United States Patent
Blackwell et al.

(10) Patent No.: US 12,122,816 B2
(45) Date of Patent: *Oct. 22, 2024

(54) LONG ACTING PEPTIDE TYROSINE TYROSINE (PYY) ANALOGS AND METHODS OF USE

(71) Applicant: Intarcia Therapeutics, Inc., Boston, MA (US)

(72) Inventors: William Blackwell, Boston, MA (US); Ved P. Srivastava, Boston, MA (US); James M. Way, Boston, MA (US)

(73) Assignee: i2o Therapeutics, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/347,246

(22) Filed: Jul. 5, 2023

(65) Prior Publication Data

US 2024/0166708 A1 May 23, 2024

Related U.S. Application Data

(63) Continuation of application No. 17/233,111, filed on Apr. 16, 2021, now Pat. No. 11,739,134.

(60) Provisional application No. 63/076,459, filed on Sep. 10, 2020, provisional application No. 63/011,649, filed on Apr. 17, 2020.

(51) Int. Cl.
*C07K 14/575* (2006.01)
*A61K 38/00* (2006.01)
*A61P 3/04* (2006.01)

(52) U.S. Cl.
CPC ............ *C07K 14/575* (2013.01); *A61P 3/04* (2018.01); *A61K 38/00* (2013.01)

(58) Field of Classification Search
None
See application file for complete search history.

(56) References Cited

U.S. PATENT DOCUMENTS 11,739,134 B2 * 8/2023 Blackwell ................. A61P 3/04
514/5.2

FOREIGN PATENT DOCUMENTS

| CN | 101065133 A | 10/2007 | |
|---|---|---|---|
| WO | WO 2004/089279 A2 | 10/2004 | |
| WO | WO 2006/066024 A2 | 6/2006 | |
| WO | WO 2011/092473 A1 | 8/2011 | |
| WO | WO 2012/101413 A1 | 8/2012 | |
| WO | WO-2014178018 A1 * | 11/2014 | ......... A61K 38/1709 |
| WO | WO 2015/177572 A1 | 11/2015 | |
| WO | WO 2015/177573 A1 | 11/2015 | |

OTHER PUBLICATIONS

Balasubramaniam et al., "Structure-Activity Studies Including a Ψ(CH$_2$-NH) Scan of Peptide YY (PYY) Active Site, PYY(22-36), for Interaction with Rat Intestinal PYY Receptors: Development of Analogues with Potent in Vivo Activity in the Intestine", *Journal of Medicinal Chemistry* 43(18):3420-3427 (2000).
International Search Report and Written Opinion received for PCT Patent Application No. PCT/US2021/027759, mailed on Oct. 6, 2021, 14 pages.
U.S. Appl. No. 17/233,111 / 2022-0002371 A1 / U.S. Pat. No. 11,739,134, filed Apr. 16, 2021 / Jan. 6, 2022 / Aug. 29, 2023, William Blackwell.

* cited by examiner

*Primary Examiner* — Christina Bradley
(74) *Attorney, Agent, or Firm* — Lathrop GPM LLP; Brian C. Trinque

(57) ABSTRACT

This invention relates to isolated polypeptides that are long acting analogs of human PYY. The disclosed PYY analog polypeptides have beneficial physicochemical properties relative to endogenous PYY and known synthetic PYY analog polypeptides, such as longer (i.e., "long-acting") elimination half-lives ($t_{1/2}$), and improved solubility and thermal stability. This invention also relates to methods of using presently disclosed PYY analog polypeptides in a variety of therapeutic indications, as well as methods of producing the same. The disclosed PYY analog polypeptides are particularly useful in methods of treating metabolic diseases or disorders, such as type 2 diabetes, treating obesity, and providing weight loss, and in methods of treating nonalcoholic fatty liver disease (NAFLD) and/or nonalcoholic steatohepatitis (NASH).

25 Claims, 9 Drawing Sheets

Specification includes a Sequence Listing.

LONG ACTING PEPTIDE TYROSINE TYROSINE (PYY) ANALOGS AND METHODS OF USE

RELATED APPLICATION

This application is a continuation of U.S. application Ser. No. 17/233,111, filed Apr. 16, 2021, which claims the benefit of U.S. Provisional Patent Application No. 63/011,649, filed Apr. 17, 2020, and U.S. Provisional Patent Application No. 63/076,459, filed Sep. 10, 2020, the disclosures of which are incorporated herein by reference in their entireties.

SEQUENCE LISTING

The instant application contains a Sequence Listing which has been submitted electronically and is hereby incorporated by reference in its entirety. Said XML copy, created on Jan. 29, 2024, is named 744345 IOT-058CON_SL2.xml and is 452,655 bytes in size.

FIELD

The present invention relates to compounds that are peptide tyrosine tyrosine (PYY) analogs and methods of preparing the same. The invention also provides pharmaceutically acceptable compositions comprising compounds of the present invention and methods of using said compositions in the treatment of various disorders.

BACKGROUND

Peptide YY (PYY) also known as peptide tyrosine tyrosine is a peptide that in humans is encoded by the PYY gene. Peptide YY is a short (36-amino acid) peptide released from cells in the ileum and colon in response to feeding. In the blood, gut, and other elements of periphery, PYY acts to reduce appetite; similarly, when injected directly into the central nervous system, PYY is also anorexigenic, i.e., it reduces appetite.

SUMMARY

It has now been found that compounds of this disclosure, and pharmaceutically acceptable compositions thereof, are effective as PYY analogs. Such compounds have a general formula as follows:
an isolated polypeptide, comprising the amino acid sequence of SEQ ID NO: 806:
$X_0PX_2PX_4X_5PX_7X_8DX_{10}SPX_{13}X_{14}X_{15}X_{16}RX_{18}X_{19}X_{20}DX_{22}X_{23}HX_{25}LX_{27}WLTRX_{32}RX_{34}$—(OH/NH$_2$) (SEQ ID NO: 806), or a pharmaceutically acceptable salt thereof;
wherein each variable is as defined and described herein.
Such exemplary compounds are provided in Table 3 herein.

Compounds of the present invention have been designed to attain long elimination half-lives ($t_1/2$) and are thus described herein as "long-acting" PYY analogs.

Compounds of the present invention, and pharmaceutically acceptable compositions thereof, are useful for treating a variety of diseases, disorders or conditions, associated with PYY receptors. Such diseases, disorders, or conditions include metabolic diseases or disorders such as type 2 diabetes, obesity and the need to attain weight loss. In certain embodiments, the invention also relates to methods of treating nonalcoholic fatty liver disease (NAFLD) and/or nonalcoholic steatohepatitis (NASH).

DETAILED DESCRIPTION

Figure 1:
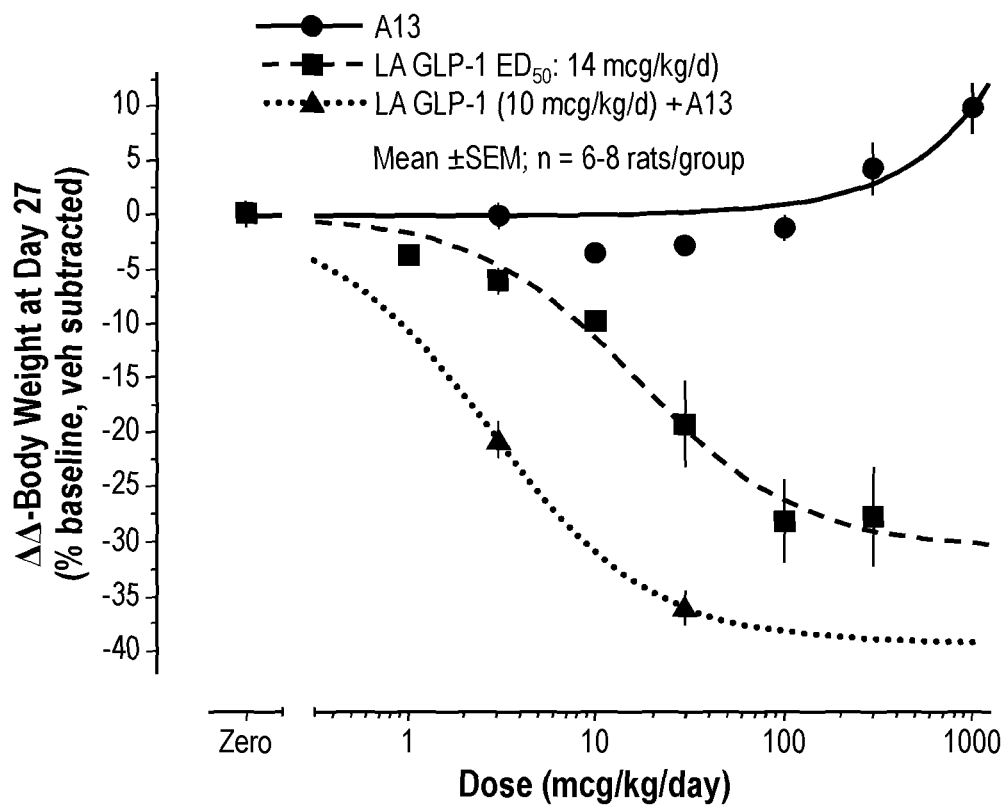
FIG. 1 depicts mean weight loss (%) from baseline and vehicle control (ΔΔ %) of a long acting PYY analog in combination with a long acting GLP-1 analog.

General description of certain embodiments of the invention Compounds of the present invention, and pharmaceutical compositions thereof, are useful as agonists of PYY receptors, particularly as agonists of human PYY receptors, including NPY1R, NPY2R, NPY4R, and NPY5R. This invention also relates to methods of producing and using such compounds, i.e., PYY analog polypeptides. Compounds of the present invention are long-acting PYY analogs. These PYY analog polypeptides are particularly useful in methods of treating metabolic diseases or disorders, such as type 2 diabetes, obesity, and in methods of providing weight loss. In certain embodiments, the invention also relates to methods of treating nonalcoholic fatty liver disease (NAFLD) and/or nonalcoholic steatohepatitis (NASH).

In certain embodiments, the present disclosure provides an isolated polypeptide comprising the amino acid sequence of SEQ ID NO: 806:

$X_0PX_2PX_4X_5PX_7X_8DX_{10}SPX_{13}X_{14}X_{15}X_{16}RX_{18}X_{19}$ $X_{20}DX_{22}X_{23}HX_{25}LX_{27}WLTRX_{32}RX_{34}$—($OH/NH_2$) (SEQ ID NO: 806), or a pharmaceutically acceptable salt thereof.

Definitions

It is to be understood that the terminology used herein is for the purpose of describing particular embodiments only, and is not intended to be limiting. As used in this specification and the appended claims, the singular forms "a," "an" and "the" include plural referents unless the context clearly dictates otherwise. Thus, for example, reference to "a solvent" includes a combination of two or more such solvents, reference to "a peptide" includes one or more peptides, or mixtures of peptides, reference to "a drug" includes one or more drugs, reference to "an osmotic delivery device" includes one or more osmotic delivery devices, and the like. Unless specifically stated or obvious from context, as used herein, the term "or" is understood to be inclusive and covers both "or" and "and".

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Unless specifically stated or obvious from context, as used herein, the term "substantially" is understood as within a narrow range of variation or otherwise normal tolerance in the art. Substantially can be understood as within 5%, 4%, 3%, 2%, 1%, 0.5%, 0.1%, 0.05%, 0.01% or 0.001% of the stated value.

Unless defined otherwise, all technical and scientific terms used herein have the same meaning as commonly understood by one of ordinary skill in the art to which the invention pertains. Although other methods and materials similar, or equivalent, to those described herein can be used in the practice of the present invention, the preferred materials and methods are described herein.

In describing and claiming the present invention, the following terminology will be used in accordance with the definitions set out below.

The terms "drug," "therapeutic agent," and "beneficial agent" are used interchangeably to refer to any therapeutically active substance that is delivered to a subject to produce a desired beneficial effect. In one embodiment of the present invention, the drug is a polypeptide. In another embodiment of the present invention, the drug is a small molecule, for example, hormones such as androgens or estrogens. The devices and methods of the present invention are well suited for the delivery of proteins, small molecules and combinations thereof.

The terms "peptide," "polypeptide," and "protein" are used interchangeably herein and typically refer to a molecule comprising a chain of two or more amino acids (e.g., most typically L-amino acids, but also including, e.g., D-amino acids, modified amino acids, amino acid analogs, and amino acid mimetics).

In some embodiments, naturally-occurring L-amino acids, are represented by either conventional three-letter, or capitalized one-letter, amino acid designations of Table 1. In other embodiments, naturally-occurring L-amino acids and D-amino acids, are both represented by either conventional three-letter, or capitalized one-letter, amino acid designations of Table 1. In still other embodiments, D-amino acids, are represented by lower-case one-letter amino acid designations corresponding to one-letter designations of Table 2, i.e., a, l, m, f, w, k, q, e, s, p, v, i, c, y, h, r, n, d, and t.

TABLE 1

| Naturally-occurring amino acids | | |
|---|---|---|
| G | Glycine | Gly |
| A | Alanine | Ala |
| L | Leucine | Leu |
| M | Methionine | Met |
| F | Phenylalanine | Phe |
| W | Tryptophan | Trp |
| K | Lysine | Lys |
| Q | Glutamine | Gln |
| E | Glutamic Acid | Glu |
| S | Serine | Ser |
| P | Proline | Pro |
| V | Valine | Val |
| I | Isoleucine | Ile |
| C | Cysteine | Cys |
| Y | Tyrosine | Tyr |
| H | Histidine | His |
| R | Arginine | Arg |
| N | Asparagine | Asn |
| D | Aspartic Acid | Asp |
| T | Threonine | Thr |

TABLE 2

| Lower case designations refer to D stereoisomers of amino acids | | |
|---|---|---|
| a | D- Alanine | D-Ala |
| l | D-Leucine | D-Leu |
| m | D-Methionine | D-Met |
| f | D-Phenylalanine | D-Phe |
| w | D-Tryptophan | D-Trp |
| k | D-Lysine | D-Lys |
| q | D-Glutamine | D-Gln |
| e | D-Glutamic Acid | D-Glu |
| s | D-Serine | D-Ser |
| p | Proline | D-Pro |
| v | D-Valine | D-Val |
| i | D-Isoleucine | D-Ile |
| c | D-Cysteine | D-Cys |
| y | D-Tyrosine | D-Tyr |
| h | D-Histidine | D-His |
| r | D-Arginine | D-Arg |
| n | D-Asparagine | D-Asn |
| d | D-Aspartic Acid | D-Asp |
| t | D-Threonine | D-Thr |

Peptides may be naturally occurring, synthetically produced, or recombinantly expressed. Peptides may also comprise additional groups modifying the amino acid chain, for example, functional groups added via post-translational modification. Examples of post-translation modifications include, but are not limited to, acetylation, alkylation (including, methylation), biotinylation, glutamylation, glycylation, glycosylation, isoprenylation, lipoylation, phosphopantetheinylation, phosphorylation, selenation, and C-terminal amidation. The term peptide also includes peptides comprising modifications of the amino terminus and/or the carboxy terminus. Modifications of the terminal amino group include, but are not limited to, des-amino, N-lower alkyl, N-di-lower alkyl, and N-acyl modifications. Modifications of the terminal carboxy group include, but are not limited to, amide, lower alkyl amide, dialkyl amide, and lower alkyl ester modifications (e.g., wherein lower alkyl is $C_1$-$C_4$ alkyl). The term peptide also includes modifications, such as but not limited to those described above, of amino acids falling between the amino and carboxy termini. In one embodiment, a peptide may be modified by addition of a small-molecule drug.

The terminal amino acid at one end of the peptide chain typically has a free amino group (i.e., the amino terminus). The terminal amino acid at the other end of the chain typically has a free carboxyl group (i.e., the carboxy terminus). Typically, the amino acids making up a peptide are numbered in order, starting at the amino terminus and increasing in the direction of the carboxy terminus of the peptide.

The phrase "amino acid residue" as used herein refers to an amino acid that is incorporated into a peptide by an amide bond or an amide bond mimetic.

The term "insulinotropic" as used herein typically refers to the ability of a compound, e.g., a peptide, to stimulate or affect the production and/or activity of insulin (e.g., an insulinotropic hormone). Such compounds typically stimulate or otherwise affect the secretion or biosynthesis of insulin in a subject. Thus, an "insulinotropic peptide" is an amino acid-containing molecule capable of stimulating or otherwise affecting secretion or biosynthesis of insulin.

The term "acylated" as used herein, in relation to disclosed polypeptides, means the disclosed polypeptide is substituted with one or more lipophilic substituents each optionally via a spacer, wherein "lipophilic substituent" and "spacer" are defined herein. Certain lipophilic substituents, each optionally via a spacer, can bind albumin and confer affinity to albumin to the resulting acylated polypeptide. The extent is variable, and depending on numerous factors, to which lipophilic substituents, each optionally via a spacer, bind albumin and confer affinity to albumin to the resulting acylated polypeptide. Numerous factors include identities of the lipophilic substituent, optional spacer, polypeptide, and the site of covalent attachment to the polypeptide.

The terms "linear" or "liner polypeptide" as used herein, refer to a "non-acylated" polypeptide, in other words, a disclosed PYY analog polypeptide without a lipophilic substituents each optionally via a spacer, wherein "lipophilic substituent" and "spacer" are defined herein.

The terms "conjugated" or conjugated polypeptide" as used herein, refer to an "acylated" polypeptide, in other words, a disclosed PYY analog polypeptide having one or more lipophilic substituents each optionally via a spacer, wherein "lipophilic substituent" and "spacer" are defined herein.

As used herein, the term "pharmaceutically acceptable salts" refers to derivatives of the disclosed polypeptides wherein the parent polypeptide is modified by converting an existing acid or base moiety to its salt form. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

The term "vehicle" as used herein refers to a medium used to carry a compound, e.g., a drug or a particle containing a drug. Vehicles of the present invention typically comprise components such as polymers and solvents. The suspension vehicles of the present invention typically comprise solvents and polymers that are used to prepare suspension formulations further comprising drug particle formulations.

The phrase "phase separation" as used herein refers to the formation of multiple phases (e.g., liquid and gel phases) in the suspension vehicle, such as when the suspension vehicle contacts the aqueous environment. In some embodiments of the present invention, the suspension vehicle is formulated to exhibit phase separation upon contact with an aqueous environment having less than approximately 10% water.

The phrase "single-phase" as used herein refers to a solid, semisolid, or liquid homogeneous system that is physically and chemically uniform throughout.

The term "dispersed" as used herein refers to dissolving, dispersing, suspending, or otherwise distributing a compound, for example, a drug particle formulation, in a suspension vehicle.

The phrase "chemically stable" as used herein refers to formation in a formulation of an acceptable percentage of degradation products produced over a defined period of time by chemical pathways, such as deamidation (usually by hydrolysis), aggregation, or oxidation.

The phrase "physically stable" as used herein refers to formation in a formulation of an acceptable percentage of aggregates (e.g., dimers and other higher molecular weight products).

Further, a physically stable formulation does not change its physical state as, for example, from liquid to solid, or from amorphous to crystal form.

The term "viscosity" as used herein typically refers to a value determined from the ratio of shear stress to shear rate (see, e.g., Considine, D. M. & Considine, G. D., Encyclopedia of Chemistry, 4th Edition, Van Nostrand, Reinhold, N.Y., 1984) essentially as follows:

$$F/A = \mu * V/L \quad \text{(Equation 1)}$$

where F/A=shear stress (force per unit area),
$\mu$=a proportionality constant (viscosity), and
V/L=the velocity per layer thickness (shear rate).

From this relationship, the ratio of shear stress to shear rate defines viscosity. Measurements of shear stress and shear rate are typically determined using parallel plate rheometry performed under selected conditions (for example, a temperature of about 37° C.). Other methods for the determination of viscosity include, measurement of a kinematic viscosity using viscometers, for example, a Cannon-Fenske viscometer, an Ubbelohde viscometer for the Cannon-Fenske opaque solution, or an Ostwald viscometer. Generally, suspension vehicles of the present invention have a viscosity sufficient to prevent a particle formulation suspended therein from settling during storage and use in a method of delivery, for example, in an implantable, drug delivery device.

The term "non-aqueous" as used herein refers to an overall moisture content, for example, of a suspension formulation, typically of less than or equal to about 10 wt %, for example, less than or equal to about 7 wt %, less than or equal to about 5 wt %, and/or less than about 4 wt %. Also, a particle formulation of the present invention comprises less than about 10 wt %, for example, less than about 5 wt %, residual moisture.

The term "subject" as used herein refers to any member of the subphylum Chordata, including, without limitation, humans and other primates, including non-human primates such as rhesus macaques and other monkey species and chimpanzees and other ape species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age or gender. Thus, both adult and newborn individuals are intended to be covered.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The term "osmotic delivery device" as used herein typically refers to a device used for delivery of a drug (e.g., a disclosed PYY analog polypeptide) to a subject, wherein the device comprises, for example, a reservoir (made, e.g., from a titanium alloy) having a lumen that contains a suspension formulation comprising a drug (e.g., a disclosed PYY analog polypeptide) and an osmotic agent formulation. A piston assembly positioned in the lumen isolates the suspension formulation from the osmotic agent formulation. A semi-permeable membrane is positioned at a first distal end of the reservoir adjacent the osmotic agent formulation and a diffusion moderator (which defines a delivery orifice through which the suspension formulation exits the device) is positioned at a second distal end of the reservoir adjacent the suspension formulation. Typically, the osmotic delivery device is implanted within the subject, for example, subdermally or subcutaneously (e.g., in the inside, outside, or back of the upper arm and in the abdominal area). An exemplary osmotic delivery device is the DUROS® (ALZA Corporation, Mountain View, Calif) delivery device. Examples of terms synonymous to "osmotic delivery device" include but are not limited to "osmotic drug delivery device", "osmotic drug delivery system", "osmotic device", "osmotic delivery device", "osmotic delivery system", "osmotic pump", "implantable drug delivery device", "drug delivery system", "drug delivery device", "implantable osmotic pump", "implantable drug delivery system", and "implantable delivery system". Other terms for "osmotic delivery device" are known in the art.

The term "continuous delivery" as used herein typically refers to a substantially continuous release of drug from an osmotic delivery device and into tissues near the implantation site, e.g., subdermal and subcutaneous tissues. For example, an osmotic delivery device releases drug essentially at a predetermined rate based on the principle of osmosis. Extracellular fluid enters the osmotic delivery device through the semi-permeable membrane directly into the osmotic engine that expands to drive the piston at a slow and consistent rate of travel. Movement of the piston forces the drug formulation to be released through the orifice of the diffusion moderator. Thus, release of the drug from the osmotic delivery device is at a slow, controlled, consistent rate.

The term "substantial steady-state delivery" as used herein typically refers to delivery of a drug at or near a target concentration over a defined period of time, wherein the amount of the drug being delivered from an osmotic delivery device is substantially zero-order delivery. Substantial zero-order delivery of an active agent (e.g., a disclosed PYY analog polypeptide) means that the rate of drug delivered is constant and is independent of the drug available in the delivery system; for example, for zero-order delivery, if the rate of drug delivered is graphed against time and a line is fitted to the data the line has a slope of approximately zero, as determined by standard methods (e.g., linear regression).

The phrase "drug half-life" as used herein refers how long it takes a drug to be eliminated from blood plasma by one half of its concentration. A drug's half-life is usually measured by monitoring how a drug degrades when it is administered via injection or intravenously. A drug is usually detected using, for example, a radioimmunoassay (RIA), a chromatographic method, an electrochemiluminescent (ECL) assay, an enzyme linked immunosorbent assay (ELISA) or an immunoenzymatic sandwich assay (IEMA).

The terms "µg" and "mcg" and "ug" are understood to mean "micrograms". Similarly, the terms "µl" and "uL" are understood to mean "microliter", and the terms "µM" and "uM" are understood to mean "micromolar".

The term "serum" is meant to mean any blood product from which a substance can be detected. Thus, the term serum includes at least whole blood, serum, and plasma. For example, "an amount of [a substance] in a subject's serum" would cover "an amount of [the substance] in a subject's plasma".

Baseline is defined as the last assessment on or before the day of the initial placement of an osmotic delivery device (containing drug or placebo).

Peptide YY (PYY) is a 36 amino acid residue peptide amide having the amino acid sequence of (YPIKPEAPGE-DASPEELNRYYASLRHYLNLVTRQRY-NH$_2$), SEQ ID NO: 800. PYY inhibits gut motility and blood flow (Laburthe, M., Trends Endocrinol Metab. 1(3):168-74 (1990), mediates intestinal secretion (Cox, H. M., et al., Br J Pharmacol 101(2):247-52 (1990); Playford, R. J., et al., Lancet 335(8705):1555-7 (1990)), and stimulate net absorption (MacFayden, R. J., et al., Neuropeptides 7(3):219-27 (1986)). Two major in vivo variants, PYY(1-36) and PYY (3-36), have been identified (e.g., Eberlein, G. A., et al., Peptides 10(4), 797-803 (1989)). The sequence of PYY, as well as peptide analogs and peptide derivatives thereof, are known in the art (e.g., U.S. Pat. Nos. 5,574,010 and 5,552, 520).

Exemplary Compounds: PYY Analog Polypeptides

Certain disclosed PYY analog polypeptides, including those of Table 3 below, exhibit one or more of: excellent solubility, stability, bioavailability, biological activity and specificity, and longer half-lives than those for endogenous PYY and known PYY analogs. Certain disclosed PYY analog polypeptides were developed to accommodate less frequent administration than is required for known PYY analogs. Certain disclosed PYY analog polypeptides were developed for administration via weekly or monthly injections. Certain disclosed PYY analog polypeptides were developed for administration via implantation of a delivery device comprising the PYY analog polypeptide, where the delivery device comprises a dose of the PYY analog polypeptide of up to 3 months, 6 months, 9 months, one year, 18 months or two years.

In some embodiments, an isolated polypeptide of the disclosure comprises an amino acid sequence selected from the group consisting of the following peptides listed in Table 3:

TABLE 3

Exemplary compounds: PYY analog polypeptides covalently bound to a lipophilic substituent, optionally via a spacer.

| Compound No. | Sequence | SEQ ID NO: |
|---|---|---|
| A1 | PKPEAPGK(γGlu-γGlu-dpeg-CO(CH$_2$)$_{18}$CO$_2$H)DASPEEWNRYYADLRHYLNWLTRQRY-(NH$_2$) | SEQ ID NO: 1 |
| A2 | PKPEAPGK(γGlu-γGlu-CO(CH$_2$)$_{18}$CO$_2$H)DASPEEWNRYYADLRHYLNWLTRQRY-(NH$_2$) | SEQ ID NO: 2 |
| A3 | PKPEAPGK(dpeg-dpeg-γGlu-CO(CH$_2$)$_{16}$CO$_2$H)DASPEEWNRYYADLRHYLNWLTRQRY-(NH$_2$) | SEQ ID NO: 3 |
| A4 | K(γGlu-γGlu-CO(CH$_2$)$_{18}$CO$_2$H)PKPEAPGKDASPEEWNRYYADARHYLNWLTRQR-(n-methyl Y)-(NH$_2$) | SEQ ID NO: 4 |
| A5 | PK(γGlu-γGlu-CO(CH$_2$)$_{18}$CO$_2$H)PEAPGKDASPEEWNRYYADARHYLNWLTRQR-(n-methyl Y)-(NH$_2$) | SEQ ID NO: 5 |
| A6 | PKPK(γGlu-γGlu-CO(CH$_2$)$_{18}$CO$_2$H)APGKDASPEEWNRYYADARHYLNWLTRQR-(n-methyl Y)-(NH$_2$) | SEQ ID NO: 6 |
| A7 | PKPEAPK(γGlu-γGlu-CO(CH$_2$)$_{18}$CO$_2$H)KDASPEEWNRYYADARHYLNWLTRQR-(n-methyl Y)-(NH$_2$) | SEQ ID NO: 7 |
| A8 | PKPEAPGKDASPK(γGlu-γGlu-CO(CH$_2$)$_{18}$CO$_2$H)EWNRYYADARHYLNWLTRQR-(n-methyl Y)-(NH$_2$) | SEQ ID NO: 8 |
| A9 | PKPEAPGKDASPEEWK(γGlu-γGlu-CO(CH$_2$)$_{18}$CO$_2$H)RYYADARHYLNWLTRQR-(n-methyl Y)-(NH$_2$) | SEQ ID NO: 9 |
| A10 | PKPEAPGK(γGlu-γGlu-CO(CH$_2$)$_{18}$CO$_2$H)DASPEEWNRYYADLRHYLNWLTRQR-(n-methyl Y)-(NH$_2$) | SEQ ID NO: 10 |
| A11 | PKPEAPGK(γGlu-γGlu-CO(CH$_2$)$_{18}$CO$_2$H)DASPEEWNRYYADLRHYLNWLTRQR-(homotyrosine)-(NH$_2$) | SEQ ID NO: 11 |
| A12 | PKPEAPGK(γGlu-γGlu-CO(CH$_2$)$_{18}$CO$_2$H)DASPEEWNRYYADLRHYLNWLTRQRy-(NH$_2$) | SEQ ID NO: 12 |
| A13 | PKPEAPGK(γGlu-γGlu-CO(CH$_2$)$_{18}$CO$_2$H)DASPEEWNRYYADLRHYLNWLTRQRF-(NH$_2$) | SEQ ID NO: 13 |
| A14 | PKPEAPGKDASPEEWNRYYk(γGlu-γGlu-CO(CH$_2$)$_{18}$CO$_2$H)DLRHYLNWLTRQRF-(NH$_2$) | SEQ ID NO: 14 |
| A15 | PKPEAPGk(γGlu-γGlu-CO(CH$_2$)$_{18}$CO$_2$H)DASPEEWNRYYADLRHYLNWLTRQRF-(NH$_2$) | SEQ ID NO: 15 |
| A16 | PKPEAPGKDASPEEWNRYYK(γGlu-dpeg-dpeg-γGlu-CO(CH$_2$)$_{18}$CO$_2$H)DLRHYLNWLTRQRF-(NH$_2$) | SEQ ID NO: 16 |
| A17 | PKPEAPGK(γGlu-dpeg-dpeg-γGlu-CO(CH$_2$)$_{18}$CO$_2$H)DASPEEWNRYYADLRHYLNWLTRQRF-(NH$_2$) | SEQ ID NO: 17 |
| A18 | PKPEAPGk(γGlu-dpeg-dpeg-γGlu-CO(CH$_2$)$_{18}$CO$_2$H)DASPEEWNRYYADLRHYLNWLTRQRF-(NH$_2$) | SEQ ID NO: 18 |

TABLE 3-continued

Exemplary compounds: PYY analog polypeptides covalently
bound to a lipophilic substituent, optionally via a spacer.

| Compound No. | Sequence | SEQ ID NO: |
|---|---|---|
| A19 | PKPEKPGK(γGlu-γGlu-CO(CH$_2$)$_{18}$CO$_2$H)DASPEEWNRYYKDLRHYLNWLTRQRF-(NH$_2$) | SEQ ID NO: 19 |
| A20 | PKPEAPGK(γGlu-γGlu-CO(CH$_2$)$_{18}$CO$_2$H)DASPKEWNRYYKDLRHYLNWLTRQRF-(NH$_2$) | SEQ ID NO: 20 |
| A21 | PKPEAPGK(γGlu-γGlu-CO(CH$_2$)$_{18}$CO$_2$H)DASPEEWNRYYkDLRHYLNWLTRQRF-(NH$_2$) | SEQ ID NO: 21 |
| A22 | PKPEAPGK(γGlu-γGlu-CO(CH$_2$)$_{18}$CO$_2$H)DASPEEWNRYY-Dap-DLRHYLNWLTRQRF-(NH$_2$) | SEQ ID NO: 22 |
| A23 | PKPEAPGK(γGlu-γGlu-CO(CH$_2$)$_{18}$CO$_2$H)DASPEEWQRYYKDLRHYLNWLTRQRF-(NH$_2$) | SEQ ID NO: 23 |
| A24 | PKPEAPGK(γGlu-γGlu-CO(CH$_2$)$_{18}$CO$_2$H)DASPEEWDRYYKDLRHYLNWLTRQRF-(NH$_2$) | SEQ ID NO: 24 |
| A25 | PKPEAPGK(γGlu-γGlu-CO(CH$_2$)$_{18}$CO$_2$H)DASPEEWSRYYKDLRHYLNWLTRQRF-(NH$_2$) | SEQ ID NO: 25 |
| A26 | PKPEAPGK(γGlu-γGlu-CO(CH$_2$)$_{18}$CO$_2$H)DASPEEWTRYYKDLRHYLNWLTRQRF-(NH$_2$) | SEQ ID NO: 26 |
| A27 | PKPEKPGK(γGlu-γGlu-CO(CH$_2$)$_{18}$CO$_2$H)DASPKEWNRYYKDLRHYLNWLTRQRF-(NH$_2$) | SEQ ID NO: 27 |
| A28 | PKPEKPGKDASPKEWNRYYK(γGlu-γGlu-CO(CH$_2$)$_{18}$CO$_2$H)DLRHYLNWLTRQRF-(NH$_2$) | SEQ ID NO: 28 |
| A29 | PKPEKPGEDASPKEWNRYYK(γGlu-γGlu-CO(CH$_2$)$_{18}$CO$_2$H)DLRHYLNWLTRQRF-(NH$_2$) | SEQ ID NO: 29 |
| A30 | PKPEAPGK(γGlu-γGlu-CO(CH$_2$)$_{18}$CO$_2$H)DASPEEW-homoSer-RYYKDLRHYLNWLTRQRF-(NH$_2$) | SEQ ID NO: 30 |
| A31 | PKPEAPGK(γGlu-γGlu-CO(CH$_2$)$_{18}$CO$_2$H)DASPEEW-(alpha-methyl-Ser)-RYYKDLRHYLNWLTRQRF-(NH$_2$) | SEQ ID NO: 31 |
| A32 | PKPEAPGK(γGlu-γGlu-CO(CH$_2$)$_{16}$CO$_2$H)DASPEEWDRYYKDLRHYLNWLTRQRF-(NH$_2$) | SEQ ID NO: 32 |
| A33 | PKPEAPGK(γGlu-γGlu-CO(CH$_2$)$_{17}$CO$_2$H)DASPEEWDRYYKDLRHYLNWLTRQRF-(NH$_2$) | SEQ ID NO: 33 |
| A34 | PKPEKPGEDASPKEWDRYYK(γGlu-γGlu-CO(CH$_2$)$_{18}$CO$_2$H)DLRHYLNWLTRQRF-(NH$_2$) | SEQ ID NO: 34 |
| A35 | PKPEK(γGlu-γGlu-CO(CH$_2$)$_{16}$CO$_2$H)PGEDASPKEWDRYYKDLRHYLNWLTRQRF-(NH$_2$) | SEQ ID NO: 35 |
| A36 | PKPEK(γGlu-γGlu-CO(CH$_2$)$_{17}$CO$_2$H)PGEDASPKEWNRYYKDLRHYLNWLTRQRF-(NH$_2$) | SEQ ID NO: 36 |

TABLE 3-continued

Exemplary compounds: PYY analog polypeptides covalently bound to a lipophilic substituent, optionally via a spacer.

| Compound No. | Sequence | SEQ ID NO: |
|---|---|---|
| A37 | PKPEK(γGlu-γGlu-CO(CH$_2$)$_{18}$CO$_2$H)PGKDASPKEWNRYYKDLRHYLNWLTRQRF-(NH$_2$) | SEQ ID NO: 37 |
| A38 | PKPEK(γGlu-γGlu-CO(CH$_2$)$_{16}$CO$_2$H)PGEDASPKEWNRYYKDLRHYLNWLTRQRF-(NH$_2$) | SEQ ID NO: 38 |
| A39 | PKPEKPGK(γGlu-γGlu-CO(CH$_2$)$_{17}$CO$_2$H)DASPKEWE*RYYK*DLRHYLNWLTRQRF-(NH$_2$) | SEQ ID NO: 39 |
| A40 | PKPEKPGK(γGlu-γGlu-CO(CH$_2$)$_{17}$CO$_2$H)DASPKEWD*RYYK*DLRHYLNWLTRQRF-(NH$_2$) | SEQ ID NO: 40 |
| A41 | PKPEAPGK(γGlu-γGlu-CO(CH$_2$)$_{18}$CO$_2$H)DASPEEWE*RYYK*DLRHYLNWLTRQRF-(NH$_2$) | SEQ ID NO: 41 |
| A42 | PKPEAPGK(γGlu-γGlu-CO(CH$_2$)$_{18}$CO$_2$H)DASPEEWD*RYYK*DLRHYLNWLTRQRF-(NH$_2$) | SEQ ID NO: 42 |
| A43 | PKPEAPGK(γGlu-γGlu-CO(CH$_2$)$_{18}$CO$_2$H)DASPEEWK*RYYE*DLRHYLNWLTRQRF-(NH$_2$) | SEQ ID NO: 43 |
| A44 | PKPEAPGK(γGlu-γGlu-CO(CH$_2$)$_{18}$CO$_2$H)DASPEEWK*RYYD*DLRHYLNWLTRQRF-(NH$_2$) | SEQ ID NO: 44 |
| A45 | PKPEAPGK(γGlu-γGlu-CO(CH$_2$)$_{18}$CO$_2$H)D*ASPK*EWDRYYKDLRHYLNWLTRQRF-(NH$_2$) | SEQ ID NO: 45 |
| A46 | PKPEAPGK(γGlu-γGlu-CO(CH$_2$)$_{18}$CO$_2$H)K*ASPE*EWDRYYKDLRHYLNWLTRQRF-(NH$_2$) | SEQ ID NO: 46 |
| A47 | PKPEAPGK(γGlu-γGlu-CO(CH$_2$)$_{18}$CO$_2$H)DASPEEWDRYYKDD*RHYK*NWLTRQRF-(NH$_2$) | SEQ ID NO: 47 |
| A48 | PKPEAPGK(γGlu-γGlu-CO(CH$_2$)$_{18}$CO$_2$H)DASPEEWDRYYKDK*RHYE*NWLTRQRF-(NH$_2$) | SEQ ID NO: 48 |
| A49 | PKPEAPGK(γGlu-γGlu-CO(CH$_2$)$_{18}$CO$_2$H)DASPEEWNRYYADLRHYLNWLTRQR-(β-homo-Tyr)-(NH$_2$) | SEQ ID NO: 49 |
| A50 | PKPEAPGKDASPEEWNRYYADLRHYLNWLTRK(γGlu-γGlu-CO(CH$_2$)$_{18}$CO2H)RF-(NH$_2$) | SEQ ID NO: 50 |
| A51 | PKPEAPGKDASPEEWNRYYADLRHYLK(γGlu-γGlu-CO(CH$_2$)$_{18}$CO$_2$H)WLTRQRF-(NH$_2$) | SEQ ID NO: 51 |
| A52 | PKPEAPGKDASPEEWNRYYADLRHK(γGlu-γGlu-CO(CH$_2$)$_{18}$CO$_2$H)LNWLTRQRF-(NH$_2$) | SEQ ID NO: 52 |
| A53 | PKPEAPGKDASPEEWNRYYADLK(γGlu-γGlu-CO(CH$_2$)$_{18}$CO$_2$H)HYLNWLTRQRF-(NH$_2$) | SEQ ID NO: 53 |
| A54 | PKPEAPGKDASPEEWNRYYK(γGlu-γGlu-CO(CH$_2$)$_{18}$CO$_2$H)DLRHYLNWLTRQRF-(NH$_2$) | SEQ ID NO: 54 |

TABLE 3-continued

Exemplary compounds: PYY analog polypeptides covalently bound to a lipophilic substituent, optionally via a spacer.

| Compound No. | Sequence | SEQ ID NO: |
|---|---|---|
| A55 | PKPEAPGKDASPEEWK(γGlu-γGlu-CO(CH$_2$)$_{18}$CO$_2$H)RYYADLRHYLNWLTRQRF-(NH$_2$) | SEQ ID NO: 55 |
| A56 | PKPEAPGK(γGlu-γGlu-CO(CH$_2$)$_{18}$CO$_2$H)DASPEEWNRYYADLRHYLNWLTRQR-(4-pyridyl Ala)-(NH$_2$) | SEQ ID NO: 56 |
| A57 | PKPEAPGK(γGlu-γGlu-CO(CH$_2$)$_{18}$CO$_2$H)DASPEEWNRYYADLRHYLNWLTRQR-(3-pyridyl Ala)-(NH$_2$) | SEQ ID NO: 57 |
| A58 | PKPEAPGK(γGlu-γGlu-CO(CH$_2$)$_{18}$CO$_2$H)DASPEEWNRYYADLRHYLNWLTRQR-(4-methyl Phe)-(NH$_2$) | SEQ ID NO: 58 |
| A59 | PKPEAPGK(γGlu-γGlu-CO(CH$_2$)$_{18}$CO$_2$H)DASPEEWNRYYADLRHYLNWLTRQR-(4-carboxy Phe)-(NH$_2$) | SEQ ID NO: 59 |
| A60 | PKPEAPGK(γGlu-γGlu-CO(CH$_2$)$_{18}$CO$_2$H)DASPEEWNRYYADLRHYLNWLTRQR-(4-fluoro Phe)-(NH$_2$) | SEQ ID NO: 60 |
| A61 | PKPEAPGK(γGlu-γGlu-CO(CH$_2$)$_{18}$CO$_2$H)DASPEEWNRYYADLRHYLNWLTRQR-(homo-Phe)-(NH$_2$) | SEQ ID NO: 61 |
| A62 | PKPEAPGK(γGlu-γGlu-CO(CH$_2$)$_{18}$CO$_2$H)DASPEEWNRYYADLRHYLNWLTRQR-(n-methyl Phe)-(NH$_2$) | SEQ ID NO: 62 |
| A63 | PKPEAPK(γGlu-γGlu-CO(CH$_2$)$_{18}$CO$_2$H)KDASPEELNRYYADARHYLNWLTRQR-(n-methyl Tyr)-(NH$_2$) | SEQ ID NO: 63 |
| A64 | PKPEAPK(γGlu-γGlu-CO(CH$_2$)$_{18}$CO$_2$H)KDASPEELNRYYADARHYLNWLTRQRF-(NH$_2$) | SEQ ID NO: 64 |
| A65 | PKPEAPGKDASPEEWNRYYk(γGlu-dpeg-dpeg-γGlu-CO(CH$_2$)$_{18}$CO$_2$H)DLRHYLNWLTRQRF-(NH$_2$) | SEQ ID NO: 65 |
| A66 | PKPEAPGK(γGlu-γGlu-CO(CH$_2$)$_{18}$CO$_2$H)DKSPEEWNRYYKDLRHYLNWLTRQRF-(NH$_2$) | SEQ ID NO: 66 |
| A67 | PKPEAPGK(γGlu-γGlu-CO(CH$_2$)$_{18}$CO$_2$H)DASPEKWNRYYKDLRHYLNWLTRQRF-(NH$_2$) | SEQ ID NO: 67 |
| A68 | PKPEAPGK(γGlu-γGlu-CO(CH$_2$)$_{18}$CO$_2$H)DASPEEWNRKYKDLRHYLNWLTRQRF-(NH$_2$) | SEQ ID NO: 68 |
| A69 | PKPEAPGK(γGlu-γGlu-CO(CH$_2$)$_{18}$CO$_2$H)DASPEEWNRYKKDLRHYLNWLTRQRF-(NH$_2$) | SEQ ID NO: 69 |
| A70 | PKPEKPGKDASPK(γGlu-γGlu-CO(CH$_2$)$_{18}$CO$_2$H)EWNRYYKDLRHYLNWLTRQRF-(NH$_2$) | SEQ ID NO: 70 |
| A71 | PKPEK(γGlu-γGlu-CO(CH$_2$)$_{18}$CO$_2$H)PGKDASPKEWNRYYKDLRHYLNWLTRQRF-(NH$_2$) | SEQ ID NO: 71 |
| A72 | PKPEK(γGlu-γGlu-CO(CH$_2$)$_{18}$CO$_2$H)PGEDASPKEWNRYYKDLRHYLNWLTRQRF-(NH$_2$) | SEQ ID NO: 72 |

TABLE 3-continued

Exemplary compounds: PYY analog polypeptides covalently bound to a lipophilic substituent, optionally via a spacer.

| Compound No. | Sequence | SEQ ID NO: |
|---|---|---|
| A73 | PKPEAPGK(γGlu-γGlu-CO(CH$_2$)$_{18}$CO$_2$H)DASPKEWNRYYKDLRHYLNWLTRQRF-(NH$_2$) | SEQ ID NO: 73 |
| A74 | PKPEKPGK(γGlu-γGlu-CO(CH$_2$)$_{18}$CO$_2$H)DASPEEWNRYYKDLRHYLNWLTRQRF-(NH$_2$) | SEQ ID NO: 74 |
| A75 | PKPEKPGK(γGlu-γGlu-CO(CH$_2$)$_{18}$CO$_2$H)DASPEEWSRYYKDLRHYLNWLTRQRF-(NH$_2$) | SEQ ID NO: 75 |
| A76 | PKPEAPGK(γGlu-γGlu-CO(CH$_2$)$_{18}$CO$_2$H)DASPKEWDRYYKDLRHYLNWLTRQRF-(NH$_2$) | SEQ ID NO: 76 |
| A77 | PKPEKPGEDASPEEWDRYYK(γGlu-γGlu-CO(CH$_2$)$_{18}$CO$_2$H)DLRHYLNWLTRQRF-(NH$_2$) | SEQ ID NO: 77 |
| A78 | PKPEK(γGlu-γGlu-CO(CH$_2$)$_{18}$CO$_2$H)PGEDASPKEWDRYYKDLRHYLNWLTRQRF-(NH$_2$) | SEQ ID NO: 78 |

Dap is diaminopimelic acid

Structural representations of certain peptides of Table 3 are provided below in Table 4:

TABLE 4

Chemical structures of exemplary peptides: PYY analog polypeptides comprising a lipophilic substituent via a spacer, two peptides of which further comprise a bridging moiety.

PKPEAPGK(γGlu-γGlu-CO(CH$_2$)$_{18}$CO$_2$H)DASPEEWNRYYADLRHLNWLTRQRY-(NH$_2$)

A2

SEQ ID NO: 2

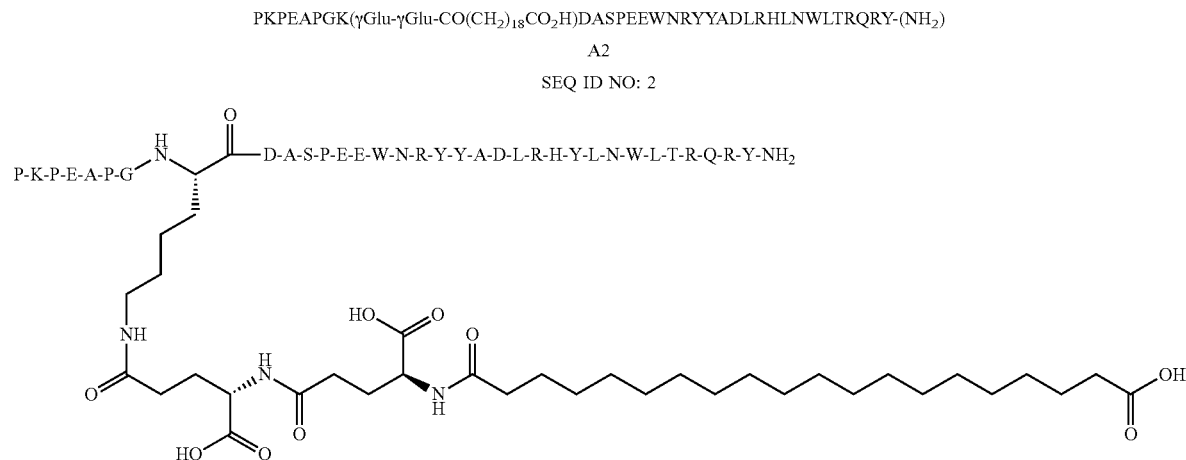

PKPEAPGK(γGly-γGlu-CO(CH$_2$)$_{18}$CO$_2$H)DASPEEWNRYYADLRHYLNWLTRQRF-(NH$_2$)

A13

SEQ ID NO: 13

TABLE 4-continued

Chemical structures of exemplary peptides: PYY analog polypeptides comprising a
lipophilic substituent via a spacer, two peptides of which further comprise a bridging moiety.

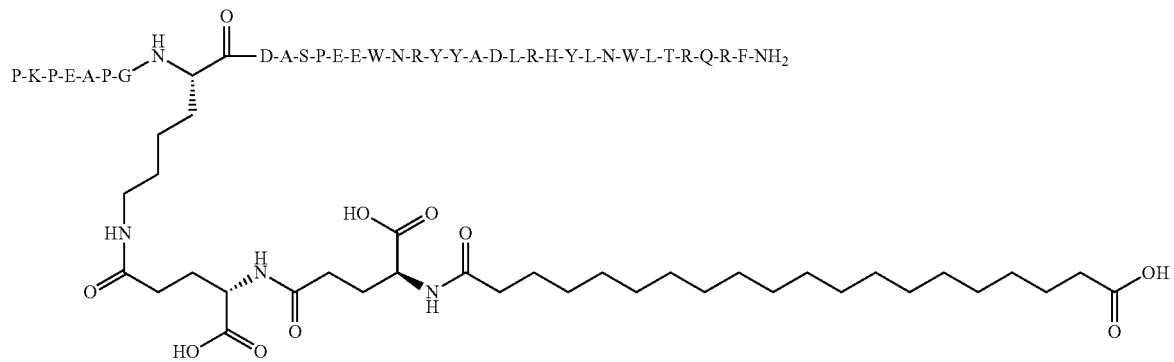

PKPEAPGK(γGlu-γGlu-CO(CH$_2$)$_{18}$CO$_2$H)DASPEEWDRYYKDLRHYLNWLTRQRF-(NH$_2$)
A24
SEQ ID NO: 24

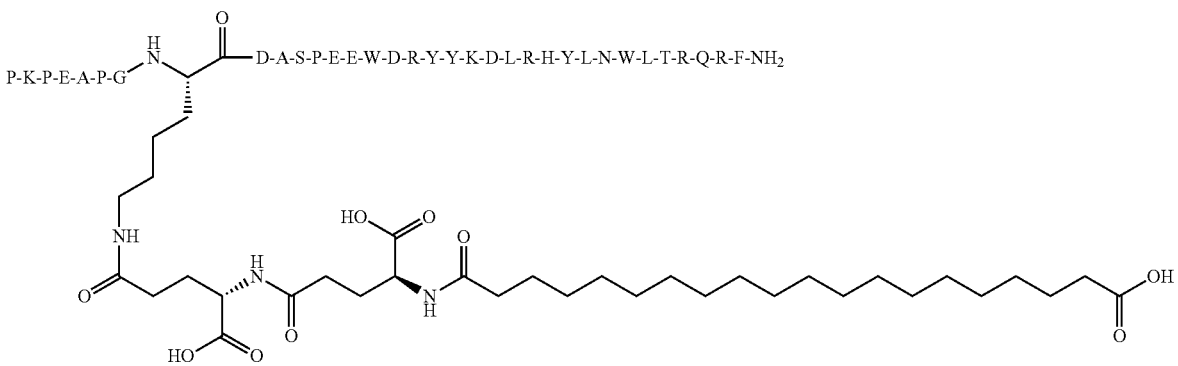

PKPEAPGK(γGlu-γGlu-CO(CH$_2$)$_{18}$CO$_2$H)DASPEEWD*RYYK*DLRHYLNWLTRQRF-(NH$_2$)
A42
SEQ ID NO: 42

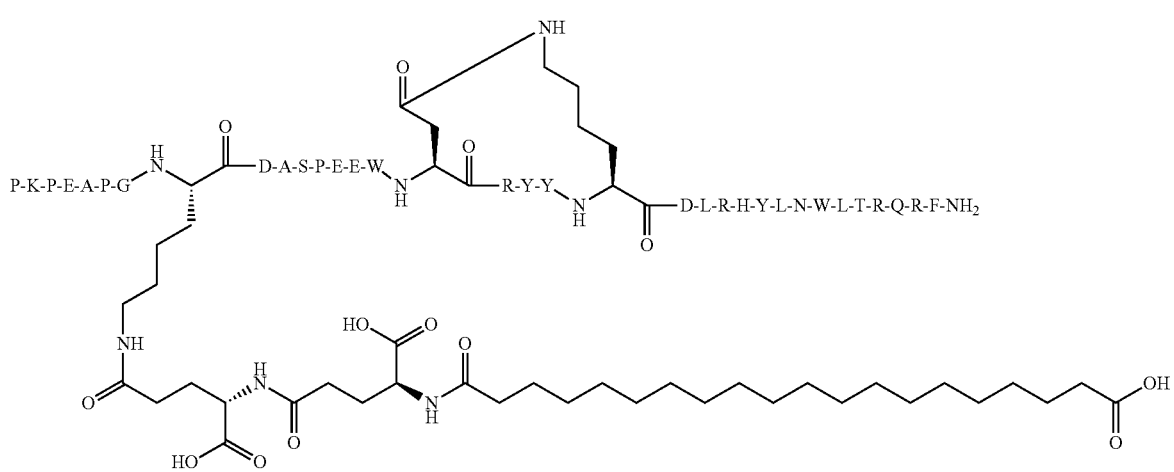

PKPEAPGK(γGlu-γGlu-CO(CH$_2$)$_{18}$CO$_2$H)DASPEEWK*RYYE*DLRHYLNWLTRQRF-(NH$_2$)
A43
SEQ ID NO: 43

TABLE 4-continued

Chemical structures of exemplary peptides: PYY analog polypeptides comprising a
lipophilic substituent via a spacer, two peptides of which further comprise a bridging moiety.

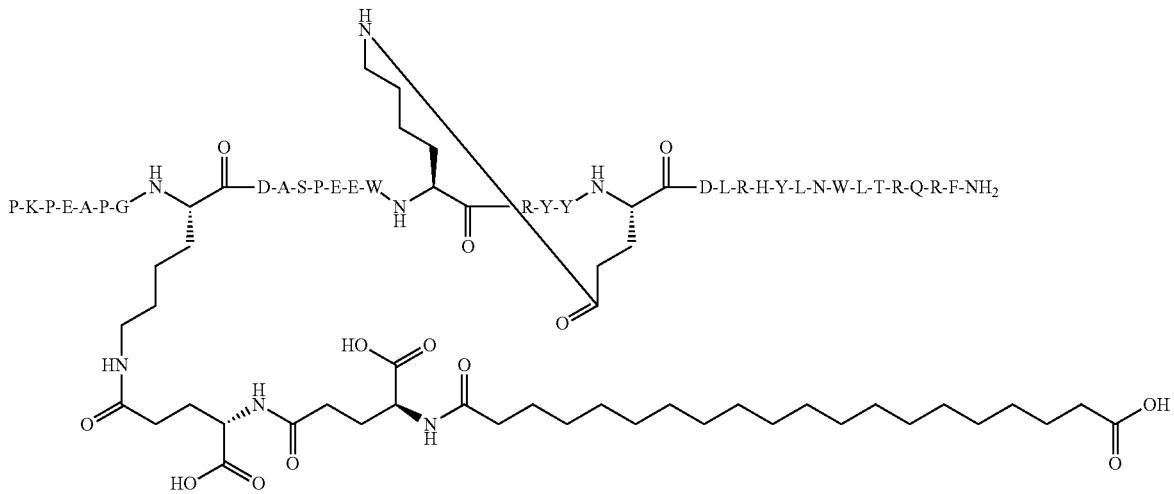

Notes:
each pairing of K* and E* and each pairing of K* and D* represent a covalent amide linkage derived from the amino sidechain of K* and the carboxy sidechain of E* or the caboxy sidechain of D* (with loss of a water molecule). For example, the segment - WD*RYYK*D- (SEQ ID NO: 807) represents:

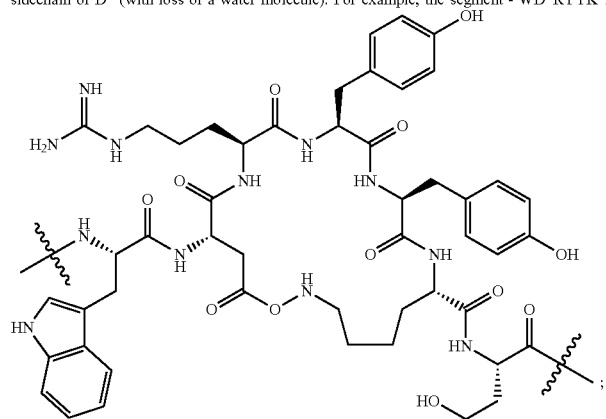

as used herein, dpeg represents —COCH$_2$O(CH$_2$)$_2$O(CH$_2$)$_2$NH—; and dpeg-dpeg represents —COCH$_2$O(CH$_2$)$_2$O(CH$_2$)$_2$NH—COCH$_2$O(CH$_2$)$_2$O(CH$_2$)$_2$NH—; and carboxy terminal amino acid, i.e. F$_{34}$, shown as —F$_{34}$—(NH$_2$), depicts —NH—CH(CH$_2$Ph)—CONH$_2$.

In some embodiments, the isolated polypeptide comprises an amino acid sequence selected from the group consisting of SEQ ID NOs: 1 to 78. or a pharmaceutically acceptable salt thereof.

In some embodiments, the isolated polypeptide comprises an amino acid sequence selected from the group consisting of SEQ ID NOs: 13, 24, 42 and 43 or a pharmaceutically acceptable salt thereof.

In some embodiments, the isolated polypeptide comprises an amino acid sequence of SEQ ID NO: 13 or a pharmaceutically acceptable salt thereof. In some embodiments, the isolated polypeptide comprises an amino acid sequence of SEQ ID NO: 24 or a pharmaceutically acceptable salt thereof. In some embodiments, the isolated polypeptide comprises an amino acid sequence of SEQ ID NO: 42 or a pharmaceutically acceptable salt thereof. In some embodiments, the isolated polypeptide comprises an amino acid sequence of SEQ ID NO: 43 or a pharmaceutically acceptable salt thereof.

In some embodiments, the present invention provides a compound set forth in Table 3, above, or a pharmaceutically acceptable salt thereof. In some embodiments, the present invention provides an isolated polypeptide that comprises an amino acid sequence selected from the group consisting of SEQ ID NOs: 1 to 78 or a pharmaceutically acceptable salt thereof. In some embodiments the pharmaceutically acceptable salt is an acetate salt. In some embodiments the pharmaceutically acceptable salt is a trifluoroacetic acid (TFA) salt. In some embodiments the pharmaceutically acceptable salt is a hydrochloric acid (HCl) salt.

In one embodiment, the compound is the isolated polypeptide comprising an amino acid sequence of SEQ ID NO: 13 or a pharmaceutically acceptable salt thereof. In some embodiments, the compound is the acetate salt of the isolated polypeptide comprising an amino acid sequence of SEQ ID NO: 13. In some embodiments, the compound is the TFA salt of the isolated polypeptide comprising an amino acid sequence of SEQ ID NO: 13. In some embodiments, the compound is the HCl salt of the isolated polypeptide comprising an amino acid sequence of SEQ ID NO: 13.

In one embodiment, the compound is the isolated polypeptide comprising an amino acid sequence of SEQ ID NO:

24 or a pharmaceutically acceptable salt thereof. In some embodiments, the compound is the acetate salt of the isolated polypeptide comprising an amino acid sequence of SEQ ID NO: 24. In some embodiments, the compound is the TFA salt of the isolated polypeptide comprising an amino acid sequence of SEQ ID NO: 24. In some embodiments, the compound is the HCl salt of the isolated polypeptide comprising an amino acid sequence of SEQ ID NO: 24.

In one embodiment, the compound is the isolated polypeptide comprising an amino acid sequence of SEQ ID NO: 42 or a pharmaceutically acceptable salt thereof. In some embodiments, the compound is the acetate salt of the isolated polypeptide comprising an amino acid sequence of SEQ ID NO: 42. In some embodiments, the compound is the TFA salt of the isolated polypeptide comprising an amino acid sequence of SEQ ID NO: 42. In some embodiments, the compound is the HCl salt of the isolated polypeptide comprising an amino acid sequence of SEQ ID NO: 42.

In one embodiment, the compound is the isolated polypeptide comprising an amino acid sequence of SEQ ID NO: 43 or a pharmaceutically acceptable salt thereof. In some embodiments, the compound is the acetate salt of the isolated polypeptide comprising an amino acid sequence of SEQ ID NO: 43. In some embodiments, the compound is the TFA salt of the isolated polypeptide comprising an amino acid sequence of SEQ ID NO: 43. In some embodiments, the compound is the HCl salt of the isolated polypeptide comprising an amino acid sequence of SEQ ID NO: 43.

In some embodiments, an isolated polypeptide of the disclosure comprises an amino acid sequence selected from the group consisting of the following peptides listed in Table 5:

TABLE 5

Exemplary compounds: PYY analog polypeptides optionally comprising a lipophilic substituent, optionally via a spacer; and optionally further comprising a bridging moiety.

| Compound No. | Sequence | SEQ ID NO: |
| --- | --- | --- |
| B1 | PKPEAPGKDASPEEWNRYYADLRHYLNWLTRQRY-(NH$_2$) | SEQ ID NO: 101 |
| B4 | KPKPEAPGKDASPEEWNRYYADARHYLNWLTRQR-(n-methyl Y)-(NH$_2$) | SEQ ID NO: 104 |
| B5 | PKPEAPGKDASPEEWNRYYADARHYLNWLTRQR-(n-methyl Y)-(NH$_2$) | SEQ ID NO: 105 |
| B6 | PKPKAPGKDASPEEWNRYYADARHYLNWLTRQR-(n-methyl Y)-(NH$_2$) | SEQ ID NO: 106 |
| B7 | PKPEAPKKDASPEEWNRYYADARHYLNWLTRQR-(n-methyl Y)-(NH$_2$) | SEQ ID NO: 107 |
| B8 | PKPEAPGKDASPKEWNRYYADARHYLNWLTRQR-(n-methyl Y)-(NH$_2$) | SEQ ID NO: 108 |
| B9 | PKPEAPGKDASPEEWKRYYADARHYLNWLTRQR-(n-methyl Y)-(NH$_2$) | SEQ ID NO: 109 |
| B10 | PKPEAPGKDASPEEWNRYYADLRHYLNWLTRQR-(n-methyl Y)-(NH$_2$) | SEQ ID NO: 110 |
| B11 | PKPEAPGKDASPEEWNRYYADLRHYLNWLTRQR-(homotyrosine)-(NH$_2$) | SEQ ID NO: 111 |
| B12 | PKPEAPGKDASPEEWNRYYADLRHYLNWLTRQRy-(NH$_2$) | SEQ ID NO: 112 |
| B13 | PKPEAPGKDASPEEWNRYYADLRHYLNWLTRQRF-(NH$_2$) | SEQ ID NO: 113 |
| B14 | PKPEAPGKDASPEEWNRYYkDLRHYLNWLTRQRF-(NH$_2$) | SEQ ID NO: 114 |
| B15 | PKPEAPGkDASPEEWNRYYADLRHYLNWLTRQRF-(NH$_2$) | SEQ ID NO: 115 |
| B16 | PKPEAPGKDASPEEWNRYYKDLRHYLNWLTRQRF-(NH$_2$) | SEQ ID NO: 116 |
| B19 | PKPEKPGKDASPEEWNRYYKDLRHYLNWLTRQRF-(NH$_2$) | SEQ ID NO: 119 |
| B20 | PKPEAPGKDASPKEWNRYYKDLRHYLNWLTRQRF-(NH$_2$) | SEQ ID NO: 120 |
| B22 | PKPEAPGKDASPEEWNRYY-Dap-DLRHYLNWLTRQRF-(NH$_2$) | SEQ ID NO: 122 |

TABLE 5-continued

Exemplary compounds: PYY analog polypeptides optionally
comprising a lipophilic substituent, optionally via a spacer;
and optionally further comprising a bridging moiety.

| Compound No. | Sequence | SEQ ID NO: |
|---|---|---|
| B23 | PKPEAPGKDASPEEWQRYYKDLRHYLNWLTRQRF-(NH$_2$) | SEQ ID NO: 123 |
| B24 | PKPEAPGKDASPEEWDRYYKDLRHYLNWLTRQRF-(NH$_2$) | SEQ ID NO: 124 |
| B25 | PKPEAPGKDASPEEWSRYYKDLRHYLNWLTRQRF-(NH$_2$) | SEQ ID NO: 125 |
| B26 | PKPEAPGKDASPEEWTRYYKDLRHYLNWLTRQRF-(NH$_2$) | SEQ ID NO: 126 |
| B27 | PKPEKPGKDASPKEWNRYYKDLRHYLNWLTRQRF-(NH$_2$) | SEQ ID NO: 127 |
| B29 | PKPEKPGEDASPKEWNRYYKDLRHYLNWLTRQRF-(NH$_2$) | SEQ ID NO: 129 |
| B30 | PKPEAPGKDASPEEW-homoSer-RYYKDLRHYLNWLTRQRF-(NH$_2$) | SEQ ID NO: 130 |
| B31 | PKPEAPGKDASPEEW-(alpha-methyl-Ser)-RYYKDLRHYLNWLTRQRF-(NH$_2$) | SEQ ID NO: 131 |
| B34 | PKPEKPGEDASPKEWDRYYKDLRHYLNWLTRQRF-(NH$_2$) | SEQ ID NO: 134 |
| B39 | PKPEKPGKDASPKEWERYYKDLRHYLNWLTRQRF-(NH$_2$) | SEQ ID NO: 139 |
| B40 | PKPEKPGKDASPKEWDRYYKDLRHYLNWLTRQRF-(NH$_2$) | SEQ ID NO: 140 |
| B41 | PKPEAPGKDASPEEWERYYKDLRHYLNWLTRQRF-(NH$_2$) | SEQ ID NO: 141 |
| B43 | PKPEAPGKDASPEEWKRYYEDLRHYLNWLTRQRF-(NH$_2$) | SEQ ID NO: 143 |
| B44 | PKPEAPGKDASPEEWKRYYDDLRHYLNWLTRQRF-(NH$_2$) | SEQ ID NO: 144 |
| B45 | PKPEAPGKDASPKEWDRYYKDLRHYLNWLTRQRF-(NH$_2$) | SEQ ID NO: 145 |
| B46 | PKPEAPGKKASPEEWDRYYKDLRHYLNWLTRQRF-(NH$_2$) | SEQ ID NO: 146 |
| B47 | PKPEAPGKDASPEEWDRYYKDDRHYKNWLTRQRF-(NH$_2$) | SEQ ID NO: 147 |
| B48 | PKPEAPGKDASPEEWDRYYKDKRHYENWLTRQRF-(NH$_2$) | SEQ ID NO: 148 |
| B49 | PKPEAPGKDASPEEWNRYYADLRHYLNWLTRQR-(β-homo Tyr)-(NH$_2$) | SEQ ID NO: 149 |
| B50 | PKPEAPGKDASPEEWNRYYADLRHYLNWLTRKRF-(NH$_2$) | SEQ ID NO: 150 |
| B51 | PKPEAPGKDASPEEWNRYYADLRHYLKWLTRQRF-(NH$_2$) | SEQ ID NO: 151 |
| B52 | PKPEAPGKDASPEEWNRYYADLRHKLNWLTRQRF-(NH$_2$) | SEQ ID NO: 152 |
| B53 | PKPEAPGKDASPEEWNRYYADLKHYLNWLTRQRF-(NH$_2$) | SEQ ID NO: 153 |
| B55 | PKPEAPGKDASPEEWKRYYADLRHYLNWLTRQRF-(NH$_2$) | SEQ ID NO: 155 |

TABLE 5-continued

Exemplary compounds: PYY analog polypeptides optionally
comprising a lipophilic substituent, optionally via a spacer;
and optionally further comprising a bridging moiety.

| Compound No. | Sequence | SEQ ID NO: |
|---|---|---|
| B56 | PKPEAPGKDASPEEWNRYYADLRHYLNWLTRQR-(4-pyridyl Ala)-(NH$_2$) | SEQ ID NO: 156 |
| B57 | PKPEAPGKDASPEEWNRYYADLRHYLNWLTRQR-(3-pyridyl Ala)-(NH$_2$) | SEQ ID NO: 157 |
| B58 | PKPEAPGKDASPEEWNRYYADLRHYLNWLTRQR-(4-methyl Phe)-(NH$_2$) | SEQ ID NO: 158 |
| B59 | PKPEAPGKDASPEEWNRYYADLRHYLNWLTRQR-(4-carboxy Phe)-(NH$_2$) | SEQ ID NO: 159 |
| B60 | PKPEAPGKDASPEEWNRYYADLRHYLNWLTRQR-(4-fluoro Phe)-(NH$_2$) | SEQ ID NO: 160 |
| B61 | PKPEAPGKDASPEEWNRYYADLRHYLNWLTRQR-(homo Phe)-(NH$_2$) | SEQ ID NO: 161 |
| B62 | PKPEAPGKDASPEEWNRYYADLRHYLNWLTRQR-(n-methyl Phe)-(NH$_2$) | SEQ ID NO: 162 |
| B63 | PKPEAPKKDASPEELNRYYADARHYLNWLTRQR-(n-methyl Tyr)-(NH$_2$) | SEQ ID NO: 163 |
| B64 | PKPEAPKKDASPEELNRYYADARHYLNWLTRQRF-(NH$_2$) | SEQ ID NO: 164 |
| B66 | PKPEAPGKDKSPEEWNRYYKDLRHYLNWLTRQRF-(NH$_2$) | SEQ ID NO: 166 |
| B67 | PKPEAPGKDASPEKWNRYYKDLRHYLNWLTRQRF-(NH$_2$) | SEQ ID NO: 167 |
| B68 | PKPEAPGKDASPEEWNRKYKDLRHYLNWLTRQRF-(NH$_2$) | SEQ ID NO: 168 |
| B69 | PKPEAPGKDASPEEWNRYKKDLRHYLNWLTRQRF-(NH$_2$) | SEQ ID NO: 169 |
| B75 | PKPEKPGKDASPEEWSRYYKDLRHYLNWLTRQRF-(NH$_2$) | SEQ ID NO: 175 |
| B77 | PKPEKPGEDASPEEWDRYYKDLRHYLNWLTRQRF-(NH$_2$) | SEQ ID NO: 177 |
| B79 | PKPEAPGKDASPEEWDRYYKDLRHYLNWLTRQRY-(NH$_2$) | SEQ ID NO: 179 |
| B80 | PKPEAPGDASPEEWDRYYKDLRHYLNWLTRQRF-(NH$_2$) | SEQ ID NO: 180 |
| B81 | PKPEAPGDASPEEWKRYYEDLRHYLNWLTRQRF-(NH$_2$) | SEQ ID NO: 181 |

In some embodiments, the isolated polypeptide comprises an amino acid sequence selected from the group consisting of SEQ ID NOs: 101 to 181. or a pharmaceutically acceptable salt thereof.

In some embodiments, the isolated polypeptide comprises an amino acid sequence selected from the group consisting of SEQ ID NOs: 113, 124, and 143 or a pharmaceutically acceptable salt thereof.

In some embodiments, the isolated polypeptide comprises an amino acid sequence of SEQ ID NO: 113 or a pharmaceutically acceptable salt thereof. In some embodiments, the isolated polypeptide comprises an amino acid sequence of SEQ ID NO: 124 or a pharmaceutically acceptable salt thereof. In some embodiments, the isolated polypeptide comprises an amino acid sequence of SEQ ID NO: 143 or a pharmaceutically acceptable salt thereof.

In some embodiments, the present invention provides a compound set forth in the Table 5, above, or a pharmaceutically acceptable salt thereof. In some embodiments, the present invention provides an isolated polypeptide that comprises an amino acid sequence selected from the group consisting of SEQ ID NOs: 101 to 181 or a pharmaceutically acceptable salt thereof. In some embodiments the pharmaceutically acceptable salt is an acetate salt. In some embodiments the pharmaceutically acceptable salt is a trifluoroacetic acid (TFA) salt. In some embodiments the pharmaceutically acceptable salt is a hydrochloric acid (HCl) salt.

In one embodiment, the compound is the isolated polypeptide comprising an amino acid sequence of SEQ ID NO: 113 or a pharmaceutically acceptable salt thereof. In some embodiments, the compound is the acetate salt of the isolated polypeptide comprising an amino acid sequence of SEQ ID NO: 113. In some embodiments, the compound is the TFA salt of the isolated polypeptide comprising an amino acid sequence of SEQ ID NO: 113. In some embodiments, the compound is the HCl salt of the isolated polypeptide comprising an amino acid sequence of SEQ ID NO: 113.

In one embodiment, the compound is the isolated polypeptide comprising an amino acid sequence of SEQ ID NO: 124 or a pharmaceutically acceptable salt thereof. In some embodiments, the compound is the acetate salt of the isolated polypeptide comprising an amino acid sequence of SEQ ID NO: 124. In some embodiments, the compound is the TFA salt of the isolated polypeptide comprising an amino acid sequence of SEQ ID NO: 124. In some embodiments, the compound is the HCl salt of the isolated polypeptide comprising an amino acid sequence of SEQ ID NO: 124.

In one embodiment, the compound is the isolated polypeptide comprising an amino acid sequence of SEQ ID NO: 143 or a pharmaceutically acceptable salt thereof. In some embodiments, the compound is the acetate salt of the isolated polypeptide comprising an amino acid sequence of SEQ ID NO: 143. In some embodiments, the compound is the TFA salt of the isolated polypeptide comprising an amino acid sequence of SEQ ID NO: 143. In some embodiments, the compound is the HCl salt of the isolated polypeptide comprising an amino acid sequence of SEQ ID NO: 143.

In some embodiments, an isolated polypeptide of the disclosure comprises an amino acid sequence selected from the group consisting of the following peptides listed in Table 6:

TABLE 6

Exemplary compounds: PYY analog polypeptides optionally covalently bound to a lipophilic substituent, optionally via a spacer

| Compound No. | Sequence | SEQ ID NO: |
|---|---|---|
| C39 | PKPEKPGKDASPKEWE*RYYK*DLRHYLNWLTRQRF-(NH₂) | SEQ ID NO: 239 |
| C40 | PKPEKPGKDASPKEWD*RYYK*DLRHYLNWLTRQRF-(NH₂) | SEQ ID NO: 240 |
| C41 | PKPEAPGKDASPEEWE*RYYK*DLRHYLNWLTRQRF-(NH₂) | SEQ ID NO: 241 |
| C42 | PKPEAPGKDASPEEWD*RYYK*DLRHYLNWLTRQRF-(NH₂) | SEQ ID NO: 242 |
| C43 | PKPEAPGKDASPEEWK*RYYE*DLRHYLNWLTRQRF-(NH₂) | SEQ ID NO: 243 |
| C44 | PKPEAPGKDASPEEWK*RYYD*DLRHYLNWLTRQRF-(NH₂) | SEQ ID NO: 244 |
| C45 | PKPEAPGKD*ASPK*EWDRYYKDLRHYLNWLTRQRF-(NH₂) | SEQ ID NO: 245 |
| C46 | PKPEAPGKK*ASPE*EWDRYYKDLRHYLNWLTRQRF-(NH₂) | SEQ ID NO: 246 |
| C47 | PKPEAPGKDASPEEWDRYYKDD*RHYK*NWLTRQRF-(NH₂) | SEQ ID NO: 247 |
| C48 | PKPEAPGKDASPEEWDRYYKDK*RHYE*NWLTRQRF-(NH₂) | SEQ ID NO: 248 |

TABLE 6-continued

Exemplary compounds: PYY analog polypeptides optionally covalently bound to a lipophilic substituent, optionally via a spacer

| Compound No. | Sequence | SEQ ID NO: |
|---|---|---|
| C80 | PKPEAPGDASPEEWD*RYYK*DLRHYLNWLTRQRF-(NH₂) | SEQ ID NO: 280 |
| C81 | PKPEAPGDASPEEWK*RYYE*DLRHYLNWLTRQRF-(NH₂) | SEQ ID NO: 281 |

Note:
Each pairing of K* and E* and each pairing of K* and D* represent a covalent amide linkage derived from the amino sidechain of K* and the carboxy sidechain of E* or the caboxy sidechain of D* (with loss of a water molecule).

In some embodiments, the isolated polypeptide comprises an amino acid sequence selected from the group consisting of SEQ ID NOs: 239, 240, 241, 242, 243, 244, 245, 246, 247, 248, 280, and 281 or a pharmaceutically acceptable salt thereof.

In some embodiments, the isolated polypeptide comprises an amino acid sequence of SEQ ID NO: 239 or a pharmaceutically acceptable salt thereof. In some embodiments, the isolated polypeptide comprises an amino acid sequence of SEQ ID NO: 240 or a pharmaceutically acceptable salt thereof. In some embodiments, the isolated polypeptide comprises an amino acid sequence of SEQ ID NO: 241 or a pharmaceutically acceptable salt thereof. In some embodiments, the isolated polypeptide comprises an amino acid sequence of SEQ ID NO: 242 or a pharmaceutically acceptable salt thereof. In some embodiments, the isolated polypeptide comprises an amino acid sequence of SEQ ID NO: 243 or a pharmaceutically acceptable salt thereof. In some embodiments, the isolated polypeptide comprises an amino acid sequence of SEQ ID NO: 244 or a pharmaceutically acceptable salt thereof. In some embodiments, the isolated polypeptide comprises an amino acid sequence of SEQ ID NO: 245 or a pharmaceutically acceptable salt thereof. In some embodiments, the isolated polypeptide comprises an amino acid sequence of SEQ ID NO: 246 or a pharmaceutically acceptable salt thereof. In some embodiments, the isolated polypeptide comprises an amino acid sequence of SEQ ID NO: 247 or a pharmaceutically acceptable salt thereof. In some embodiments, the isolated polypeptide comprises an amino acid sequence of SEQ ID NO: 248 or a pharmaceutically acceptable salt thereof. In some embodiments, the isolated polypeptide comprises an amino acid sequence of SEQ ID NO: 280 or a pharmaceutically acceptable salt thereof. In some embodiments, the isolated polypeptide comprises an amino acid sequence of SEQ ID NO: 281 or a pharmaceutically acceptable salt thereof.

In some embodiments the pharmaceutically acceptable salt is an acetate salt. In some embodiments the pharmaceutically acceptable salt is a trifluoroacetic acid (TFA) salt. In some embodiments the pharmaceutically acceptable salt is a hydrochloric acid (HCl) salt.

In one embodiment, the compound is the isolated polypeptide comprising an amino acid sequence of SEQ ID NO: 242 or a pharmaceutically acceptable salt thereof. In some embodiments, the compound is the acetate salt of the isolated polypeptide comprising an amino acid sequence of SEQ ID NO: 242. In some embodiments, the compound is the TFA salt of the isolated polypeptide comprising an amino acid sequence of SEQ ID NO: 242. In some embodiments, the compound is the HCl salt of the isolated polypeptide comprising an amino acid sequence of SEQ ID NO: 242.

In one embodiment, the compound is the isolated polypeptide comprising an amino acid sequence of SEQ ID NO: 243 or a pharmaceutically acceptable salt thereof. In some embodiments, the compound is the acetate salt of the isolated polypeptide comprising an amino acid sequence of SEQ ID NO: 243. In some embodiments, the compound is the TFA salt of the isolated polypeptide comprising an amino acid sequence of SEQ ID NO: 243. In some embodiments, the compound is the HCl salt of the isolated polypeptide comprising an amino acid sequence of SEQ ID NO: 243.

Description of Exemplary Embodiments

In certain embodiments, the present disclosure provides an isolated polypeptide comprising the amino acid sequence of SEQ ID NO: 90:

$X_0PX_2PX_4X_5PX_7X_8X_9X_{10}SPX_{13}X_{14}X_{15}X_{16}RX_{18}$ $X_{19}X_{20}DX_{22}X_{23}HX_{25}X_{26}X_{27}WLTRX_{32}RX_{34}$—(OH/NH$_2$) (SEQ ID NO: 90), or a pharmaceutically acceptable salt thereof, wherein:

$X_0$ is absent or K;
$X_2$ is K;
$X_4$ is E or K;
$X_5$ is A or K;
$X_7$ is G or K
$X_8$ is E, K, or k;
$X_9$ is D or K;
$X_{10}$ is A or K;
$X_{13}$ is E or K;
$X_{14}$ is E or K;
$X_{15}$ is L or W;
$X_{16}$ is D, E, K, N, Q, S, T, α-methylserine, or homoserine;
$X_{18}$ is K or Y;
$X_{19}$ is K or Y;
$X_{20}$ is A, D, E, K, k, or Dap;
$X_{22}$ is A, D, K, or L;
$X_{23}$ is K or R;
$X_{25}$ is K or Y;
$X_{26}$ is E, K, or L;
$X_{27}$ is K or N;
$X_{32}$ is K or Q;
$X_{34}$ is F, y, 3-pyridinylalanine, 4-pyridinylalanine, 4-carboxyphenylalanine, 4-fluorophenylalanine, 4-methylphenylalanine, N-methylphenylalanine, homophenylalanine, (3-homotyrosine, homotyrosine, or N-methyltyrosine;

wherein when $X_0$, $X_2$, $X_4$, $X_5$, $X_7$, $X_8$, $X_{13}$, $X_{20}$, $X_{23}$, $X_{25}$, $X_{27}$, or $X_{32}$ are K, the lysine residue is optionally covalently bound to a lipophilic substituent, optionally via a spacer, and wherein when $X_8$ or $X_{20}$ are k, the D-lysine residue is optionally covalently bound to a lipophilic substituent, optionally via a spacer, provided that the polypeptide comprises at least one residue covalently bound to lipophilic substituent, optionally via a spacer; and wherein the polypeptide optionally further comprises a lactam bridge formed via an amide bond between the side chains of a lysine and an aspartic acid or between the side chains of a lysine and a glutamic acid, wherein the residues that form the lactam bridge are located at positions $X_9$ and $X_{13}$ or at positions $X_{16}$ and $X_{20}$ or at positions $X_{22}$ and $X_{26}$.

In some embodiments, when $X_{15}$ is L, $X_{22}$ is A.
In some embodiment, when $X_{16}$ is N, $X_{20}$ is not A.

In some embodiments, when $X_8$ is E, $X_5$ is K and $X_{20}$ is K, and the lysine residue at either of $X_5$ or $X_{20}$ is covalently bound to a lipophilic substituent, optionally via a spacer.

In some embodiments, $X_8$ is K. In some embodiments, the lysine residue at the 8$^{th}$ position of the polypeptide sequence is covalently bound to a lipophilic substituent, optionally via a spacer.

In some embodiments, $X_{15}$ is W.
In some embodiments, $X_{34}$ is F.

In some embodiments, the peptide further comprises a lactam bridge formed via an amide bond between the side chains of a lysine and a glutamic acid at positions $X_9$ and $X_{13}$, respectively.

In some embodiments, the peptide further comprises a lactam bridge formed via an amide bond between the side chains of an aspartic acid and a lysine at positions $X_9$ and $X_{13}$, respectively.

In some embodiments, the peptide further comprises a lactam bridge formed via an amide bond between the side chains of a lysine and an aspartic acid at positions $X_{16}$ and $X_{20}$, respectively.

In some embodiments, the peptide further comprises a lactam bridge formed via an amide bond between the side chains of a lysine and a glutamic acid at positions $X_{16}$ and $X_{20}$, respectively. In some embodiments, the peptide further comprises a lactam bridge formed via an amide bond between the side chains of an aspartic acid and a lysine at positions $X_{16}$ and $X_{20}$, respectively. In some embodiments, the peptide further comprises a lactam bridge formed via an amide bond between the side chains of a glutamic acid and a lysine at positions $X_{16}$ and $X_{20}$, respectively. In some embodiments, the peptide further comprises a lactam bridge formed via an amide bond between the side chains of a lysine and a glutamic acid at positions $X_{22}$ and $X_{26}$, respectively. In some embodiments, the peptide further comprises a lactam bridge formed via an amide bond between the side chains of an aspartic acid and a lysine at positions $X_{22}$ and $X_{26}$, respectively.

In some embodiments, $X_0$ is absent. In some embodiments, $X_0$ is K. In some embodiments, $X_0$ is K covalently bound to a lipophilic substituent, optionally via a spacer.

In some embodiments, $X_2$ is K. In some embodiments, $X_2$ is K covalently bound to a lipophilic substituent, optionally via a spacer.

In some embodiments, $X_4$ is E. In some embodiments, $X_4$ is K. In some embodiments, $X_4$ is K covalently bound to a lipophilic substituent, optionally via a spacer.

In some embodiments, $X_5$ is A. In some embodiments, $X_5$ is K. In some embodiments, $X_5$ is K covalently bound to a lipophilic substituent, optionally via a spacer.

In some embodiments, $X_7$ is G. In some embodiments, $X_7$ is K. In some embodiments, $X_7$ is K covalently bound to a lipophilic substituent, optionally via a spacer.

In some embodiments, $X_8$ is E. In some embodiments, $X_8$ is K. In some embodiments, $X_8$ is K covalently bound to a lipophilic substituent, optionally via a spacer. In some embodiments, $X_8$ is k. In some embodiments, $X_8$ is k covalently bound to a lipophilic substituent, optionally via a spacer.

As used herein, k refers to D-lysine.

In some embodiments, $X_9$ is D. In some embodiments, $X_9$ is K.

In some embodiments, $X_{10}$ is A. In some embodiments, $X_{10}$ is K. In some embodiments, $X_{10}$ is K covalently bound to a lipophilic substituent, optionally via a spacer.

In some embodiments, $X_{13}$ is E. In some embodiments, $X_{13}$ is K. In some embodiments, $X_{13}$ is K covalently bound to a lipophilic substituent, optionally via a spacer.

In some embodiments, $X_{14}$ is E. In some embodiments, $X_{14}$ is K.

In some embodiments, $X_{15}$ is L. In some embodiments, $X_{15}$ is W.

In some embodiments, $X_{16}$ is D. In some embodiments, $X_{16}$ is E. In some embodiments, $X_{15}$ is K. In some embodiments, $X_{15}$ is N. In some embodiments, $X_{16}$ is Q. In some embodiments, $X_{16}$ is S. In some embodiments, $X_{16}$ is T. In some embodiments, $X_{15}$ is α-methylserine. In some embodiments, $X_{16}$ is homoserine.

In some embodiments, $X_{15}$ is K. In some embodiments, $X_{15}$ is Y.

In some embodiments, $X_{19}$ is K. In some embodiments, $X_{19}$ is Y.

In some embodiments, $X_{20}$ is A. In some embodiments, $X_{20}$ is D. In some embodiments, $X_{20}$ is E. In some embodiments, $X_{20}$ is K. In some embodiments, $X_{20}$ is K covalently bound to a lipophilic substituent, optionally via a spacer. In some embodiments, $X_{20}$ is k. In some embodiments, $X_{20}$ is k covalently bound to a lipophilic substituent, optionally via a spacer. In some embodiments, $X_{20}$ is Dap.

As used herein, Dap refers to diaminopimelic acid.

In some embodiments, $X_{22}$ is A. In some embodiments, $X_{22}$ is D. In some embodiments, $X_{22}$ is K. In some embodiments, $X_{22}$ is L.

In some embodiments, $X_{23}$ is K. In some embodiments, $X_{23}$ is K covalently bound to a lipophilic substituent, optionally via a spacer. In some embodiments, $X_{23}$ is R.

In some embodiments, $X_{25}$ is K. In some embodiments, $X_{25}$ is K covalently bound to a lipophilic substituent, optionally via a spacer. In some embodiments, $X_{25}$ is Y.

In some embodiments, $X_{26}$ is E. In some embodiments, $X_{26}$ is K. In some embodiments, $X_{26}$ is L.

In some embodiments, $X_{27}$ is K. In some embodiments, $X_{27}$ is K covalently bound to a lipophilic substituent, optionally via a spacer. In some embodiments, $X_{27}$ is N.

In some embodiments, $X_{32}$ is K. In some embodiments, $X_{32}$ is K covalently bound to a lipophilic substituent, optionally via a spacer. In some embodiments, $X_{32}$ is Q.

In some embodiments, $X_{34}$ is F. In some embodiments, $X_{34}$ is y. In some embodiments, $X_{34}$ is 3-pyridinylalanine. In some embodiments, $X_{34}$ is 4-pyridinylalanine. In some embodiments, $X_{34}$ is 4-carboxyphenylalanine. In some embodiments, $X_{34}$ is 4-fluorophenylalanine. In some embodiments, $X_{34}$ is 4-methylphenylalanine. In some embodiments, $X_{34}$ is N-methylphenylalanine. In some embodiments, $X_{34}$ is homophenylalanine. In some embodiments, $X_{34}$ is β-homotyrosine. In some embodiments, $X_{34}$ is homotyrosine. In some embodiments, $X_{34}$ is N-methyltyrosine.

As used herein, y refers to D-tyrosine.

In some embodiments, carboxy terminal amino acid, i.e. $X_{34}$, is —$X_{34}$—(NH$_2$). In some embodiments, carboxy terminal amino acid $X_{34}$ is —$X_{34}$—(OH).

In some embodiments, certain amino acids represented by the consensus sequence of SEQ ID NO: 90 include the following:

In some embodiments, $X_5$ is A and $X_8$ is K covalently bound to a lipophilic substituent, optionally via a spacer. In some embodiments, $X_5$ is A and $X_{15}$ is W. In some embodiments, $X_5$ is A and $X_{16}$ is D. In some embodiments, $X_5$ is A and $X_{16}$ is K. In some embodiments, $X_5$ is A and $X_{15}$ is N. In some embodiments, $X_5$ is A and $X_{20}$ is K. In some embodiments, $X_5$ is A and $X_{20}$ is E. In some embodiments, $X_5$ is A and $X_{20}$ is A. In some embodiments, $X_5$ is A and $X_{34}$ is F.

In some embodiments, $X_5$ is K covalently bound to a lipophilic substituent, optionally via a spacer, and $X_8$ is E. In some embodiments, $X_5$ is K covalently bound to a lipophilic substituent, optionally via a spacer, and $X_{15}$ is W. In some embodiments, $X_5$ is K covalently bound to a lipophilic substituent, optionally via a spacer, and $X_{16}$ is N. In some embodiments, $X_8$ is K covalently bound to a lipophilic substituent, optionally via a spacer, and $X_{16}$ is D. In some embodiments, $X_5$ is K covalently bound to a lipophilic substituent, optionally via a spacer, and $X_{20}$ is K. In some embodiments, $X_5$ is K covalently bound to a lipophilic substituent, optionally via a spacer, and $X_{34}$ is F.

In some embodiments, $X_5$ is K and $X_8$ is E. In some embodiments, $X_5$ is K and $X_{15}$ is W. In some embodiments, $X_5$ is K and $X_{15}$ is N. In some embodiments, $X_5$ is K and $X_{16}$ is D. In some embodiments, $X_5$ is K and $X_{20}$ is K. In some embodiments, $X_5$ is K and $X_{20}$ is K covalently bound to a lipophilic substituent, optionally via a spacer. In some embodiments, $X_5$ is K and $X_{34}$ is F.

In some embodiments, $X_8$ is E and $X_{15}$ is W. In some embodiments, $X_8$ is E and $X_{15}$ is D. In some embodiments, $X_8$ is E and $X_{15}$ is N. In some embodiments, $X_8$ is E and $X_{20}$ is K. In some embodiments, $X_8$ is E and $X_{20}$ is K covalently bound to a lipophilic substituent, optionally via a spacer. In some embodiments, $X_8$ is E and $X_{34}$ is F.

In some embodiments, $X_8$ is K covalently bound to a lipophilic substituent, optionally via a spacer, and $X_{15}$ is W. In some embodiments, $X_8$ is K covalently bound to a lipophilic substituent, optionally via a spacer, and $X_{16}$ is D. In some embodiments, $X_8$ is K covalently bound to a lipophilic substituent, optionally via a spacer, and $X_{16}$ is K. In some embodiments, $X_8$ is K covalently bound to a lipophilic substituent, optionally via a spacer, and $X_{16}$ is N. In some embodiments, $X_8$ is K covalently bound to a lipophilic substituent, optionally via a spacer, and $X_{20}$ is K. In some embodiments, $X_8$ is K covalently bound to a lipophilic substituent, optionally via a spacer, and $X_{20}$ is E. In some embodiments, $X_8$ is K covalently bound to a lipophilic substituent, optionally via a spacer, and $X_{20}$ is A. In some embodiments, $X_8$ is K covalently bound to a lipophilic substituent, optionally via a spacer, and $X_{34}$ is F.

In some embodiments, $X_{15}$ is W and $X_{15}$ is D. In some embodiments, $X_{15}$ is W and $X_{16}$ is K. In some embodiments, $X_{15}$ is W and $X_{15}$ is N. In some embodiments, $X_{15}$ is W and $X_{20}$ is K. In some embodiments, $X_{15}$ is W and $X_{20}$ is E. In some embodiments, $X_{15}$ is W and $X_{20}$ is A. In some embodiments, $X_{15}$ is W and $X_{34}$ is F.

In some embodiments, $X_{16}$ is D and $X_{20}$ is K. In some embodiments, $X_{15}$ is D and $X_{34}$ is F.

In some embodiments, $X_{15}$ is K and $X_{20}$ is E. In some embodiments, $X_{15}$ is K and $X_{20}$ is D. In some embodiments, $X_{15}$ is K and $X_{34}$ is F.

In some embodiments, $X_{15}$ is N and $X_{20}$ is A. In some embodiments, $X_{16}$ is N and $X_{20}$ is K. In some embodiments, $X_{15}$ is N and $X_{34}$ is F.

In some embodiments, $X_{20}$ is K and $X_{34}$ is F.
In some embodiments, $X_{20}$ is E and $X_{34}$ is F.
In some embodiments, $X_{20}$ is A and $X_{34}$ is F.

In some embodiments, certain amino acids represented by the consensus sequence of SEQ ID NO: 90 include the following:

In some embodiments, $X_5$ is A, $X_8$ is K covalently bound to a lipophilic substituent, optionally via a spacer, and $X_{15}$ is W. In some embodiments, $X_5$ is A, $X_8$ is K covalently bound to a lipophilic substituent, optionally via a spacer, and $X_{16}$ is D. In some embodiments, $X_5$ is A, $X_8$ is K covalently bound to a lipophilic substituent, optionally via a spacer, and $X_{16}$ is K. In some embodiments, $X_5$ is A, $X_8$ is K covalently bound to a lipophilic substituent, optionally via a spacer, and $X_{16}$ is N. In some embodiments, $X_5$ is A, $X_8$ is K covalently bound to a lipophilic substituent, optionally via a spacer, and $X_{20}$ is K. In some embodiments, $X_5$ is A, $X_8$ is K covalently bound to a lipophilic substituent, optionally via a spacer, and $X_{20}$ is E. In some embodiments, $X_5$ is A, $X_8$ is K covalently bound to a lipophilic substituent, optionally via a spacer, and $X_{20}$ is A. In some embodiments, $X_5$ is A, $X_8$ is K covalently bound to a lipophilic substituent, optionally via a spacer, and $X_{34}$ is F.

In some embodiments, $X_5$ is A, $X_{15}$ is W, and $X_{16}$ is D. In some embodiments, $X_5$ is A, $X_{15}$ is W, and $X_{16}$ is D. In some embodiments, $X_5$ is A, $X_{15}$ is W, and $X_{16}$ is K. In some embodiments, $X_5$ is A, $X_{15}$ is W, and $X_{16}$ N. In some embodiments, $X_5$ is A, $X_{15}$ is W, and $X_{20}$ is K. In some embodiments, $X_5$ is A, $X_{15}$ is W, and $X_{20}$ is E. In some embodiments, $X_5$ is A, $X_{15}$ is W, and $X_{20}$ is A. In some embodiments, $X_5$ is A, $X_{15}$ is W, and $X_{34}$ is F.

In some embodiments, $X_5$ is A, $X_{16}$ is D, and $X_{20}$ is K. In some embodiments, $X_5$ is A, $X_{16}$ is D, and $X_{34}$ is F.

In some embodiments, $X_5$ is A, $X_{16}$ is K, and $X_{20}$ is E. In some embodiments, $X_5$ is A, $X_{16}$ is K, and $X_{20}$ is D. In some embodiments, $X_5$ is A, $X_{16}$ is K, and $X_{34}$ is F.

In some embodiments, $X_5$ is A, $X_{16}$ is N, and $X_{20}$ is A. In some embodiments, $X_5$ is A, $X_{16}$ is N, and $X_{20}$ is K. In some embodiments, $X_5$ is A, $X_{16}$ is N, and $X_{34}$ is F.

In some embodiments, $X_5$ is A, $X_{20}$ is K, and $X_{34}$ is F.
In some embodiments, $X_5$ is A, $X_{20}$ is E, and $X_{34}$ is F.
In some embodiments, $X_5$ is A, $X_{20}$ is A, and $X_{34}$ is F.

In some embodiments, $X_5$ is K covalently bound to a lipophilic substituent, optionally via a spacer, $X_5$ is E, and $X_{15}$ is W. In some embodiments, $X_5$ is K covalently bound to a lipophilic substituent, optionally via a spacer, $X_8$ is E, and $X_{15}$ is N. In some embodiments, $X_5$ is K covalently bound to a lipophilic substituent, optionally via a spacer, $X_8$ is E, and $X_{15}$ is D. In some embodiments, $X_5$ is K covalently bound to a lipophilic substituent, optionally via a spacer, $X_8$ is E, and $X_{20}$ is K. In some embodiments, $X_5$ is K covalently bound to a lipophilic substituent, optionally via a spacer, $X_8$ is E, and $X_{34}$ is F.

In some embodiments, $X_5$ is K, $X_8$ is E, and $X_{15}$ is W. In some embodiments, $X_5$ is K, $X_8$ is E, and $X_{15}$ is N. In some embodiments, $X_5$ is K, $X_8$ is E, and $X_{15}$ is D. In some embodiments, $X_5$ is K, $X_8$ is E, and $X_{20}$ is K covalently bound to a lipophilic substituent, optionally via a spacer.

In some embodiments, $X_5$ is K, $X_8$ is E, and $X_{34}$ is F. In some embodiments, $X_8$ is E, $X_{15}$ is W, and $X_{15}$ is N. In some embodiments, $X_8$ is E, Xis is W, and $X_{20}$ is K. In some embodiments, $X_8$ is E, $X_{15}$ is W, and $X_{20}$ is K covalently bound to a lipophilic substituent, optionally via a spacer. In some embodiments, $X_8$ is E, $X_{15}$ is W, and $X_{34}$ is F.

In some embodiments, $X_8$ is K covalently bound to a lipophilic substituent, optionally via a spacer, $X_{15}$ is W, and $X_{16}$ is D. In some embodiments, $X_8$ is K covalently bound to a lipophilic substituent, optionally via a spacer, $X_{15}$ is W, and $X_{16}$ is K. In some embodiments, $X_8$ is K covalently bound to a lipophilic substituent, optionally via a spacer, $X_{15}$ is W, and $X_{16}$ is N. In some embodiments, $X_8$ is K covalently bound to a lipophilic substituent, optionally via a spacer, $X_{15}$ is W, and $X_{20}$ is K. In some embodiments, $X_8$ is K covalently bound to a lipophilic substituent, optionally via a spacer, $X_{15}$ is W, and $X_{20}$ is E. In some embodiments, $X_8$ is K covalently bound to a lipophilic substituent, optionally via a spacer, $X_{15}$ is W, and $X_{20}$ is A. In some embodiments, $X_8$ is K covalently bound to a lipophilic substituent, optionally via a spacer, $X_{15}$ is W, and $X_{34}$ is F.

In some embodiments, $X_8$ is K covalently bound to a lipophilic substituent, optionally via a spacer, $X_{15}$ is D, and $X_{20}$ is K. In some embodiments, $X_8$ is K covalently bound to a lipophilic substituent, optionally via a spacer, $X_{15}$ is D, and $X_{34}$ is F.

In some embodiments, $X_8$ is K covalently bound to a lipophilic substituent, optionally via a spacer, $X_{15}$ is K, and $X_{20}$ is E. In some embodiments, $X_8$ is K covalently bound to a lipophilic substituent, optionally via a spacer, $X_{15}$ is K, and $X_{20}$ is D. In some embodiments, $X_8$ is K covalently bound to a lipophilic substituent, optionally via a spacer, $X_{16}$ is K, and $X_{34}$ is F.

In some embodiments, $X_8$ is K covalently bound to a lipophilic substituent, optionally via a spacer, $X_{16}$ is N, and $X_{20}$ is A. In some embodiments, $X_8$ is K covalently bound to a lipophilic substituent, optionally via a spacer, $X_{15}$ is N, and $X_{20}$ is K. In some embodiments, $X_8$ is K covalently bound to a lipophilic substituent, optionally via a spacer, $X_{16}$ is N, and $X_{34}$ is F.

In some embodiments, $X_8$ is K covalently bound to a lipophilic substituent, optionally via a spacer, $X_{20}$ is K, and $X_{34}$ is F.

In some embodiments, $X_8$ is K covalently bound to a lipophilic substituent, optionally via a spacer, $X_{20}$ is E, and $X_{34}$ is F.

In some embodiments, $X_8$ is K covalently bound to a lipophilic substituent, optionally via a spacer, $X_{20}$ is A, and $X_{34}$ is F.

In some embodiments, $X_{15}$ is W, $X_{15}$ is D, and $X_{20}$ is K.
In some embodiments, $X_{15}$ is W, $X_{16}$ is D, and $X_{34}$ is F.
In some embodiments, $X_{15}$ is W, $X_{15}$ is K, and $X_{20}$ is E.
In some embodiments, $X_{15}$ is W, $X_{15}$ is K, and $X_{20}$ is D. In some embodiments, $X_{15}$ is W, $X_{15}$ is K, and $X_{34}$ is F.
In some embodiments, $X_{15}$ is W, $X_{15}$ is N, and $X_{20}$ is A.
In some embodiments, $X_{15}$ is W, $X_{16}$ is N, and $X_{20}$ is K. In some embodiments, $X_{15}$ is W, $X_{16}$ is N, and $X_{34}$ is F.
In some embodiments, $X_{15}$ is W, $X_{20}$ is K, and $X_{34}$ is F.
In some embodiments, $X_{15}$ is W, $X_{20}$ is E, and $X_{34}$ is F.
In some embodiments, $X_{15}$ is W, $X_{20}$ is A, and $X_{34}$ is F.
In some embodiments, $X_{16}$ is D, $X_{20}$ is K, and $X_{34}$ is F.
In some embodiments, $X_{15}$ is K, $X_{20}$ is E, and $X_{34}$ is F.
In some embodiments, $X_{16}$ is K, $X_{20}$ is D, and $X_{34}$ is F.
In some embodiments, $X_{15}$ is N, $X_{20}$ is A, and $X_{34}$ is F.
In some embodiments, $X_{15}$ is N, $X_{20}$ is K, and $X_{34}$ is F.

In certain embodiments, the present disclosure provides an isolated polypeptide comprising the amino acid sequence of SEQ ID NO: 91:

PKPEX$_5$PX$_7$X$_8$DASPX$_{13}$EX$_{15}$X$_{15}$RYYX$_{20}$DX$_{22}$R-HYLNWLTRQRX$_{34}$—(OH/NH$_2$) (SEQ ID NO: 91), or a pharmaceutically acceptable salt thereof, wherein:
  $X_5$ is A or K;
  $X_7$ is G or K;
  $X_8$ is E, K, or k;
  $X_{13}$ is E or K;
  $X_{15}$ is L or W;
  $X_{16}$ is D, E, K, N, S, α-methylserine, or homoserine;
  $X_{20}$ is A, D, E, K, or k,
  $X_{22}$ is A or L;
  $X_{34}$ is F, 3-pyridinylalanine, 4-pyridinylalanine, 4-carboxyphenylalanine, 4-fluorophenylalanine, 4-methylphenylalanine, N-methylphenylalanine, homophenylalanine, (3-homotyrosine, homotyrosine, or N-methyltyrosine;

wherein when $X_5$, $X_7$, $X_8$, $X_{13}$, or $X_{20}$ are K, the lysine residue is optionally covalently bound to a lipophilic substituent, optionally via a spacer, and wherein when $X_8$ or $X_{20}$ are k, the D-lysine residue is optionally covalently bound to a lipophilic substituent, optionally via a spacer, provided that the polypeptide comprises at least one residue covalently bound to lipophilic substituent, optionally via a spacer; and wherein the polypeptide optionally further comprises a lactam bridge formed via an amide bond between the side chains of a lysine and an aspartic acid or between the side chains of a lysine and a glutamic acid, wherein the residues that form the lactam bridge are located at positions $X_{16}$ and $X_{20}$.

In some embodiments, when $X_{15}$ is L, $X_{22}$ is A.

In some embodiment, when $X_{16}$ is N, $X_{20}$ is not A.

In some embodiments, when $X_8$ is E, $X_5$ is K and $X_{20}$ is K, and the lysine residue at either of $X_5$ or $X_{20}$ is covalently bound to a lipophilic substituent, optionally via a spacer.

In some embodiments, $X_8$ is K. In some embodiments, the lysine residue at the 8$^{th}$ position of the polypeptide sequence is covalently bound to a lipophilic substituent, optionally via a spacer.

In some embodiments, $X_{15}$ is W.

In some embodiments, $X_{34}$ is F.

In some embodiments, the peptide further comprises a lactam bridge formed via an amide bond between the side chains of a lysine and an aspartic acid at positions $X_{16}$ and $X_{20}$, respectively.

In some embodiments, the peptide further comprises a lactam bridge formed via an amide bond between the side chains of a lysine and a glutamic acid at positions $X_{16}$ and $X_{20}$, respectively. In some embodiments, the peptide further comprises a lactam bridge formed via an amide bond between the side chains of an aspartic acid and a lysine at positions $X_{16}$ and $X_{20}$, respectively. In some embodiments, the peptide further comprises a lactam bridge formed via an amide bond between the side chains of a glutamic acid and a lysine at positions $X_{16}$ and $X_{20}$, respectively.

In some embodiments, $X_5$ is A. In some embodiments, $X_5$ is K. In some embodiments, $X_8$ is K covalently bound to a lipophilic substituent, optionally via a spacer.

In some embodiments, $X_7$ is G. In some embodiments, $X_7$ is K. In some embodiments, $X_7$ is K covalently bound to a lipophilic substituent, optionally via a spacer.

In some embodiments, $X_8$ is E. In some embodiments, $X_8$ is K. In some embodiments, $X_8$ is K covalently bound to a lipophilic substituent, optionally via a spacer. In some embodiments, $X_8$ is k. In some embodiments, $X_8$ is k covalently bound to a lipophilic substituent, optionally via a spacer.

In some embodiments, $X_{13}$ is E. In some embodiments, $X_{13}$ is K. In some embodiments, $X_{13}$ is K covalently bound to a lipophilic substituent, optionally via a spacer.

In some embodiments, $X_{15}$ is L. In some embodiments, $X_{15}$ is W.

In some embodiments, $X_{16}$ is D. In some embodiments, $X_{16}$ is E. In some embodiments, $X_{16}$ is K. In some embodiments, $X_{16}$ is N. In some embodiments, $X_{16}$ is S. In some embodiments, $X_{16}$ is α-methylserine. In some embodiments, $X_{16}$ is homoserine.

In some embodiments, $X_{20}$ is A. In some embodiments, $X_{20}$ is D. In some embodiments, $X_{20}$ is E. In some embodiments, $X_{20}$ is K. In some embodiments, $X_{20}$ is K covalently bound to a lipophilic substituent, optionally via a spacer. In some embodiments, $X_{20}$ is k. In some embodiments, $X_{20}$ is k covalently bound to a lipophilic substituent, optionally via a spacer.

In some embodiments, $X_{22}$ is A. In some embodiments, $X_{22}$ is L.

In some embodiments, $X_{34}$ is F. In some embodiments, $X_{34}$ is 3-pyridinylalanine. In some embodiments, $X_{34}$ is 4-pyridinylalanine. In some embodiments, $X_{34}$ is 4-carboxyphenylalanine. In some embodiments, $X_{34}$ is 4-fluorophenylalanine. In some embodiments, $X_{34}$ is 4-methylphenylalanine. In some embodiments, $X_{34}$ is N-methylphenylalanine. In some embodiments, $X_{34}$ is homophenylalanine. In some embodiments, $X_{34}$ is β-homotyrosine. In some embodiments, $X_{34}$ is homotyrosine. In some embodiments, $X_{34}$ is N-methyltyrosine.

In some embodiments, carboxy terminal amino acid, i.e. $X_{34}$, is —$X_{34}$—(NH$_2$). In some embodiments, carboxy terminal amino acid $X_{34}$ is —$X_{34}$—(OH).

In some embodiments, certain amino acids represented by the consensus sequence of SEQ ID NO: 91 include the following:

In some embodiments, $X_5$ is A and $X_8$ is K covalently bound to a lipophilic substituent, optionally via a spacer. In some embodiments, $X_5$ is A and $X_{15}$ is W. In some embodiments, $X_5$ is A and $X_{16}$ is D. In some embodiments, $X_5$ is A and $X_{16}$ is K. In some embodiments, $X_5$ is A and $X_{16}$ is N. In some embodiments, $X_5$ is A and $X_{20}$ is K. In some embodiments, $X_5$ is A and $X_{20}$ is E. In some embodiments, $X_5$ is A and $X_{20}$ is A. In some embodiments, $X_5$ is A and $X_{34}$ is F.

In some embodiments, $X_5$ is K covalently bound to a lipophilic substituent, optionally via a spacer, and $X_8$ is E. In some embodiments, $X_5$ is K covalently bound to a lipophilic substituent, optionally via a spacer, and $X_{15}$ is W. In some embodiments, $X_5$ is K covalently bound to a lipophilic substituent, optionally via a spacer, and $X_{16}$ is N. In some embodiments, $X_5$ is K covalently bound to a lipophilic substituent, optionally via a spacer, and $X_{16}$ is D. In some embodiments, $X_5$ is K covalently bound to a lipophilic substituent, optionally via a spacer, and $X_{20}$ is K. In some embodiments, $X_5$ is K covalently bound to a lipophilic substituent, optionally via a spacer, and $X_{34}$ is F.

In some embodiments, $X_5$ is K and $X_5$ is E. In some embodiments, $X_5$ is K and $X_{15}$ is W. In some embodiments, $X_5$ is K and $X_{16}$ is N. In some embodiments, $X_5$ is K and $X_{16}$ is D. In some embodiments, $X_5$ is K and $X_{20}$ is K. In some embodiments, $X_5$ is K and $X_{20}$ is K covalently bound to a lipophilic substituent, optionally via a spacer. In some embodiments, $X_5$ is K and $X_{34}$ is F.

In some embodiments, $X_5$ is E and $X_{15}$ is W. In some embodiments, $X_5$ is E and $X_{16}$ is D. In some embodiments, $X_8$ is E and $X_{16}$ is N. In some embodiments, $X_8$ is E and $X_{20}$ is K. In some embodiments, $X_8$ is E and $X_{20}$ is K covalently bound to a lipophilic substituent, optionally via a spacer. In some embodiments, $X_8$ is E and $X_{34}$ is F.

In some embodiments, $X_8$ is K covalently bound to a lipophilic substituent, optionally via a spacer, and $X_{15}$ is W. In some embodiments, $X_8$ is K covalently bound to a lipophilic substituent, optionally via a spacer, and $X_{16}$ is D. In some embodiments, $X_8$ is K covalently bound to a lipophilic substituent, optionally via a spacer, and $X_{16}$ is K. In some embodiments, $X_8$ is K covalently bound to a lipophilic substituent, optionally via a spacer, and $X_{16}$ is N. In some embodiments, $X_8$ is K covalently bound to a lipophilic substituent, optionally via a spacer, and $X_{20}$ is K. In some embodiments, $X_8$ is K covalently bound to a lipophilic substituent, optionally via a spacer, and $X_{20}$ is E.

In some embodiments, $X_8$ is K covalently bound to a lipophilic substituent, optionally via a spacer, and $X_{20}$ is A. In some embodiments, $X_5$ is K covalently bound to a lipophilic substituent, optionally via a spacer, and $X_{34}$ is F.

In some embodiments, $X_{15}$ is W and $X_{16}$ is D. In some embodiments, $X_{15}$ is W and $X_{16}$ is K. In some embodiments, $X_{15}$ is W and $X_{16}$ is N. In some embodiments, $X_{15}$ is W and $X_{20}$ is K. In some embodiments, $X_{15}$ is W and $X_{20}$ is E. In some embodiments, $X_{15}$ is W and $X_{20}$ is A. In some embodiments, $X_{15}$ is W and $X_{34}$ is F.

In some embodiments, $X_{16}$ is D and $X_{20}$ is K. In some embodiments, $X_{16}$ is D and $X_{34}$ is F.

In some embodiments, $X_{16}$ is K and $X_{20}$ is E. In some embodiments, $X_{16}$ is K and $X_{20}$ is D. In some embodiments, $X_{15}$ is K and $X_{34}$ is F.

In some embodiments, $X_{15}$ is N and $X_{20}$ is A. In some embodiments, $X_{16}$ is N and $X_{20}$ is K. In some embodiments, $X_{15}$ is N and $X_{34}$ is F.

In some embodiments, $X_{20}$ is K and $X_{34}$ is F.
In some embodiments, $X_{20}$ is E and $X_{34}$ is F.
In some embodiments, $X_{20}$ is A and $X_{34}$ is F.

In some embodiments, certain amino acids represented by the consensus sequence of SEQ ID NO: 91 include the following:

In some embodiments, $X_5$ is A, $X_5$ is K covalently bound to a lipophilic substituent, optionally via a spacer, and $X_{15}$ is W. In some embodiments, $X_5$ is A, $X_8$ is K covalently bound to a lipophilic substituent, optionally via a spacer, and $X_{16}$ is D. In some embodiments, $X_5$ is A, $X_8$ is K covalently bound to a lipophilic substituent, optionally via a spacer, and $X_{16}$ is K. In some embodiments, $X_5$ is A, $X_8$ is K covalently bound to a lipophilic substituent, optionally via a spacer, and $X_{16}$ is N. In some embodiments, $X_5$ is A, $X_8$ is K covalently bound to a lipophilic substituent, optionally via a spacer, and $X_{20}$ is K. In some embodiments, $X_5$ is A, $X_8$ is K covalently bound to a lipophilic substituent, optionally via a spacer, and $X_{20}$ is E. In some embodiments, $X_5$ is A, $X_8$ is K covalently bound to a lipophilic substituent, optionally via a spacer, and $X_{20}$ is A. In some embodiments, $X_5$ is A, $X_8$ is K covalently bound to a lipophilic substituent, optionally via a spacer, and $X_{34}$ is F.

In some embodiments, $X_5$ is A, $X_{15}$ is W, and $X_{16}$ is D. In some embodiments, $X_5$ is A, $X_{15}$ is W, and $X_{16}$ is D. In some embodiments, $X_5$ is A, $X_{15}$ is W, and $X_{16}$ is K. In some embodiments, $X_5$ is A, $X_{15}$ is W, and $X_{16}$ is N. In some embodiments, $X_5$ is A, $X_{15}$ is W, and $X_{20}$ is K. In some embodiments, $X_5$ is A, $X_{15}$ is W, and $X_{20}$ is E. In some embodiments, $X_5$ is A, $X_{15}$ is W, and $X_{20}$ is A. In some embodiments, $X_5$ is A, $X_{15}$ is W, and $X_{34}$ is F.

In some embodiments, $X_5$ is A, $X_{16}$ is D, and $X_{20}$ is K. In some embodiments, $X_5$ is A, $X_{16}$ is D, and $X_{34}$ is F.

In some embodiments, $X_5$ is A, $X_{16}$ is K, and $X_{20}$ is E. In some embodiments, $X_5$ is A, $X_{16}$ is K, and $X_{20}$ is D. In some embodiments, $X_5$ is A, $X_{16}$ is K, and $X_{34}$ is F.

In some embodiments, $X_5$ is A, $X_{16}$ is N, and $X_{20}$ is A. In some embodiments, $X_8$ is A, $X_{16}$ is N, and $X_{20}$ is K. In some embodiments, $X_5$ is A, $X_{16}$ is N, and $X_{34}$ is F.

In some embodiments, $X_5$ is A, $X_{20}$ is K, and $X_{34}$ is F.
In some embodiments, $X_5$ is A, $X_{20}$ is E, and $X_{34}$ is F.
In some embodiments, $X_5$ is A, $X_{20}$ is A, and $X_{34}$ is F.

In some embodiments, $X_5$ is K covalently bound to a lipophilic substituent, optionally via a spacer, $X_8$ is E, and $X_{15}$ is W. In some embodiments, $X_5$ is K covalently bound to a lipophilic substituent, optionally via a spacer, $X_8$ is E, and $X_{15}$ is N. In some embodiments, $X_5$ is K covalently bound to a lipophilic substituent, optionally via a spacer, $X_8$ is E, and $X_{15}$ is D. In some embodiments, $X_5$ is K covalently bound to a lipophilic substituent, optionally via a spacer, $X_8$ is E, and $X_{20}$ is K. In some embodiments, $X_5$ is K covalently bound to a lipophilic substituent, optionally via a spacer, $X_8$ is E, and $X_{34}$ is F.

In some embodiments, $X_5$ is K, $X_8$ is E, and $X_{15}$ is W. In some embodiments, $X_5$ is K, $X_8$ is E, and $X_{16}$ is N. In some embodiments, $X_5$ is K, $X_8$ is E, and $X_{16}$ is D. In some embodiments, $X_5$ is K, $X_8$ is E, and $X_{20}$ is K covalently bound to a lipophilic substituent, optionally via a spacer. In some embodiments, $X_5$ is K, $X_8$ is E, and $X_{34}$ is F.

In some embodiments, $X_8$ is E, $X_{15}$ is W, and $X_{15}$ is N. In some embodiments, $X_8$ is E, Xis is W, and $X_{20}$ is K. In some embodiments, $X_8$ is E, $X_{15}$ is W, and $X_{20}$ is K covalently bound to a lipophilic substituent, optionally via a spacer. In some embodiments, $X_8$ is E, $X_{15}$ is W, and $X_{34}$ is F.

In some embodiments, $X_8$ is K covalently bound to a lipophilic substituent, optionally via a spacer, $X_{15}$ is W, and $X_{15}$ is D. In some embodiments, $X_8$ is K covalently bound to a lipophilic substituent, optionally via a spacer, $X_{15}$ is W, and $X_{15}$ is K. In some embodiments, $X_8$ is K covalently bound to a lipophilic substituent, optionally via a spacer, $X_{15}$ is W, and $X_{16}$ is N. In some embodiments, $X_8$ is K covalently bound to a lipophilic substituent, optionally via a spacer, $X_{15}$ is W, and $X_{20}$ is K. In some embodiments, $X_8$ is K covalently bound to a lipophilic substituent, optionally via a spacer, $X_{15}$ is W, and $X_{20}$ is E. In some embodiments, $X_8$ is K covalently bound to a lipophilic substituent, optionally via a spacer, $X_{15}$ is W, and $X_{20}$ is A. In some embodiments, $X_8$ is K covalently bound to a lipophilic substituent, optionally via a spacer, $X_{15}$ is W, and $X_{34}$ is F.

In some embodiments, $X_8$ is K covalently bound to a lipophilic substituent, optionally via a spacer, $X_{15}$ is D, and $X_{20}$ is K. In some embodiments, $X_8$ is K covalently bound to a lipophilic substituent, optionally via a spacer, $X_{16}$ is D, and $X_{34}$ is F.

In some embodiments, $X_8$ is K covalently bound to a lipophilic substituent, optionally via a spacer, $X_{15}$ is K, and $X_{20}$ is E. In some embodiments, $X_8$ is K covalently bound to a lipophilic substituent, optionally via a spacer, $X_{15}$ is K, and $X_{20}$ is D. In some embodiments, $X_8$ is K covalently bound to a lipophilic substituent, optionally via a spacer, $X_{16}$ is K, and $X_{34}$ is F.

In some embodiments, $X_8$ is K covalently bound to a lipophilic substituent, optionally via a spacer, $X_{15}$ is N, and $X_{20}$ is A. In some embodiments, $X_8$ is K covalently bound to a lipophilic substituent, optionally via a spacer, $X_{15}$ is N, and $X_{20}$ is K. In some embodiments, $X_8$ is K covalently bound to a lipophilic substituent, optionally via a spacer, $X_{16}$ is N, and $X_{34}$ is F.

In some embodiments, $X_8$ is K covalently bound to a lipophilic substituent, optionally via a spacer, $X_{20}$ is K, and $X_{34}$ is F.

In some embodiments, $X_8$ is K covalently bound to a lipophilic substituent, optionally via a spacer, $X_{20}$ is E, and $X_{34}$ is F.

In some embodiments, $X_8$ is K covalently bound to a lipophilic substituent, optionally via a spacer, $X_{20}$ is A, and $X_{34}$ is F.

In some embodiments, $X_{15}$ is W, $X_{16}$ is D, and $X_{20}$ is K. In some embodiments, $X_{15}$ is W, $X_{16}$ is D, and $X_{34}$ is F.

In some embodiments, $X_{15}$ is W, $X_{15}$ is K, and $X_{20}$ is E. In some embodiments, $X_{15}$ is W, $X_{15}$ is K, and $X_{20}$ is D. In some embodiments, $X_{15}$ is W, $X_{15}$ is K, and $X_{34}$ is F.

In some embodiments, $X_{15}$ is W, $X_{15}$ is N, and $X_{20}$ is A. In some embodiments, $X_{15}$ is W, $X_{16}$ is N, and $X_{20}$ is K. In some embodiments, $X_{15}$ is W, $X_{16}$ is N, and $X_{34}$ is F.

In some embodiments, $X_{15}$ is W, $X_{20}$ is K, and $X_{34}$ is F.

In some embodiments, $X_{15}$ is W, $X_{20}$ is E, and $X_{34}$ is F.
In some embodiments, $X_{15}$ is W, $X_{20}$ is A, and $X_{34}$ is F.
In some embodiments, $X_{15}$ is D, $X_{20}$ is K, and $X_{34}$ is F.
In some embodiments, $X_{16}$ is K, $X_{20}$ is E, and $X_{34}$ is F.
In some embodiments, $X_{15}$ is K, $X_{20}$ is D, and $X_{34}$ is F.
In some embodiments, $X_{15}$ is N, $X_{20}$ is A, and $X_{34}$ is F.
In some embodiments, $X_{16}$ is N, $X_{20}$ is K, and $X_{34}$ is F.

In certain embodiments, the present disclosure provides an isolated polypeptide comprising the amino acid sequence of SEQ ID NO: 92:

PKPEX$_5$PX$_7$X$_8$DASPX$_{13}$EX$_{15}$X$_{16}$RYYX$_{20}$DX$_{22}$RH-YLNWLTRQRX$_{34}$—(OH/NH$_2$) (SEQ ID NO: 92), or a pharmaceutically acceptable salt thereof, wherein:
  $X_5$ is A or K;
  $X_7$ is G or K;
  $X_8$ is E, K, or k;
  $X_{13}$ is E or K;
  $X_{15}$ is L or W;
  $X_{16}$ is D, E, K, S, α-methylserine, or homoserine;
  $X_{20}$ is A, D, E, K, or k,
  $X_{22}$ is A or L;
  $X_{34}$ is F, 3-pyridinylalanine, 4-pyridinylalanine, 4-carboxyphenylalanine, 4-fluorophenylalanine, 4-methylphenylalanine, N-methylphenylalanine, homophenylalanine, (3-homotyrosine, homotyrosine, or N-methyltyrosine;
  wherein when $X_5$, $X_7$, $X_8$, $X_{13}$, or $X_{20}$ are K, the lysine residue is optionally covalently bound to a lipophilic substituent, optionally via a spacer, and
  wherein when $X_8$ or $X_{20}$ are k, the D-lysine residue is optionally covalently bound to a lipophilic substituent, optionally via a spacer,
  provided that the polypeptide comprises at least one residue covalently bound to lipophilic substituent, optionally via a spacer; and
  wherein the polypeptide optionally further comprises a lactam bridge formed via an amide bond between the side chains of a lysine and an aspartic acid or between the side chains of a lysine and a glutamic acid, wherein the residues that form the lactam bridge are located at positions $X_{16}$ and $X_{20}$.

In some embodiments, when $X_{15}$ is L, $X_{22}$ is A.

In some embodiments, when $X_8$ is E, $X_5$ is K and $X_{20}$ is K, and the lysine residue at either of $X_5$ or $X_{20}$ is covalently bound to a lipophilic substituent, optionally via a spacer.

In some embodiments, $X_8$ is K. In some embodiments, the lysine residue at the 8$^{th}$ position of the polypeptide sequence is covalently bound to a lipophilic substituent, optionally via a spacer.

In some embodiments, $X_{15}$ is W.
In some embodiments, $X_{34}$ is F.

In some embodiments, the peptide further comprises a lactam bridge formed via an amide bond between the side chains of a lysine and an aspartic acid at positions $X_{16}$ and $X_{20}$, respectively. In some embodiments, the peptide further comprises a lactam bridge formed via an amide bond between the side chains of a lysine and a glutamic acid at positions $X_{16}$ and $X_{20}$, respectively. In some embodiments, the peptide further comprises a lactam bridge formed via an amide bond between the side chains of an aspartic acid and a lysine at positions $X_{16}$ and $X_{20}$, respectively. In some embodiments, the peptide further comprises a lactam bridge formed via an amide bond between the side chains of a glutamic acid and a lysine at positions $X_{16}$ and $X_{20}$, respectively.

In some embodiments, $X_5$ is A. In some embodiments, $X_5$ is K. In some embodiments, $X_5$ is K covalently bound to a lipophilic substituent, optionally via a spacer.

In some embodiments, $X_7$ is G. In some embodiments, $X_7$ is K. In some embodiments, $X_7$ is K covalently bound to a lipophilic substituent, optionally via a spacer.

In some embodiments, $X_8$ is E. In some embodiments, $X_8$ is K. In some embodiments, $X_8$ is K covalently bound to a lipophilic substituent, optionally via a spacer. In some embodiments, $X_8$ is k. In some embodiments, $X_8$ is k covalently bound to a lipophilic substituent, optionally via a spacer.

In some embodiments, $X_{13}$ is E. In some embodiments, $X_{13}$ is K. In some embodiments, $X_{13}$ is K covalently bound to a lipophilic substituent, optionally via a spacer.

In some embodiments, $X_{15}$ is L. In some embodiments, $X_{15}$ is W.

In some embodiments, $X_{15}$ is D. In some embodiments, $X_{15}$ is E. In some embodiments, $X_{16}$ is K. In some embodiments, $X_{16}$ is S. In some embodiments, $X_{16}$ is α-methylserine. In some embodiments, $X_{15}$ is homoserine.

In some embodiments, $X_{20}$ is A. In some embodiments, $X_{20}$ is D. In some embodiments, $X_{20}$ is E. In some embodiments, $X_{20}$ is K. In some embodiments, $X_{20}$ is K covalently bound to a lipophilic substituent, optionally via a spacer. In some embodiments, $X_{20}$ is k. In some embodiments, $X_{20}$ is k covalently bound to a lipophilic substituent, optionally via a spacer.

In some embodiments, $X_{22}$ is A. In some embodiments, $X_{22}$ is L.

In some embodiments, $X_{34}$ is F. In some embodiments, $X_{34}$ is 3-pyridinylalanine. In some embodiments, $X_{34}$ is 4-pyridinylalanine. In some embodiments, $X_{34}$ is 4-carboxyphenylalanine. In some embodiments, $X_{34}$ is 4-fluorophenylalanine. In some embodiments, $X_{34}$ is 4-methylphenylalanine. In some embodiments, $X_{34}$ is N-methylphenylalanine. In some embodiments, $X_{34}$ is homophenylalanine. In some embodiments, $X_{34}$ is β-homotyrosine. In some embodiments, $X_{34}$ is homotyrosine. In some embodiments, $X_{34}$ is N-methyltyrosine.

In some embodiments, carboxy terminal amino acid, i.e. $X_{34}$, is —$X_{34}$—(NH$_2$). In some embodiments, carboxy terminal amino acid $X_{34}$ is —$X_{34}$—(OH).

In some embodiments, certain amino acids represented by the consensus sequence of SEQ ID NO: 92 include the following:

In some embodiments, $X_5$ is A and $X_8$ is K covalently bound to a lipophilic substituent, optionally via a spacer. In some embodiments, $X_5$ is A and $X_{15}$ is W. In some embodiments, $X_5$ is A and $X_{16}$ is D. In some embodiments, $X_5$ is A and $X_{16}$ is K. In some embodiments, $X_5$ is A and $X_{20}$ is K. In some embodiments, $X_5$ is A and $X_{20}$ is E. In some embodiments, $X_5$ is A and $X_{20}$ is A. In some embodiments, $X_5$ is A and $X_{34}$ is F.

In some embodiments, $X_5$ is K covalently bound to a lipophilic substituent, optionally via a spacer, and $X_8$ is E. In some embodiments, $X_5$ is K covalently bound to a lipophilic substituent, optionally via a spacer, and $X_{15}$ is W. In some embodiments, $X_5$ is K covalently bound to a lipophilic substituent, optionally via a spacer, and $X_{16}$ is D. In some embodiments, $X_5$ is K covalently bound to a lipophilic substituent, optionally via a spacer, and $X_{20}$ is K. In some embodiments, $X_5$ is K covalently bound to a lipophilic substituent, optionally via a spacer, and $X_{34}$ is F.

In some embodiments, $X_5$ is K and $X_8$ is E. In some embodiments, $X_5$ is K and $X_{15}$ is W. In some embodiments, $X_5$ is K and $X_{16}$ is D. In some embodiments, $X_5$ is K and $X_{20}$ is K. In some embodiments, $X_5$ is K and $X_{20}$ is K covalently bound to a lipophilic substituent, optionally via a spacer. In some embodiments, $X_5$ is K and $X_{34}$ is F.

In some embodiments, $X_8$ is E and $X_{15}$ is W. In some embodiments, $X_8$ is E and $X_{15}$ is D. In some embodiments, $X_8$ is E and $X_{20}$ is K. In some embodiments, $X_8$ is E and $X_{20}$ is K covalently bound to a lipophilic substituent, optionally via a spacer. In some embodiments, $X_8$ is E and $X_{34}$ is F.

In some embodiments, $X_8$ is K covalently bound to a lipophilic substituent, optionally via a spacer, and $X_{15}$ is W. In some embodiments, $X_8$ is K covalently bound to a lipophilic substituent, optionally via a spacer, and $X_{16}$ is D. In some embodiments, $X_8$ is K covalently bound to a lipophilic substituent, optionally via a spacer, and $X_{16}$ is K. In some embodiments, $X_8$ is K covalently bound to a lipophilic substituent, optionally via a spacer, and $X_{20}$ is K. In some embodiments, $X_8$ is K covalently bound to a lipophilic substituent, optionally via a spacer, and $X_{20}$ is E. In some embodiments, $X_8$ is K covalently bound to a lipophilic substituent, optionally via a spacer, and $X_{20}$ is A. In some embodiments, $X_8$ is K covalently bound to a lipophilic substituent, optionally via a spacer, and $X_{34}$ is F.

In some embodiments, $X_{15}$ is W and $X_{16}$ is D. In some embodiments, $X_{15}$ is W and $X_{16}$ is K. In some embodiments, $X_{15}$ is W and $X_{20}$ is K. In some embodiments, $X_{15}$ is W and $X_{20}$ is E. In some embodiments, $X_{15}$ is W and $X_{20}$ is A. In some embodiments, $X_{15}$ is W and $X_{34}$ is F.

In some embodiments, $X_{15}$ is D and $X_{20}$ is K. In some embodiments, $X_{15}$ is D and $X_{34}$ is F.

In some embodiments, $X_{16}$ is K and $X_{20}$ is E. In some embodiments, $X_{16}$ is K and $X_{20}$ is D. In some embodiments, $X_{16}$ is K and $X_{34}$ is F.

In some embodiments, $X_{20}$ is K and $X_{34}$ is F.
In some embodiments, $X_{20}$ is E and $X_{34}$ is F.
In some embodiments, $X_{20}$ is A and $X_{34}$ is F.

In some embodiments, certain amino acids represented by the consensus sequence of SEQ ID NO: 92 include the following:

In some embodiments, $X_5$ is A, $X_8$ is K covalently bound to a lipophilic substituent, optionally via a spacer, and $X_{15}$ is W. In some embodiments, $X_5$ is A, $X_8$ is K covalently bound to a lipophilic substituent, optionally via a spacer, and $X_{16}$ is D. In some embodiments, $X_5$ is A, $X_8$ is K covalently bound to a lipophilic substituent, optionally via a spacer, and $X_{16}$ is K. In some embodiments, $X_5$ is A, $X_8$ is K covalently bound to a lipophilic substituent, optionally via a spacer, and $X_{20}$ is K. In some embodiments, $X_5$ is A, $X_8$ is K covalently bound to a lipophilic substituent, optionally via a spacer, and $X_{20}$ is E. In some embodiments, $X_5$ is A, $X_8$ is K covalently bound to a lipophilic substituent, optionally via a spacer, and $X_{20}$ is A. In some embodiments, $X_5$ is A, $X_8$ is K covalently bound to a lipophilic substituent, optionally via a spacer, and $X_{34}$ is F.

In some embodiments, $X_5$ is A, $X_{15}$ is W, and $X_{16}$ is D. In some embodiments, $X_5$ is A, $X_{15}$ is W, and $X_{15}$ is D. In some embodiments, $X_5$ is A, $X_{15}$ is W, and $X_{16}$ is K. In some embodiments, $X_5$ is A, $X_{15}$ is W, and $X_{20}$ is K. In some embodiments, $X_5$ is A, $X_{15}$ is W, and $X_{20}$ is E. In some embodiments, $X_5$ is A, $X_{15}$ is W, and $X_{20}$ is A. In some embodiments, $X_5$ is A, $X_{15}$ is W, and $X_{34}$ is F.

In some embodiments, $X_5$ is A, $X_{16}$ is D, and $X_{20}$ is K. In some embodiments, $X_5$ is A, $X_{16}$ is D, and $X_{34}$ is F.

In some embodiments, $X_5$ is A, $X_{16}$ is K, and $X_{20}$ is E. In some embodiments, $X_5$ is A, $X_{16}$ is K, and $X_{20}$ is D. In some embodiments, $X_5$ is A, $X_{16}$ is K, and $X_{34}$ is F.

In some embodiments, $X_5$ is A, $X_{20}$ is K, and $X_{34}$ is F.
In some embodiments, $X_5$ is A, $X_{20}$ is E, and $X_{34}$ is F.

In some embodiments, $X_5$ is A, $X_{20}$ is A, and $X_{34}$ is F.

In some embodiments, $X_5$ is K covalently bound to a lipophilic substituent, optionally via a spacer, $X_8$ is E, and $X_{15}$ is W. In some embodiments, $X_5$ is K covalently bound to a lipophilic substituent, optionally via a spacer, $X_8$ is E, and $X_{15}$ is D. In some embodiments, $X_5$ is K covalently bound to a lipophilic substituent, optionally via a spacer, $X_5$ is E, and $X_{20}$ is K. In some embodiments, $X_5$ is K covalently bound to a lipophilic substituent, optionally via a spacer, $X_5$ is E, and $X_{34}$ is F.

In some embodiments, $X_5$ is K, $X_8$ is E, and $X_{15}$ is W. In some embodiments, $X_5$ is K, $X_8$ is E, and $X_{16}$ is D. In some embodiments, $X_5$ is K, $X_5$ is E, and $X_{20}$ is K covalently bound to a lipophilic substituent, optionally via a spacer. In some embodiments, $X_5$ is K, $X_8$ is E, and $X_{34}$ is F.

In some embodiments, $X_8$ is E, $X_{15}$ is W, and $X_{20}$ is K. In some embodiments, $X_8$ is E, $X_{15}$ is W, and $X_{20}$ is K covalently bound to a lipophilic substituent, optionally via a spacer. In some embodiments, $X_8$ is E, $X_{15}$ is W, and $X_{34}$ is F.

In some embodiments, $X_8$ is K covalently bound to a lipophilic substituent, optionally via a spacer, $X_{15}$ is W, and $X_{16}$ is D. In some embodiments, $X_8$ is K covalently bound to a lipophilic substituent, optionally via a spacer, $X_{15}$ is W, and $X_{16}$ is K. In some embodiments, $X_8$ is K covalently bound to a lipophilic substituent, optionally via a spacer, $X_{15}$ is W, and $X_{20}$ is K. In some embodiments, $X_8$ is K covalently bound to a lipophilic substituent, optionally via a spacer, $X_{15}$ is W, and $X_{20}$ is E. In some embodiments, $X_8$ is K covalently bound to a lipophilic substituent, optionally via a spacer, $X_{15}$ is W, and $X_{20}$ is A. In some embodiments, $X_5$ is K covalently bound to a lipophilic substituent, optionally via a spacer, $X_{15}$ is W, and $X_{34}$ is F.

In some embodiments, $X_8$ is K covalently bound to a lipophilic substituent, optionally via a spacer, $X_{16}$ is D, and $X_{20}$ is K. In some embodiments, $X_8$ is K covalently bound to a lipophilic substituent, optionally via a spacer, $X_{16}$ is D, and $X_{34}$ is F.

In some embodiments, $X_8$ is K covalently bound to a lipophilic substituent, optionally via a spacer, $X_{16}$ is K, and $X_{20}$ is E. In some embodiments, $X_8$ is K covalently bound to a lipophilic substituent, optionally via a spacer, $X_{15}$ is K, and $X_{20}$ is D. In some embodiments, $X_8$ is K covalently bound to a lipophilic substituent, optionally via a spacer, $X_{16}$ is K, and $X_{34}$ is F.

In some embodiments, $X_8$ is K covalently bound to a lipophilic substituent, optionally via a spacer, $X_{20}$ is K, and $X_{34}$ is F.

In some embodiments, $X_8$ is K covalently bound to a lipophilic substituent, optionally via a spacer, $X_{20}$ is E, and $X_{34}$ is F.

In some embodiments, $X_8$ is K covalently bound to a lipophilic substituent, optionally via a spacer, $X_{20}$ is A, and $X_{34}$ is F.

In some embodiments, $X_{15}$ is W, $X_{16}$ is D, and $X_{20}$ is K. In some embodiments, $X_{15}$ is W, $X_{16}$ is D, and $X_{34}$ is F.

In some embodiments, $X_{15}$ is W, $X_{15}$ is K, and $X_{20}$ is E. In some embodiments, $X_{15}$ is W, $X_{15}$ is K, and $X_{20}$ is D. In some embodiments, $X_{15}$ is W, $X_{15}$ is K, and $X_{34}$ is F.

In some embodiments, $X_{15}$ is W, $X_{20}$ is K, and $X_{34}$ is F.
In some embodiments, $X_{15}$ is W, $X_{20}$ is E, and $X_{34}$ is F.
In some embodiments, $X_{15}$ is W, $X_{20}$ is A, and $X_{34}$ is F.
In some embodiments, $X_{15}$ is D, $X_{20}$ is K, and $X_{34}$ is F.
In some embodiments, $X_{15}$ is K, $X_{20}$ is E, and $X_{34}$ is F.
In some embodiments, $X_{15}$ is K, $X_{20}$ is D, and $X_{34}$ is F.

In certain embodiments, the present disclosure provides an isolated polypeptide comprising the amino acid sequence of SEQ ID NO: 93:

PKPEX$_5$PX$_7$X$_8$DASPX$_{13}$EX$_{15}$X$_{16}$RYYX$_{20}$DX$_{22}$RH-YLNWLTRQRX$_{34}$—(OH/NH$_2$) (SEQ ID NO: 93), or a pharmaceutically acceptable salt thereof, wherein:

X$_5$ is A or K;
X$_7$ is G or K;
X$_8$ is E, K, or k;
X$_{13}$ is E or K;
X$_{15}$ is L or W;
X$_{16}$ is D, E, K, N, S, α-methylserine, or homoserine;
X$_{20}$ is D, E, K, or k,
X$_{22}$ is A or L;
X$_{34}$ is F, 3-pyridinylalanine, 4-pyridinylalanine, 4-carboxyphenylalanine, 4-fluorophenylalanine, 4-methylphenylalanine, N-methylphenylalanine, homophenylalanine, β-homotyrosine, homotyrosine, or N-methyltyrosine;

wherein when X$_5$, X$_7$, X$_8$, X$_{13}$, or X$_{20}$ are K, the lysine residue is optionally covalently bound to a lipophilic substituent, optionally via a spacer, and wherein when X$_8$ or X$_{20}$ are k, the D-lysine residue is optionally covalently bound to a lipophilic substituent, optionally via a spacer, provided that the polypeptide comprises at least one residue covalently bound to lipophilic substituent, optionally via a spacer; and wherein the polypeptide optionally further comprises a lactam bridge formed via an amide bond between the side chains of a lysine and an aspartic acid or between the side chains of a lysine and a glutamic acid, wherein the residues that form the lactam bridge are located at positions X$_{16}$ and X$_{20}$.

In some embodiments, when X$_{15}$ is L, X$_{22}$ is A.

In some embodiments, when X$_8$ is E, X$_5$ is K and X$_{20}$ is K, and the lysine residue at either of X$_5$ or X$_{20}$ is covalently bound to a lipophilic substituent, optionally via a spacer.

In some embodiments, X$_8$ is K. In some embodiments, the lysine residue at the 8$^{th}$ position of the polypeptide sequence is covalently bound to a lipophilic substituent, optionally via a spacer.

In some embodiments, X$_{15}$ is W.

In some embodiments, X$_{34}$ is F.

In some embodiments, the peptide further comprises a lactam bridge formed via an amide bond between the side chains of a lysine and an aspartic acid at positions X$_{16}$ and X$_{20}$, respectively. In some embodiments, the peptide further comprises a lactam bridge formed via an amide bond between the side chains of a lysine and a glutamic acid at positions X$_{16}$ and X$_{20}$, respectively. In some embodiments, the peptide further comprises a lactam bridge formed via an amide bond between the side chains of an aspartic acid and a lysine at positions X$_{16}$ and X$_{20}$, respectively. In some embodiments, the peptide further comprises a lactam bridge formed via an amide bond between the side chains of a glutamic acid and a lysine at positions X$_{16}$ and X$_{20}$, respectively.

In some embodiments, X$_5$ is A. In some embodiments, X$_5$ is K. In some embodiments, X$_5$ is K covalently bound to a lipophilic substituent, optionally via a spacer.

In some embodiments, X$_7$ is G. In some embodiments, X$_7$ is K. In some embodiments, X$_7$ is K covalently bound to a lipophilic substituent, optionally via a spacer.

In some embodiments, X$_8$ is E. In some embodiments, X$_8$ is K. In some embodiments, X$_8$ is K covalently bound to a lipophilic substituent, optionally via a spacer. In some embodiments, X$_8$ is k. In some embodiments, X$_8$ is k covalently bound to a lipophilic substituent, optionally via a spacer.

In some embodiments, X$_{13}$ is E. In some embodiments, X$_{13}$ is K. In some embodiments, X$_{13}$ is K covalently bound to a lipophilic substituent, optionally via a spacer.

In some embodiments, X$_{15}$ is L. In some embodiments, X$_{15}$ is W.

In some embodiments, X$_{16}$ is D. In some embodiments, X$_{16}$ is E. In some embodiments, X$_{16}$ is K. In some embodiments, X$_{16}$ is N. In some embodiments, X$_{16}$ is S. In some embodiments, X$_{16}$ is α-methylserine. In some embodiments, X$_{16}$ is homoserine.

In some embodiments, X$_{20}$ is D. In some embodiments, X$_{20}$ is E. In some embodiments, X$_{20}$ is K. In some embodiments, X$_{20}$ is K covalently bound to a lipophilic substituent, optionally via a spacer. In some embodiments, X$_{20}$ is k. In some embodiments, X$_{20}$ is k covalently bound to a lipophilic substituent, optionally via a spacer.

In some embodiments, X$_{22}$ is A. In some embodiments, X$_{22}$ is L.

In some embodiments, X$_{34}$ is F. In some embodiments, X$_{34}$ is 3-pyridinylalanine. In some embodiments, X$_{34}$ is 4-pyridinylalanine. In some embodiments, X$_{34}$ is 4-carboxyphenylalanine. In some embodiments, X$_{34}$ is 4-fluorophenylalanine. In some embodiments, X$_{34}$ is 4-methylphenylalanine. In some embodiments, X$_{34}$ is N-methylphenylalanine. In some embodiments, X$_{34}$ is homophenylalanine. In some embodiments, X$_{34}$ is β-homotyrosine. In some embodiments, X$_{34}$ is homotyrosine. In some embodiments, X$_{34}$ is N-methyltyrosine.

In some embodiments, carboxy terminal amino acid, i.e. X$_{34}$, is —X$_{34}$—(NH$_2$). In some embodiments, carboxy terminal amino acid X$_{34}$ is —X$_{34}$—(OH).

In some embodiments, certain amino acids represented by the consensus sequence of SEQ ID NO: 93 include the following:

In some embodiments, X$_5$ is A and X$_8$ is K covalently bound to a lipophilic substituent, optionally via a spacer. In some embodiments, X$_5$ is A and X$_{15}$ is W. In some embodiments, X$_5$ is A and X$_{16}$ is D. In some embodiments, X$_5$ is A and X$_{16}$ is K. In some embodiments, X$_5$ is A and X$_{16}$ is N. In some embodiments, X$_5$ is A and X$_{20}$ is K. In some embodiments, X$_5$ is A and X$_{20}$ is E. In some embodiments, X$_5$ is A and X$_{34}$ is F.

In some embodiments, X$_5$ is K covalently bound to a lipophilic substituent, optionally via a spacer, and X$_8$ is E. In some embodiments, X$_5$ is K covalently bound to a lipophilic substituent, optionally via a spacer, and X$_{15}$ is W. In some embodiments, X$_5$ is K covalently bound to a lipophilic substituent, optionally via a spacer, and X$_{16}$ is N. In some embodiments, X$_5$ is K covalently bound to a lipophilic substituent, optionally via a spacer, and X$_{16}$ is D. In some embodiments, X$_5$ is K covalently bound to a lipophilic substituent, optionally via a spacer, and X$_{20}$ is K. In some embodiments, X$_5$ is K covalently bound to a lipophilic substituent, optionally via a spacer, and X$_{34}$ is F.

In some embodiments, X$_5$ is K and X$_8$ is E. In some embodiments, X$_5$ is K and X$_{15}$ is W. In some embodiments, X$_5$ is K and X$_{16}$ is N. In some embodiments, X$_5$ is K and X$_{16}$ is D. In some embodiments, X$_5$ is K and X$_{20}$ is K. In some embodiments, X$_5$ is K and X$_{20}$ is K covalently bound to a lipophilic substituent, optionally via a spacer. In some embodiments, X$_5$ is K and X$_{34}$ is F.

In some embodiments, X$_5$ is E and X$_{15}$ is W. In some embodiments, X$_5$ is E and X$_{16}$ is D. In some embodiments, X$_8$ is E and X$_{16}$ is N. In some embodiments, X$_8$ is E and X$_{20}$ is K. In some embodiments, $X_8$ is E and $X_{20}$ is K covalently bound to a lipophilic substituent, optionally via a spacer. In some embodiments, $X_8$ is E and $X_{34}$ is F.

In some embodiments, $X_8$ is K covalently bound to a lipophilic substituent, optionally via a spacer, and $X_{15}$ is W. In some embodiments, $X_8$ is K covalently bound to a lipophilic substituent, optionally via a spacer, and $X_{16}$ is D. In some embodiments, $X_8$ is K covalently bound to a lipophilic substituent, optionally via a spacer, and $X_{16}$ is K. In some embodiments, $X_8$ is K covalently bound to a lipophilic substituent, optionally via a spacer, and $X_{16}$ is N. In some embodiments, $X_8$ is K covalently bound to a lipophilic substituent, optionally via a spacer, and $X_{20}$ is K. In some embodiments, $X_8$ is K covalently bound to a lipophilic substituent, optionally via a spacer, and $X_{20}$ is E. In some embodiments, $X_8$ is K covalently bound to a lipophilic substituent, optionally via a spacer, and $X_{34}$ is F.

In some embodiments, $X_{15}$ is W and $X_{16}$ is D. In some embodiments, $X_{15}$ is W and $X_{16}$ is K. In some embodiments, $X_{15}$ is W and $X_{16}$ is N. In some embodiments, $X_{15}$ is W and $X_{20}$ is K. In some embodiments, $X_{15}$ is W and $X_{20}$ is E. In some embodiments, $X_{15}$ is W and $X_{34}$ is F.

In some embodiments, $X_{15}$ is D and $X_{20}$ is K. In some embodiments, $X_{16}$ is D and $X_{34}$ is F.

In some embodiments, $X_{16}$ is K and $X_{20}$ is E. In some embodiments, $X_{16}$ is K and $X_{20}$ is D. In some embodiments, $X_{15}$ is K and $X_{34}$ is F.

In some embodiments, $X_{15}$ is N and $X_{20}$ is K. In some embodiments, $X_{16}$ is N and $X_{34}$ is F.

In some embodiments, $X_{20}$ is K and $X_{34}$ is F.

In some embodiments, $X_{20}$ is E and $X_{34}$ is F.

In some embodiments, certain amino acids represented by the consensus sequence of SEQ ID NO: 93 include the following:

In some embodiments, $X_5$ is A, $X_8$ is K covalently bound to a lipophilic substituent, optionally via a spacer, and $X_{15}$ is W. In some embodiments, $X_5$ is A, $X_8$ is K covalently bound to a lipophilic substituent, optionally via a spacer, and $X_{16}$ is D. In some embodiments, $X_5$ is A, $X_8$ is K covalently bound to a lipophilic substituent, optionally via a spacer, and $X_{16}$ is K. In some embodiments, $X_5$ is A, $X_8$ is K covalently bound to a lipophilic substituent, optionally via a spacer, and $X_{16}$ is N. In some embodiments, $X_5$ is A, $X_8$ is K covalently bound to a lipophilic substituent, optionally via a spacer, and $X_{20}$ is K. In some embodiments, $X_5$ is A, $X_5$ is K covalently bound to a lipophilic substituent, optionally via a spacer, and $X_{20}$ is E. In some embodiments, $X_5$ is A, $X_8$ is K covalently bound to a lipophilic substituent, optionally via a spacer, and $X_{34}$ is F.

In some embodiments, $X_5$ is A, $X_{15}$ is W, and $X_{16}$ is D. In some embodiments, $X_5$ is A, $X_{15}$ is W, and $X_{16}$ is D. In some embodiments, $X_5$ is A, $X_{15}$ is W, and $X_{16}$ is K. In some embodiments, $X_5$ is A, $X_{15}$ is W, and $X_{16}$ N. In some embodiments, $X_5$ is A, $X_{15}$ is W, and $X_{20}$ is K. In some embodiments, $X_5$ is A, $X_{15}$ is W, and $X_{20}$ is E. In some embodiments, $X_5$ is A, $X_{15}$ is W, and $X_{34}$ is F.

In some embodiments, $X_5$ is A, $X_{16}$ is D, and $X_{20}$ is K. In some embodiments, $X_5$ is A, $X_{16}$ is D, and $X_{34}$ is F.

In some embodiments, $X_5$ is A, $X_{16}$ is K, and $X_{20}$ is E. In some embodiments, $X_5$ is A, $X_{16}$ is K, and $X_{20}$ is D. In some embodiments, $X_5$ is A, $X_{16}$ is K, and $X_{34}$ is F.

In some embodiments, $X_5$ is A, $X_{16}$ is N, and $X_{20}$ is K. In some embodiments, $X_5$ is A, $X_{16}$ is N, and $X_{34}$ is F.

In some embodiments, $X_5$ is A, $X_{20}$ is K, and $X_{34}$ is F.

In some embodiments, $X_5$ is A, $X_{20}$ is E, and $X_{34}$ is F.

In some embodiments, $X_5$ is K covalently bound to a lipophilic substituent, optionally via a spacer, $X_8$ is E, and $X_{15}$ is W. In some embodiments, $X_5$ is K covalently bound to a lipophilic substituent, optionally via a spacer, $X_8$ is E, and $X_{15}$ is N. In some embodiments, $X_5$ is K covalently bound to a lipophilic substituent, optionally via a spacer, $X_8$ is E, and $X_{15}$ is D. In some embodiments, $X_5$ is K covalently bound to a lipophilic substituent, optionally via a spacer, $X_8$ is E, and $X_{20}$ is K. In some embodiments, $X_5$ is K covalently bound to a lipophilic substituent, optionally via a spacer, $X_8$ is E, and $X_{34}$ is F.

In some embodiments, $X_5$ is K, $X_8$ is E, and $X_{15}$ is W. In some embodiments, $X_5$ is K, $X_8$ is E, and $X_{15}$ is N. In some embodiments, $X_5$ is K, $X_8$ is E, and $X_{15}$ is D. In some embodiments, $X_5$ is K, $X_8$ is E, and $X_{20}$ is K covalently bound to a lipophilic substituent, optionally via a spacer. In some embodiments, $X_5$ is K, $X_8$ is E, and $X_{34}$ is F.

In some embodiments, $X_8$ is E, $X_{15}$ is W, and $X_{16}$ is N. In some embodiments, $X_8$ is E, $X_{15}$ is W, and $X_{20}$ is K. In some embodiments, $X_8$ is E, $X_{15}$ is W, and $X_{20}$ is K covalently bound to a lipophilic substituent, optionally via a spacer. In some embodiments, $X_8$ is E, $X_{15}$ is W, and $X_{34}$ is F.

In some embodiments, $X_8$ is K covalently bound to a lipophilic substituent, optionally via a spacer, $X_{15}$ is W, and $X_{15}$ is D. In some embodiments, $X_8$ is K covalently bound to a lipophilic substituent, optionally via a spacer, $X_{15}$ is W, and $X_{16}$ is K. In some embodiments, $X_8$ is K covalently bound to a lipophilic substituent, optionally via a spacer, $X_{15}$ is W, and $X_{16}$ is N. In some embodiments, $X_8$ is K covalently bound to a lipophilic substituent, optionally via a spacer, $X_{15}$ is W, and $X_{20}$ is K. In some embodiments, $X_8$ is K covalently bound to a lipophilic substituent, optionally via a spacer, $X_{15}$ is W, and $X_{20}$ is E. In some embodiments, $X_8$ is K covalently bound to a lipophilic substituent, optionally via a spacer, $X_{15}$ is W, and $X_{34}$ is F.

In some embodiments, $X_8$ is K covalently bound to a lipophilic substituent, optionally via a spacer, $X_{15}$ is D, and $X_{20}$ is K. In some embodiments, $X_8$ is K covalently bound to a lipophilic substituent, optionally via a spacer, $X_{15}$ is D, and $X_{34}$ is F.

In some embodiments, $X_8$ is K covalently bound to a lipophilic substituent, optionally via a spacer, $X_{16}$ is K, and $X_{20}$ is E. In some embodiments, $X_8$ is K covalently bound to a lipophilic substituent, optionally via a spacer, $X_{15}$ is K, and $X_{20}$ is D. In some embodiments, $X_8$ is K covalently bound to a lipophilic substituent, optionally via a spacer, $X_{16}$ is K, and $X_{34}$ is F.

In some embodiments, $X_8$ is K covalently bound to a lipophilic substituent, optionally via a spacer, $X_{15}$ is N, and $X_{20}$ is K. In some embodiments, $X_8$ is K covalently bound to a lipophilic substituent, optionally via a spacer, $X_{16}$ is N, and $X_{34}$ is F.

In some embodiments, $X_8$ is K covalently bound to a lipophilic substituent, optionally via a spacer, $X_{20}$ is K, and $X_{34}$ is F.

In some embodiments, $X_8$ is K covalently bound to a lipophilic substituent, optionally via a spacer, $X_{20}$ is E, and $X_{34}$ is F.

In some embodiments, $X_{15}$ is W, $X_{16}$ is D, and $X_{20}$ is K. In some embodiments, $X_{15}$ is W, $X_{16}$ is D, and $X_{34}$ is F.

In some embodiments, $X_{15}$ is W, $X_{15}$ is K, and $X_{20}$ is E. In some embodiments, $X_{15}$ is W, $X_{15}$ is K, and $X_{20}$ is D. In some embodiments, $X_{15}$ is W, $X_{15}$ is K, and $X_{34}$ is F.

In some embodiments, $X_{15}$ is W, $X_{16}$ is N, and $X_{20}$ is K. In some embodiments, $X_{15}$ is W, $X_{16}$ is N, and $X_{34}$ is F.

In some embodiments, $X_{15}$ is W, $X_{20}$ is K, and $X_{34}$ is F.

In some embodiments, $X_{15}$ is W, $X_{20}$ is E, and $X_{34}$ is F.

In some embodiments, $X_{16}$ is D, $X_{20}$ is K, and $X_{34}$ is F.

In some embodiments, $X_{15}$ is K, $X_{20}$ is E, and $X_{34}$ is F.

In some embodiments, $X_{16}$ is K, $X_{20}$ is D, and $X_{34}$ is F.
In some embodiments, $X_{15}$ is N, $X_{20}$ is K, and $X_{34}$ is F.

In certain embodiments, the present invention provides an isolated polypeptide comprising the amino acid sequence of SEQ ID NO: 94:

PKPEX$_5$PGX$_8$DASPX$_{13}$EWX$_{16}$RYYX$_{20}$DX$_{22}$RHY-LNWLTRQRX$_{34}$—(OH/NH$_2$) (SEQ ID NO: 94), or a pharmaceutically acceptable salt thereof, wherein:

$X_5$ is A or K;
$X_8$ is E, K, or k;
$X_{13}$ is E or K;
$X_{15}$ is D, E, K, or N;
$X_{20}$ is A, D, E, K, or k,
$X_{22}$ is A or L;
$X_{34}$ is F or N-methyltyrosine;
wherein when $X_5$, $X_8$, $X_{13}$, or $X_{20}$ are K, the lysine residue is optionally covalently bound to a lipophilic substituent, optionally via a spacer, and
wherein when $X_8$ or $X_{20}$ are k, the D-lysine residue is optionally covalently bound to a lipophilic substituent, optionally via a spacer,
provided that the polypeptide comprises at least one residue covalently bound to lipophilic substituent, optionally via a spacer; and
wherein the polypeptide optionally further comprises a lactam bridge formed via an amide bond between the side chains of a lysine and an aspartic acid or between the side chains of a lysine and a glutamic acid, wherein the residues that form the lactam bridge are located at positions $X_{16}$ and $X_{20}$.

In some embodiment, when $X_{16}$ is N, $X_{20}$ is not A.

In some embodiments, when $X_8$ is E, $X_5$ is K and $X_{20}$ is K, and the lysine residue at either of $X_5$ or $X_{20}$ is covalently bound to a lipophilic substituent, optionally via a spacer.

In some embodiments, $X_5$ is K. In some embodiments, the lysine residue at the 8$^{th}$ position of the polypeptide sequence is covalently bound to a lipophilic substituent, optionally via a spacer.

In some embodiments, $X_{34}$ is F.

In some embodiments, the peptide further comprises a lactam bridge formed via an amide bond between the side chains of a lysine and an aspartic acid at positions $X_{16}$ and $X_{20}$, respectively.

In some embodiments, the peptide further comprises a lactam bridge formed via an amide bond between the side chains of a lysine and a glutamic acid at positions $X_{16}$ and $X_{20}$, respectively. In some embodiments, the peptide further comprises a lactam bridge formed via an amide bond between the side chains of an aspartic acid and a lysine at positions $X_{16}$ and $X_{20}$, respectively. In some embodiments, the peptide further comprises a lactam bridge formed via an amide bond between the side chains of a glutamic acid and a lysine at positions $X_{16}$ and $X_{20}$, respectively.

In some embodiments, $X_5$ is A. In some embodiments, $X_5$ is K. In some embodiments, $X_5$ is K covalently bound to a lipophilic substituent, optionally via a spacer.

In some embodiments, $X_8$ is E. In some embodiments, $X_8$ is K. In some embodiments, $X_8$ is K covalently bound to a lipophilic substituent, optionally via a spacer. In some embodiments, $X_5$ is k. In some embodiments, $X_5$ is k covalently bound to a lipophilic substituent, optionally via a spacer.

In some embodiments, $X_{13}$ is E. In some embodiments, $X_{13}$ is K. In some embodiments, $X_{13}$ is K covalently bound to a lipophilic substituent, optionally via a spacer.

In some embodiments, $X_{16}$ is D. In some embodiments, $X_{16}$ is E. In some embodiments, $X_{15}$ is K. In some embodiments, $X_{15}$ is N.

In some embodiments, $X_{20}$ is A. In some embodiments, $X_{20}$ is D. In some embodiments, $X_{20}$ is E. In some embodiments, $X_{20}$ is K. In some embodiments, $X_{20}$ is K covalently bound to a lipophilic substituent, optionally via a spacer. In some embodiments, $X_{20}$ is k. In some embodiments, $X_{20}$ is k covalently bound to a lipophilic substituent, optionally via a spacer.

In some embodiments, $X_{22}$ is A. In some embodiments, $X_{22}$ is L.

In some embodiments, $X_{34}$ is F. In some embodiments, $X_{34}$ is N-methyltyrosine.

In some embodiments, carboxy terminal amino acid, i.e. $X_{34}$, is —X$_{34}$—(NH$_2$). In some embodiments, carboxy terminal amino acid $X_{34}$ is —X$_{34}$—(OH).

In some embodiments, certain amino acids represented by the consensus sequence of SEQ ID NO: 94 include the following:

In some embodiments, $X_5$ is A and $X_8$ is K covalently bound to a lipophilic substituent, optionally via a spacer. In some embodiments, $X_5$ is A and $X_{16}$ is D. In some embodiments, $X_8$ is A and $X_{16}$ is K. In some embodiments, $X_5$ is A and $X_{16}$ is N. In some embodiments, $X_5$ is A and $X_{20}$ is K. In some embodiments, $X_5$ is A and $X_{20}$ is E. In some embodiments, $X_5$ is A and $X_{20}$ is A. In some embodiments, $X_5$ is A and $X_{34}$ is F.

In some embodiments, $X_5$ is K covalently bound to a lipophilic substituent, optionally via a spacer, and $X_8$ is E. In some embodiments, $X_5$ is K covalently bound to a lipophilic substituent, optionally via a spacer, and $X_{16}$ is N. In some embodiments, $X_5$ is K covalently bound to a lipophilic substituent, optionally via a spacer, and $X_{16}$ is D. In some embodiments, $X_8$ is K covalently bound to a lipophilic substituent, optionally via a spacer, and $X_{20}$ is K. In some embodiments, $X_5$ is K covalently bound to a lipophilic substituent, optionally via a spacer, and $X_{34}$ is F.

In some embodiments, $X_5$ is K and $X_8$ is E. In some embodiments, $X_5$ is K and $X_{15}$ is N. In some embodiments, $X_5$ is K and $X_{15}$ is D. In some embodiments, $X_5$ is K and $X_{20}$ is K. In some embodiments, $X_5$ is K and $X_{20}$ is K covalently bound to a lipophilic substituent, optionally via a spacer. In some embodiments, $X_5$ is K and $X_{34}$ is F.

In some embodiments, $X_8$ is E and $X_{15}$ is D. In some embodiments, $X_8$ is E and $X_{16}$ is N. In some embodiments, $X_8$ is E and $X_{20}$ is K. In some embodiments, $X_8$ is E and $X_{20}$ is K covalently bound to a lipophilic substituent, optionally via a spacer. In some embodiments, $X_8$ is E and $X_{34}$ is F.

In some embodiments, $X_8$ is K covalently bound to a lipophilic substituent, optionally via a spacer, and $X_{15}$ is D. In some embodiments, $X_8$ is K covalently bound to a lipophilic substituent, optionally via a spacer, and $X_{16}$ is K. In some embodiments, $X_8$ is K covalently bound to a lipophilic substituent, optionally via a spacer, and $X_{16}$ is N. In some embodiments, $X_8$ is K covalently bound to a lipophilic substituent, optionally via a spacer, and $X_{20}$ is K. In some embodiments, $X_8$ is K covalently bound to a lipophilic substituent, optionally via a spacer, and $X_{20}$ is E. In some embodiments, $X_8$ is K covalently bound to a lipophilic substituent, optionally via a spacer, and $X_{20}$ is A. In some embodiments, $X_8$ is K covalently bound to a lipophilic substituent, optionally via a spacer, and $X_{34}$ is F.

In some embodiments, $X_{16}$ is D and $X_{20}$ is K. In some embodiments, $X_{16}$ is D and $X_{34}$ is F.

In some embodiments, $X_{16}$ is K and $X_{20}$ is E. In some embodiments, $X_{16}$ is K and $X_{20}$ is D. In some embodiments, $X_{15}$ is K and $X_{34}$ is F.

In some embodiments, $X_{15}$ is N and $X_{20}$ is A. In some embodiments, $X_{16}$ is N and $X_{20}$ is K. In some embodiments, $X_{16}$ is N and $X_{34}$ is F.

In some embodiments, $X_{20}$ is K and $X_{34}$ is F.

In some embodiments, $X_{20}$ is E and $X_{34}$ is F.

In some embodiments, $X_{20}$ is A and $X_{34}$ is F.

In some embodiments, certain amino acids represented by the consensus sequence of SEQ ID NO: 94 include the following:

In some embodiments, $X_5$ is A, $X_8$ is K covalently bound to a lipophilic substituent, optionally via a spacer, and $X_{16}$ is D. In some embodiments, $X_5$ is A, $X_8$ is K covalently bound to a lipophilic substituent, optionally via a spacer, and $X_{16}$ is K. In some embodiments, $X_8$ is A, $X_8$ is K covalently bound to a lipophilic substituent, optionally via a spacer, and $X_{16}$ is N. In some embodiments, $X_5$ is A, $X_8$ is K covalently bound to a lipophilic substituent, optionally via a spacer, and $X_{20}$ is K. In some embodiments, $X_5$ is A, $X_8$ is K covalently bound to a lipophilic substituent, optionally via a spacer, and $X_{20}$ is E. In some embodiments, $X_5$ is A, $X_8$ is K covalently bound to a lipophilic substituent, optionally via a spacer, and $X_{20}$ is A. In some embodiments, $X_5$ is A, $X_8$ is K covalently bound to a lipophilic substituent, optionally via a spacer, and $X_{34}$ is F.

In some embodiments, $X_5$ is A, $X_{16}$ is D, and $X_{20}$ is K. In some embodiments, $X_5$ is A, $X_{16}$ is D, and $X_{34}$ is F.

In some embodiments, $X_5$ is A, $X_{16}$ is K, and $X_{20}$ is E. In some embodiments, $X_8$ is A, $X_{16}$ is K, and $X_{20}$ is D. In some embodiments, $X_5$ is A, $X_{16}$ is K, and $X_{34}$ is F.

In some embodiments, $X_5$ is A, $X_{16}$ is N, and $X_{20}$ is A. In some embodiments, $X_8$ is A, $X_{16}$ is N, and $X_{20}$ is K. In some embodiments, $X_5$ is A, $X_{16}$ is N, and $X_{34}$ is F.

In some embodiments, $X_5$ is A, $X_{20}$ is K, and $X_{34}$ is F.

In some embodiments, $X_5$ is A, $X_{20}$ is E, and $X_{34}$ is F.

In some embodiments, $X_5$ is A, $X_{20}$ is A, and $X_{34}$ is F.

In some embodiments, $X_5$ is K covalently bound to a lipophilic substituent, optionally via a spacer, $X_8$ is E, and $X_{15}$ is N. In some embodiments, $X_5$ is K covalently bound to a lipophilic substituent, optionally via a spacer, $X_8$ is E, and $X_{16}$ is D. In some embodiments, $X_5$ is K covalently bound to a lipophilic substituent, optionally via a spacer, $X_8$ is E, and $X_{20}$ is K. In some embodiments, $X_5$ is K covalently bound to a lipophilic substituent, optionally via a spacer, $X_8$ is E, and $X_{34}$ is F.

In some embodiments, $X_5$ is K, $X_8$ is E, and $X_{16}$ is N. In some embodiments, $X_8$ is K, $X_8$ is E, and $X_{15}$ is D. In some embodiments, $X_5$ is K, $X_8$ is E, and $X_{20}$ is K covalently bound to a lipophilic substituent, optionally via a spacer. In some embodiments, $X_5$ is K, $X_8$ is E, and $X_{34}$ is F.

In some embodiments, $X_8$ is K covalently bound to a lipophilic substituent, optionally via a spacer, $X_{15}$ is D, and $X_{20}$ is K. In some embodiments, $X_8$ is K covalently bound to a lipophilic substituent, optionally via a spacer, $X_{15}$ is D, and $X_{34}$ is F.

In some embodiments, $X_8$ is K covalently bound to a lipophilic substituent, optionally via a spacer, $X_{15}$ is K, and $X_{20}$ is E. In some embodiments, $X_8$ is K covalently bound to a lipophilic substituent, optionally via a spacer, $X_{15}$ is K, and $X_{20}$ is D. In some embodiments, $X_8$ is K covalently bound to a lipophilic substituent, optionally via a spacer, $X_{16}$ is K, and $X_{34}$ is F.

In some embodiments, $X_8$ is K covalently bound to a lipophilic substituent, optionally via a spacer, $X_{16}$ is N, and $X_{20}$ is A. In some embodiments, $X_8$ is K covalently bound to a lipophilic substituent, optionally via a spacer, $X_{16}$ is N, and $X_{20}$ is K. In some embodiments, $X_8$ is K covalently bound to a lipophilic substituent, optionally via a spacer, $X_{16}$ is N, and $X_{34}$ is F.

In some embodiments, $X_5$ is K covalently bound to a lipophilic substituent, optionally via a spacer, $X_{20}$ is K, and $X_{34}$ is F.

In some embodiments, $X_8$ is K covalently bound to a lipophilic substituent, optionally via a spacer, $X_{20}$ is E, and $X_{34}$ is F.

In some embodiments, $X_8$ is K covalently bound to a lipophilic substituent, optionally via a spacer, $X_{20}$ is A, and $X_{34}$ is F.

In some embodiments, $X_{15}$ is D, $X_{20}$ is K, and $X_{34}$ is F.

In some embodiments, $X_{16}$ is K, $X_{20}$ is E, and $X_{34}$ is F.

In some embodiments, $X_{15}$ is K, $X_{20}$ is D, and $X_{34}$ is F.

In some embodiments, $X_{15}$ is N, $X_{20}$ is A, and $X_{34}$ is F.

In some embodiments, $X_{15}$ is N, $X_{20}$ is K, and $X_{34}$ is F.

In certain embodiments, the present disclosure provides an isolated polypeptide comprising the amino acid sequence of SEQ ID NO: 95:

PKPEX$_5$PGK$_8$DASPX$_{13}$EWX$_{16}$RYYX$_{20}$DLR-HYLNWLTRQRF-(OH/NH$_2$) (SEQ ID NO: 95), or a pharmaceutically acceptable salt thereof, wherein:

$X_5$ is A or K;

$X_{13}$ is E or K;

$X_{16}$ is D, E, K, or N;

$X_{20}$ is A, D, E, K, or k; and wherein when $X_5$, $X_{13}$, or $X_{20}$ are K, the lysine residue is optionally covalently bound to a lipophilic substituent, optionally via a spacer, wherein $K_8$ is optionally covalently bound to a lipophilic substituent, optionally via a spacer, and wherein when $X_{20}$ is k, the D-lysine residue is optionally covalently bound to a lipophilic substituent, optionally via a spacer, provided that the polypeptide comprises at least one residue covalently bound to lipophilic substituent, optionally via a spacer; and wherein the polypeptide optionally further comprises a lactam bridge formed via an amide bond between the side chains of a lysine and an aspartic acid or between the side chains of a lysine and a glutamic acid, wherein the residues that form the lactam bridge are located at positions $X_{16}$ and $X_{20}$.

In some embodiment, when $X_{16}$ is N, $X_{20}$ is not A.

In some embodiments, K is covalently bound to a lipophilic substituent, optionally via a spacer.

In some embodiments, the peptide further comprises a lactam bridge formed via an amide bond between the side chains of a lysine and an aspartic acid at positions $X_{16}$ and $X_{20}$, respectively.

In some embodiments, the peptide further comprises a lactam bridge formed via an amide bond between the side chains of a lysine and a glutamic acid at positions $X_{16}$ and $X_{20}$, respectively. In some embodiments, the peptide further comprises a lactam bridge formed via an amide bond between the side chains of an aspartic acid and a lysine at positions $X_{16}$ and $X_{20}$, respectively. In some embodiments, the peptide further comprises a lactam bridge formed via an amide bond between the side chains of a glutamic acid and a lysine at positions $X_{16}$ and $X_{20}$, respectively.

In some embodiments, $X_5$ is A. In some embodiments, $X_5$ is K. In some embodiments, $X_5$ is K covalently bound to a lipophilic substituent, optionally via a spacer.

In some embodiments, $K_8$ is unsubstituted. In some embodiments, $K_8$ is covalently bound to a lipophilic substituent, optionally via a spacer.

In some embodiments, $X_{13}$ is E. In some embodiments, $X_{13}$ is K. In some embodiments, $X_{13}$ is K covalently bound to a lipophilic substituent, optionally via a spacer.

In some embodiments, $X_{16}$ is D. In some embodiments, $X_{15}$ is E. In some embodiments, $X_{15}$ is K. In some embodiments, $X_{15}$ is N.

In some embodiments, $X_{20}$ is A. In some embodiments, $X_{20}$ is D. In some embodiments, $X_{20}$ is E. In some embodiments, $X_{20}$ is K. In some embodiments, $X_{20}$ is K covalently bound to a lipophilic substituent, optionally via a spacer. In some embodiments, $X_{20}$ is k. In some embodiments, $X_{20}$ is k covalently bound to a lipophilic substituent, optionally via a spacer.

In some embodiments, carboxy terminal amino acid, i.e. $F_{34}$, is $—F_{34}—(NH_2)$. In some embodiments, carboxy terminal amino acid $F_{34}$ is $—F_{34}—(OH)$.

In some embodiments, certain amino acids represented by the consensus sequence of SEQ ID NO: 95 include the following:

In some embodiments, $X_5$ is A and $K_5$ is covalently bound to a lipophilic substituent, optionally via a spacer. In some embodiments, $X_5$ is A and $X_{16}$ is D. In some embodiments, $X_8$ is A and $X_{16}$ is K. In some embodiments, $X_5$ is A and $X_{16}$ is N. In some embodiments, $X_5$ is A and $X_{20}$ is K. In some embodiments, $X_5$ is A and $X_{20}$ is E. In some embodiments, $X_5$ is A and $X_{20}$ is A.

In some embodiments, $X_5$ is K covalently bound to a lipophilic substituent, optionally via a spacer, and $X_{15}$ is N. In some embodiments, $X_5$ is K covalently bound to a lipophilic substituent, optionally via a spacer, and $X_{16}$ is D. In some embodiments, $X_5$ is K covalently bound to a lipophilic substituent, optionally via a spacer, and $X_{20}$ is K.

In some embodiments, $X_5$ is K and $X_{15}$ is N. In some embodiments, $X_5$ is K and $X_{16}$ is D. In some embodiments, $X_5$ is K and $X_{20}$ is K. In some embodiments, $X_5$ is K and $X_{20}$ is K covalently bound to a lipophilic substituent, optionally via a spacer.

In some embodiments, $K_8$ is covalently bound to a lipophilic substituent, optionally via a spacer, and $X_{15}$ is D. In some embodiments, $K_8$ is covalently bound to a lipophilic substituent, optionally via a spacer, and $X_{15}$ is K. In some embodiments, $K_8$ is covalently bound to a lipophilic substituent, optionally via a spacer, and $X_{15}$ is N. In some embodiments, $K_8$ is covalently bound to a lipophilic substituent, optionally via a spacer, and $X_{20}$ is K. In some embodiments, $K_5$ is covalently bound to a lipophilic substituent, optionally via a spacer, and $X_{20}$ is E. In some embodiments, $K_8$ is covalently bound to a lipophilic substituent, optionally via a spacer, and $X_{20}$ is A.

In some embodiments, $X_{16}$ is D and $X_{20}$ is K.

In some embodiments, $X_{15}$ is K and $X_{20}$ is E. In some embodiments, $X_{15}$ is K and $X_{20}$ is D.

In some embodiments, $X_{16}$ is N and $X_{20}$ is A. In some embodiments, $X_{16}$ is N and $X_{20}$ is K.

In some embodiments, certain amino acids represented by the consensus sequence of SEQ ID NO: 95 include the following:

In some embodiments, $X_5$ is A, $K_8$ is covalently bound to a lipophilic substituent, optionally via a spacer, and $X_{16}$ is D. In some embodiments, $X_5$ is A, $K_8$ is covalently bound to a lipophilic substituent, optionally via a spacer, and $X_{16}$ is K. In some embodiments, $X_5$ is A, $K_8$ is covalently bound to a lipophilic substituent, optionally via a spacer, and $X_{16}$ is N. In some embodiments, $X_5$ is A, $K_8$ is covalently bound to a lipophilic substituent, optionally via a spacer, and $X_{20}$ is K. In some embodiments, $X_5$ is A, $K_8$ is covalently bound to a lipophilic substituent, optionally via a spacer, and $X_{20}$ is E. In some embodiments, $X_5$ is A, $K_8$ is covalently bound to a lipophilic substituent, optionally via a spacer, and $X_{20}$ is A.

In some embodiments, $X_5$ is A, $X_{16}$ is D, and $X_{20}$ is K.

In some embodiments, $X_5$ is A, $X_{16}$ is K, and $X_{20}$ is E. In some embodiments, $X_5$ is A, $X_{16}$ is K, and $X_{20}$ is D.

In some embodiments, $X_5$ is A, $X_{16}$ is N, and $X_{20}$ is A. In some embodiments, $X_5$ is A, $X_{16}$ is N, and $X_{20}$ is K.

In some embodiments, $K_8$ is covalently bound to a lipophilic substituent, optionally via a spacer, $X_{16}$ is D, and $X_{20}$ is K.

In some embodiments, $K_8$ is covalently bound to a lipophilic substituent, optionally via a spacer, $X_{16}$ is K, and $X_{20}$ is E. In some embodiments, $K_8$ is covalently bound to a lipophilic substituent, optionally via a spacer, $X_{16}$ is K, and $X_{20}$ is D.

In some embodiments, $K_8$ is covalently bound to a lipophilic substituent, optionally via a spacer, $X_{16}$ is N, and $X_{20}$ is A. In some embodiments, $K_8$ is covalently bound to a lipophilic substituent, optionally via a spacer, $X_{16}$ is N, and $X_{20}$ is K.

Conjugation of a Lipophilic Substituent to any of the Peptides, Optionally Via a Spacer In some embodiments, any of the disclosed polypeptides is optionally substituted with one or more lipophilic substituents each optionally via a spacer, wherein "lipophilic substituent" and "spacer" are defined herein. In some embodiments, any of the disclosed polypeptides, comprising an amino acid sequence selected from the group consisting of amino acid sequences represented by any of the consensus sequences of SEQ ID NO: 1 through SEQ ID NO: 78 either comprises one or more lipophilic substituents each optionally via a spacer, or can be modified, or further modified, by covalent attachment of one or more lipophilic substituents each optionally via a spacer. In some embodiments, any of the disclosed polypeptides, comprising an amino acid sequence selected from the group consisting of amino acid sequences represented by any of the consensus sequences of SEQ ID NO: 101 through SEQ ID NO: 181 can be modified by covalent attachment of one or more lipophilic substituents each optionally via a spacer. In some embodiments, any of the disclosed polypeptides, comprising an amino acid sequence selected from the group consisting of amino acid sequences represented by any of the consensus sequences of SEQ ID NO: 239, 240, 241, 242, 243, 244, 245, 246, 247, 248, 280, or 281 can be modified by covalent attachment of one or more lipophilic substituents each optionally via a spacer. In some embodiments, the lipophilic substituent may be attached to an amino group of the polypeptide (e.g., an ε-amino group of a lysine residue) by means of a carboxyl group of the lipophilic substituent, or optionally an amino group of the spacer, wherein a carboxyl group of the spacer forms an amide bond with an ε-amino group of a lysine residue.

Lipophilic Substituent

Conjugation of one or more "lipophilic substituents", each optionally via a "spacer," to any of the disclosed polypeptides of this invention is intended to prolong the action of the polypeptide by facilitating binding to serum albumin and delayed renal clearance of the conjugated polypeptide. As used herein, a "lipophilic substituent" comprises a substituent comprising 4 to 40 carbon atoms, 8 to 25 carbon atoms, 12 to 22 carbon atoms, or 6 to 20 carbon atoms. The lipophilic substituent may be attached to an amino group of the polypeptide (e.g., an ε-amino group of a lysine residue) by means of a carboxyl group of the lipophilic substituent, or optionally an amino group of the spacer, which carboxyl group of the spacer in turn forms an amide bond with an amino group of the amino acid (e.g., lysine) residue to which it is attached. In some embodiments, the polypeptide comprises three, two, or preferably one lipophilic substituent each with or without an optional spacer, which is defined in greater detail below.

In some embodiments, the lipophilic substituent comprises a straight-chain or branched alkyl group. In some embodiments, the lipophilic substituent is an acyl group of a straight-chain or branched fatty acid. In some embodiments, the lipophilic substituent is an acyl group of a straight-chain or branched fatty acid, further substituted with one or more carboxylic acid and/or hydroxamic acid groups.

In some embodiments, the polypeptide comprises three, two, or preferably one lipophilic substituents each without an optional spacer. In some embodiments, the lipophilic substituent is —CO(CH$_2$)$_{16}$CO$_2$H. In some embodiments, the lipophilic substituent is —CO(CH$_2$)$_{18}$CO$_2$H. In some embodiments, the lipophilic substituent is —CO(CH$_2$)$_{20}$CO$_2$H.

In some embodiments, the polypeptide comprises three, two, or preferably one lipophilic substituents each without an optional spacer. In some embodiments, the lipophilic substituent is a monovalent group of Formula I:

—CO—(CH$_2$)$_m$—Z      Formula I wherein
Z is —CH$_3$ or —CO$_2$H; and
m is from 4 to 24,
which lipophilic substituent forms an amide bond between an amino group (e.g., ε-amino group of a lysine) of the disclosed polypeptide and a CO group of the lipophilic substituent.

In some embodiments, Z is —CO$_2$H. In some embodiments, m is from 14 to 20. In some embodiments, the lipophilic substituent is covalently bound to the isolated polypeptide via a spacer. In some embodiments, the lipophilic substituent, —CO—(CH$_2$)$_m$—Z, is linked to an amino group of the isolated polypeptide via the spacer, wherein the spacer forms a bridge between the amino group of the isolated polypeptide and a CO— group of the lipophilic substituent.

In some embodiments, m is selected from the group consisting of 4-20, 8-20, 12-20, 14-20, 16-20, 14, 16, 18, and 20.

In some embodiments, Z is —CO$_2$H, and the lipophilic substituent has the formula —CO—(CH$_2$)$_m$—CO$_2$H. In some embodiments, —CO—(CH$_2$)$_m$—Z is selected from the group consisting of —CO—(CH$_2$)$_4$—CO$_2$H, —CO—(CH$_2$)$_5$—CO$_2$H, —CO—(CH$_2$)$_6$—CO$_2$H, —CO—(CH$_2$)$_7$—CO$_2$H, —CO—(CH$_2$)$_8$—CO$_2$H, —CO—(CH$_2$)$_9$—CO$_2$H, —CO—(CH$_2$)$_{10}$—CO$_2$H, —CO—(CH$_2$)$_{11}$—CO$_2$H, —CO—(CH$_2$)$_{12}$—CO$_2$H, —CO—(CH$_2$)$_{13}$—CO$_2$H, —CO—(CH$_2$)$_{14}$—CO$_2$H, —CO—(CH$_2$)$_{15}$—CO$_2$H, —CO—(CH$_2$)$_{16}$—CO$_2$H, —CO—(CH$_2$)$_{17}$—CO$_2$H, —CO—(CH$_2$)$_{18}$—CO$_2$H, —CO—(CH$_2$)$_{19}$—CO$_2$H, —CO—(CH$_2$)$_{20}$—CO$_2$H.

In some embodiments, the lipophilic substituent is —CO—(CH$_2$)$_{14}$—CO$_2$H. In some embodiments, the lipophilic substituent is —CO—(CH$_2$)$_{16}$—CO$_2$H. In some embodiments, the lipophilic substituent is —CO—(CH$_2$)$_{18}$—CO$_2$H. In some embodiments, the lipophilic substituent is —CO—(CH$_2$)$_{20}$—CO$_2$H.

In some embodiments, Z is —CH$_3$, and the lipophilic substituent has the formula —CO—(CH$_2$)$_m$—CH$_3$. In some embodiments, —CO—(CH$_2$)$_m$—Z is selected from the group consisting of —CO—(CH$_2$)$_4$—CH$_3$, —CO—(CH$_2$)$_5$—CH$_3$, —CO—(CH$_2$)$_6$—CH$_3$, —CO—(CH$_2$)$_7$—CH$_3$, —CO—(CH$_2$)$_8$—CH$_3$, —CO—(CH$_2$)$_9$—CH$_3$, —CO—(CH$_2$)$_{10}$—CH$_3$, —CO—(CH$_2$)$_{11}$—CH$_3$, —CO—(CH$_2$)$_{12}$—CH$_3$, —CO—(CH$_2$)$_{13}$—CH$_3$, —CO—(CH$_2$)$_{14}$—CH$_3$, —CO—(CH$_2$)$_{15}$—CH$_3$, —CO—(CH$_2$)$_{16}$—CH$_3$, —CO—(CH$_2$)$_{17}$—CH$_3$, —CO—(CH$_2$)$_{18}$—CH$_3$, —CO—(CH$_2$)$_{19}$—CH$_3$, and —CO—(CH$_2$)$_{20}$—CH$_3$.

Lipophilic Substituent & Spacer

In some embodiments, the lipophilic substituent is attached to the parent peptide by means of a "spacer." In some embodiments, provided herein is any of the disclosed polypeptides, comprising an amino acid sequence selected from the group consisting of amino acid sequences represented by any of the consensus sequences of SEQ ID NO:1 through SEQ ID NO: 143, comprising a lipophilic substituent, wherein the lipophilic substituent is linked to the ε-amino group of a lysine via a spacer, which spacer forms a bridge between an amino group of the disclosed polypeptide and a CO— group of the lipophilic substituent.

In some embodiments, the spacer comprises one or more amino acids, for example, single amino acid such as Glu, Asp, Gly or Lys, dipeptide such as 2(Glu), Glu-Gly, or polypeptide such as 3(Glu), 4(Glu) (SEQ ID NO: 814), 2(Glu)-Gly etc. In some embodiments, when the spacer comprises one or more amino acids, e.g., Glu, Asp, Gly or Lys, one carboxyl group of the spacer may form an amide bond with an amino group of the disclosed polypeptide, and an amino group of the spacer may form an amide bond with a carboxyl group of the lipophilic substituent.

In some embodiments, when the spacer comprises Glu or Asp, that further include a carboxylic acid-terminating sidechain, the terminal carboxyl group of the sidechain of the Glu or Asp-containing spacer may form an amide bond with an amino group of the disclosed polypeptide, and an amino group of the Glu or Asp-containing spacer may form an amide bond with a carboxyl group of the lipophilic substituent, i.e., γGlu or βAsp.

In some embodiments, the spacer is -γGlu-γGlu-. In some embodiments, the spacer is -γGlu-γGlu-dpeg-. In some embodiments, the spacer is -dpeg-dpeg-γGlu-. In some embodiments, the spacer is -γGlu-dpeg-dpeg-γGlu-. In some embodiments, the spacer is -γGlu-γGlu-dpeg-γGlu-γGlu-. In some embodiments, the spacer is —[COCH$_2$(OCH$_2$CH$_2$)$_2$NH]$_2$-γGlu-.

In some embodiments, the polypeptide comprises three, two, or preferably one lipophilic substituent each with a spacer. In some non-limiting embodiments, the lipophilic substituent and spacer form a monovalent group selected from the group consisting of those listed in Table 7:

TABLE 7 representative lipophilic substituent and spacer moieties

-γGlu-γGlu-CO(CH$_2$)$_{16}$CO$_2$H
-γGlu-γGlu-CO(CH$_2$)$_{17}$CO$_2$H
-γGlu-γGlu-CO(CH$_2$)$_{18}$CO$_2$H
-γGlu-γGlu-dpeg-CO(CH$_2$)$_{16}$CO$_2$H
-γGlu-γGlu-dpeg-CO(CH$_2$)$_{18}$CO$_2$H
-γGlu-γGlu-dpeg-γGlu-CO(CH$_2$)$_{16}$CO$_2$H
-γGlu-γGlu-dpeg-γGlu-CO(CH$_2$)$_{18}$CO$_2$H
-γGlu-γGlu-dpeg-γGlu-γGlu-CO(CH$_2$)$_{16}$CO$_2$H
-γGlu-γGlu-dpeg-γGlu-γGlu-CO(CH$_2$)$_{18}$CO$_2$H
-γGlu-γGlu-dpeg-dpeg-CO(CH$_2$)$_{16}$CO$_2$H
-γGlu-γGlu-dpeg-dpeg-CO(CH2)$_{18}$CO$_2$H
-γGlu-γGlu-dpeg-dpeg-γGlu-CO(CH$_2$)$_{16}$CO$_2$H
-γGlu-γGlu-dpeg-dpeg-γGlu-CO(CH$_2$)$_{18}$CO$_2$H

TABLE 7-continued representative lipophilic substituent and spacer moieties

-γGlu-γGlu-γGlu-CO(CH$_2$)$_{16}$CO$_2$H
-γGlu-γGlu-γGlu-CO(CH$_2$)$_{18}$CO$_2$H
-dpeg-dpeg-γGlu-CO(CH$_2$)$_{16}$CO$_2$H
-dpeg-dpeg-γGlu-CO(CH$_2$)$_{18}$CO$_2$H
-γGlu-dpeg-dpeg-γGlu-CO(CH$_2$)$_{16}$CO$_2$H
-γGlu-dpeg-dpeg-γGlu-CO(CH$_2$)$_{18}$CO$_2$H
-γGlu-γGlu-γGlu-dpeg-CO(CH$_2$)$_{16}$CO$_2$H
-γGlu-γGlu-γGlu-dpeg-CO(CH$_2$)$_{18}$CO$_2$H
-γGlu-dpeg-CO(CH$_2$)$_{16}$CO$_2$H
-γGlu-dpeg-CO(CH$_2$)$_{18}$CO$_2$H
—[COCH$_2$(OCH$_2$CH$_2$)$_2$NH]$_2$-γGlu-CO(CH$_2$)$_{16}$CO$_2$H Preferably, the lipophilic substituent and spacer are attached to an amino group of the polypeptide. In particular, a carboxyl group of the lipophilic substituent, or optionally a carboxyl group of the spacer, forms an amide bond with an ε-amino group of a lysine residue. The lysine residue bound to the lipophilic substituent, optionally via a spacer, may be L-lysine or D-lysine. Structural representations of representative spacer moieties and lipophilic substituents are provided in Table 8:

TABLE 8

Structures of Representative Spacers Moieties & Lipophillic Substituents Bound to Lysine

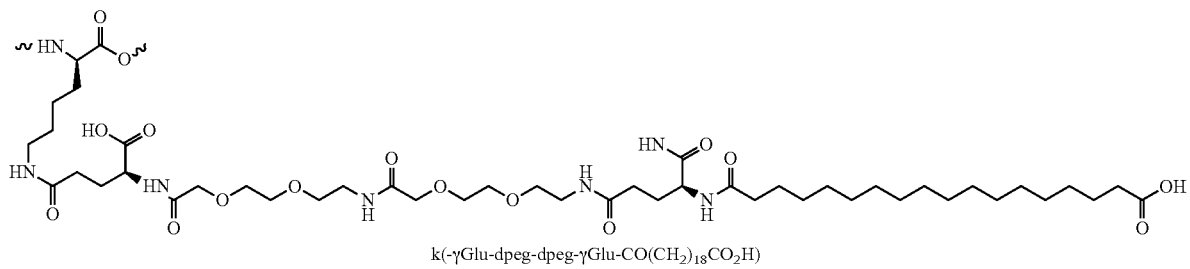

k(-γGlu-dpeg-dpeg-γGlu-CO(CH$_2$)$_{18}$CO$_2$H)

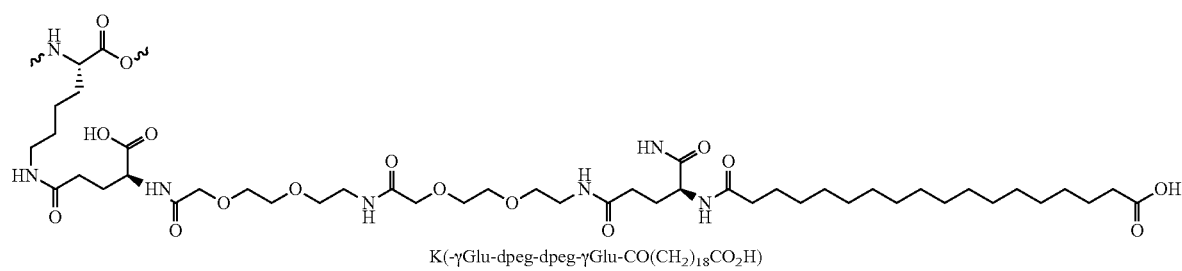

K(-γGlu-dpeg-dpeg-γGlu-CO(CH$_2$)$_{18}$CO$_2$H)

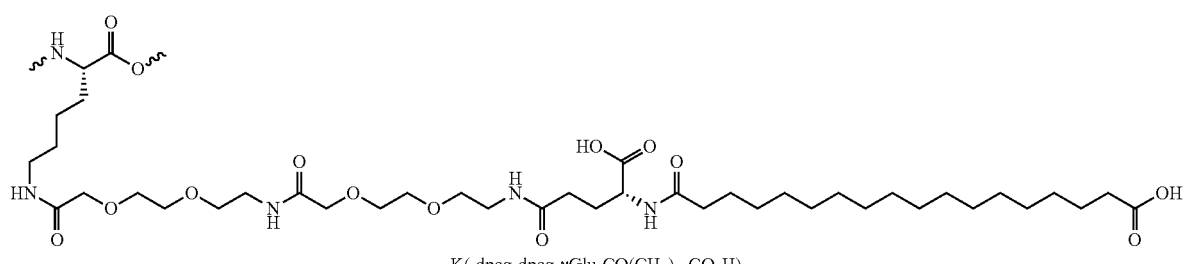

K(-dpeg-dpeg-γGlu-CO(CH$_2$)$_{16}$CO$_2$H)

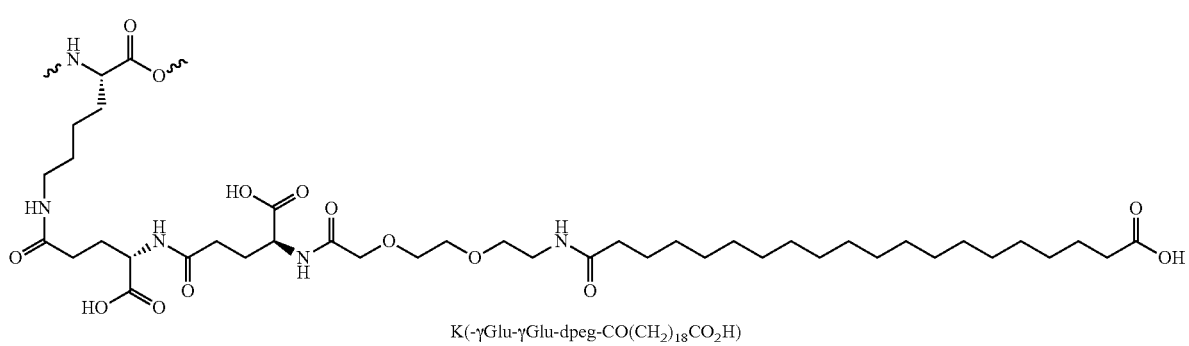

K(-γGlu-γGlu-dpeg-CO(CH$_2$)$_{18}$CO$_2$H)

TABLE 8-continued
Structures of Representative Spacers Moieties & Lipophillic Substituents Bound to Lysine
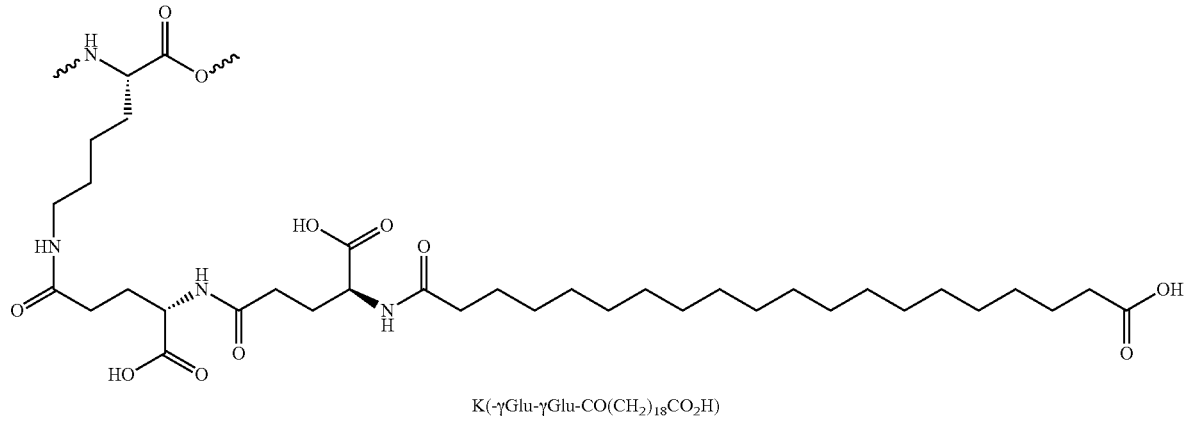
K(-γGlu-γGlu-CO(CH$_2$)$_{18}$CO$_2$H)
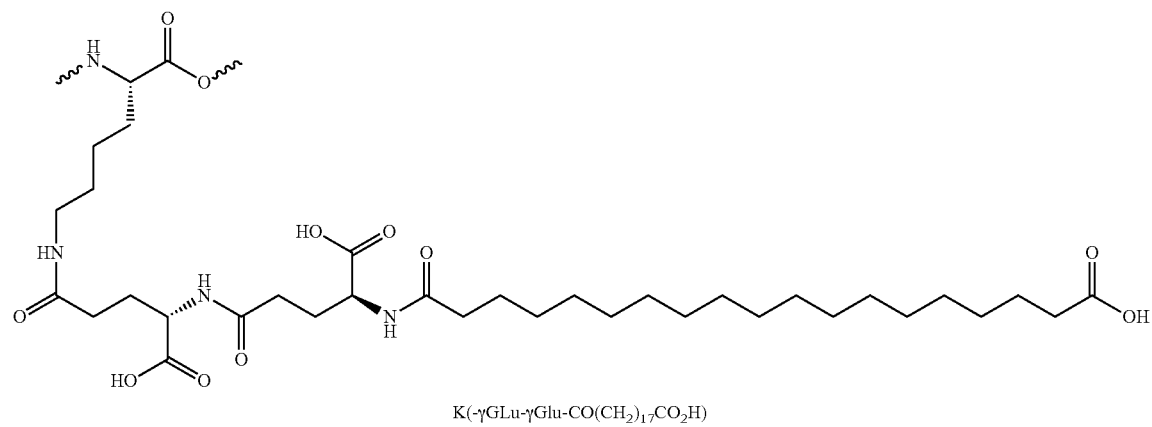
K(-γGLu-γGlu-CO(CH$_2$)$_{17}$CO$_2$H)
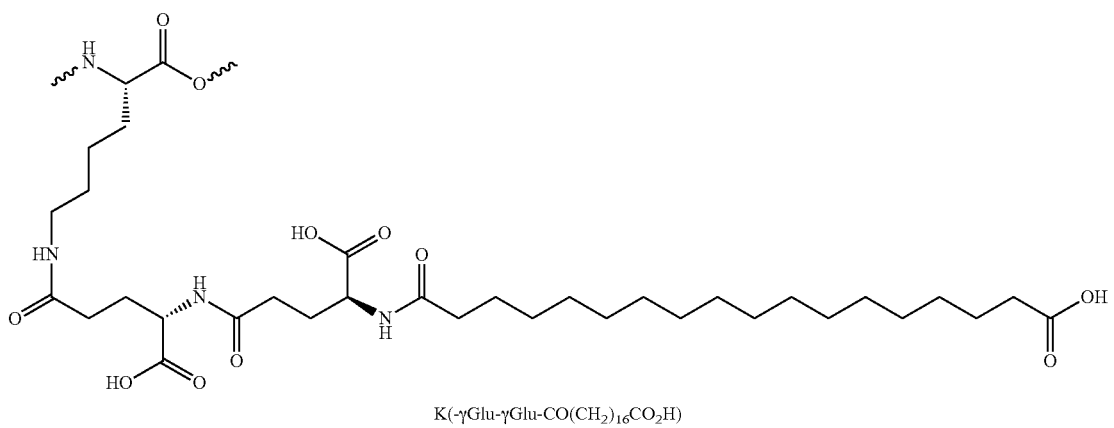
K(-γGlu-γGlu-CO(CH$_2$)$_{16}$CO$_2$H)

TABLE 8-continued

Structures of Representative Spacers Moieties & Lipophillic Substituents Bound to Lysine

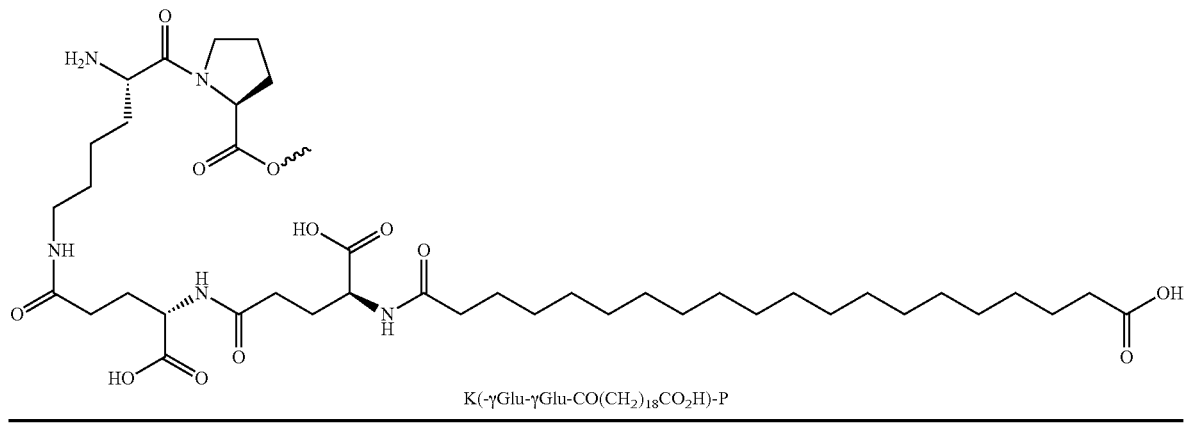

K(-γGlu-γGlu-CO(CH₂)₁₈CO₂H)-P

In some embodiments, the lipophilic substituent and spacer form a monovalent group of Formula II:

—(Y)$_n$—CO—(CH$_2$)$_m$—Z    Formula II wherein
Y is selected from the group consisting of γGlu, Asp, Lys and Gly;
Z is —CH$_3$ or —CO$_2$H;
m is from 4 to 24; and
n is from 1 to 10.

In some embodiments, Z is —CO$_2$H. In some embodiments, m is from 14 to 20. In some embodiments, Y is γGlu. In some embodiments, n is from 1 to 5.

In some embodiments, Y is selected from the group consisting of γGlu and Gly. In some embodiments, Y is γGlu. In some embodiments, Y is Gly.

In some embodiments, the polypeptide comprises three, two, or preferably one lipophilic substituent each with a spacer. In some embodiments, the lipophilic substituent and spacer are a monovalent group of Formula III:

—(V)$_r$—(Y)$_n$—CO—(CH$_2$)$_m$—Z    Formula III wherein,
V is —[COCH$_2$(OCH$_2$CH$_2$)$_t$NH]—;
Y is selected from the group consisting of γGlu, Asp, and Gly;
Z is —CH$_3$ or —CO$_2$H;
m is from 4 to 24;
n is from 1 to 10;
r is from 1 to 6; and
t is from 1 to 6.

In some embodiments, Z is —CO$_2$H. In some embodiments, Z is —CH$_3$.

In some embodiments, Y is γGlu. In some embodiments, Y is Asp. In some embodiments, Y is Gly.

In some embodiments, m is selected from the group consisting of 4-20, 8-20, 12-20, 14-20, 16-20, 14, 16, 18, and 20. In some embodiments, m is from 14 to 20.

In some embodiments, n is selected from the group consisting of 1, 2, 3, 4, 5, 6, 7, 8, 9 and 10. In some embodiments, n is from 1 to 5. In some embodiments, n is 1. In some embodiments, n is 2. In some embodiments, n is 3. In some embodiments, n is 4. In some embodiments, n is 5.

In some embodiments, r is from 1 to 3. In some embodiments, r is 1. In some embodiments, r is 2. In some embodiments, r is 3. In some embodiments, r is 4. In some embodiments, r is 5.

In some embodiments, t is from 1 to 3. In some embodiments, t is selected from the group consisting of 1, 2, 3, 4, 5 and 6.

In some embodiments, Y is γGlu; Z is —CO$_2$H; m is 16; n is 1; r is 2; and t is 2.

In an embodiment, —(V)$_r$—(Y)$_n$— is —[COCH$_2$(OCH$_2$CH$_2$)$_2$NH]$_2$-γGlu-.

In some embodiments, the polypeptide comprises three, two, or preferably one lipophilic substituent each with a spacer. In some embodiments, the lipophilic substituent and spacer are a monovalent group of Formula IV:

—(Y1)$_{n1}$-(dpeg)$_r$-(Y2)$_{n2}$—CO—(CH$_2$)$_m$—Z    Formula IV wherein
Z is —CH$_3$ or —CO$_2$H;
m is from 4 to 24;
Y1 is selected from the group consisting of γGlu, Asp, and Gly;
Y2 is selected from the group consisting of γGlu, Asp, and Gly;
dpeg is —[CO(CH$_2$)O(CH$_2$)$_2$O(CH$_2$)NH]—;
r is from 1 to 8;
n1 is from 0 to 10; and
n2 is from 0 to 10.

In some embodiments, Z is —CO$_2$H. In some embodiments, Z is —CH$_3$.

In some embodiments, m is selected from the group consisting of 4-20, 8-20, 12-20, 14-20, 16-20, 14, 16, 18, and 20. In some embodiments, m is from 14 to 20.

In some embodiments, Y1 is γGlu. In some embodiments, Y1 is Asp. In some embodiments, Y1 is Gly.

In some embodiments, Y2 is γGlu. In some embodiments, Y2 is Asp. In some embodiments, Y2 is Gly.

In some embodiments, n1 is selected from the group consisting of 0, 1, 2, 3, 4, 5, 6, 7, 8, 9 and 10. In some embodiments, n1 is from 0 to 3. In some embodiments, n1 is 0. In some embodiments, n1 is 1. In some embodiments, n1 is 2. In some embodiments, n1 is 3. In some embodiments, n1 is 4. In some embodiments, n1 is 5.

In some embodiments, n2 is selected from the group consisting of 0, 1, 2, 3, 4, 5, 6, 7, 8, 9 and 10. In some embodiments, n2 is from 0 to 3. In some embodiments, n2 is 0. In some embodiments, n2 is 1. In some embodiments, n2 is 2. In some embodiments, n2 is 3. In some embodiments, n2 is 4. In some embodiments, n2 is 5.

In some embodiments, r is from 1 to 3. In some embodiments, r is 1. In some embodiments, r is 2. In some embodiments, r is 3. In some embodiments, r is 4. In some embodiments, r is 5.

In some embodiments, r is 6. In some embodiments, r is 7. In some embodiments, r is 8.

In some embodiments, r is 1, n1 is 2, and n2 is 0.
In some embodiments, r is 1, n1 is 2, and n2 is 2.
In some embodiments, Y1 is γGlu and Y2 is γGlu.
In some embodiments, Y1 is γGlu and n2 is 0.
In some embodiments, Y1 is γGlu, r is 1, n1 is 2, and n2 is 0.

In some embodiments, $-(Y1)_{n1}$-(dpeg)$_r$-(Y2)$_{n2}$- is selected from the group consisting of -γGlu-γGlu-dpeg-, -γGlu-γGlu-dpeg-γGlu-γGlu-, -γGlu-γGlu-dpeg-γGlu-, -γGlu-γGlu-dpeg-dpeg-, -γGlu-γGlu-dpeg-dpeg-γGlu-, -dpeg-dpeg-γGlu-, -γGlu-γGlu-γGlu-dpeg-, and -γGlu-dpeg-.

In some embodiments, the polypeptide comprises three, two, or preferably one lipophilic substituent each with a spacer. In some embodiments, the lipophilic substituent and spacer are a monovalent group of Formula V:

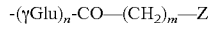    Formula V wherein
Z is —CH$_3$ or —CO$_2$H;
m is from 4 to 24; and
n is from 1 to 10 ("(γGlu)$_n$", where n is from 1 to 10 disclosed as SEQ ID NO: 808).

In some embodiments, Z is —CH$_3$. In some embodiments, Z is —CO$_2$H.

In some embodiments, m is from 14 to 20.

In some embodiments, m is selected from the group consisting of 4-20, 8-20, 12-20, 14-20, 16-20, 14, 16, 18, and 20.

In some embodiments, n is selected from the group consisting of 1, 2, 3, 4, 5, 6, 7, 8, 9 and 10. In some embodiments, n is 1. In some embodiments, n is 2. In some embodiments, n is 3. In some embodiments, n is 4. In some embodiments, n is 5.

In some embodiments, the polypeptide comprises three, two, or preferably one lipophilic substituent each with a spacer. In some embodiments, the lipophilic substituent and spacer are a monovalent group of Formula VI:

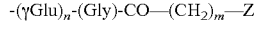    Formula VI wherein
Z is —CH$_3$ or —CO$_2$H;
m is from 4 to 24; and
n is from 1 to 10 ("(γGlu)$_n$-(Gly)", where n is from 1 to 10 disclosed as SEQ ID NO: 809).

In some embodiments, (γGlu)$_n$ is selected from the group consisting of γGlu; 2(γGlu); 3(γGlu); 4(γGlu) (SEQ ID NO: 810); and 5(γGlu) (SEQ ID NO: 811). In some embodiments, -(γGlu)$_n$-(Gly)- is selected from the group consisting of 2(γGlu),Gly; and 3(γGlu),Gly (SEQ ID NO: 812).

In some embodiments, the polypeptide comprises three, two, or preferably one lipophilic substituent each with a spacer. In some embodiments, the lipophilic substituent and spacer are a monovalent group of Formula VII:

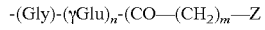    Formula VII wherein
Z is —CH$_3$ or —CO$_2$H;
m is from 4 to 24; and
n is from 1 to 10 ("-(Gly)-(γGlu)$_n$", where n is from 1 to 10 disclosed as SEQ ID NO: 813).

In some embodiments, certain variables represented in certain of the preceding Formulae include the following:

In some embodiments, Z is —CH$_3$. In some embodiments, Z is —CO$_2$H.

In some embodiments, m is selected from the group consisting of 4-20, 8-20, 12-20, 14-20, 16-20, 14, 16, 18, and 20.

In some embodiments, n is selected from the group consisting of 1, 2, 3, 4, 5, 6, 7, 8, 9 and 10. In some embodiments, n is 1. In some embodiments, n is 2. In some embodiments, n is 3. In some embodiments, n is 4. In some embodiments, n is 5.

In some embodiments, n is 1 and Z is —CO$_2$H. In some embodiments, n is 1 and Z is —CH$_3$. In some embodiments, n is 2 and Z is —CO$_2$H. In some embodiments, n is 2 and Z is —CH$_3$. In some embodiments, n is 3 and Z is —CO$_2$H. In some embodiments, n is 3 and Z is —CH$_3$. In some embodiments, n is 4 and Z is —CO$_2$H. In some embodiments, n is 4 and Z is —CH$_3$. In some embodiments, n is 5 and Z is —CO$_2$H. In some embodiments, n is 5 and Z is —CH$_3$.

In some embodiments, n is 1, Z is —CO$_2$H, and m is 14-20. In some embodiments, n is 1, Z is —CO$_2$H, and m is 14. In some embodiments, n is 1, Z is —CO$_2$H, and m is 16. In some embodiments, n is 1, Z is —CO$_2$H, and m is 18.

In some embodiments, n is 1, Z is —CH$_3$, and m is 14-20. In some embodiments, n is 1, Z is —CH$_3$ and m is 14. In some embodiments, n is 1, Z is —CH$_3$, and m is 16. In some embodiments, n is 1, Z is —CH$_3$, and m is 18.

In some embodiments, n is 2, Z is —CO$_2$H, and m is 14-20. In some embodiments, n is 2, Z is —CO$_2$H, and m is 14. In some embodiments, n is 2, Z is —CO$_2$H, and m is 16. In some embodiments, n is 2, Z is —CO$_2$H, and m is 18.

In some embodiments, n is 2, Z is —CH$_3$, and m is 14-20. In some embodiments, n is 2, Z is —CH$_3$ and m is 14. In some embodiments, n is 2, Z is —CH$_3$, and m is 16. In some embodiments, n is 2, Z is —CH$_3$, and m is 18.

In some embodiments, n is 3, Z is —CO$_2$H, and m is 14-20. In some embodiments, n is 3, Z is —CO$_2$H, and m is 14. In some embodiments, n is 3, Z is —CO$_2$H, and m is 16. In some embodiments, n is 3, Z is —CO$_2$H, and m is 18.

In some embodiments, n is 3, Z is —CH$_3$, and m is 14-20. In some embodiments, n is 3, Z is —CH$_3$ and m is 14. In some embodiments, n is 3, Z is —CH$_3$, and m is 16. In some embodiments, n is 3, Z is —CH$_3$, and m is 18.

In some embodiments, n is 4, Z is —CO$_2$H, and m is 14-20. In some embodiments, n is 4, Z is —CO$_2$H, and m is 14. In some embodiments, n is 4, Z is —CO$_2$H, and m is 16. In some embodiments, n is 4, Z is —CO$_2$H, and m is 18.

In some embodiments, n is 4, Z is —CH$_3$, and m is 14-20. In some embodiments, n is 4, Z is —CH$_3$ and m is 14. In some embodiments, n is 4, Z is —CH$_3$, and m is 16. In some embodiments, n is 4, Z is —CH$_3$, and m is 18.

In some embodiments, n is 5, Z is —CO$_2$H, and m is 14-20. In some embodiments, n is 5, Z is —CO$_2$H, and m is 14. In some embodiments, n is 5, Z is —CO$_2$H, and m is 16. In some embodiments, n is 5, Z is —CO$_2$H, and m is 18.

In some embodiments, n is 5, Z is —CH$_3$, and m is 14-20. In some embodiments, n is 5, Z is —CH$_3$ and m is 14. In some embodiments, n is 5, Z is —CH$_3$, and m is 16. In some embodiments, n is 5, Z is —CH$_3$, and m is 18.

In some embodiments, the polypeptide comprises three, two, or preferably one lipophilic substituent each with a spacer. In some embodiments, the lipophilic substituent and spacer are a monovalent group of Formula VIII:

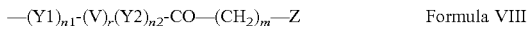
—(Y1)$_{n1}$-(V)$_r$-(Y2)$_{n2}$-CO—(CH$_2$)$_m$—Z    Formula VIII wherein
Z is —CH$_3$ or —CO$_2$H;
m is from 4 to 24;
Y1 is selected from the group consisting of γGlu, Asp, and Gly;
Y2 is selected from the group consisting of γGlu, Asp, and Gly;
V is —[COCH$_2$(OCH$_2$CH$_2$)$_t$NH]—;
r is from 1 to 6;
n1 is from 0 to 10;
n2 is from 0 to 10; and
t is from 1 to 6.

In some embodiments, the polypeptide comprises three, two, or preferably one lipophilic substituent each with a spacer. In some embodiments, the lipophilic substituent and spacer are a monovalent group of Formula IX:

—(Y)$_n$—(V)$_r$CO—(CH$_2$)$_m$—Z    Formula IX wherein
Z is —CH$_3$ or —CO$_2$H;
m is from 4 to 24;
Y is selected from the group consisting of γGlu, Asp, and Gly;
V is —[COCH$_2$(OCH$_2$CH$_2$)$_t$NH]—;
r is from 1 to 6; and
n is from 1 to 10; and
t is from 1 to 6.

In some embodiments, the polypeptide comprises three, two, or preferably one lipophilic substituent each with a spacer. In some embodiments, the lipophilic substituent and spacer are a monovalent group of Formula X:

-(dpeg)$_r$-(Y2)$_{n2}$-CO—(CH$_2$)$_m$—Z    Formula X wherein
Z is —CH$_3$ or —CO$_2$H;
m is from 4 to 24;
dpeg is —[CO(CH$_2$)O(CH$_2$)$_2$O(CH$_2$)NH]—;
Y2 is selected from the group consisting of γGlu, Asp, and Gly;
r is from 1 to 8; and
n2 is from 0 to 10.

In some embodiments, -(dpeg)$_r$-(Y2)$_{n2}$- is selected from the group consisting of dpeg,γGlu; and dpeg,dpeg,γGlu.

In an embodiment, -(dpeg)$_r$-(Y2)$_{n2}$- is -dpeg-dpeg-γGlu-.

In some embodiments, the polypeptide comprises three, two, or preferably one lipophilic substituent each with a spacer. In some embodiments, the lipophilic substituent and spacer are a monovalent group of Formula XI:

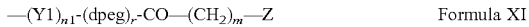
—(Y1)$_{n1}$-(dpeg)$_r$-CO—(CH$_2$)$_m$—Z    Formula XI wherein
Z is —CH$_3$ or —CO$_2$H;
m is from 4 to 24;
Y1 is selected from the group consisting of γGlu, Asp, and Gly;
dpeg is —[CO(CH$_2$)O(CH$_2$)$_2$O(CH$_2$)NH]—;
r is from 1 to 8; and
n1 is from 0 to 10.

In some embodiments, Z is —CO$_2$H.

In some embodiments, m is selected from the group consisting of 4-20, 8-20, 12-20, 14-20, 16-20, 14, 16, 18, and 20. In some embodiments, m is from 14 to 20.

In some embodiments, Y1 is γGlu. In some embodiments, Y1 is Asp. In some embodiments, Y1 is Gly.

In some embodiments, n1 is selected from the group consisting of 0, 1, 2, 3, 4, 5, 6, 7, 8, 9 and 10. In some embodiments, n1 is from 0 to 3. In some embodiments, n1 is 0. In some embodiments, n1 is 1. In some embodiments, n1 is 2. In some embodiments, n1 is 3. In some embodiments, n1 is 4. In some embodiments, n1 is 5.

In some embodiments, r is from 1 to 3. In some embodiments, r is 1. In some embodiments, r is 2. In some embodiments, r is 3. In some embodiments, r is 4. In some embodiments, r is 5.

In some embodiments, r is 6. In some embodiments, r is 7. In some embodiments, r is 8.

In some embodiments, r is 1 and n1 is 2.

In some embodiments, Y1 is γGlu, r is 1, and n1 is 2.

In some embodiments, —(Y1)$_{n1}$-(dpeg)$_r$- is selected from the group consisting of -γGlu-γGlu-dpeg-, -γGlu-γGlu-dpeg-dpeg-, -γGlu-γGlu-γGlu-dpeg-, and -γGlu-dpeg-.

Further Exemplary Spacers

In some embodiments, the spacer comprises a bivalent group of Formula XII:

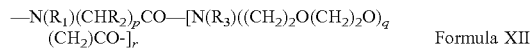
—N(R$_1$)(CHR$_2$)$_p$CO—[N(R$_3$)((CH$_2$)$_2$O(CH$_2$)$_2$O)$_q$(CH$_2$)CO-]$_r$    Formula XII wherein
each R$_1$ and R$_3$ is hydrogen or C$_1$-C$_4$ alkyl;
each R$_2$ is H or CO$_2$H;
p is 1, 2, 3, 4, 5 or 6;
q is 1, 2 or 3;
r is 0 or 1.
which spacer forms a bridge between an amino group of the disclosed polypeptide and a CO group of the lipophilic substituent.

In some embodiments, the spacer comprises a bivalent group of Formula XIII:

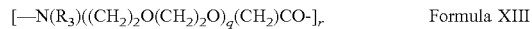
[—N(R$_3$)((CH$_2$)$_2$O(CH$_2$)$_2$O)$_q$(CH$_2$)CO-]$_r$    Formula XIII wherein
each R$_3$ is hydrogen or C$_1$-C$_4$ alkyl;
q is 1, 2 or 3;
r is 0 or 1.
which spacer forms a bridge between an amino group of the disclosed polypeptide and a CO group of the lipophilic substituent.

In some embodiments, certain variables represented in certain Formulae include the following:

In some embodiments, each R$_1$ is hydrogen. In some embodiments, each R$_3$ is hydrogen.

In some embodiments, each R$_1$ and each R$_3$ are hydrogen.

In some embodiments, at least one R$_2$ is CO$_2$H. In some embodiments, one R$_2$ is CO$_2$H.

In some embodiments, p is 1. In some embodiments, p is 2. In some embodiments, p is 3.

In some embodiments, p is 4. In some embodiments, p is 5. In some embodiments, p is 6.

In some embodiments, q is 1. In some embodiments, q is 2. In some embodiments, q is 3.

In some embodiments, r is 0. In some embodiments, r is 1.

In some embodiments, the spacer is γ-glutamyl, i.e., —NH(CHCO$_2$H)(CH$_2$)$_2$CO—. In some embodiments, the spacer is γ-aminobutanoyl, i.e., —NH(CH$_2$)$_3$CO—. In some embodiments, the spacer is β-asparagyl, i.e., —NH(CHCO$_2$H)(CH$_2$)CO—. In some embodiments, the spacer is —NH(CH$_2$)$_2$CO—. In some embodiments, the spacer is glycyl. In some embodiments, the spacer is β-alanyl.

In some embodiments, the spacer is —NHCH(CO$_2$H)(CH$_2$)$_2$CO—[N(R$_3$)((CH$_2$)$_2$O(CH$_2$)$_{20}$)$_q$(CH$_2$)CO]$_r$-. In some embodiments, the spacer is —NH(CH$_2$)$_3$CO—[N(R$_3$)((CH$_2$)$_2$O(CH$_2$)$_{20}$)$_q$(CH$_2$)CO-]$_r$-. In some embodiments, the spacer is —NHCH(CO$_2$H)(CH$_2$)$_2$CO—NH((CH$_2$)$_2$O(CH$_2$)$_{20}$)$_2$(CH$_2$)CO—. In some embodiments, the spacer is —NH(CH$_2$)$_3$CO—NH((CH$_2$)$_2$O(CH$_2$)$_{20}$)$_2$(CH$_2$)CO—. In some embodiments, the spacer is —NHCH(CO$_2$H)CH$_2$CO—[N(R$_3$)((CH$_2$)$_2$O(CH$_2$)$_{20}$)$_q$(CH$_2$)CO]$_r$-. In some embodiments, the spacer is —NH(CH$_2$)$_2$CO—[N(R$_3$)((CH$_2$)$_2$O(CH$_2$)$_{20}$)$_q$(CH$_2$)CO-]$_r$-.

In some embodiments, the spacer comprises a bivalent group of Formula XIV:

—(Y)$_n$—      Formula XIV wherein

Y is selected from the group consisting of γGlu, Asp, Lys and Gly;

n is from 1 to 10.

In some embodiments, Y is selected from the group consisting of γGlu and Gly. In some embodiments, Y is γGlu. In some embodiments, Y is Gly.

In some embodiments, the spacer forms a bridge between an amino group of the disclosed polypeptide and a CO group of a lipophilic substituent. In some embodiments, one end of the spacer forms a covalent bond with an amino group of the disclosed polypeptide and the other end of the spacer forms a covalent bond with a hydrogen atom or a protecting group.

In some embodiments, the spacer comprises a bivalent group of Formula XV:

-(γGlu)$_n$-      Formula XV wherein n is from 1 to 10 ("(γGlu)$_n$", where n is from 1 to 10 disclosed as SEQ ID NO: 808).

In some embodiments, n is selected from the group consisting of 1, 2, 3, 4, 5, 6, 7, 8, 9 and 10. In some embodiments, n is 1. In some embodiments, n is 2. In some embodiments, n is 3. In some embodiments, n is 4. In some embodiments, n is 5.

In some embodiments, the spacer forms a bridge between an amino group of the disclosed polypeptide and a CO— group of a lipophilic substituent. In some embodiments, one end of the spacer forms a covalent bond with an amino group of the disclosed polypeptide and the other end of the spacer forms a covalent bond with a hydrogen atom or a protecting group.

In some embodiments, the spacer comprises a bivalent group of Formula XVI:

-(γGlu)$_n$-(Gly)-      Formula XVI wherein n is from 1 to 10 ("(γGlu)$_n$-(Gly)", where n is from 1 to 10 disclosed as SEQ ID NO: 809).

In some embodiments, (γGlu)$_n$ is selected from the group consisting of γGlu; 2(γGlu); 3(γGlu); 4(γGlu) (SEQ ID NO: 810); and 5(γGlu) (SEQ ID NO: 811). In some embodiments, -(γGlu)$_n$-(Gly)- is selected from the group consisting of 2(γGlu),Gly; and 3(γGlu),Gly (SEQ ID NO: 812).

In some embodiments, the spacer forms a bridge between an amino group of the disclosed polypeptide and a CO group of a lipophilic substituent. In some embodiments, one end of the spacer forms a covalent bond with an amino group of the disclosed polypeptide and the other end of the spacer forms a covalent bond with a hydrogen atom or a protecting group.

In some embodiments, the spacer comprises a bivalent group of Formula XVII:

-(Gly)-(γGlu)$_n$-      Formula XVII wherein n is from 1 to 10 ("-(Gly)-(γGlu)$_n$", where n is from 1 to 10 disclosed as SEQ ID NO: 813).

In some embodiments, the spacer forms a bridge between an amino group of the disclosed polypeptide and a CO group of a lipophilic substituent. In some embodiments, one end of the spacer forms a covalent bond with an amino group of the disclosed polypeptide and the other end of the spacer forms a covalent bond with a hydrogen atom or a protecting group.

In some embodiments, n is selected from the group consisting of 1, 2, 3, 4, 5, 6, 7, 8, 9 and 10. In some embodiments, n is 1. In some embodiments, n is 2. In some embodiments, n is 3. In some embodiments, n is 4. In some embodiments, n is 5.

In some embodiments, the spacer comprises a bivalent group of Formula XVIII:

—(V)$_r$—(Y)$_t$—      Formula XVIII wherein

Y is selected from the group consisting of γGlu, Asp, and Gly;

V is —[COCH$_2$(OCH$_2$CH$_2$)$_t$NH]—;

r is from 1 to 6;

n is from 1 to 10; and t is from 1 to 6.

In some embodiments, Y is γGlu. In some embodiments, Y is Asp. In some embodiments, Y is Gly.

In some embodiments, n is selected from the group consisting of 1, 2, 3, 4, 5, 6, 7, 8, 9 and 10. In some embodiments, n is from 1 to 5. In some embodiments, n is 1. In some embodiments, n is 2. In some embodiments, n is 3. In some embodiments, n is 4. In some embodiments, n is 5.

In some embodiments, r is from 1 to 3. In some embodiments, r is 1. In some embodiments, r is 2. In some embodiments, r is 3. In some embodiments, r is 4. In some embodiments, r is 5.

In some embodiments, t is from 1 to 3. In some embodiments, t is selected from the group consisting of 1, 2, 3, 4, 5 and 6.

In an embodiment, —(V)$_r$—(Y)$_n$— is —[COCH$_2$(OCH$_2$CH$_2$)$_2$NH]$_2$-γGlu-.

In some embodiments, the spacer forms a bridge between an amino group of the disclosed polypeptide and a CO group of a lipophilic substituent. In some embodiments, one end of the spacer forms a covalent bond with an amino group of the disclosed polypeptide and the other end of the spacer forms a covalent bond with a hydrogen atom or a protecting group.

In some embodiments, the spacer comprises a bivalent group of Formula XIX:

—(Y1)$_{n1}$-(dpeg)$_r$-(Y2)$_{n2}$-      Formula XIX wherein

Y1 is selected from the group consisting of γGlu, Asp, and Gly;

Y2 is selected from the group consisting of γGlu, Asp, and Gly;

dpeg is —[CO(CH$_2$)O(CH$_2$)$_2$O(CH$_2$)NH]—;

r is from 1 to 8;

n1 is from 0 to 10; and n2 is from 0 to 10.

In some embodiments, Y1 is γGlu. In some embodiments, Y1 is Asp. In some embodiments, Y1 is Gly.

In some embodiments, Y2 is γGlu. In some embodiments, Y2 is Asp. In some embodiments, Y2 is Gly.

In some embodiments, n1 is selected from the group consisting of 0, 1, 2, 3, 4, 5, 6, 7, 8, 9 and 10. In some embodiments, n1 is from 0 to 3. In some embodiments, n1 is 0. In some embodiments, n1 is 1. In some embodiments, n1 is 2. In some embodiments, n1 is 3. In some embodiments, n1 is 4. In some embodiments, n1 is 5.

In some embodiments, n2 is selected from the group consisting of 0, 1, 2, 3, 4, 5, 6, 7, 8, 9 and 10. In some embodiments, n2 is from 0 to 3. In some embodiments, n2 is 0. In some embodiments, n2 is 1. In some embodiments, n2 is 2. In some embodiments, n2 is 3. In some embodiments, n2 is 4. In some embodiments, n2 is 5.

In some embodiments, r is from 1 to 3. In some embodiments, r is 1. In some embodiments, r is 2. In some embodiments, r is 3. In some embodiments, r is 4. In some embodiments, r is 5.

In some embodiments, r is 6. In some embodiments, r is 7. In some embodiments, r is 8.

In some embodiments, r is 1, n1 is 2, and n2 is 0.
In some embodiments, r is 1, n1 is 2, and n2 is 2.
In some embodiments, Y1 is γGlu and Y2 is γGlu.
In some embodiments, Y1 is γGlu and n2 is 0.
In some embodiments, Y1 is γGlu, r is 1, n1 is 2, and n2 is 0.

In some embodiments, $-(Y1)_{n1}$-(dpeg)$_r$-(Y2)$_{n2}$- is selected from the group consisting of -γGlu-γGlu-dpeg-, -γGlu-γGlu-dpeg-γGlu-γGlu-, -γGlu-γGlu-dpeg-γGlu-, -γGlu-γGlu-dpeg-dpeg-, -γGlu-γGlu-dpeg-dpeg-γGlu-, -dpeg-dpeg-γGlu-, -γGlu-γGlu-γGlu-dpeg-, and -γGlu-dpeg-.

In some embodiments, the spacer forms a bridge between an amino group of the disclosed polypeptide and a CO group of a lipophilic substituent. In some embodiments, one end of the spacer forms a covalent bond with an amino group of the disclosed polypeptide and the other end of the spacer forms a covalent bond with a hydrogen atom or a protecting group.

Accordingly, in some embodiments, an isolated polypeptide provided herein comprises an amino acid sequence, or a pharmaceutically acceptable salt thereof, selected from the group consisting of amino acid sequences represented by a consensus sequence selected from the group consisting of SEQ ID NO: 101 through SEQ ID NO: 181 and SEQ ID NOs: 239, 240, 241, 242, 243, 244, 245, 246, 247, 248, 280, and 281, wherein the isolated peptide further comprises a lipophilic substituent, and optionally comprises a spacer.

In some embodiments, an isolated polypeptide provided herein comprises an amino acid sequence, or a pharmaceutically acceptable salt thereof, selected from the group consisting of amino acid sequences represented by a consensus sequence selected from the group consisting of SEQ ID NO: 101 through SEQ ID NO: 181 and SEQ ID NOs: 239, 240, 241, 242, 243, 244, 245, 246, 247, 248, 280, and 281, wherein the isolated peptide further comprises a lipophilic substituent of Formula I.

In some embodiments, an isolated polypeptide provided herein comprises an amino acid sequence, or a pharmaceutically acceptable salt thereof, selected from the group consisting of amino acid sequences represented by a consensus sequence selected from the group consisting of SEQ ID NO: 101 through SEQ ID NO: 181 and SEQ ID NOs: 239, 240, 241, 242, 243, 244, 245, 246, 247, 248, 280, and 281, wherein the isolated peptide further comprises a lipophilic substituent of Formula I and a spacer selected from the group consisting of those described by Formula XII, XIII, XIV, XV, XVI, XVII, XVIII, and XIX.

In some embodiments, an isolated polypeptide provided herein comprises an amino acid sequence, or a pharmaceutically acceptable salt thereof, selected from the group consisting of amino acid sequences represented by a consensus sequence selected from the group consisting of SEQ ID NO: 101 through SEQ ID NO: 157 and SEQ ID NOs: 239, 240, 241, 242, 243, 244, 245, 246, 247, 248, 280, and 281, wherein the isolated peptide further comprises a lipophilic substituent and a spacer selected from the group consisting of those described by Formula I, II, III, IV, V, VI, VII, VIII, IX, X, and XI.

In some embodiments, an isolated polypeptide provided herein comprises an amino acid sequence, or a pharmaceutically acceptable salt thereof, selected from the group consisting of amino acid sequences represented by a consensus sequence selected from the group consisting of SEQ ID NO: 101 through SEQ ID NO: 181 and SEQ ID NOs: 239, 240, 241, 242, 243, 244, 245, 246, 247, 248, 280, and 281, wherein the isolated peptide further comprises a lipophilic substituent and a spacer selected from the group consisting of those described by Formula I.

In some embodiments, an isolated polypeptide provided herein comprises an amino acid sequence, or a pharmaceutically acceptable salt thereof, selected from the group consisting of amino acid sequences represented by a consensus sequence selected from the group consisting of SEQ ID NO: 101 through SEQ ID NO: 181 and SEQ ID NOs: 239, 240, 241, 242, 243, 244, 245, 246, 247, 248, 280, and 281, wherein the isolated peptide further comprises a lipophilic substituent and a spacer selected from the group consisting of those described by Formula II.

In some embodiments, an isolated polypeptide provided herein comprises an amino acid sequence, or a pharmaceutically acceptable salt thereof, selected from the group consisting of amino acid sequences represented by a consensus sequence selected from the group consisting of SEQ ID NO: 101 through SEQ ID NO: 181 and SEQ ID NOs: 239, 240, 241, 242, 243, 244, 245, 246, 247, 248, 280, and 281, wherein the isolated peptide further comprises a lipophilic substituent and a spacer selected from the group consisting of those described by Formula III.

In some embodiments, an isolated polypeptide provided herein comprises an amino acid sequence, or a pharmaceutically acceptable salt thereof, selected from the group consisting of amino acid sequences represented by a consensus sequence selected from the group consisting of SEQ ID NO: 101 through SEQ ID NO: 181 and SEQ ID NOs: 239, 240, 241, 242, 243, 244, 245, 246, 247, 248, 280, and 281, wherein the isolated peptide further comprises a lipophilic substituent and a spacer selected from the group consisting of those described by Formula IV. As used herein, (γGlu)$_2$ and 2(γGlu) both mean -(γGlu)-(γGlu)- or —CO(CH$_2$)$_2$CH(CO$_2$H)NH—CO(CH$_2$)$_2$CH(CO$_2$H)NH—; (γGlu)$_3$ and 3(γGlu) both mean -(γGlu)-(γGlu)-(γGlu)- or —CO(CH$_2$)$_2$CH(CO$_2$H)NH—CO(CH$_2$)$_2$CH(CO$_2$H)NH—CO(CH$_2$)$_2$CH(CO$_2$H)NH—; etc.; where a variable is present more than once in a given formula, each occurrence of that variable is independently determined. For example, for group —(Y)$_3$—, where Y may be γGlu, Asp, Lys, or Gly, each Y is independently selected to be one of the four amino acids. Accordingly, by non-limiting example, —(Y)$_3$— may be -(γGlu)-(γGlu)-(γGlu)-, -(γGlu)-(Asp)-(γGlu)-, -(Gly)-(Asp)-(γGlu)-, or -(Gly)-(γGlu)-(γGlu)-.

Bridging Moiety

In some embodiments, any of the disclosed polypeptides is optionally substituted with one or more bridging moieties. As used herein, the term "bridging moiety" means a covalent bond or any bivalent linker or moiety that joins two side-chains of two separate amino acid residues. In some embodiments, any of the disclosed polypeptides is optionally substituted with one or more lactam bridging moieties. As used herein, the term "lactam bridging moiety" means a lactam bridge or lactam bond that joins amino-containing and carboxy-containing sidechains of two separate amino acid residues. In some embodiments, the lactam bridging moiety is formed between a lysine residue and an aspartic acid residue, and the amino-containing sidechain of lysine and the carboxy-containing sidechain of aspartic acid are covalently joined, with loss of water, to form a lactam bridging moiety. In some embodiments, the lactam bridging moiety is formed between a lysine residue and a glutamic acid residue, and the amino-containing sidechain of lysine and the carboxy-containing sidechain of glutamic acid are covalently joined, with loss of water, to form a lactam bridging moiety. In some embodiments, the lactam bridging moiety is formed between two amino acids that are spaced three, four, or five residues apart on the peptide. In some embodiments, the lactam bridging moiety is formed between two amino acids that are spaced four residues apart on the peptide.

Polypeptide Intermediates & General Methods of Providing the Present Compounds

The compounds of this invention may be prepared or isolated in general by synthetic and/or semi-synthetic methods known in general to those skilled in the art for analogous compounds and by methods described in detail in the Examples, herein.

In the Schemes below, where a particular protecting group ("PG"), leaving group ("LG"), or transformation condition is depicted, one of ordinary skill in the art will appreciate that other protecting groups, leaving groups, and transformation conditions are also suitable and are contemplated. Such groups and transformations are described in detail in *March's Advanced Organic Chemistry: Reactions, Mechanisms, and Structure*, M. B. Smith and J. March, 5$^{th}$ Edition, John Wiley & Sons, 2001, *Comprehensive Organic Transformations*, R. C. Larock, 2$^{nd}$ Edition, John Wiley & Sons, 1999, and *Protecting Groups in Organic Synthesis*, T. W. Greene and P. G. M. Wuts, 3$^{rd}$ edition, John Wiley & Sons, 1999, the entirety of each of which is hereby incorporated herein by reference.

As used herein, the phrase "leaving group" (LG) includes, but is not limited to, halogens (e.g. fluoride, chloride, bromide, iodide), sulfonates (e.g. mesylate, tosylate, benzenesulfonate, brosylate, nosylate, triflate), diazonium, and the like.

As used herein, the phrase "oxygen protecting group" includes, for example, carbonyl protecting groups, hydroxyl protecting groups, etc. Hydroxyl protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Examples of suitable hydroxyl protecting groups include, but are not limited to, esters (e.g., acetyl, benzyl), allyl ethers, ethers, silyl ethers, alkyl ethers, arylalkyl ethers, benzyl ethers and alkoxyalkyl ethers. Examples of such esters include formates, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetyl), crotonate, 4-methoxy-crotonate, benzoate, p-benylbenzoate, 2,4,6-trimethylbenzoate, carbonates such as methyl, 9-fluorenylmethyl, ethyl, 2,2,2-trichloroethyl, 2-(trimethylsilyl)ethyl, 2-(phenylsulfonyl) ethyl, vinyl, allyl, and p-nitrobenzyl. Examples of such silyl ethers include trimethylsilyl, triethylsilyl, t-butyldimethylsilyl, t-butyldiphenylsilyl, triisopropylsilyl, and other trialkylsilyl ethers. Alkyl ethers include methyl, benzyl, p-methoxybenzyl, 3,4-dimethoxybenzyl, trityl, t-butyl, allyl, and allyloxycarbonyl ethers or derivatives. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyranyl ethers. Examples of arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, and 2- and 4-picolyl.

Amino protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Suitable amino protecting groups include, but are not limited to, aralkylamines, carbamates, cyclic imides, allyl amines, amides, and the like. Examples of such groups include t-butyloxycarbonyl (Boc), ethyloxycarbonyl, methyloxycarbonyl, trichloroethyloxycarbonyl, allyloxycarbonyl (Alloc), benzyloxocarbonyl (Cbz), allyl, phthalimide, benzyl (Bn), dimethyl-2,6-dioxocyclohex-1-ylidene)ethyl (Dmb), 1-(4,4-dimethyl-2,6-dioxocyclohex-1-ylidene)-3-methylbutyl (ivDde), fluorenylmethylcarbonyl (Fmoc), formyl, acetyl, chloroacetyl, dichloroacetyl, trichloroacetyl, phenylacetyl, trifluoroacetyl, benzoyl, and the like.

In certain embodiments, the present invention also relates to synthetic peptide intermediates of disclosed PYY analogs. In some embodiments, a polypeptide intermediate of the disclosure is an isolated polypeptide comprising the amino acid sequence of any of SEQ ID NO: 101 through SEQ ID NO: 181 or SEQ ID NOs: 239, 240, 241, 242, 243, 244, 245, 246, 247, 248, 280, and 281, wherein at least one amino acid is covalently bound to a protecting group. In some embodiments, a polypeptide intermediate of the disclosure is an isolated polypeptide comprising the amino acid sequence of any of SEQ ID NO: 101 through SEQ ID NO: 181 or SEQ ID NOs: 239, 240, 241, 242, 243, 244, 245, 246, 247, 248, 280, and 281, wherein at least one amino acid is covalently bound to a spacer as defined herein, wherein the spacer is further covalently bound to a protecting group or a hydrogen atom. In some embodiments, the polypeptide intermediate comprises a lysine residue bound to a protecting group via the amino group of its sidechain. In some embodiments, the lysine residue is covalently bound to a Alloc or ivDde. In some embodiments, the polypeptide intermediate comprises an aspartic acid residue bound to a protecting group via the carboxyl group of its sidechain. In some embodiments, the aspartic acid residue is covalently bound to an allyl group. In some embodiments, the polypeptide intermediate comprises a glutamic acid residue bound to a protecting group via the carboxyl group of its sidechain. In some embodiments, the glutamic acid residue is covalently bound to an allyl group.

Exemplary Polypeptide Intermediates

The compounds of this invention may be prepared or isolated in general by synthetic and/or semi-synthetic methods known to those skilled in the art for analogous compounds and by methods described in detail in the Examples, herein.

In certain embodiments, the present invention also relates to synthetic peptide intermediates of disclosed PYY analogs. In some embodiments, a polypeptide intermediate of the disclosure is an isolated polypeptide comprising the amino acid sequence of SEQ ID NO: 390:

$X_0PX_2PX_4X_5PX_7X_8X_9X_{10}SPX_{13}X_{14}X_{15}X_{16}RX_{18}X_{19}X_{20}DX_{22}X_{23}HX_{25}X_{26}X_{27}WLTRX_{32}RX_{34}$—(OH/NH$_2$) (SEQ ID NO: 390), or a pharmaceutically acceptable salt thereof, wherein:

$X_0$ is absent or K;
$X_2$ is K;
$X_4$ is E or K;
$X_5$ is A or K;
$X_7$ is G or K
$X_8$ is E, K, or k;
$X_9$ is D or K;
$X_{10}$ is A or K;
$X_{13}$ is E or K;
$X_{14}$ is E or K;
$X_{15}$ is L or W;
$X_{16}$ is D, E, K, N, Q, S, T, α-methylserine, or homoserine;
$X_{18}$ is K or Y;
$X_{19}$ is K or Y;
$X_{20}$ is A, D, E, K, k, or Dap;
$X_{22}$ is A, D, K, or L;
$X_{23}$ is K or R;
$X_{25}$ is K or Y;
$X_{26}$ is E, K, or L;
$X_{27}$ is K or N;
$X_{32}$ is K or Q;
$X_{34}$ is F, y, 3-pyridinylalanine, 4-pyridinylalanine, 4-carboxyphenylalanine, 4-fluorophenylalanine, 4-methylphenylalanine, N-methylphenylalanine, homophenylalanine, β-homotyrosine, homotyrosine, or N-methyltyrosine;
wherein when $X_0$, $X_2$, $X_4$, $X_5$, $X_7$, $X_8$, $X_{13}$, $X_{20}$, $X_{23}$, $X_{25}$, $X_{27}$, or $X_{32}$ are K, the lysine residue is optionally covalently bound to a protecting group or to a spacer optionally bound to a protecting group, and
wherein when $X_8$ or $X_{20}$ are k, the D-lysine residue is optionally covalently bound to a protecting group or to a spacer optionally bound to a protecting group.

In some embodiments, when $X_{15}$ is L, $X_{22}$ is A.

In some embodiment, when $X_{16}$ is N, $X_{20}$ is not A.

In some embodiments, when $X_5$ is E, $X_5$ is K and $X_{20}$ is K.

In some embodiments, $X_5$ is K. In some embodiments, $X_5$ is K covalently bound to a protecting group. In some embodiments, $X_8$ is K covalently bound to a spacer optionally bound to a protecting group.

In some embodiments, $X_{15}$ is W.

In some embodiments, $X_{34}$ is F.

In some embodiments, $X_0$ is absent. In some embodiments, $X_0$ is K. In some embodiments, $X_0$ is K covalently bound to a protecting group. In some embodiments, $X_0$ is K covalently bound to a spacer optionally bound to a protecting group.

In some embodiments, $X_2$ is K. In some embodiments, $X_2$ is K covalently bound to a protecting group. In some embodiments, $X_2$ is K covalently bound to a spacer optionally bound to a protecting group.

In some embodiments, $X_4$ is E. In some embodiments, $X_4$ is K. In some embodiments, $X_4$ is K covalently bound to a protecting group. In some embodiments, $X_4$ is K covalently bound to a spacer optionally bound to a protecting group.

In some embodiments, $X_5$ is A. In some embodiments, $X_5$ is K. In some embodiments, $X_5$ is K covalently bound to a protecting group. In some embodiments, $X_5$ is K covalently bound to a spacer optionally bound to a protecting group.

In some embodiments, $X_7$ is G. In some embodiments, $X_7$ is K. In some embodiments, $X_7$ is K covalently bound to a protecting group. In some embodiments, $X_7$ is K covalently bound to a spacer optionally bound to a protecting group.

In some embodiments, $X_8$ is E. In some embodiments, $X_8$ is K. In some embodiments, $X_8$ is K covalently bound to a protecting group. In some embodiments, $X_8$ is K covalently bound to a spacer optionally bound to a protecting group. In some embodiments, $X_8$ is k. In some embodiments, $X_8$ is k covalently bound to a protecting group. In some embodiments, $X_8$ is k covalently bound to a spacer optionally bound to a protecting group.

In some embodiments, $X_9$ is D. In some embodiments, $X_9$ is K.

In some embodiments, $X_{10}$ is A. In some embodiments, $X_{10}$ is K. In some embodiments, $X_{10}$ is K covalently bound to a protecting group. In some embodiments, $X_{10}$ is K covalently bound to a spacer optionally bound to a protecting group.

In some embodiments, $X_{13}$ is E. In some embodiments, $X_{13}$ is K. In some embodiments, $X_{13}$ is K covalently bound to a protecting group. In some embodiments, $X_{13}$ is K covalently bound to a spacer optionally bound to a protecting group.

In some embodiments, $X_{14}$ is E. In some embodiments, $X_{14}$ is K.

In some embodiments, $X_{15}$ is L. In some embodiments, $X_{15}$ is W.

In some embodiments, $X_{16}$ is D. In some embodiments, $X_{16}$ is E. In some embodiments, $X_{16}$ is K. In some embodiments, $X_{15}$ is N. In some embodiments, $X_{16}$ is Q. In some embodiments, $X_{16}$ is S. In some embodiments, $X_{16}$ is T. In some embodiments, $X_{16}$ is α-methylserine. In some embodiments, $X_{15}$ is homoserine.

In some embodiments, $X_{18}$ is K. In some embodiments, $X_{18}$ is Y.

In some embodiments, $X_{19}$ is K. In some embodiments, $X_{19}$ is Y.

In some embodiments, $X_{20}$ is A. In some embodiments, $X_{20}$ is D. In some embodiments, $X_{20}$ is E. In some embodiments, $X_{20}$ is K. In some embodiments, $X_{20}$ is K covalently bound to a protecting group. In some embodiments, $X_{20}$ is K covalently bound to a spacer optionally bound to a protecting group. In some embodiments, $X_{20}$ is k. In some embodiments, $X_{20}$ is k covalently bound to a protecting group. In some embodiments, $X_{20}$ is k covalently bound to a spacer optionally bound to a protecting group. In some embodiments, $X_{20}$ is Dap.

In some embodiments, $X_{22}$ is A. In some embodiments, $X_{22}$ is D. In some embodiments, $X_{22}$ is K. In some embodiments, $X_{22}$ is L.

In some embodiments, $X_{23}$ is K. In some embodiments, $X_{23}$ is K covalently bound to a protecting group. In some embodiments, $X_{23}$ is K covalently bound to a spacer optionally bound to a protecting group. In some embodiments, $X_{23}$ is R.

In some embodiments, $X_{25}$ is K. In some embodiments, $X_{25}$ is K covalently bound to a protecting group. In some embodiments, $X_{25}$ is K covalently bound to a spacer optionally bound to a protecting group. In some embodiments, $X_{25}$ is Y.

In some embodiments, $X_{26}$ is E. In some embodiments, $X_{26}$ is K. In some embodiments, $X_{26}$ is L.

In some embodiments, $X_{27}$ is K. In some embodiments, $X_{27}$ is K covalently bound to a protecting group. In some embodiments, $X_{27}$ is K covalently bound to a spacer optionally bound to a protecting group. In some embodiments, $X_{27}$ is N.

In some embodiments, $X_{32}$ is K. In some embodiments, $X_{32}$ is K covalently bound to a protecting group. In some embodiments, $X_{32}$ is K covalently bound to a spacer optionally bound to a protecting group. In some embodiments, $X_{32}$ is Q.

In some embodiments, $X_{34}$ is F. In some embodiments, $X_{34}$ is y. In some embodiments, $X_{34}$ is 3-pyridinylalanine. In some embodiments, $X_{34}$ is 4-pyridinylalanine. In some embodiments, $X_{34}$ is 4-carboxyphenylalanine. In some embodiments, $X_{34}$ is 4-fluorophenylalanine. In some embodiments, $X_{34}$ is 4-methylphenylalanine. In some embodiments, $X_{34}$ is N-methylphenylalanine. In some embodiments, $X_{34}$ is homophenylalanine. In some embodiments, $X_{34}$ is β-homotyrosine. In some embodiments, $X_{34}$ is homotyrosine. In some embodiments, $X_{34}$ is N-methyltyrosine.

In some embodiments, a polypeptide intermediate of the disclosure is an isolated polypeptide comprising the amino acid sequence of SEQ ID NO: SEQ ID NO: 394:
PKPEX$_5$PGX$_8$DASPX$_{13}$EWX$_{15}$RYYX$_{20}$DX$_{22}$RHY-LNWLTRQRX$_{34}$—(OH/NH$_2$) (SEQ ID NO: 394), or a pharmaceutically acceptable salt thereof, wherein:
$X_5$ is A or K;
$X_8$ is E, K, or k;
$X_{13}$ is E or K;
$X_{15}$ is D, E, K, or N;
$X_{20}$ is A, D, E, K, or k,
$X_{22}$ is A or L;
$X_{34}$ is F or N-methyltyrosine;
wherein when $X_5$, $X_8$, $X_{13}$, or $X_{20}$ are K, the lysine residue is optionally covalently bound to a protecting group or to a spacer optionally bound to a protecting group, and
wherein when $X_8$ or $X_{20}$ are k, the D-lysine residue is optionally covalently bound to a protecting group or to a spacer optionally bound to a protecting group.

In some embodiment, when $X_{16}$ is N, $X_{20}$ is not A.

In some embodiments, when $X_8$ is E, $X_5$ is K and $X_{20}$ is K.

In some embodiments, $X_8$ is K. In some embodiments, $X_8$ is K covalently bound to a protecting group. In some embodiments, $X_8$ is K covalently bound to a spacer optionally bound to a protecting group.

In some embodiments, $X_{34}$ is F.

In some embodiments, $X_5$ is A. In some embodiments, $X_5$ is K. In some embodiments, $X_5$ is K covalently bound to a protecting group. In some embodiments, $X_5$ is K covalently bound to a spacer optionally bound to a protecting group.

In some embodiments, $X_5$ is E. In some embodiments, $X_5$ is K. In some embodiments, $X_8$ is K covalently bound to a protecting group. In some embodiments, $X_8$ is K covalently bound to a spacer optionally bound to a protecting group. In some embodiments, $X_8$ is k. In some embodiments, $X_5$ is k covalently bound to a protecting group. In some embodiments, $X_5$ is k covalently bound to a spacer optionally bound to a protecting group.

In some embodiments, $X_{13}$ is E. In some embodiments, $X_{13}$ is K. In some embodiments, $X_{13}$ is K covalently bound to a protecting group. In some embodiments, $X_{13}$ is K covalently bound to a spacer optionally bound to a protecting group.

In some embodiments, $X_{15}$ is D. In some embodiments, $X_{15}$ is E. In some embodiments, $X_{16}$ is K. In some embodiments, $X_{16}$ is N.

In some embodiments, $X_{20}$ is A. In some embodiments, $X_{20}$ is D. In some embodiments, $X_{20}$ is E. In some embodiments, $X_{20}$ is K. In some embodiments, $X_{20}$ is K covalently bound to a protecting group. In some embodiments, $X_{20}$ is K covalently bound to a spacer optionally bound to a protecting group. In some embodiments, $X_{20}$ is k. In some embodiments, $X_{20}$ is k covalently bound to a protecting group. In some embodiments, $X_{20}$ is k covalently bound to a spacer optionally bound to a protecting group.

In some embodiments, $X_{22}$ is A. In some embodiments, $X_{22}$ is L.

In some embodiments, $X_{34}$ is F. In some embodiments, $X_{34}$ is N-methyltyrosine.

In some embodiments, an isolated polypeptide of the disclosure comprises an amino acid sequence selected form the group consisting of the following peptides listed in Tables 9, 10, 11, and 12.

TABLE 9

Exemplary polypeptide intermediates of SEQ ID NOs: 24, 42, and 43.

Intermediate to A24 (SEQ ID NO: 24):

P-K-P-E-A-P-G-[Lys(Alloc)]-D-A-S-P-E-E-W-D-R-Y-Y-K-D-L-R-H-Y-L-N-W-L-T-R-Q-R-F-NH$_2$

SEQ ID NO: 524 (F24)

Intermediate to A42 (SEQ ID NO: 42):

TABLE 9-continued
Exemplary polypeptide intermediates of SEQ ID NOs: 24, 42, and 43.
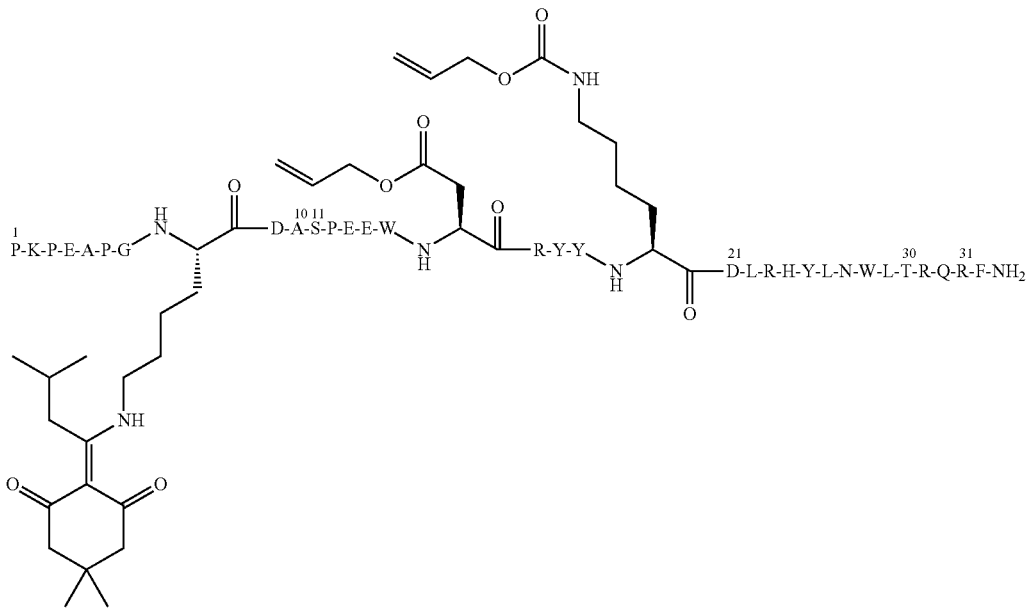
SEQ ID NO: 742 (H42)
Intermediate to A43 (SEQ ID NO: 43)
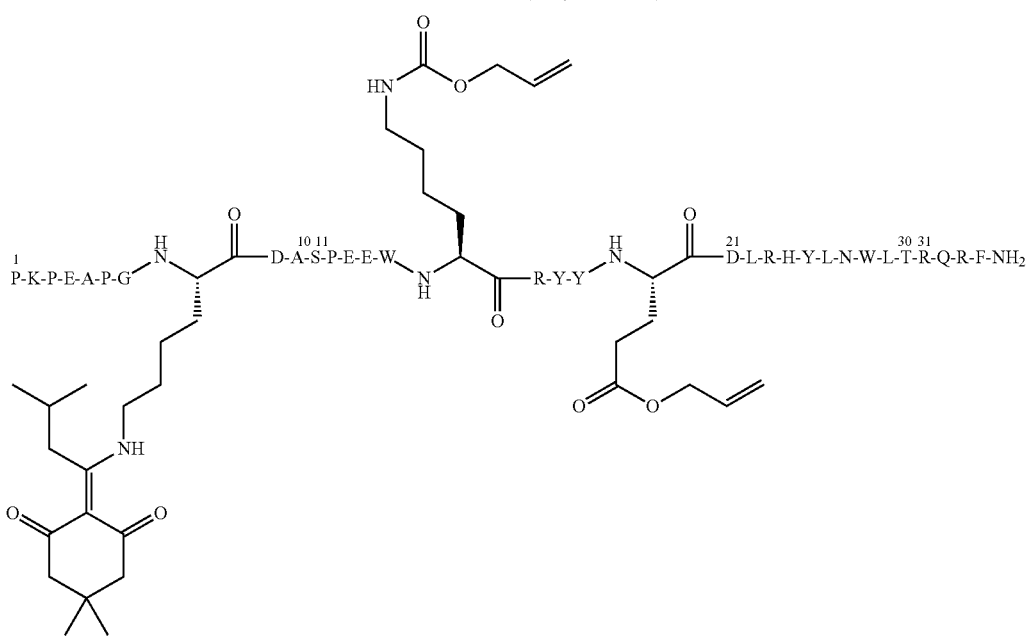
SEQ ID NO: 743 (H43)

TABLE 10

Compound A24 and exemplary polypeptide intermediates thereof

| Compound No. | Sequence | SEQ ID NO: |
|---|---|---|
| A24 | PKPEAPGK(γGlu-γGlu-CO(CH$_2$)$_{18}$CO$_2$H)DASPEEWDRYYKDLRHYLNWLTRQRF-(NH$_2$) | SEQ ID NO: 24 |
| D24 | PKPEAPGK(γGlu-γGlu)DASPEEWDRYYKDLRHYLNWLTRQRF-(NH$_2$) | SEQ ID NO: 324 |
| E24 | PKPEAPGK(γGlu)DASPEEWDRYYKDLRHYLNWLTRQRF-(NH$_2$) | SEQ ID NO: 424 |
| B24 | PKPEAPGKDASPEEWDRYYKDLRHYLNWLTRQRF-(NH$_2$) | SEQ ID NO: 124 |
| F24 | PKPEAPGK(alloc)DASPEEWDRYYKDLRHYLNWLTRQRF-(NH$_2$) | SEQ ID NO: 524 |

Notes:
alloc = allyloxycarbonyl protecting group

In some embodiments, the present invention provides a peptide intermediate of Compound A24 (SEQ ID NO: 24). In some embodiments, the peptide intermediate of Compound A24 comprises at least one amino acid covalently bound to a protecting group. In some embodiments, the peptide intermediate of Compound A24 comprises a lysine residue bound to a protecting group via the amino group of its sidechain. In some embodiments, the lysine residue is covalently bound to a Alloc or ivDde. In some embodiments, the peptide intermediate of Compound A24 comprises an aspartic acid residue bound to a protecting group via the carboxyl group of its sidechain. In some embodiments, the aspartic acid residue is covalently bound to an allyl group. In some embodiments, the peptide intermediate of Compound A24 comprises a glutamic acid residue bound to a protecting group via the carboxyl group of its sidechain. In some embodiments, the glutamic acid residue is covalently bound to an allyl group. In some embodiments, the peptide intermediate of Compound A24 comprises at least one amino acid covalently bound to a spacer as defined herein, wherein the spacer is further covalently bound to a protecting group or a hydrogen atom. In some embodiments, the present invention provides a peptide intermediate set forth in the Table 10, above. In some embodiments, the peptide intermediate is a peptide having the amino acid sequence of SEQ ID NO: 324. In some embodiments, the peptide intermediate is a peptide having the amino acid sequence of SEQ ID NO: 424. In some embodiments, the peptide intermediate is a peptide having the amino acid sequence of SEQ ID NO: 124. In some embodiments, the peptide intermediate is a peptide having the amino acid sequence of SEQ ID NO: 524.

In some embodiments, the present invention provides a method for preparing compounds of the invention, such as Compound A24 (SEQ ID NO: 24), comprising the step of acylating a polypeptide intermediates, such as Compound D24 (SEQ ID NO: 324), with the following activated acyl group, (LG)CO(CH$_2$)$_{zz}$CO$_2$H, wherein ZZ is from 14 to 22 and LG is a leaving group, as defined herein, as exemplified below in Scheme 1:

Scheme 1

PKPEAPGK(γGlu-γGlu)DASPEEWDRYYKDLRHYLNWLTRQRF-(NH$_2$)
(D24; SEQ ID NO: 324)

solid-phase peptide synthesis (SPPS) conditions"

(LG)CO(CH$_2$)$_{18}$CO$_2$H

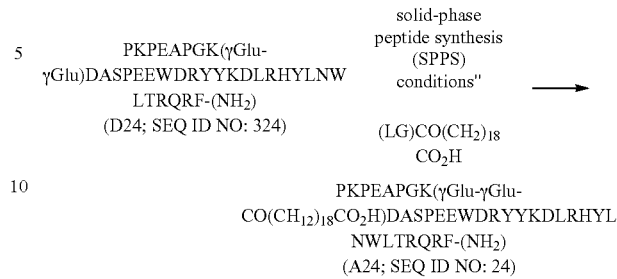

PKPEAPGK(γGlu-γGlu-CO(CH$_{12}$)$_{18}$CO$_2$H)DASPEEWDRYYKDLRHYLNWLTRQRF-(NH$_2$)
(A24; SEQ ID NO: 24)

TABLE 11

Compound A42 and exemplary polypeptide intermediates thereof.

| Compound No. | Sequence | SEQ ID NO: |
|---|---|---|
| A42 | PKPEAPGK(γGlu-γGlu-CO(CH$_2$)$_{18}$CO$_2$H)DASPEEWD*RYYK*DLRHYLNWLTRQRF-(NH$_2$) | SEQ ID NO: 42 |
| D42 | PKPEAPGK(γGlu-γGlu)DASPEEWD*RYYK*DLRHYLNWLTRQRF-(NH$_2$) | SEQ ID NO: 342 |
| E42 | PKPEAPGK(γGlu)DASPEEWD*RYYK*DLRHYLNWLTRQRF-(NH$_2$) | SEQ ID NO: 442 |
| C42 | PKPEAPGKDASPEEWD*RYYK*DLRHYLNWLTRQRF-(NH$_2$) | SEQ ID NO: 242 |
| F42 | PKPEAPGK(ivDde)DASPEEWD*RYYK*DLRHYLNWLTRQRF-(NH$_2$) | SEQ ID NO: 542 |
| G42 | PKPEAPGK(ivDde)DASPEEWDRYYKDLRHYLNWLTRQRF-(NH$_2$) | SEQ ID NO: 642 |
| H42 | PKPEAPGK(ivDde)DASPEEWD(allyl)RYYK(alloc)DLRHYLNWLTRQRF-(NH$_2$) | SEQ ID NO: 742 |

Notes:
Each pairing of K* and D* represents a covalent amide linkage derived from the amino sidechain of K* and the carboxy sidechain of D* (with loss of a water molecule).
alloc = allyloxycarbonyl protecting group
allyl = allyl (CH$_2$=CH-CH$_2$-) protecting group
ivDde = 1-(4,4-dimethyl-2,6-dioxocyclohex-1-ylidene)-3-methylbutyl protecting group In some embodiments, the present invention provides a peptide intermediate of Compound A42 (SEQ ID NO: 42). In some embodiments, the peptide intermediate of Compound A42 comprises at least one amino acid covalently bound to a protecting group. In some embodiments, the peptide intermediate of Compound A42 comprises a lysine residue bound to a protecting group via the amino group of its sidechain. In some embodiments, the lysine residue is covalently bound to a Alloc or ivDde. In some embodiments, the peptide intermediate of Compound A42 comprises an aspartic acid residue bound to a protecting group via the carboxyl group of its sidechain. In some embodiments, the aspartic acid residue is covalently bound to an allyl group. In some embodiments, the peptide intermediate of Compound A42 comprises a glutamic acid residue bound to a protecting group via the carboxyl group of its sidechain. In some embodiments, the glutamic acid residue is covalently bound to an allyl group. In some embodiments, the peptide intermediate of Compound A42 comprises at least one amino acid covalently bound to a spacer as defined herein, wherein the spacer is further covalently bound to a protecting group or a hydrogen atom. In some embodiments, the present invention provides a peptide intermediate set forth in the Table 11, above. In some embodiments, the peptide intermediate is a peptide having the amino acid sequence of SEQ ID NO: 342. In some embodiments, the peptide intermediate is a peptide having the amino acid sequence of SEQ ID NO: 442. In some embodiments, the peptide intermediate is a peptide having the amino acid sequence of SEQ ID NO: 242. In some embodiments, the peptide intermediate is a peptide having the amino acid sequence of SEQ ID NO: 542. In some embodiments, the peptide intermediate is a peptide having the amino acid sequence of SEQ ID NO: 642. In some embodiments, the peptide intermediate is a peptide having the amino acid sequence of SEQ ID NO: 742.

In some embodiments, the present invention provides a method for preparing compounds of the invention, such as Compound A42 (SEQ ID NO: 42), comprising the step of acylating a polypeptide intermediates, such as Compound D42 (SEQ ID NO: 342), with the following activated acyl group, $(LG)CO(CH_2)_{zz}CO_2H$, wherein ZZ is from 14 to 22 and LG is a leaving group, as defined herein, as exemplified below in Scheme 2:

Scheme 2

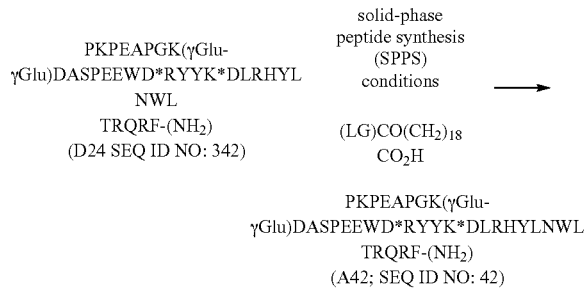

TABLE 12

Compound A43 and exemplary polypeptide intermediates thereof.

| Compound No. | Sequence | SEQ ID NO: |
|---|---|---|
| A43 | PKPEAPGK(γGlu-γGlu-CO(CH$_2$)$_{18}$CO$_2$H)DASPEEWK*RYYE*DLRHYLNWLTRQRF-(NH$_2$) | SEQ ID NO: 43 |
| D43 | PKPEAPGK(γGlu-γGlu)DASPEEWK*RYYE*DLRHYLNWLTRQRF-(NH$_2$) | SEQ ID NO: 343 |
| E43 | PKPEAPGK(γGlu)DASPEEWK*RYYE*DLRHYLNWLTRQRF-(NH$_2$) | SEQ ID NO: 443 |
| C43 | PKPEAPGKDASPEEWK*RYYE*DLRHYLNWLTRQRF-(NH$_2$) | SEQ ID NO: 243 |
| F43 | PKPEAPGK(ivDde)DASPEEWK*RYYE*DLRHYLNWLTRQRF-(NH$_2$) | SEQ ID NO: 543 |
| G43 | PKPEAPGK(ivDde)DASPEEWKRYYEDLRHYLNWLTRQRF-(NH$_2$) | SEQ ID NO: 643 |

TABLE 12-continued

Compound A43 and exemplary polypeptide intermediates thereof.

| Compound No. | Sequence | SEQ ID NO: |
|---|---|---|
| H43 | PKPEAPGK(ivDde)DASPEEWK(alloc)RYYE(allyl)DLRHYLNWLTRQRF-(NH$_2$) | SEQ ID NO: 743 |

Notes:
Each pairing of K* and E* represents a covalent amide linkage derived from the amino sidechain of K* and the carboxy sidechain of E* (with loss of a water molecule).
alloc = allyloxycarbonyl protecting group
allyl = allyl (CH$_2$=CH–CH$_2$–) protecting group
ivDde = 1-(4,4-dimethyl-2,6-dioxocyclohex-1-ylidene)-3-methylbutyl protecting group In some embodiments, the present invention provides a peptide intermediate of Compound A43 (SEQ ID NO: 43). In some embodiments, the peptide intermediate of Compound A43 comprises at least one amino acid covalently bound to a protecting group. In some embodiments, the peptide intermediate of Compound A43 comprises a lysine residue bound to a protecting group via the amino group of its sidechain. In some embodiments, the lysine residue is covalently bound to a Alloc or ivDde. In some embodiments, the peptide intermediate of Compound A43 comprises an aspartic acid residue bound to a protecting group via the carboxyl group of its sidechain. In some embodiments, the aspartic acid residue is covalently bound to an allyl group. In some embodiments, the peptide intermediate of Compound A43 comprises a glutamic acid residue bound to a protecting group via the carboxyl group of its sidechain. In some embodiments, the glutamic acid residue is covalently bound to an allyl group. In some embodiments, the peptide intermediate of Compound A43 comprises at least one amino acid covalently bound to a spacer as defined herein, wherein the spacer is further covalently bound to a protecting group or a hydrogen atom. In some embodiments, the present invention provides a peptide intermediate set forth in the Table 12, above. In some embodiments, the peptide intermediate is a peptide having the amino acid sequence of SEQ ID NO: 343. In some embodiments, the peptide intermediate is a peptide having the amino acid sequence of SEQ ID NO: 443. In some embodiments, the peptide intermediate is a peptide having the amino acid sequence of SEQ ID NO: 243. In some embodiments, the peptide intermediate is a peptide having the amino acid sequence of SEQ ID NO: 543. In some embodiments, the peptide intermediate is a peptide having the amino acid sequence of SEQ ID NO: 643. In some embodiments, the peptide intermediate is a peptide having the amino acid sequence of SEQ ID NO: 743.

In some embodiments, the present invention provides a method for preparing compounds of the invention, such as Compound A43 (SEQ ID NO: 43), comprising the step of acylating a polypeptide intermediates, such as Compound D43 (SEQ ID NO: 343), with the following activated acyl group, $(LG)CO(CH_2)_{zz}CO_2H$, wherein ZZ is from 14 to 22 and LG is a leaving group, as defined herein, as exemplified below in Scheme 3:

Scheme 3

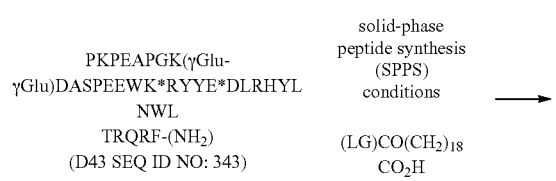

-continued

PKPEAPGK(γGlu-
γGlu)DASPEEWK*RYYE*DLRHYLNWL
TRQRF-(NH₂)
(A43; SEQ ID NO: 43)

Methods of Use

According to another embodiment, the invention relates to a method of treating metabolic disease or disorder in a subject in need of treatment, comprising providing the subject with an effective amount of a PYY analog polypeptide of the disclosure or a pharmaceutical composition thereof. Metabolic diseases or disorders include type 1 diabetes, type 2 diabetes, and obesity. Additionally, the invention relates to a method of effecting weight loss in a subject, including a diabetic subject, comprising providing the subject with an effective amount of a PYY analog polypeptide of the disclosure. In certain embodiments, the invention also relates to methods of treating nonalcoholic fatty liver disease (NAFLD) and/or nonalcoholic steatohepatitis (NASH).

In some embodiments, provided is a method of treating obesity in a human subject, providing weight loss to the human subject, or suppressing appetite in the human subject, comprising administering to the subject any of the polypeptides disclosed herein, a pharmaceutical composition comprising any of the disclosed polypeptides, or an osmotic delivery device comprising any of the disclosed polypeptides.

In some embodiments, provided is a method of treating diabetes in a human subject, comprising administering to the subject any of the polypeptides disclosed herein, a pharmaceutical composition comprising any of the disclosed polypeptides, or an osmotic delivery device comprising any of the disclosed polypeptides. In some embodiments, the diabetes is type 1 diabetes. In some embodiments, the diabetes is type 2 diabetes.

In some embodiments, provided is a method of treating nonalcoholic fatty liver disease (NAFLD) in a human subject, comprising administering to the subject any of the polypeptides disclosed herein, a pharmaceutical composition comprising any of the disclosed polypeptides, or an osmotic delivery device comprising any of the disclosed polypeptides.

In some embodiments, provided is a method of treating nonalcoholic steatohepatitis (NASH) in a human subject, comprising administering to the subject any of the polypeptides disclosed herein, a pharmaceutical composition comprising any of the disclosed polypeptides, or an osmotic delivery device comprising any of the disclosed polypeptides.

PYY analog polypeptides of the disclosure are particularly useful for the treatment of diabetes, the method comprising providing a diabetic subject with an effective amount of a PYY analog polypeptide. In some embodiments, a PYY analog polypeptide of the disclosure is used for the treatment of a subject with type 1 or type 2 diabetes to control, or reduce, concentrations of blood sugar in the subject, where blood sugar levels can be monitored or approximated based on measured blood concentrations of glycated hemoglobin (hemoglobin A1c, HbA1c).

(i) In some embodiments, a PYY analog polypeptide of the disclosure is used for the treatment of a subject with type 1 diabetes;

(ii) In some embodiments, a PYY analog polypeptide of the disclosure is used for the treatment of a subject with type 2 diabetes;

(iii) In some embodiments, a PYY analog polypeptide of the disclosure is used for the treatment of obesity; and (iv) In some embodiments, a PYY analog polypeptide of the disclosure is used to provide weight loss to a subject, such as a diabetic subject, (v) In some embodiments, a PYY analog polypeptide of the disclosure is used for the treatment of nonalcoholic fatty liver disease (NAFLD), (vi) In some embodiments, a PYY analog polypeptide of the disclosure is used for the treatment of nonalcoholic steatohepatitis (NASH), wherein the PYY analog polypeptide of usage (i), (ii), (iii), (iv), (v) or (vi) comprises any isolated polypeptide of this disclosure including those represented by any of the consensus sequences of SEQ ID NO: 1 through SEQ ID NO: 78, or a pharmaceutically acceptable salt thereof.

In some embodiments, the PYY analog polypeptide of usage (i), (ii), (iii), (iv), (v) or (vi) comprises any isolated polypeptide of this disclosure including those selected from the group consisting of SEQ ID NOs: 13, 24, 42 and 43 or a pharmaceutically acceptable salt thereof.

In some embodiments, the PYY analog polypeptide of usage (i), (ii), (iii), (iv), (v) or (vi) comprises the isolated polypeptide of SEQ ID NO: 13 or a pharmaceutically acceptable salt thereof. In some embodiments, the PYY analog polypeptide of usage (i), (ii), (iii), (iv), (v) or (vi) comprises the isolated polypeptide of SEQ ID NO: 24 or a pharmaceutically acceptable salt thereof. In some embodiments, the PYY analog polypeptide of usage (i), (ii), (iii), (iv), (v) or (vi) comprises the isolated polypeptide of SEQ ID NO: 42 or a pharmaceutically acceptable salt thereof. In some embodiments, the PYY analog polypeptide of usage (i), (ii), (iii), (iv), (v) or (vi) comprises the isolated polypeptide of SEQ ID NO: 43 or a pharmaceutically acceptable salt thereof.

In some embodiments, the PYY analog polypeptide is used for the treatment of a subject with type 1 diabetes wherein the isolated polypeptide is of SEQ ID NO: 13 or a pharmaceutically acceptable salt thereof. In some embodiments, the PYY analog polypeptide is used for the treatment of a subject with type 1 diabetes wherein the isolated polypeptide is of SEQ ID NO: 24 or a pharmaceutically acceptable salt thereof. In some embodiments, the PYY analog polypeptide is used for the treatment of a subject with type 1 diabetes wherein the isolated polypeptide is of SEQ ID NO: 42 or a pharmaceutically acceptable salt thereof. In some embodiments, the PYY analog polypeptide is used for the treatment of a subject with type 1 diabetes wherein the isolated polypeptide is of SEQ ID NO: 43 or a pharmaceutically acceptable salt thereof.

In some embodiments, the PYY analog polypeptide is used for the treatment of a subject with type 2 diabetes wherein the isolated polypeptide is of SEQ ID NO: 13 or a pharmaceutically acceptable salt thereof. In some embodiments, the PYY analog polypeptide is used for the treatment of a subject with type 2 diabetes wherein the isolated polypeptide is of SEQ ID NO: 24 or a pharmaceutically acceptable salt thereof. In some embodiments, the PYY analog polypeptide is used for the treatment of a subject with type 2 diabetes wherein the isolated polypeptide is of SEQ ID NO: 42 or a pharmaceutically acceptable salt thereof. In some embodiments, the PYY analog polypeptide is used for the treatment of a subject with type 2 diabetes wherein the isolated polypeptide is of SEQ ID NO: 43 or a pharmaceutically acceptable salt thereof.

In some embodiments, the PYY analog polypeptide is used for the treatment of a subject with obesity wherein the isolated polypeptide is of SEQ ID NO: 13 or a pharmaceutically acceptable salt thereof. In some embodiments, the PYY analog polypeptide is used for the treatment of a subject with obesity wherein the isolated polypeptide is of SEQ ID NO: 24 or a pharmaceutically acceptable salt thereof. In some embodiments, the PYY analog polypeptide is used for the treatment of a subject with obesity wherein the isolated polypeptide is of SEQ ID NO: 42 or a pharmaceutically acceptable salt thereof. In some embodiments, the PYY analog polypeptide is used for the treatment of a subject with obesity wherein the isolated polypeptide is of SEQ ID NO: 43 or a pharmaceutically acceptable salt thereof.

In some embodiments, the PYY analog polypeptide is used to provide weight loss to a subject wherein the isolated polypeptide is of SEQ ID NO: 13 or a pharmaceutically acceptable salt thereof. In some embodiments, the PYY analog polypeptide is used to provide weight loss to a subject wherein the isolated polypeptide is of SEQ ID NO: 23 or a pharmaceutically acceptable salt thereof. In some embodiments, the PYY analog polypeptide is used to provide weight loss to a subject wherein the isolated polypeptide is of SEQ ID NO: 42 or a pharmaceutically acceptable salt thereof. In some embodiments, the PYY analog polypeptide is used to provide weight loss to a subject wherein the isolated polypeptide is of SEQ ID NO: 43 or a pharmaceutically acceptable salt thereof.

In some embodiments, the PYY analog polypeptide is used for the treatment of a subject with NAFLD wherein the isolated polypeptide is of SEQ ID NO: 13 or a pharmaceutically acceptable salt thereof. In some embodiments, the PYY analog polypeptide is used for the treatment of a subject with NAFLD wherein the isolated polypeptide is of SEQ ID NO: 24 or a pharmaceutically acceptable salt thereof. In some embodiments, the PYY analog polypeptide is used for the treatment of a subject with NAFLD wherein the isolated polypeptide is of SEQ ID NO: 42 or a pharmaceutically acceptable salt thereof. In some embodiments, the PYY analog polypeptide is used for the treatment of a subject with NAFLD wherein the isolated polypeptide is of SEQ ID NO: 43 or a pharmaceutically acceptable salt thereof.

In some embodiments, the PYY analog polypeptide is used for the treatment of a subject with NASH wherein the isolated polypeptide is of SEQ ID NO: 13 or a pharmaceutically acceptable salt thereof. In some embodiments, the PYY analog polypeptide is used for the treatment of a subject with NASH wherein the isolated polypeptide is of SEQ ID NO: 24 or a pharmaceutically acceptable salt thereof. In some embodiments, the PYY analog polypeptide is used for the treatment of a subject with NASH wherein the isolated polypeptide is of SEQ ID NO: 42 or a pharmaceutically acceptable salt thereof. In some embodiments, the PYY analog polypeptide is used for the treatment of a subject with NASH wherein the isolated polypeptide is of SEQ ID NO: 43 or a pharmaceutically acceptable salt thereof.

Certain PYY analog polypeptides of the disclosure, while capable of eliciting anorectic and weight-loss effects when administered in combination with a GLP-1 receptor agonist, can induce dose-dependent orexigenic and weight-gain effects when administered alone. This property of select PYY analog polypeptides of the disclosure is useful in the treatment of a variety of wasting disorders. Accordingly, in some embodiments, a PYY analog polypeptide of the disclosure is used for the treatment of anorexia nervosa, sarcopenia, frailty, cachexia, and the like. In some embodiments, the PYY analog is SEQ ID NO: 13. In some embodiments, the PYY analog is SEQ ID NO: 24.

The terms "patient" or "subject" as used herein, refer to a rodent or an animal, preferably a mammal, and most preferably a human.

Combinations

In some embodiments, a PYY analog polypeptide of the disclosure is co-formulated in combination with a second agent. In some embodiments, a PYY analog polypeptide of the disclosure is co-formulated in combination with a second agent, wherein the second agent is an incretin mimetic. In some embodiments, a PYY analog polypeptide of the disclosure is co-formulated in combination with a second agent, wherein the second agent is an insulinotropic compound.

The phrase "incretin mimetics" as used herein includes, but is not limited to GLP-1 peptide; GLP-1 (7-36); GLP-1 receptor agonists; peptide derivatives of GLP-1; peptide analogs of GLP-1; exenatide; exenatide having the amino acid sequence of exendin-4 (the naturally-occurring form of exenatide; exenatide-LAR; lixisenatide; liraglutide; semaglutide; dulaglutide; albiglutide; taspoglutide; tirzepatide (Eli Lilly's LY3298176 or Y-(Aib)-EGTFTSDYSI-(Aib)-LDKIAQ-[diacid-gamma-Glu-(AEEA)$_2$-Lys]-AF-VQWLIAGGPSSGAPPPS-NH2) SEQ ID NO: 805); glucagon as well as peptide analogs and peptide derivatives thereof; glucagon like polypeptide-2 (GLP-2); PYY as well as peptide analogs and peptide derivatives thereof; PYY(3-36); oxyntomodulin as well as peptide analogs and peptide derivatives thereof); amylin as well as peptide analogs and peptide derivatives thereof; and gastric inhibitory peptide (GIP). Incretin mimetics are also referred to herein as "insulinotropic peptides." Incretin mimetics which target the GLP-1 receptor are also known in the literature as "GLP-1 receptor agonists" or "GLP-1 agonists," with both terms being used interchangeably herein.

Some embodiments of the present invention comprise use of a disclosed PYY analog polypeptide of the present invention in combination with a second therapeutic agent, such as a second polypeptide, such as, by way of, non-limiting example, insulinotropic peptides. In some embodiments, a pharmaceutical composition comprising a PYY analog polypeptide in combination with a second agent is used to treat type 2 diabetes.

In some embodiments, provided is a pharmaceutical composition comprising any of the isolated polypeptides as disclosed herein. In some embodiments, provided is a pharmaceutical composition comprising any of the isolated polypeptides as disclosed herein and further comprising a second polypeptide. In some embodiments, the second polypeptide is a glucagon analog. In some embodiments, the second polypeptide is an amylin analog. In a preferred embodiment, the second polypeptide is a GLP-1 receptor agonist.

The term "GLP-1" refers to a polypeptide, glucagon-like peptide-1(7-36)amide, a 30-residue peptide hormone released from intestinal L cells following nutrient consumption. GLP-1 has the amino acid sequence of (HAEGTFTSDVSSYLEGQAAKEFIAWLVKGR-NH$_2$), SEQ ID NO: 801. GLP-1 is a regulatory peptide that binds to the extracellular region of the GLP-1 receptor (GLP-1R), a G-coupled protein receptor on β cell and via adenyl cyclase activity and production of cAMP stimulates the insulin response to the nutrients that are absorbed from the gut

[Baggio 2007, "Biology of incretins: GLP-1 and GIP," Gastroenterology, vol. 132(6):2131-57; Holst 2008, "The incretin system and its role in type 2 diabetes mellitus," Mol Cell Endocrinology, vol. 297(1-2):127-36]. The effects of GLP-1R agonism are multiple. GLP-1 maintains glucose homeostasis by enhancing endogenous glucose dependent insulin secretion, rendering the R cells glucose competent and sensitive to GLP-1, suppressing glucagon release, restoring first and second phase insulin secretion, slowing gastric emptying, decreasing food intake, and increasing satiety [Holst 2008 Mol. Cell Endocrinology; Kjems 2003 "The influence of GLP-1 on glucose-stimulated insulin secretion: effects on beta-cell sensitivity in type 2 and nondiabetic subjects," Diabetes, vol. 52(2): 380-86; Holst 2013 "Incretin hormones and the satiation signal," Int J Obes (Lond), vol. 37(9):1161-69; Seufert 2014, "The extra-pancreatic effects of GLP-1 receptor agonists: a focus on the cardiovascular, gastrointestinal and central nervous systems," Diabetes Obes Metab, vol. 16(8): 673-88]. The risk of hypoglycemia is minimal given the mode of action of GLP-1. Glucagon-like peptide-1(7-36)amide (GLP-1) is a 30-residue peptide hormone released from intestinal L cells following nutrient consumption. It potentiates the glucose-induced secretion of insulin from pancreatic beta cells, increases insulin expression, inhibits beta-cell apoptosis, promotes beta-cell neogenesis, reduces glucagon secretion, delays gastric emptying, promotes satiety and increases peripheral glucose disposal. These multiple effects have generated a great deal of interest in the discovery of long-lasting agonists of the GLP-1 receptor (GLP-1R) in order to treat type 2 diabetes. The term "exenatide" as used herein includes, but is not limited to exenatide, exenatide having the amino acid sequence of (HGEGTFTSDLSKQMEEE-AVRLFIEWLKNGGPSSGAPPPS-$NH_2$), SEQ ID NO: 802, native exendin-4, exenatide peptides, exenatide peptide analogs, and exenatide peptide derivatives.

Endogenous GLP-1 is released from the gut in response to nutrient ingestion. Following food intake and digestion, carbohydrates and fats appear in the lumen of the gut, which stimulate a so-called incretin effect, the release of incretins such as GLP-1 from intestinal L-cells. GLP-1, once released, targets the pancreas where it enhances secretion of insulin in a "glucose dependent manner." In other words, this GLP-1-mediated effect upon insulin persists when glucose levels are high yet safely dissipates as glucose levels fall. GLP-1 activity thus self-regulates to reduce the risk of hypoglycemia (the condition by which glucose levels drop dangerously low). Since GLP-1 has a short elimination half-life ($t_{1/2}$) of less than five minutes, this endogenous peptide is unsuitably short-lived for use as a therapeutic.

Synthetic analogs of GLP-1 have been designed to have longer half-lives and similarly enhance secretion of insulin in a glucose dependent manner like endogenous GLP-1, for use in the treatment of type 2 diabetes and for providing weight loss.

Numerous GLP-1 receptor agonists (e.g., GLP-1 peptide derivatives and peptide analogs) demonstrating insulinotropic action are known in the art (see, e.g., U.S. Pat. Nos. 5,118,666; 5,120,712; 5,512,549; 5,545,618; 5,574,008; 5,574,008; 5,614,492; 5,958,909; 6,191,102; 6,268,343; 6,329,336; 6,451,974; 6,458,924; 6,514,500; 6,593,295; 6,703,359; 6,706,689; 6,720,407; 6,821,949; 6,849,708; 6,849,714; 6,887,470; 6,887,849; 6,903,186; 7,022,674; 7,041,646; 7,084,243; 7,101,843; 7,138,486; 7,141,547; 7,144,863; and 7,199,217), as well as in clinical trials (e.g., taspoglutide and albiglutide).

Certain GLP-1 receptor agonists, including Bydureon® (exenatide), marketed by AstraZeneca of Cambridge, U.K.; Trulicity® (dulaglutide), marketed by Eli Lilly and Co., of Indianapolis, IN, U.S.A.; and Victoza® (liraglutide), Ozempic® (injectable semaglutide) & Rybelsus® (orally administered semaglutide), marketed by Novo Nordisk A/S of Bagsvord, Denmark, have each been approved by numerous regulatory authorities, including the United States Food and Drug Administration (U.S. FDA) and European Medicines Agency (EMA) for the treatment of patients suffering from type 2 diabetes. These marketed GLP-1 receptor agonists were developed and formulated for injectable and/or oral administration to patients. However, patient adherence to injectable and orally administered therapies for type 2 diabetes is notoriously poor which prohibits many patients from realizing a full and lasting therapeutic potential of GLP-1 receptor agonists. Many patients skip or cease periodic self-administrations of prescribed injectable and orally administered GLP-1 receptor agonists and thus fail to adequately treat and control their own type 2 diabetic condition.

The PYY analog polypeptides of the disclosure in combination with a GLP-1 receptor agonist have been found to deliver bariatric surgery-like efficacy for weight loss. The observation that improved glycemic control following Roux-en-Y gastric bypass surgery (RYGB) in obese or obese T2D patients precedes the weight loss seen following RYGB, suggests that surgical rearrangement of the gut leads to physiological adaptations beyond those driven by weight loss alone. Indeed, RYGB leads to enhanced post-prandial secretion of GLP-1 and PYY, both of which are released from L-cells lining the distal gut. The gut peptide hormones GLP-1 and peptide tyrosine-tyrosine (PYY) each play a role in whole body energy balance through several overlapping biological responses to energy input. These responses principally include potentiation of glucose-induced insulin secretion, inhibition of gastric emptying, inducing satiety, and inhibition of food intake.

Accordingly, combinations of a PYY analog polypeptide of the disclosure together with a GLP-1 receptor agonist are suitable for the treatment of the diseases and disorders disclosed herein. In some embodiments, the GLP-1 receptor agonist is a long acting GLP-1 receptor agonist.

Oxyntomodulin is a naturally occurring 37 amino acid peptide hormone found in the colon that has been found to suppress appetite and facilitate weight loss (Wynne K, et al., Int J Obes (Lond) 30(12):1729-36(2006)). The sequence of oxyntomodulin, as well as peptide analogs and peptide derivatives thereof, are known in the art (e.g., Bataille D, et al., Peptides 2(Suppl 2):41-44 (1981); and U.S. Patent Publication Nos. 2005/0070469 and 2006/0094652).

Gastric Inhibitory Peptide (GIP) is an insulinotropic peptide hormone (Efendic, S., et al., Horm Metab Res. 36:742-6 (2004)) and is secreted by the mucosa of the duodenum and jejunum in response to absorbed fat and carbohydrate that stimulate the pancreas to secrete insulin. GIP circulates as a biologically active 42-amino acid peptide. GIP is also known as glucose-dependent insulinotropic protein. GIP is a 42-amino acid gastrointestinal regulatory peptide that stimulates insulin secretion from pancreatic beta cells in the presence of glucose (Tseng, C., et al., PNAS 90:1992-1996 (1993)). The sequence of GIP, as well as peptide analogs and peptide derivatives thereof, are known in the art (e.g., Meier J. J., Diabetes Metab Res Rev. 21(2):91-117 (2005) and Efendic S., Horm Metab Res. 36(11-12):742-6 (2004)).

Glucagon is a peptide hormone, produced by alpha cells of the pancreas, which raises the concentration of glucose in the bloodstream. Its effect is opposite that of insulin, which lowers the glucose concentration. The pancreas releases glucagon when the concentration of glucose in the bloodstream falls too low. Glucagon causes the liver to convert stored glycogen into glucose, which is released into the bloodstream. High blood glucose levels stimulate the release of insulin. Insulin allows glucose to be taken up and used by insulin-dependent tissues. Thus, glucagon and insulin are part of a feedback system that keeps blood glucose levels at a stable level.

Human amylin, or islet amyloid polypeptide (IAPP), is a 37-residue polypeptide hormone. Amylin is co-secreted with insulin from pancreatic β-cells in the ratio of approximately 100:1 (insulin:amylin). Pro-islet amyloid polypeptide (i.e., pro-IAPP) is produced in the pancreatic β-cells as a 67 amino acid, 7404 Dalton pro-peptide that undergoes post-translational modifications including protease cleavage to produce the 37-residue amylin. Loss of β-cell function that occurs early in type 1 diabetics and can occur late in type 2 diabetics leads to deficiencies in the secretion of insulin and amylin.

Amylin functions as part of the endocrine pancreas, those cells within the pancreas that synthesize and secrete hormones. Amylin contributes to glycemic control; it is secreted from the pancreatic islets into the blood circulation and is cleared by peptidases in the kidney. Amylin's metabolic function is well-characterized as an inhibitor of the appearance of nutrients, such as glucose, in the plasma. It thus functions as a synergistic partner to insulin, a peptide that regulates blood glucose levels and coordinates the body's distribution and uptake of glucose. Insulin's role in the body is, among other things, to prevent blood glucose levels from rising too high, particularly after a meal.

Amylin is believed to play a role in glycemic regulation by slowing gastric emptying and promoting satiety (i.e., feeling of fullness), thereby preventing post-prandial (i.e., after-meal) spikes in blood glucose levels. The overall effect is to slow the rate of appearance of glucose in the blood after eating. Amylin also lowers the secretion of glucagon by the pancreas. Glucagon's role in the body is, among other things, to prevent blood glucose levels dropping too low. This is significant because certain type 1 diabetics, for example, are prone to secrete excess amounts of the blood glucose-raising glucagon just after meals.

For numerous reasons, human amylin, having a half-life in serum of about 13 minutes, is not amenable for use as a therapeutic agent. Rather, pramlintide (Symlin®, developed by Amylin Pharmaceuticals, Inc., San Diego, CA, USA and marketed by AstraZeneca plc, Cambridge, UK) was developed as a synthetic analogue of human amylin for the treatment of patients with types 1 or 2 diabetes, who use meal-time insulin but cannot achieve desired glycemic control despite optimal insulin therapy. Pramlintide differs from human amylin in 3 of its 37 amino acids. These modifications provide pramlintide a longer half-life of approximately 48 minutes in humans and reduce its propensity to aggregate, a characteristic found of human amylin. Further analogues of human amylin have been disclosed such as those in U.S. patent application Ser. No. 16/598,915 (corresponding to PCT International Application No. PCT/US2019/055696), both filed Oct. 10, 2019.

Implantable Delivery

In some embodiments, provided is an osmotic delivery device, as described herein, comprising any of the long acting PYY analog polypeptides, as disclosed herein, or a pharmaceutical composition comprising any of the long acting PYY analog polypeptides.

In some embodiments, the osmotic delivery device comprises an impermeable reservoir comprising interior and exterior surfaces and first and second open ends; a semi-permeable membrane in sealing relationship with the first open end of the reservoir; an osmotic engine within the reservoir and adjacent the semi-permeable membrane; a piston adjacent the osmotic engine, wherein the piston forms a movable seal with the interior surface of the reservoir, the piston divides the reservoir into a first chamber and a second chamber, the first chamber comprising the osmotic engine; a suspension formulation, wherein the second chamber comprises the suspension formulation and the suspension formulation is flowable and comprises the isolated polypeptide; and a diffusion moderator inserted in the second open end of the reservoir, the diffusion moderator adjacent the suspension formulation.

An implantable, osmotic delivery device typically includes a reservoir having at least one orifice through which the suspension formulation is delivered. The suspension formulation may be stored within the reservoir. In a preferred embodiment, the implantable, drug delivery device is an osmotic delivery device, wherein delivery of the drug is osmotically driven. Some osmotic delivery devices and their component parts have been described, for example, the DUROS® delivery device or similar devices (see, e.g., U.S. Pat. Nos. 5,609,885; 5,728,396; 5,985,305; 5,997,527; 6,113,938; 6,132,420; 6,156,331; 6,217,906; 6,261,584; 6,270,787; 6,287,295; 6,375,978; 6,395,292; 6,508,808; 6,544,252; 6,635,268; 6,682,522; 6,923,800; 6,939,556; 6,976,981; 6,997,922; 7,014,636; 7,207,982; and 7,112,335; 7,163,688; U.S. Patent Publication Nos. 2005/0175701, 2007/0281024, 2008/0091176, and 2009/0202608).

The osmotic delivery device typically consists of a cylindrical reservoir which contains the osmotic engine, piston, and drug formulation. The reservoir is capped at one end by a controlled-rate, semi-permeable membrane and capped at the other end by a diffusion moderator through which suspension formulation, comprising the drug, is released from the drug reservoir. The piston separates the drug formulation from the osmotic engine and utilizes a seal to prevent the water in the osmotic engine compartment from entering the drug reservoir. The diffusion moderator is designed, in conjunction with the drug formulation, to prevent body fluid from entering the drug reservoir through the orifice.

The osmotic device releases a drug at a predetermined rate based on the principle of osmosis. Extracellular fluid enters the osmotic delivery device through a semi-permeable membrane directly into a salt engine that expands to drive the piston at a slow and even delivery rate. Movement of the piston forces the drug formulation to be released through the orifice or exit port at a predetermined shear rate. In one embodiment of the present invention, the reservoir of the osmotic device is loaded with a suspension formulation wherein the device is capable of delivering the suspension formulation to a subject over an extended period of time (e.g., about 1, about 3, about 6, about 9, about 10, and about 12 months) at a pre-determined, therapeutically effective delivery rate.

The release rate of the drug from the osmotic delivery device typically provides a subject with a predetermined target dose of a drug, for example, a therapeutically effective daily dose delivered over the course of a day; that is, the release rate of the drug from the device, provides substantial steady-state delivery of the drug at a therapeutic concentration to the subject.

Typically, for an osmotic delivery device, the volume of a beneficial agent chamber comprising the beneficial agent formulation is between about 100 µl to about 1000 µl, more preferably between about 120 µl and about 500 µl, more preferably between about 150 µl and about 200 µl.

Typically, the osmotic delivery device is implanted within the subject, for example, subdermally or subcutaneously to provide subcutaneous drug delivery. The device(s) can be implanted subdermally or subcutaneously into either or both arms (e.g., in the inside, outside, or back of the upper arm) or the abdomen. Preferred locations in the abdominal area are under the abdominal skin in the area extending below the ribs and above the belt line. To provide a number of locations for implantation of one or more osmotic delivery device within the abdomen, the abdominal wall can be divided into 4 quadrants as follows: the upper right quadrant extending at least 2-3 centimeters below the right ribs, e.g., at least about 5-8 centimeters below the right ribs, and at least 2-3 centimeters to the right of the midline, e.g., at least about 5-8 centimeters to the right of the midline; the lower right quadrant extending at least 2-3 centimeters above the belt line, e.g., at least about 5-8 centimeters above the belt line, and at least 2-3 centimeters to the right of the midline, e.g., at least about 5-8 centimeters to the right of the midline; the upper left quadrant extending at least 2-3 centimeters below the left ribs, e.g., at least about 5-8 centimeters below the left ribs, and at least 2-3 centimeters to the left of the midline, e.g., at least about 5-8 centimeters to the left of the midline; and the lower left quadrant extending at least 2-3 centimeters above the belt line, e.g., at least about 5-8 centimeters above the belt line, and at least 2-3 centimeters to the left of the midline, e.g., at least about 5-8 centimeters to the left of the midline. This provides multiple available locations for implantation of one or more devices on one or more occasions. Implantation and removal of osmotic delivery devices are generally carried out by medical professionals using local anesthesia (e.g., lidocaine).

Termination of treatment by removal of an osmotic delivery device from a subject is straightforward, and provides the important advantage of immediate cessation of delivery of the drug to the subject.

Preferably, the osmotic delivery device has a fail-safe mechanism to prevent an inadvertent excess or bolus delivery of drug in a theoretical situation like the plugging or clogging of the outlet (diffusion moderator) through which the drug formulation is delivered. To prevent an inadvertent excess or bolus delivery of drug the osmotic delivery device is designed and constructed such that the pressure needed to partially or wholly dislodge or expel the diffusion moderator from the reservoir exceeds the pressure needed to partially or wholly dislodge or expel the semi-permeable membrane to the extent necessary to de-pressurize the reservoir. In such a scenario, pressure would build within the device until it would push the semi-permeable membrane at the other end outward, thereby releasing the osmotic pressure. The osmotic delivery device would then become static and no longer deliver the drug formulation provided that the piston is in a sealing relationship with the reservoir.

A dose and delivery rate can be selected to achieve a desired blood concentration of a drug generally within less than about 6 half-lives of the drug within the subject after implantation of the device. The blood concentration of the drug is selected to give the optimal therapeutic effects of the drug while avoiding undesirable side effects that may be induced by excess concentration of the drug, while at the same time avoiding peaks and troughs that may induce side effects associated with peak or trough plasma concentrations of the drug.

The suspension formulations may also be used in infusion pumps, for example, the ALZET® (DURECT Corporation, Cupertino, Calif.) osmotic pumps which are miniature, infusion pumps for the continuous dosing of laboratory animals (e.g., mice and rats).

Modes of Administration

In some embodiments, the method comprises providing a PYY analog polypeptide of the disclosure or a pharmaceutical composition thereof, to a subject in need of treatment, via injection. In some embodiments, the method comprises providing a PYY analog polypeptide of the disclosure or a pharmaceutical composition thereof, formulated for oral administration, to a subject in need of treatment.

In some embodiments, the method comprises providing a PYY analog polypeptide of the disclosure or a pharmaceutical composition thereof, to a subject in need of treatment, via implantation. In some embodiments, the method comprises providing continuous delivery of a PYY analog polypeptide, to a subject in need of treatment, from an osmotic delivery device. The delivery device, such as an osmotic delivery device, comprises sufficient PYY analog polypeptide of the disclosure for continuous administration for up to 3 months, 6 months, 9 months, 12 months, 18 months or 24 months. As such, continuous administration of a PYY analog polypeptide of the disclosure via osmotic delivery device eliminates daily, or multiple daily dosing of marketed PYY analog polypeptides.

The substantial steady-state delivery of the PYY analog polypeptide from the osmotic delivery device is continuous over an administration period. In some embodiments, the subject or patient is a human subject or human patient.

In some embodiments of the present invention, the administration period is, for example, at least about 3 months, at least about 3 months to about a year, at least about 4 months to about a year, at least about 5 months to about a year, at least about 6 months to about a year, at least about 8 months to about a year, at least about 9 months to about a year, at least about 10 months to about a year, at least about one year to about two years, at least about two years to about three years.

In further embodiments, the treatment methods of the present invention provide significant decrease in the subject's fasting plasma glucose concentration after implantation of the osmotic delivery device in the subject (relative to the subject's fasting plasma glucose concentration before implantation of the osmotic delivery device) that is achieved within about 7 days, 6 days, 5 days, 4 days, 3 days, 2 days, 1 day or less after implantation of the osmotic delivery device in the subject. The significant decrease in fasting plasma glucose is typically statistically significant as demonstrated by application of an appropriate statistical test or is considered significant for the subject by a medical practitioner. A significant decrease in fasting plasma glucose relative to the baseline before implantation is typically maintained over the administration period.

In some embodiments, the present invention relates to a method of treating a disease or condition in a subject in need of treatment. The method comprises providing continuous delivery of a drug from an osmotic delivery device, wherein substantial steady-state delivery of the drug at therapeutic concentrations is achieved in the subject. The substantial steady-state delivery of the drug from the osmotic delivery device is continuous over an administration period of at least about 3 months. The drug has a known or determined half-life in a typical subject. Humans are preferred subjects for the practice of the present invention. The present invention includes a drug effective for treatment of the disease or condition, as well as an osmotic delivery device comprising the drug for use in the present methods of treating the disease or condition in a subject in need of treatment. Advantages of the present invention include mitigation of peak-associated drug toxicities and attenuation of sub-optimal drug therapy associated with troughs.

In some embodiments, the substantial steady-state delivery of a drug at therapeutic concentrations is achieved within a period of about 1 month, 7 days, 5 days, 3 days or 1 day after implantation of the osmotic delivery device in the subject.

The invention also provides a method for promoting weight loss in a subject in need thereof, a method for treating excess weight or obesity in a subject in need thereof, and/or a method for suppressing appetite in a subject in need thereof. The method comprises providing delivery of an isolated PYY analog polypeptide. In some embodiments, the isolated PYY analog polypeptide is continuously delivered from an implantable osmotic delivery device. In some embodiments, substantial steady-state delivery of the PYY analog polypeptide from the osmotic delivery device is achieved and is substantially continuous over an administration period. In some embodiments, the subject is human.

The present invention includes an osmotic delivery device comprising a PYY analog polypeptide for use in the present methods in a subject in need of treatment. The subject may have type 2 diabetes. The subject in need thereof may have a baseline HbA1c % of greater than 10.0%, i.e., a high baseline (HBL) subject. The subject may not have previously received a drug for treating type 2 diabetes mellitus.

In further embodiments, the treatment methods of the present invention provide significant decrease in the subject's fasting plasma glucose concentration after implantation of the osmotic delivery device in the subject (relative to the subject's fasting plasma glucose concentration before implantation of the osmotic delivery device) that is achieved within about 7 days or less after implantation of the osmotic delivery device in the subject, within about 6 days or less after implantation of the osmotic delivery device in the subject, within about 5 days or less after implantation of the osmotic delivery device in the subject, within about 4 days or less after implantation of the osmotic delivery device in the subject, within about 3 days or less after implantation of the osmotic delivery device in the subject, within about 2 days or less after implantation of the osmotic delivery device in the subject, or within about 1 day or less after implantation of the osmotic delivery device in the subject. In preferred embodiments of the present invention, the significant decrease in the subject's fasting plasma glucose concentration after implantation of the osmotic delivery device, relative to the subject's fasting plasma glucose concentration before implantation, is achieved within about 2 days or less, preferably within about 1 day or less after implantation of the osmotic delivery device in the subject, or more preferably within about 1 day after implantation of the osmotic delivery device in the subject. The significant decrease in fasting plasma glucose is typically statistically significant as demonstrated by application of an appropriate statistical test or is considered significant for the subject by a medical practitioner. A significant decrease in fasting plasma glucose relative to the baseline before implantation is typically maintained over the administration period.

In embodiments of all aspects of the present invention relating to methods of treating a disease or condition in a subject, an exemplary osmotic delivery device comprises the following: an impermeable reservoir comprising interior and exterior surfaces and first and second open ends; a semi-permeable membrane in sealing relationship with the first open end of the reservoir; an osmotic engine within the reservoir and adjacent the semi-permeable membrane; a piston adjacent the osmotic engine, wherein the piston forms a movable seal with the interior surface of the reservoir, the piston divides the reservoir into a first chamber and a second chamber, the first chamber comprising the osmotic engine; a drug formulation or suspension formulation comprising the drug, wherein the second chamber comprises the drug formulation or suspension formulation and the drug formulation or suspension formulation is flowable; and a diffusion moderator inserted in the second open end of the reservoir, the diffusion moderator adjacent the suspension formulation. In preferred embodiments, the reservoir comprises titanium or a titanium alloy.

In embodiments of all aspects of the present invention relating to methods of treating a disease or condition in a subject, the drug formulation can comprise the drug and a vehicle formulation. Alternatively, suspension formulations are used in the methods and can, for example, comprise a particle formulation comprising the drug and a vehicle formulation. Vehicle formulations for use in forming the suspension formulations of the present invention can, for example, comprise a solvent and a polymer.

The reservoir of the osmotic delivery devices may, for example, comprise titanium or a titanium alloy.

In embodiments of all aspects of the present invention the implanted osmotic delivery device can be used to provide subcutaneous delivery.

In embodiments of all aspects of the present invention the continuous delivery can, for example, be zero-order, controlled continuous delivery.

Pharmaceutical Compositions

According to another embodiment, the invention provides a pharmaceutical composition comprising a compound, i.e., isolated polypeptide, of this invention or a pharmaceutically acceptable derivative thereof and a pharmaceutically acceptable carrier, adjuvant, or vehicle.

In some embodiments, provided is a pharmaceutical composition comprising any of the disclosed polypeptides formulated as pharmaceutically acceptable salts thereof, such as a trifluoroacetate salt, acetate salt or hydrochloride salt. In some embodiments, provided is a pharmaceutical composition comprising any of the disclosed polypeptides formulated as a trifluoroacetate salt. In some embodiments, provided is a pharmaceutical composition comprising any of the disclosed polypeptides formulated as an acetate salt. In some embodiments, provided is a pharmaceutical composition comprising any of the disclosed polypeptides formulated as a hydrochloride salt.

The term "pharmaceutically acceptable carrier, adjuvant, or vehicle" refers to a non-toxic carrier, adjuvant, or vehicle that does not destroy the pharmacological activity of the compound with which it is formulated.

As used herein, the term "pharmaceutically acceptable carrier" is intended to include any and all solvents, polymers, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

Representative pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

In some embodiments, provided is a pharmaceutical composition comprising a pharmaceutically acceptable derivative of any of the disclosed polypeptides formulated as pharmaceutically acceptable salts thereof, such as a trifluoroacetate salt, acetate salt or hydrochloride salt. A "pharmaceutically acceptable derivative" means any non-toxic salt, ester, salt of an ester or other derivative of a compound of this invention that, upon administration to a recipient, is capable of providing, either directly or indirectly, a compound of this invention or an active metabolite or residue thereof.

The pharmaceutical composition comprises a drug and may be formulated as a "particle formulation" as described in greater detail below. The pharmaceutical composition and/or particle formulation may include stabilizing components (also referred to herein as "excipients"). Examples of stabilizing components include, but are not limited to, carbohydrates, antioxidants, amino acids, buffers, inorganic compounds, and surfactants.

The amount of compound in compositions of this invention is such that is effective to measurably activate one or more PYY receptors (e.g., human, rat, monkey etc.), in a biological sample or in a patient. In certain embodiments, the amount of compound in compositions of this invention is such that is effective to measurably activate human PYY receptors in the absence or presence of human serum albumin, in a biological sample or in a patient. In certain embodiments, a composition of this invention is formulated for administration to a patient in need of such composition. In some embodiments, a composition of this invention is formulated for injectable administration to a patient. In some embodiments, a composition of this invention is formulated for administration to a patient via an implantable delivery device such as an osmotic deliver device.

The isolated polypeptides of the disclosure (also referred to herein as "active compounds"), and derivatives, fragments, analogs and homologs thereof, can be incorporated into pharmaceutical compositions suitable for administration. Such compositions typically comprise the isolated polypeptide, or a pharmaceutically acceptable salt thereof, and a pharmaceutically acceptable carrier.

A pharmaceutical composition of the invention is formulated to be compatible with its intended route of administration. Examples of routes of administration include parenteral, (e.g., intravenous, intradermal, subdermal, subcutaneous), oral (e.g., inhalation), transdermal (i.e., topical), transmucosal, rectal, or combinations thereof. In some embodiments, a pharmaceutical composition or an isolated polypeptide of the disclosure is formulated for administration by topical administration. In some embodiments, a pharmaceutical composition or an isolated polypeptide of the disclosure is formulated for administration by inhalation administration. In some embodiments, the pharmaceutical composition is formulated for administration by a device or other suitable delivery mechanism that is suitable for subdermal or subcutaneous implantation and delivers the pharmaceutical composition subcutaneously. In some embodiments, the pharmaceutical composition is formulated for administration by an implant device that is suitable for subdermal or subcutaneous implantation and delivers the pharmaceutical composition subcutaneously. In some embodiments, the pharmaceutical composition is formulated for administration by an osmotic delivery device, e.g., an implantable osmotic delivery device, that is suitable for subdermal or subcutaneous placement or other implantation and delivers the pharmaceutical composition subcutaneously. Solutions or suspensions used for parenteral application, intradermal application, subdermal application, subcutaneous application, or combinations thereof can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Drug Particle Formulations

Compounds, i.e., isolated polypeptides or pharmaceutically acceptable salts thereof, for use in the practice of the present invention are typically added to particle formulations, which are used to make polypeptide-containing particles that are uniformly suspended, dissolved or dispersed in a suspension vehicle to form a suspension formulation. In some embodiments, the PYY analog polypeptide is formulated in a particle formulation and converted (e.g., spray dried) to particles. In some embodiments, the particles comprising the PYY analog polypeptide are suspended in a vehicle formulation, resulting in a suspension formulation of vehicle and suspended particles comprising the PYY analog polypeptide.

Preferably, particle formulations are formable into particles using processes such as spray drying, lyophilization, desiccation, freeze-drying, milling, granulation, ultrasonic drop creation, crystallization, precipitation, or other techniques available in the art for forming particles from a mixture of components. In one embodiment of the invention the particles are spray dried. The particles are preferably substantially uniform in shape and size.

In some embodiments, the present invention provides drug particle formulations for pharmaceutical use. The particle formulation typically comprises a drug and includes one or more stabilizing component (also referred to herein as "excipients"). Examples of stabilizing components include, but are not limited to, carbohydrates, antioxidants, amino acids, buffers, inorganic compounds, and surfactants. The amounts of stabilizers in the particle formulation can be determined experimentally based on the activities of the stabilizers and the desired characteristics of the formulation, in view of the teachings of the present specification.

In any of the embodiments, the particle formulation may comprise about 50 wt % to about 90 wt % drug, about 50 wt % to about 85 wt % drug, about 55 wt % to about 90 wt % drug, about 60 wt % to about 90 wt % drug, about 65 wt % to about 85 wt % drug, about 65 wt % to about 90 wt % drug, about 70 wt % to about 90 wt % drug, about 70 wt % to about 85 wt % drug, about 70 wt % to about 80 wt % drug, or about 70 wt % to about 75 wt % drug.

Typically, the amount of carbohydrate in the particle formulation is determined by aggregation concerns. In general, the carbohydrate amount should not be too high so as to avoid promoting crystal growth in the presence of water due to excess carbohydrate unbound to drug.

Typically, the amount of antioxidant in the particle formulation is determined by oxidation concerns, while the amount of amino acid in the formulation is determined by oxidation concerns and/or formability of particles during spray drying.

Typically, the amount of buffer in the particle formulation is determined by pre-processing concerns, stability concerns, and formability of particles during spray drying. Buffer may be required to stabilize drug during processing, e.g., solution preparation and spray drying, when all stabilizers are solubilized.

Examples of carbohydrates that may be included in the particle formulation include, but are not limited to, monosaccharides (e.g., fructose, maltose, galactose, glucose, D-mannose, and sorbose), disaccharides (e.g., lactose, sucrose, trehalose, and cellobiose), polysaccharides (e.g., raffinose, melezitose, maltodextrins, dextrans, and starches), and alditols (acyclic polyols; e.g., mannitol, xylitol, maltitol, lactitol, xylitol sorbitol, pyranosyl sorbitol, and myoinsitol). Suitable carbohydrates include disaccharides and/or non-reducing sugars, such as sucrose, trehalose, and raffinose.

Examples of antioxidants that may be included in the particle formulation include, but are not limited to, methionine, ascorbic acid, sodium thiosulfate, catalase, platinum, ethylenediaminetetraacetic acid (EDTA), citric acid, cysteine, thioglycerol, thioglycolic acid, thiosorbitol, butylated hydroxanisol, butylated hydroxyltoluene, and propyl gallate. Further, amino acids that readily oxidize can be used as antioxidants, for example, cysteine, methionine, and tryptophan.

Examples of amino acids that may be included in the particle formulation include, but are not limited to, arginine, methionine, glycine, histidine, alanine, leucine, glutamic acid, iso-leucine, L-threonine, 2-phenylamine, valine, norvaline, proline, phenylalanine, tryptophan, serine, asparagines, cysteine, tyrosine, lysine, and norleucine. Suitable amino acids include those that readily oxidize, e.g., cysteine, methionine, and tryptophan.

Examples of buffers that may be included in the particle formulation include, but are not limited to, citrate, histidine, succinate, phosphate, maleate, tris, acetate, carbohydrate, and gly-gly. Suitable buffers include citrate, histidine, succinate, and tris.

Examples of inorganic compounds that may be included in the particle formulation include, but are not limited to, NaCl, $Na_2SO_4$, $NaHCO_3$, KCl, $KH_2PO_4$, $CaCl_2$, and $MgCl_2$.

In addition, the particle formulation may include other stabilizers/excipients, such as surfactants and salts. Examples of surfactants include, but are not limited to, Polysorbate 20, Polysorbate 80, PLURONIC® (BASF Corporation, Mount Olive, N.J.) F68, and sodium dodecyl sulfate (SDS). Examples of salts include, but are not limited to, sodium chloride, calcium chloride, and magnesium chloride.

The particles are typically sized such that they can be delivered via an implantable osmotic delivery device. Uniform shape and size of the particles typically helps to provide a consistent and uniform rate of release from such a delivery device; however, a particle preparation having a non-normal particle size distribution profile may also be used. For example, in a typical implantable osmotic delivery device having a delivery orifice, the size of the particles is less than about 30%, more preferably is less than about 20%, more preferably is less than about than 10%, of the diameter of the delivery orifice. In an embodiment of the particle formulation for use with an osmotic delivery system, wherein the delivery orifice diameter of the implant is about 0.5 mm, particle sizes may be, for example, less than about 150 microns to about 50 microns. In an embodiment of the particle formulation for use with an osmotic delivery system, wherein the delivery orifice diameter of the implant is about 0.1 mm, particle sizes may be, for example, less than about 30 microns to about 10 microns. In one embodiment, the orifice is about 0.25 mm (250 microns) and the particle size is about 2 microns to about 5 microns.

Those of ordinary skill in the art will appreciate that a population of particles follow principles of particle size distribution. Widely used, art-recognized methods of describing particle size distributions include, for example, average diameters and D values, such as the D50 value, which is commonly used to represent the mean diameter of the range of the particle sizes of a given sample.

Particles of a particle formulation have diameters of between about 2 microns to about 150 microns, e.g., less than 150 microns in diameter, less than 100 microns in diameter, less than 50 microns in diameter, less than 30 microns in diameter, less than 10 microns in diameter, less than 5 microns in diameter, and about 2 microns in diameter. Preferably, particles have diameters of between about 2 microns and about 50 microns.

Particles of a particle formulation comprising an isolated PYY analog polypeptide have average diameters of between about 0.3 microns to about 150 microns. Particles of a particle formulation comprising an isolated PYY analog polypeptide have average diameters of between about 2 microns to about 150 microns, e.g., less than 150 microns in average diameter, less than 100 microns in average diameter, less than 50 microns in average diameter, less than 30 microns in average diameter, less than 10 microns in average diameter, less than 5 microns in average diameter, and about 2 microns in average diameter. In some embodiments, particles have average diameters of between about 0.3 microns and 50 microns, for example, between about 2 microns and about 50 microns. In some embodiments, the particles have an average diameter between 0.3 microns and 50 microns, for example, between about 2 microns and about 50 microns, where each particle is less than about 50 microns in diameter.

Typically, the particles of the particle formulations, when incorporated in a suspension vehicle, do not settle in less than about 3 months, preferably do not settle in less than about 6 months, more preferably do not settle in less than about 12 months, more preferably do not settle in less than about 24 months at delivery temperature, and most preferably do not settle in less than about 36 months at delivery temperature. The suspension vehicles typically have a viscosity of between about 5,000 to about 30,000 poise, preferably between about 8,000 to about 25,000 poise, more preferably between about 10,000 to about 20,000 poise. In one embodiment, the suspension vehicle has a viscosity of about 15,000 poise, plus or minus about 3,000 poise. Generally speaking, smaller particles tend to have a lower settling rate in viscous suspension vehicles than larger particles. Accordingly, micron- to nano-sized particles are typically desirable. In viscous suspension formulation, particles of about 2 microns to about 7 microns of the present invention will not settle for at least 20 years at room temperature based on simulation modeling studies. In an embodiment of the particle formulation of the present invention, for use in an implantable osmotic delivery device, comprises particles of sizes less than about 50 microns, more preferably less than about 10 microns, more preferably in a range from about 2 microns to about 7 microns.

In summary, disclosed polypeptides, or pharmaceutically acceptable salts thereof, are formulated into dried powders in solid state particles, which preserve maximum chemical and biological stability of the drug. Particles offers long-term storage stability at high temperature, and therefore, allows delivery to a subject of stable and biologically effective drug for extended periods of time. Particles are suspended in suspension vehicles for administration to patients.

Particle Suspensions in Vehicles

In one aspect, the suspension vehicle provides a stable environment in which the drug particle formulation is dispersed. The drug particle formulations are chemically and physically stable (as described above) in the suspension vehicle. The suspension vehicle typically comprises one or more polymer and one or more solvent that form a solution of sufficient viscosity to uniformly suspend the particles comprising the drug. The suspension vehicle may comprise further components, including, but not limited to, surfactants, antioxidants, and/or other compounds soluble in the vehicle.

The viscosity of the suspension vehicle is typically sufficient to prevent the drug particle formulation from settling during storage and use in a method of delivery, for example, in an implantable, osmotic delivery device. The suspension vehicle is biodegradable in that the suspension vehicle disintegrates or breaks down over a period of time in response to a biological environment, while the drug particle is dissolved in the biological environment and the active pharmaceutical ingredient (i.e., the drug) in the particle is absorbed.

In embodiments, the suspension vehicle is a "single-phase" suspension vehicle, which is a solid, semisolid, or liquid homogeneous system that is physically and chemically uniform throughout.

The solvent in which the polymer is dissolved may affect characteristics of the suspension formulation, such as the behavior of drug particle formulation during storage. A solvent may be selected in combination with a polymer so that the resulting suspension vehicle exhibits phase separation upon contact with the aqueous environment. In some embodiments of the invention, the solvent may be selected in combination with the polymer so that the resulting suspension vehicle exhibits phase separation upon contact with the aqueous environment having less than approximately about 10% water.

The solvent may be an acceptable solvent that is not miscible with water. The solvent may also be selected so that the polymer is soluble in the solvent at high concentrations, such as at a polymer concentration of greater than about 30%. Examples of solvents useful in the practice of the present invention include, but are not limited to, lauryl alcohol, benzyl benzoate, benzyl alcohol, lauryl lactate, decanol (also called decyl alcohol), ethyl hexyl lactate, and long chain (C8 to C24) aliphatic alcohols, esters, or mixtures thereof. The solvent used in the suspension vehicle may be "dry," in that it has a low moisture content. Preferred solvents for use in formulation of the suspension vehicle include lauryl lactate, lauryl alcohol, benzyl benzoate, and mixtures thereof.

Examples of polymers for formulation of the suspension vehicles of the present invention include, but are not limited to, a polyester (e.g., polylactic acid and polylacticpolyglycolic acid), a polymer comprising pyrrolidones (e.g., polyvinylpyrrolidone having a molecular weight ranging from approximately 2,000 to approximately 1,000,000), ester or ether of an unsaturated alcohol (e.g., vinyl acetate), polyoxyethylenepolyoxypropylene block copolymer, or mixtures thereof. Polyvinylpyrrolidone can be characterized by its K-value (e.g., K-17), which is a viscosity index. In one embodiment, the polymer is polyvinylpyrrolidone having a molecular weight of 2,000 to 1,000,000. In a preferred embodiment, the polymer is polyvinylpyrrolidone K-17 (typically having an approximate average molecular weight range of 7,900-10,800). The polymer used in the suspension vehicle may include one or more different polymers or may include different grades of a single polymer. The polymer used in the suspension vehicle may also be dry or have a low moisture content.

Generally speaking, a suspension vehicle for use in the present invention may vary in composition based on the desired performance characteristics. In one embodiment, the suspension vehicle may comprise about 40 wt % to about 80 wt % polymer(s) and about 20 wt % to about 60 wt % solvent(s). Preferred embodiments of a suspension vehicle include vehicles formed of polymer(s) and solvent(s) combined at the following ratios: about 25 wt % solvent and about 75 wt % polymer; about 50 wt % solvent and about 50 wt % polymer; about 75 wt % solvent and about 25 wt % polymer. Accordingly, in some embodiments, the suspension vehicle may comprise selected components and in other embodiments consist essentially of selected components.

The suspension vehicle may exhibit Newtonian behavior. The suspension vehicle is typically formulated to provide a viscosity that maintains a uniform dispersion of the particle formulation for a predetermined period of time. This helps facilitate making a suspension formulation tailored to provide controlled delivery of the drug contained in the drug particle formulation. The viscosity of the suspension vehicle may vary depending on the desired application, the size and type of the particle formulation, and the loading of the particle formulation in the suspension vehicle. The viscosity of the suspension vehicle may be varied by altering the type or relative amount of the solvent or polymer used.

The suspension vehicle may have a viscosity ranging from about 100 poise to about 1,000,000 poise, preferably from about 1,000 poise to about 100,000 poise. In preferred embodiments, the suspension vehicles typically have a viscosity, at 33° C., of between about 5,000 to about 30,000 poise, preferably between about 8,000 to about 25,000 poise, more preferably between about 10,000 to about 20,000 poise. In one embodiment, the suspension vehicle has a viscosity of about 15,000 poise, plus or minus about 3,000 poise, at 33° C. The viscosity may be measured at 33° C., at a shear rate of 10-4/sec, using a parallel plate rheometer.

The suspension vehicle may exhibit phase separation when contacted with the aqueous environment; however, typically the suspension vehicle exhibits substantially no phase separation as a function of temperature. For example, at a temperature ranging from approximately 0° C. to approximately 70° C. and upon temperature cycling, such as cycling from 4° C. to 37° C. to 4° C., the suspension vehicle typically exhibits no phase separation.

The suspension vehicle may be prepared by combining the polymer and the solvent under dry conditions, such as in a dry box. The polymer and solvent may be combined at an elevated temperature, such as from approximately 40° C. to approximately 70° C., and allowed to liquefy and form the single phase. The ingredients may be blended under vacuum to remove air bubbles produced from the dry ingredients. The ingredients may be combined using a conventional mixer, such as a dual helix blade or similar mixer, set at a speed of approximately 40 rpm. However, higher speeds may also be used to mix the ingredients. Once a liquid solution of the ingredients is achieved, the suspension vehicle may be cooled to room temperature. Differential scanning calorimetry (DSC) may be used to verify that the suspension vehicle is a single phase. Further, the components of the vehicle (e.g., the solvent and/or the polymer) may be treated to substantially reduce or substantially remove peroxides (e.g., by treatment with methionine; see, e.g., U.S., Patent Application Publication No. 2007-0027105).

The drug particle formulation is added to the suspension vehicle to form a suspension formulation. In some embodiments, the suspension formulation may comprise a drug particle formulation and a suspension vehicle and in other embodiments consist essentially of a drug particle formulation and a suspension vehicle.

The suspension formulation may be prepared by dispersing the particle formulation in the suspension vehicle. The suspension vehicle may be heated and the particle formulation added to the suspension vehicle under dry conditions. The ingredients may be mixed under vacuum at an elevated temperature, such as from about 40° C. to about 70° C. The ingredients may be mixed at a sufficient speed, such as from about 40 rpm to about 120 rpm, and for a sufficient amount of time, such as about 15 minutes, to achieve a uniform dispersion of the particle formulation in the suspension vehicle. The mixer may be a dual helix blade or other suitable mixer. The resulting mixture may be removed from the mixer, sealed in a dry container to prevent water from contaminating the suspension formulation, and allowed to cool to room temperature before further use, for example, loading into an implantable, drug delivery device, unit dose container, or multiple-dose container.

The suspension formulation typically has an overall moisture content of less than about 10 wt %, preferably less than about 5 wt %, and more preferably less than about 4 wt %.

In preferred embodiments, the suspension formulations of the present invention are substantially homogeneous and flowable to provide delivery of the drug particle formulation from the osmotic delivery device to the subject.

In summary, the components of the suspension vehicle provide biocompatibility. Components of the suspension vehicle offer suitable chemico-physical properties to form stable suspensions of drug particle formulations. These properties include, but are not limited to, the following: viscosity of the suspension; purity of the vehicle; residual moisture of the vehicle; density of the vehicle; compatibility with the dry powders; compatibility with implantable devices; molecular weight of the polymer; stability of the vehicle; and hydrophobicity and hydrophilicity of the vehicle. These properties can be manipulated and controlled, for example, by variation of the vehicle composition and manipulation of the ratio of components used in the suspension vehicle.

The suspension formulations described herein may be used in an implantable, osmotic delivery device to provide zero-order, continuous, controlled, and sustained delivery of a compound over an extended period of time, such as over weeks, months, or up to about one year or more. Such an implantable osmotic delivery device is typically capable of delivering the suspension formulation, comprising the drug, at a desired flow rate over a desired period of time. The suspension formulation may be loaded into the implantable, osmotic delivery device by conventional techniques.

EXAMPLES

The following examples are put forth so as to provide those of ordinary skill in the art with a complete disclosure and description of how to practice the present invention, and are not intended to limit the scope of what the inventors regard as the invention. Efforts have been made to ensure accuracy with respect to numbers used (e.g., amounts, concentrations, and percent changes) but some experimental errors and deviations should be accounted for. Unless indicated otherwise, temperature is in degrees Centigrade and pressure is at or near atmospheric.

Example 1: Generation of a Long Acting PYY Analog Polypeptides

Long acting PYY analogs of the invention, as provided in Table 3, were synthesized on a Prelude peptide synthesizer (Protein Technologies Inc., Tucson, AZ)) by solid-phase methods using Fmoc strategy with N-[(dimethylamino)-1H-1,2,3-triazolo-[4,5-b]pyridin-1-ylmethylene]-N-methyl-methanaminium hexafluorophosphate N-oxide (HATU) or 2-(6-chloro-1-H-benzotriazole-1-yl)-1,1,3,3-tetramethylaminium hexafluorophosphate (HCTU) activation (5-fold molar excess to amino acid) in N,N-dimethylformamide (DMF), and N'N-diisopropylethylamine (DIEA) was used as base. A 20% piperidine/DMF solution was used for Fmoc deprotection. The resin used was Rink Amide MBHA LL (Novabiochem) with loading of (0.30-0.40) mmol/g on a (20-400) μmol scale.

Upon completion of solid phase synthesis of the linear polypeptide, the resin was washed with dichloromethane (DCM) and dried under vacuum for 30 minutes. For analogs containing the allyloxycarbonyl (Alloc) protecting group, removal was accomplished via a solution of Pd $(PPh_3)_3$ in (chloroform/acetic acid/n-methyl-morpholine, 37:2:1). For analogs containing the tert-butyloxycarbonyl (BOC)-Lys-fluorenylmethyloxycarbonyl (Fmoc)-OH, the Fmoc protecting group was removed using 20% piperidine/DMF. The resulting Fmoc-deprotected resin was washed with DMF (6×30 secs). Next, elongation of the spacer region was carried out in step-wise manner with the manual addition of each building block under pre-activation conditions. Addition of the lipophilic substituent (also referred to as "acyl chain") was carried out under solid-phase peptide synthesis (SPPS) conditions with no pre-activation step. Final deprotection and cleavage of the peptide from the solid support were performed by treatment of the resin with (95% TFA, 2% water, 2% thioanisole, and 1% triisopropylsilane) for 2-3 hours. The cleaved peptide was precipitated using cold diethyl ether. The diethyl ether layer was decanted, and the solids triturated again with cold diethyl ether and pelleted by centrifugation.

For analogs containing a lactam bridge, the appropriate allyl-protected amino acid building blocks were installed under normal solid-phase conditions as described above. Also, Fmoc-Lys-ε-1-(4,4-dimethyl-2,6-dioxocyclohex-1-ylidene)-3-methylbutyl(ivDde)-OH was installed as a handle to later incorporate the acyl spacer and side-chain. Upon completion of the linear peptide the allyl-protecting groups were removed as described above. Lactam-bridge formation was afforded via solid-phase protocol using benzotriazol-1-yl-oxytripyrrolidinophosphonium hexafluorophosphate (PyBOP, 0.5M) activation and DIEA as the base. Deprotection of the Fmoc & ivDde groups was afforded via 4% solution of hydrazine in DMF. The resulting de-protected resin was washed with DMF (6×30 secs). Elongation of the spacer region and addition of a lipophilic substituent was carried out as described in the preceding paragraphs. Final deprotection and cleavage of the peptide from the solid support was performed by treatment of the resin with (95% TFA, 2% water, 2% thioanisole, and 1% triisopropylsilane) for 2-3 hours. The cleaved peptide was precipitated using cold diethyl ether. The diethyl ether was decanted, and the solids triturated again with cold diethyl ether and pelleted by centrifugation.

The crude product was next dissolved in a solution of acetonitrile (ACN)/$H_2O$, 0.1% TFA. A 10% solution of acetic acid was added to each solution of crude peptide product and allowed to stir until analysis via LC/MS indicated removal of any $CO_2$ adducts. The solution was frozen and lyophilized. Purification was afforded via the methods described in Example 2.

Example 2: Purification and Characterization of Long Acting PYY Analog Polypeptides, i.e., Linear Polypeptide, without any Lipophilic Substituent and Optional Spacer The product of Example 1 was lyophilized and analyzed by electrospray ionization-liquid chromatography/mass spectrometry (ESI-LC/MS) and analytical high-pressure liquid chromatography (HPLC) and was demonstrated to be pure (>98%). Mass results were consistent with calculated values.

Characterizations of peptide analogs were performed via C18 HPLC and LC/MS analysis (Acquity SQD Waters Corp, Milford, MA) and UV detection provided by dual absorbance signals at 215 nm and 280 nm, using one of Method A, Method B, Method C or Method D.

Method A, LC/MS conditions: performed using a Phenomenex HPLC Aeris™ Peptide XB C18 35 column, 1.7 µm, 2.1×100 mm or Acquity BEH300 or BEH130 CT8 column, 1.77 µm. 2.1×100 mm using 5-65% acetonitrile/water with 0.05% TFA over 30 minutes with a flow rate 0.5 mL/min, λ–215 nm, 280 nm.

Method B, C18 HPLC conditions: HPLC analysis was conducted on an Acquity BEH130, C18 column, 1.7 µm, 100×2.10 mm column at 25° C., 5-65% acetonitrile/water with 0.05% TFA over 30 minutes, flow rate 0.5 mL/min, λ–215 nm, 280 nm.

Method C, HPLC conditions: HPLC analysis was conducted on an Acquity BEH130, C18 column, 1.7 µm, 100×2.10 mm column at 25° C., 5-65% acetonitrile/water with 0.05% TFA over 20 minutes, flow rate 0.5 mL/min, λ–215 nm, 280 nm.

Method D, HPLC conditions: HPLC analysis was conducted on an Acquity BEH130, C18 column, 1.7 µm, 100×2.10 mm column at 25° C., 5-65% acetonitrile/water with 0.05% TFA over 10 minutes, flow rate 0.5 mL/min, λ–215 nm, 280 nm. 5.0 µL of sample was injected using a PLNO (partial loop w/needle over-fill) injection mode.

Polypeptide analogs without a lipophilic substituent and optional spacer are sometimes referred to herein as "linear polypeptides." Polypeptide analogs having at least one covalently bound lipophilic substituent and optional spacer are sometimes referred to herein as "conjugated polypeptides." Table 13 provides characterization data for exemplary long acting PYY analog polypeptides of the disclosure.

Polypeptide analogs without a lipophilic substituent and optional spacer are sometimes referred to herein as "linear polypeptides." Polypeptide analogs having at least one covalently bound lipophilic substituent and optional spacer are sometimes referred to herein as "conjugated polypeptides."

TABLE 13

Exemplary compounds: PYY analog polypeptides

| Compound No. | SEQ ID NO: | Parent MW | Calculated Mass (Parent MW) M + 3 | Observed Mass (Parent MW) M + 3 | Calculated Mass (Parent MW) M + 4 | Observed Mass (Parent MW) M + 4 |
|---|---|---|---|---|---|---|
| A1 | SEQ ID NO: 1 | 4948.58 | 1650.53 | 1651.7 | — | — |
| A2 | SEQ ID NO: 2 | 4803.43 | 1602.14 | 1603.4 | — | — |
| A3 | SEQ ID NO: 3 | 4936.57 | 1646.52 | 1647.7 | — | — |
| A4 | SEQ ID NO: 4 | 4903.55 | 1637.2 | 1635.52 | — | — |
| A5 | SEQ ID NO: 5 | 4775.37 | 1595 | 1592.79 | — | — |
| A6 | SEQ ID NO: 6 | 4774.43 | 1594 | 1592.48 | — | — |
| A7 | SEQ ID NO: 7 | 4846.5 | 1617.9 | 1616.5 | — | — |
| A8 | SEQ ID NO: 8 | 4774.43 | 1593.5 | 1592.48 | — | — |
| A9 | SEQ ID NO: 9 | 4789.44 | 1599.2 | 1597.48 | — | — |
| A10 | SEQ ID NO: 10 | 4817.45 | 1606.82 | 1608.6 | — | — |
| A11 | SEQ ID NO: 11 | 4817.45 | 1606.82 | 1608.5 | — | — |
| A12 | SEQ ID NO: 12 | 4803.43 | 1602.14 | 1603.4 | — | — |
| A13 | SEQ ID NO: 13 | 4787.43 | 1596.81 | 1598.9 | — | — |
| A14 | SEQ ID NO: 14 | 4844.52 | 1615.84 | 1617.8 | — | — |
| A15 | SEQ ID NO: 15 | 4787.43 | 1596.81 | 1597.5 | — | — |
| A16 | SEQ ID NO: 16 | 5134.84 | 1712.61 | 1714.3 | — | — |
| A17 | SEQ ID NO: 17 | 5077.74 | 1693.58 | 1694.7 | — | — |
| A18 | SEQ ID NO: 18 | 5134.84 | 1712.61 | 1714.2 | — | — |
| A19 | SEQ ID NO: 19 | 4901.62 | 1634.87 | 1637.2 | — | — |
| A20 | SEQ ID NO: 20 | 4844.57 | 1615.85 | 1617.8 | — | — |
| A21 | SEQ ID NO: 21 | 4844.52 | 1615.84 | 1617.1 | — | — |
| A22 | SEQ ID NO: 22 | 4802.44 | 1601.81 | 1603.2 | — | — |
| A23 | SEQ ID NO: 23 | 4858.55 | 1620.52 | 1622.4 | — | — |
| A24 | SEQ ID NO: 24 | 4845.51 | 1616.17 | 1617.8 | — | — |
| A25 | SEQ ID NO: 25 | 4817.5 | 1606.83 | 1608.4 | — | — |
| A26 | SEQ ID NO: 26 | 4831.52 | 1611.51 | 1612.4 | — | — |
| A27 | SEQ ID NO: 27 | 4900.68 | — | — | 1226.17 | 1227.1 |
| A28 | SEQ ID NO: 28 | 4900.68 | — | — | 1226.17 | 1227.1 |
| A29 | SEQ ID NO: 29 | 4901.62 | — | — | 1226.41 | 1227.1 |
| A30 | SEQ ID NO: 30 | 4831.52 | — | — | 1208.88 | 1209.8 |
| A31 | SEQ ID NO: 31 | 4831.52 | — | — | 1208.88 | 1209.8 |
| A32 | SEQ ID NO: 32 | 4817.45 | — | — | 1205.36 | 1206.5 |
| A33 | SEQ ID NO: 33 | 4831.48 | 1611.49 | 1612.6 | — | — |
| A34 | SEQ ID NO: 34 | 4902.6 | 1635.2 | 1637 | — | — |
| A35 | SEQ ID NO: 35 | 4874.55 | 1625.85 | 1626.1 | — | — |
| A36 | SEQ ID NO: 36 | 4887.59 | 1630.2 | 1631.7 | — | — |
| A37 | SEQ ID NO: 37 | 4900.68 | 1634.56 | 1635.9 | — | — |
| A38 | SEQ ID NO: 38 | 4873.57 | 1626.1 | 1626.1 | — | — |
| A39 | SEQ ID NO: 39 | 4897.68 | — | — | 1225.42 | 1226.3 |
| A40 | SEQ ID NO: 40 | 4883.65 | — | — | 1221.91 | 1222.7 |
| A41 | SEQ ID NO: 41 | 4841.52 | — | — | 1211.38 | 1212.7 |

TABLE 13-continued

Exemplary compounds: PYY analog polypeptides

| Compound No. | SEQ ID NO: | Parent MW | Calculated Mass (Parent MW) M + 3 | Observed Mass (Parent MW) M + 3 | Calculated Mass (Parent MW) M + 4 | Observed Mass (Parent MW) M + 4 |
|---|---|---|---|---|---|---|
| A42 | SEQ ID NO: 42 | 4827.49 | — | — | 1207.87 | 1208.9 |
| A43 | SEQ ID NO: 43 | 4841.52 | — | — | 1211.38 | 1212.7 |
| A44 | SEQ ID NO: 44 | 4827.49 | — | — | 1207.87 | 1209 |
| A49 | SEQ ID NO: 49 | 4817.45 | 1606.82 | 1607.7 | — | — |
| A50 | SEQ ID NO: 50 | 4787.47 | 1596.82 | 1598.6 | — | — |
| A51 | SEQ ID NO: 51 | 4801.5 | 1601.5 | 1602.4 | — | — |
| A52 | SEQ ID NO: 52 | 4752.43 | 1585.14 | 1587.5 | — | — |
| A53 | SEQ ID NO: 53 | 4759.41 | 1587.47 | 1588.4 | — | — |
| A54 | SEQ ID NO: 54 | 4844.52 | 1615.84 | 1617.7 | — | — |
| A55 | SEQ ID NO: 55 | 4801.5 | 1601.5 | 1603.1 | — | — |

"—" = not determined

Example 3: Stability and Solubility of Long Acting PYY Analog Polypeptides

The analog polypeptides described herein were tested for solubility in saline or in aqueous (DI water) at room temperature. Samples were visually inspected for clarity of the sample, any appearance of turbidity or haziness. The results of this analysis are shown in Table 14.

Several Long-acting PYY analog analogs described herein were tested, as the trifluoro acetate salt, for stability in aqueous (i.e., in DI water) or in saline (at 1 mg/ml solution. These analog polypeptides were incubated at 37° C., and samples were withdrawn at various time intervals and analyzed by LC/MS and HPLC determination of purity and mass of the parent peptide and extent of any degradation products. The purity results of these analyses are shown in Table 14 and are considered indicative of stability.

TABLE 14

Solubility and Stability of long-acting PYY Analog Polypeptides

| Compound No. | Salt form | Solubility (in Water, RT) mg/mL | Stability (37° C./RT, T0: Mar. 25, 2020) | Stability (37° C./RT, 14 days) | Stability (37° C./RT, 28 days) |
|---|---|---|---|---|---|
| A1 | TFA | 58 | 98 | — | — |
| A3 | TFA | 48 | 96.3 | — | — |
| A10 | TFA | 53 | 94.2 | — | — |
| A13 | TFA | 40 | 93.9 | — | — |
| A14 | TFA | 79 | 94.2 | — | — |
| A18 | TFA | 95 | 94.5 | — | — |
| A19 | TFA | 59 | 88.8 | — | — |
| A20 | TFA | 103 | 98.6 | — | — |
| A21 | TFA | 114 | 96.4 | — | — |
| A22 | TFA | 57 | 96.1 | — | — |
| A24 | TFA | 90 | 98.1 | — | — |
| A24 | Acetate | <0.8 | 97.7 | — | — |
| A25 | TFA | 37 | 97.6 | — | — |
| A26 | TFA | 68 | 99.8 | — | — |
| A39 | TFA | 16 | 95.9 | — | — |
| A40 | TFA | 27 | 98.1 | — | — |
| A41 | TFA | 26 | 95.7 | — | — |
| A42 | TFA | 53 | 98 | — | — |

"—" = not determined

Example 4: Human and Rat NPY Receptor Functional Assay

The NPY family of G-protein coupled receptors include Y1, Y2, Y4, and Y5 in humans and rats. Each receptor binds a pharmacologically distinct set of endogenous peptide agonist hormones or neurotransmitters belonging to the NPY family, and include neuropeptide Y (NPY), peptide tyrosine-tyrosine (PYY), and pancreatic polypeptide (PP). While NPY and PYY (1-36) bind Y1, Y2, and Y5 receptors with relative high affinity, PYY (3-36) selectively binds the Y2 receptor, and PP is selective for the Y4 receptor. Following agonist binding, the receptor-G protein complex activates a downstream intracellular signaling cascade which leads to inhibition of adenylate cyclase and a reduction in intracellular cAMP levels.

Cell Handling and cAMP Accumulation Assays

HEK-CNG cells stably expressing the human or rat Y1, Y2, Y4 or Y5 receptors (Codex Biosolutions) were used to characterize the functional potency of peptide agonists using the ActOne™ membrane potential dye kit (Codex Biosolutions). In addition to each NPY receptor, each cell line encodes a proprietary exogenous Cyclic Nucleotide-Gated (CNG) channel (Codex Biosolutions). The channel is activated by elevated intracellular levels of cAMP, resulting in ion flux and cell membrane depolarization which can be detected with a calcium sensitive dye or fluorescent membrane potential (MP) dye. Cells were carried in growth media containing 90% DMEM, 10% FBS, 250 mcg/mL G418 and 1 mcg/mL puromycin for no more than 15 passages.

Prior to testing, cells were counted and dispensed at 14,000 cells per well (Y1, Y4 and Y5) or 28,000 cells per well (Y2) into black 384 well Poly-D-Lysine plates at 20 mcL per well. Covered plates were then incubated at room temperature for 30 minutes followed by an overnight incubation at 37° C. in 5% C02. The following day, media was removed and wells were washed once with 40 mcL Dulbecco's phosphate buffered saline. Twenty microliters of DMEM followed by 20 mcL of dye loading solution containing 1×ACTOne™ membrane potential dye dilution buffer, 1×ACTOne™ membrane potential dye solution (Codex Biosolutions) and 50 mcM of the phosphodiesterase inhibitor Ro20-1724 was added to each well, covered and pre-incubated at room temperature for 2 hours in the dark. During this pre-incubation, experimental peptides and standards (NPY for Y1 and Y5, PYY (3-36) for Y2, and PP for Y4) were serially diluted over 12 concentrations to a 5× concentration (ranging from 5×10−7 M to 5×10−13 M) in agonist dilution buffer containing 1×DPBS, 0.5% casein, 125 mcM Ro20-1724 and 1.5 mcM isoproterenol to stimulate b1/b2-adrenoreceptor mediated cAMP production. Following the pre-incubation, an initial read (Ex530/Em590)

was performed on a Flexstation 3 fluorescent plate reader (Molecular Devices, Sunnyvale, CA). Ten microliters of experimental peptide or peptide standard was added in triplicate to wells and incubated for 50 minutes at room temperature in the dark. Following this incubation step, plates were read again as before (final read).

Data Analysis and Interpretation

NPY receptor activation, leading to a reduction in intracellular cAMP levels, is detected as a decrease in isoproterenol induced fluorescent signal. Peptide standard and experimental values were initially transformed in excel using the formula: final read/initial read. Transformed values were then normalized to receptor specific standard values ($1\times10^{-13}$ M minimum and $1\times10^{-7}$ M maximum) using the formula: (test value−standard minavg)/(standard maxavg−standard minavg)*100. Normalized experimental values represent a baseline corrected percentage of the receptor-system max response produced by the control peptide for each assay (NPY for Y1R and Y5R, PYY(3-36) for Y2R, and PP for Y4R). Analogs whose activity was ≤70% of the control peptide maximum are identified as partial agonists. Normalized data was analyzed from triplicate tests and used to estimate the EC50 for each test peptide on each receptor. Data was fit in GraphPad Prism software (v8.2.1) using a 3-parameter logistic curve model: Y=Bottom+(Top−Bottom)/(1+10^((LogEC50−X))). EC50 values were converted to pEC50 values using the formula: pEC50=−Log(EC50). All reported values met the curve fitting parameter $r^2 \geq 0.8$.

The results of these analyses are reported in Table 15.

TABLE 15

Activity of PYY analog polypeptides against PYY Receptors

| Compound No. | NPY1R pEC50 | NPY2R pEC50 | NPY4R pEC50 | NPY5R pEC50 |
|---|---|---|---|---|
| PYY (3-36) | 8.5 | 10.3 | <7.0 | 9.4 |
| A1 | 9.1* | 10.5 | 8.8 | 8.8 |
| A2 | 9.3* | 10.5 | 9.2 | 8.9 |
| A3 | 9.1* | 10.7 | 9.1 | 9 |
| A4 | nr | 8.7 | inactive | 7.3 |
| A5 | nr | 7.7 | inactive | 8 |
| A6 | nr | 8.9 | inactive | 7.7 |
| A7 | nr | 9.7 | inactive | 6 |
| A8 | nr | 9.6 | inactive | 7.1 |
| A9 | nr | 9.6 | inactive | 6 |
| A10 | 8.4* | 9.7 | inactive | 7.7 |
| A11 | nr | 9.5 | inactive | 7.1 |
| A12 | nr | 9.7 | inactive | 7.1 |
| A13 | inactive | 10.2 | inactive | 8.7 |
| A19 | nr | 10.5 | nr | 8.7 |
| A20 | nr | 10.5 | nr | 8.7 |
| A21 | nr | 10.4 | nr | 8.3 |
| A22 | nr | 10.5 | nr | 8.7 |
| A23 | nr | 10.4 | nr | 8.6 |
| A24 | inactive | 10.5 | inactive | 8.7 |
| A25 | nr | 10.9 | nr | 8.4 |
| A26 | nr | 10.7 | nr | 8.5 |
| A14 | 8.5* | 10.1 | nr | 8.3 |
| A15 | 9.6* | 10.2 | nr | 8 |
| A16 | nr | 10.2 | nr | 9.1 |
| A17 | 8.3* | 10.2 | nr | 8.7 |
| A18 | nr | 10.3 | nr | 9.3 |
| A27 | nr | 10.7 | nr | 8.9 |
| A28 | nr | 10.5 | nr | 8.8 |
| A29 | nr | 10.9 | nr | 9 |
| A30 | nr | 10.3 | nr | 8.5 |
| A31 | nr | 10.4 | nr | 8.7 |
| A32 | nr | 10.8 | nr | 9 |
| A33 | nr | 10.4 | nr | 8.9 |
| A34 | nr | 10.2 | nr | 8.8 |
| A35 | nr | 10.5 | nr | 9.1 |
| A36 | nr | 10.9 | nr | 8.7 |
| A37 | nr | 10.8 | nr | 8.6 |
| A38 | 8.6* | 11.1 | nr | 8.4 |
| A39 | 9.1* | 10.4 | nr | 8.9 |
| A40 | nr | 10.1 | nr | 9 |
| A41 | nr | 10.5 | nr | 9.3* |
| A42 | nr | 10.3 | nr | 9.1 |
| A43 | 9.2* | 10.5 | nr | 8.5 |
| A44 | 8.1* | 9.7 | nr | 9.2 |
| A49 | nr | 7.6 | inactive | 6 |
| A50 | nr | 6 | inactive | 6 |
| A51 | nr | 6 | inactive | 6 |
| A52 | nr | 8.4 | inactive | 8 |
| A53 | nr | 8.7 | inactive | 7.3 |
| A54 | nr | 7.7 | inactive | 8.0 |
| A55 | nr | 8.9 | inactive | 7.7 |
| A56 | nr | 9.7 | inactive | inactive |
| A57 | nr | 9.6 | inactive | 7.1 |
| A58 | 8.8* | 10.3 | inactive | 8.8 |
| A59 | nr | 8.8 | inactive | 6 |
| A60 | 8.9* | 10.3 | inactive | 8.6 |
| A61 | 8.6* | 10 | inactive | 8.3 |
| A62 | 8.1* | 9.4 | inactive | 8.2 |
| A63 | nr | 7.5 | inactive | 6 |
| A64 | nr | 8.6 | inactive | 7.9 |
| A65 | 8.0* | 10.2 | nr | 8.6 |
| A66 | nr | 10.3 | nr | 8.3 |
| A67 | nr | 10.3 | nr | 8.5 |
| A68 | nr | 9.7 | nr | 7.9 |
| A69 | nr | 10 | nr | 8.3 |
| A70 | nr | 10.4 | nr | 8.7 |
| A71 | nr | 10.7 | nr | 8.8 |
| A72 | 9.0* | 10.8 | nr | 8.8 |
| A73 | nr | 10.3 | nr | 8.6 |
| A74 | 9.3* | 10.3 | nr | 9 |
| A75 | nr | 10.6 | nr | 9.3 |
| A76 | 10.6* | 10.4 | nr | 8.9 |
| A77 | nr | 10.3 | nr | 9.2 |
| A78 | nr | 10.2 | nr | 8.5 |

*maximal response ≤70% when compared to NPY maximal response on NPY1R.
nr; not reported Example 5: In Vitro Metabolic Stability Pharmacokinetics Studies (T½) of PYY Analogs Rat and Human Kidney Brush Border Membranes In vitro incubations in kidney brush border membrane (kBBM) preparations were used to characterize the ability of peptides to resist degradation by proteases and peptidases in the systemic circulation. kBBM were selected because they contain a high concentration of a diverse set of proteases and peptidases, many of which are present throughout the body. Generally, peptides with low in vivo CL are stable in this assay, while peptides with high in vivo CL are unstable in this assay.

Brush border membranes from rat and human kidney tissue were prepared via centrifugation and stored at −70° C. Thawed stocks of rat or human kBBM were diluted to the appropriate concentration in 25 mM HEPES buffer (pH 7.4) containing 1% casein and aliquoted into a 96-well plate. The kBBM solutions were pre-warmed for 10 minutes at 37° C. Reactions were initiated by the addition of test peptide (1 mcM final concentration) also dissolved in 25 mM HEPES buffer (pH 7.4) containing 1% casein. The final concentration of kBBM in each incubation was 50 mcg protein/mL. Reactions were maintained at 37° C. in a shaking water bath. At 0, 0.25, 0.5, 1.0, 2.0, and 4.0 h post-initiation, 30 mcL of the reaction mixture was removed and placed into a 96-well plate containing 120 mcL of ice-cold methanol containing 2.5% formic acid. Quenched samples were centrifuged at 2178×g for 10 min and then a portion of the supernatants were transferred to a clean 96-well plate and diluted 1:1 with water. Samples were analyzed by UPLC-MS/MS. The results of these analyses are shown in Tables 16, 17, and 18.

Human Subcutaneous Tissue Homogenates

In vitro incubations in subcutaneous (SC) tissue homogenates were used to characterize the ability of peptides to resist pre-systemic degradation by proteases and peptidases after SC administration. In vivo nonclinical studies have shown that peptidase activity in the SC space can limit the bioavailability of a peptide after SC administration. Peptides with high SC bioavailability are stable in this assay, while peptides with low SC bioavailability are unstable in this assay.

Human SC tissue was homogenized in cold 25 mM HEPES buffer (pH 7.4, 10-fold volume based on sample weight), and then filtered through a double layer of cheesecloth. The filtrates were aliquoted, flash frozen on a methanol/dry ice bath and stored at −80° C. The protein concentration of each pooled batch was determined using the BCA protein assay. Thawed stocks of human SC tissue homogenates were diluted to 1.0 mg protein/mL in 25 mM HEPES buffer (pH 7.4) and aliquoted into a 96-well plate. The diluted SC homogenates were pre-warmed for 10 minutes at 37° C. Reactions were initiated by the addition of test peptide (10 mcM final concentration) also dissolved in 25 mM HEPES buffer (pH 7.4). Reactions were maintained at 37° C. in a shaking water bath. At 0, 0.25, 0.5, 1.0, 2.0, and 4.0 h post-initiation, 50 mcL of the reaction mixture was removed and placed into a 96-well plate containing 150 mcL of ice-cold methanol containing 2.5% formic acid. Quenched samples were centrifuged at 2178×g for 10 min and then a portion of the supernatants were transferred to a clean 96-well plate and diluted 1:10 with water. Samples were analyzed by UPLC-MS/MS. The results of these analyses are shown in Tables 16, 17, and 18.

Fraction Unbound ($f_u$) in Plasma

Conventional methods of measuring plasma protein binding, such as equilibrium dialysis, ultrafiltration and ultracentrifugation, are not reliable with peptides because of their tendency to adsorb to the surface of plastic tubing, dialysis membranes and molecular weight cut-off filters. As a result, the extent to which acylated peptides bind to serum albumin was evaluated using surface plasmon resonance (SPR). The utility of this technique to provide a reasonable estimation of the fraction of a drug bound to plasma protein has been demonstrated in the literature. The results of this analysis for compounds A13 (SEQ ID NO: 24) and A24 (SEQ ID NO: 24) are shown in Tables 17 and 18. The estimated half life of compounds A13 and A24 in humans based off this data is approximately 4 days, each.

TABLE 16

Metabolic stability pharmacokinetics of PYY analog polypeptides

| Compound No. | rkBBM t½(hr) | hkBBM t½(hr) | (H)SC tissue stability t½(hr) |
|---|---|---|---|
| A27 | — | 10 | 0.2 |
| A28 | — | 5.2 | 0.2 |
| A29 | — | 8.7 | 1.1 |
| A35 | — | 5.6 | 1.3 |
| A21 | >12 | >12 | 2.5 |
| A26 | >12 | >12 | 4 |
| A14 | >12 | >12 | 4.5 |

TABLE 16-continued

Metabolic stability pharmacokinetics of PYY analog polypeptides

| Compound No. | rkBBM t½(hr) | hkBBM t½(hr) | (H)SC tissue stability t½(hr) |
|---|---|---|---|
| A23 | >12 | >12 | 4.5 |
| A25 | >12 | >12 | 4.7 |
| A34 | — | 6.7 | 4.9 |
| A30 | — | >12 | 5.1 |
| A31 | — | >12 | 5.6 |
| A22 | >12 | >12 | 7.2 |
| A16 | >12 | >12 | 7.3 |
| A15 | >12 | >12 | 9.6 |
| A17 | >12 | >12 | 9.7 |
| A33 | — | >12 | 9.9 |
| A12 | >12 | — | 10.2 |
| A2 | >12 | >12 | 10.6 |
| A24 | >12 | >12 | 10.8 |
| A13 | >12 | >72 | 10.8 |
| A10 | >12 | >72 | 11.2 |
| A11 | >12 | — | >12 |

TABLE 17

Metabolic stability pharmacokinetics and fraction unbound of PYY analog compound A13

| | kBBM t½(hr) | SC tissue stability t½(hr) | % $f_u$ |
|---|---|---|---|
| Rat | >12 | 2.9 | 0.68% |
| Monkey | >12 | ND | 0.43% |
| Human | >72 | 10.8 | 0.44% |

ND = not determined

TABLE 18

Metabolic stability pharmacokinetics and fraction unbound of PYY analog compound A24

| | kBBM t½(hr) | SC tissue stability t½(hr) | % $f_u$ |
|---|---|---|---|
| Rat | >12 | 7.1 | 0.27% |
| Monkey | ND | ND | 0.17% |
| Human | >12 | 10.8 | 0.22% |

ND = not determined

Example 6: Pharmacokinetic Analysis of PYY Analog Polypeptides

Intravenous Infusion of Long-Acting PYY Analog Polypeptides to Assess Clearance (CL) of Peptides Peptides were dissolved in 0.05% Tween-20 in PBS (pH7.4) and administered as a 1-hour subcutaneous infusion to non-fasted male Sprague-Dawley rats (n=3 per group) at a final dose of 0.033 mg/kg via a cannula placed into the femoral vein. Formulations were administered at a rate of 0.150 mL/h/kg. Blood samples (approximately 250 μL) were collected for pharmacokinetic analysis via a jugular vein cannula at 0.25, 0.5, 0.75, 1, 1.17, 1.33, 1.5, 2, 4, 8, 24, 48, 72, 96, and 120 hr post-start of infusion into microtainer tubes containing K₂EDTA as anticoagulant and 25 μL of a protease inhibitor cocktail. Plasma was prepared by centrifugation and stored at −80° C. until analysis.

Subcutaneous Bolus Injection of Long-Acting PYY Analog Polypeptides to Assess Bioavailability (F) of Polypeptides Peptides were dissolved in sterile saline and administered to non-fasted male Sprague-Dawley rats (n=3 per group) at a dose of 0.1 mg/kg via a single bolus injection into the subcutaneous space between the scapulae. Blood samples (approximately 250 μL) were collected for pharmacokinetic analysis via a jugular vein cannula at 0.083, 0.25, 0.5, 1, 2, 4, 8, 24, 48, 72, 96, and 120 hr post-dose into microtainer tubes containing K$_2$EDTA as anticoagulant and 25 μL of a protease inhibitor cocktail. Plasma was prepared by centrifugation and stored at −80° C. until analysis.

Plasma Sample Preparation for Pharmacokinetic Studies

A 70 μL aliquot of each plasma sample was placed into to a 96-well plate. To each well was added 210 μL of 0.1% TFA in 2:1 ethanol:acetonitrile containing an appropriate internal standard. Plates were vortex mixed for 10 min at 1300 rpm, and then centrifuged for 10 min at 500×g. Supernatants (210 μL) were placed into a clean 96-well plate and evaporated under a nitrogen stream at 45° C. Residues were reconstituted in 80 μL of 20% acetonitrile (aq) containing 0.1% formic acid.

LC/MS Quantification of PYY Polypeptides in Plasma

All calibration standards were prepared in control rat plasma containing K$_2$EDTA and protease inhibitor cocktail.

Figure 4:
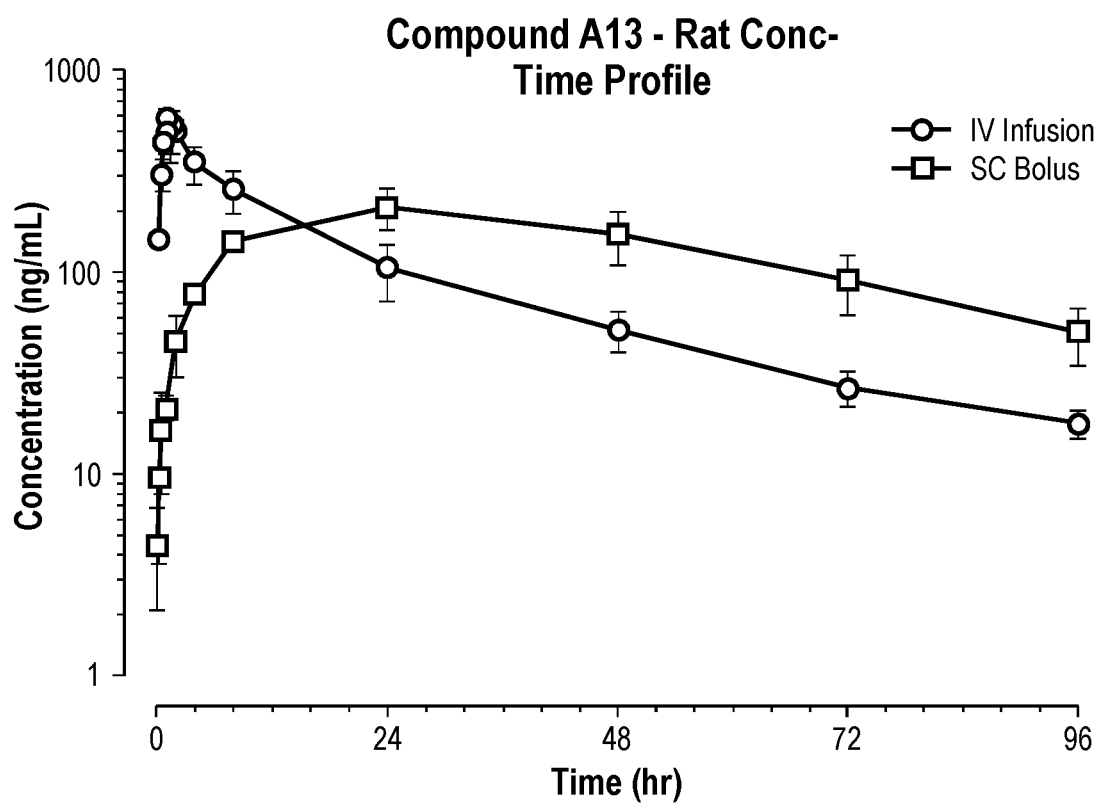
FIG. 4 depicts the change in plasma concentration of A13 following bolus or intravenous infusion.
Figure 5:
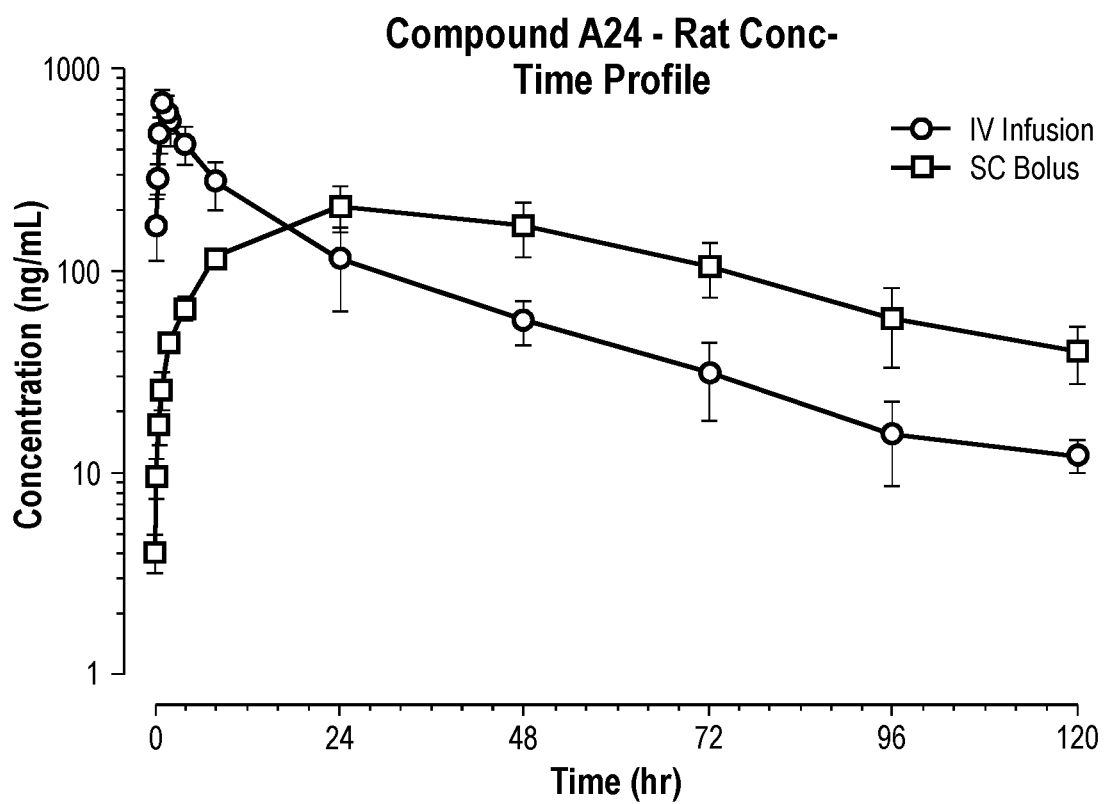
FIG. 5 depicts the change in plasma concentration of A24 following bolus or intravenous infusion.

Samples and standards were analyzed by electrospray ionization (ESI) UPLC-MS/MS using a system consisting of a CTC HTS PAL auto-injector (Leap, Carrboro, NC), an Agilent Infinity 1290 system with column oven (Palo Alto, CA), a Valco switching valve (Houston, TX), and a Sciex TripleTOF® 5600 mass spectrometer (Framingham, MA). Samples were injected onto a 2.1×50 mm reverse phase C18 analytical column, typically a Waters CORTECS UPLC C18+, 1.6 μm (Waters Corporation, Milford, MA) or similar. Chromatographic separation was achieved with a gradient method using water containing 0.1% formic acid (A) and acetonitrile containing 0.1% formic acid (B) as mobile phase. Initial conditions consisted of 95% A and 5% B. The organic component was increased to 95% B over a period of 3-4 minutes, depending on the peptide. Typical flow rates were 550 μL/min. The column temperature was held constant at 45° C. Peptides were quantified by monitoring one or more product ions produced from a multiply charged parent ion. The results of these analyses are provided in Table 19. Comprehensive pharmacokinetic and ADME profiles for compounds A13 (SEQ ID NO: 13) and A24 (SEQ ID NO: 24) are shown in Tables 20 and 21, respectively. The change in plasma concentration of A13 and A24 following bolus and intravenous infusion are presented in FIGS. 4 and 5.

TABLE 19

Quantification of PYY in plasma

| Compound No. | CL (mL/min/kg) | IV $t_{1/2}$ (hr) | F (%) |
|---|---|---|---|
| A2 | 0.0749 | 26.6 | 46.2 |
| A7 | 0.326 | 6.44 | 66.7 |
| A10 | 0.0600 | 43.2 | 58.7 |
| A13 | 0.0589 | 32.4 | 51.4 |
| A24 | 0.0564 | 28.7 | 49.8 |
| A25 | 0.0696 | 16.2 | 28.4 |

TABLE 20

Pharmacokinetic and ADME profile of compound A13 in a rat model

| Route | Dose (mg/kg) | CL (mL/min/kg) | $V_{ss}$ (mL/kg) | $T_{1/2}$ (hr) | $T_{max}$ (hr) | $C_{max}$ (ng/mL) | F (%) |
|---|---|---|---|---|---|---|---|
| IV infusion | 0.033 | 0.0589 | 119 | 32.4 | ND | ND | ND |
| SC bolus | 0.100 | ND | ND | 30.9 | 24 | 211 | 51.4 |

ND = not determined

TABLE 21

Pharmacokinetic and ADME profile of compound A24 in a rat model

| Route | Dose (mg/kg) | CL (mL/min/kg) | $V_{ss}$ (mL/kg) | $T_{1/2}$ (hr) | $T_{max}$ (hr) | $C_{max}$ (ng/mL) | F (%) |
|---|---|---|---|---|---|---|---|
| IV infusion | 0.033 | 0.0564 | 101 | 28.7 | ND | ND | ND |
| SC bolus | 0.100 | ND | ND | 33.5 | 24 | 210 | 49.8 |

ND = not determined

Figure 6:
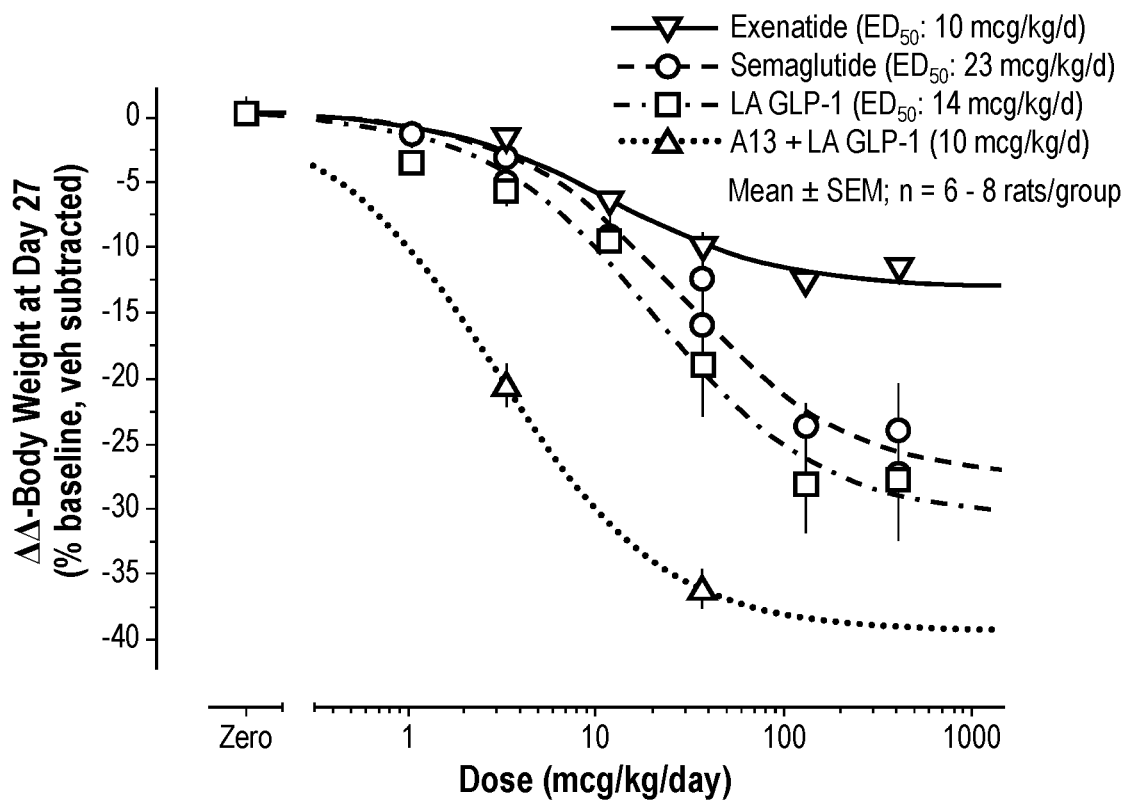
FIG. 6 is a graph depicting weight loss in the diet-induced-obese rat model of obesity and highlighting that the combination of the PYY analog peptide A13 with a long acting GLP-1 receptor agonist is significantly more effective and potent than the industry benchmarks exenatide or semaglutide alone.

Example 7a: Weight-Loss Efficacy of PYY Analog in Combination with a Long-Acting GLP-1 Receptor Agonist in LE DIO Rats Chronic weight loss efficacy studies were conducted in a rodent model for obesity Long Evans (LE) diet-induced obese (DIO) rat to investigate the efficacy and durability of long acting PYY analog(s) singly and in combination with a long acting GLP-1 analog (LA GLP-1). Male LE DIO rats were used (Envigo Laboratories, Inc., Indianapolis, IN) and beginning at weaning, the rats were fed a high fat chow (Teklad TD 95217, 40% kcal from fat, Harlan Laboratories, Madison, WI). The rats were housed 1 per cage and given ad libitum access to high fat diet (Harlan TD.95217) and water, maintained on a 12 hr light/dark cycle from 5:00 AM to 5:00 PM at 21° C. and 50% relative humidity and allowed to acclimate for at least 10 days post shipping prior to use. Rats were 16-18 weeks old at the start of the study. All procedures were performed in compliance with the Animal Welfare Act, USDA regulations and approved by the Mispro Institutional Animal Care and Use Committee. Animals were randomized into treatment groups according to body weight and fat mass (n=8 rats/group). DIO LE rats were dosed by subcutaneous (SC) injection with every other day dosing (eod) with either a long acting PYY and/or GLP-1 receptor agonist polypeptide at the specified doses or vehicle control (saline). The mean weight loss (%)±SEM from baseline and vehicle control (AA) results from the chronic combination studies of compound A13 (SEQ ID NO: 13) with the LA GLP-1 are shown in FIG. 1. Comparative data with respect to exenatide and semaglutide is provided in FIG. 6.

Figure 8:
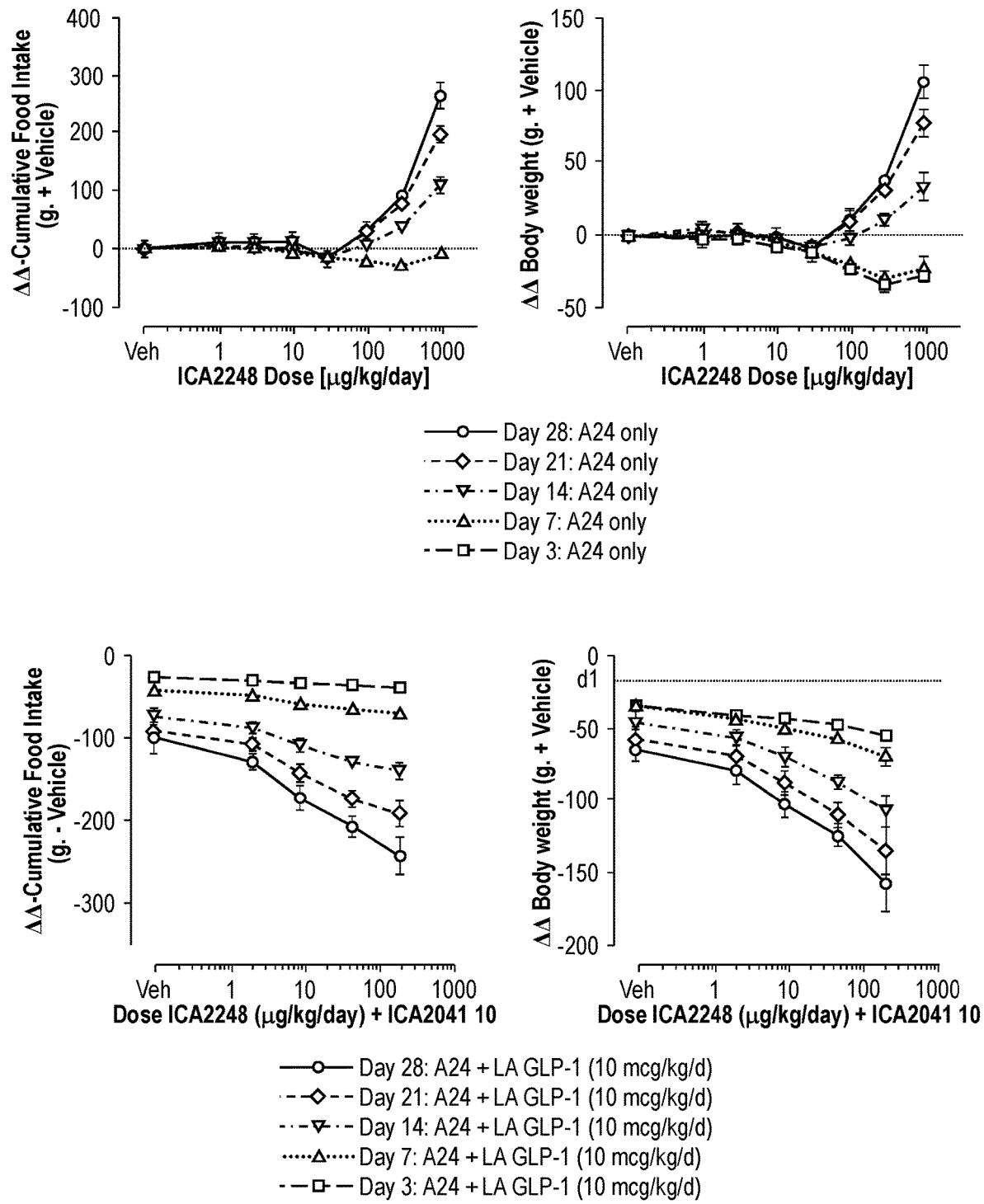
FIG. 8 is a panel of graphs depicting changes in food intake (ΔΔ g) over different durations of treatment with different doses (left panels) and corresponding changes in body weight (ΔΔ g, right panels) in the diet-induced-obese rat model of obesity. The upper panels correspond to repeated administrations of the PYY analog A24 alone, while the lower panels correspond to combined administrations of the PYY analog A24 and a long acting GLP-1 receptor agonist.

Example 7b: Weight-Gain Efficacy of PYY Analog Administered Alone in LE DIO Rats The experiments described in Example 7a where responses to a long-acting PYY agonist in combination with a long-acting GLP-1 agonist were analyzed were separately analyzed in LE DIO rats that received a long-acting PYY agonist (compound A24; SEQ ID NO: 24) alone. Surprisingly, in contrast to the synergistic reduction in food intake and synergistic weight loss of the combination of compound A24 (SEQ ID NO: 24) and the long acting GLP-1 receptor agonist shown as the lower panels in FIG. 8, the PYY agonist alone invoked a dose-dependent increase in food intake and gain in body weight as shown in the upper panels of FIG. 8. A similar pattern of increase in food intake and weight gain was also observed with another long-acting PYY agonist (compound A13; SEQ ID NO: 13) when administered alone. The orexigenic (food intake-stimulating) and weight-gain effects of both PYY agonists (A13 and A24) administered alone contrast with previously-described patterns of weight change with similarly-selective (Y2) PYY agonists. This is the first example of an agent, orexigenic on its own, that when combined with a GLP-1 agonist, promotes an anorectic effect more profound than that observed with the GLP-1 agonist on its own.

The orexigenic effect of SEQ ID NO: 13 and SEQ ID NO: 24 is not easily ascribed to the long duration of effect per se of these peptides. Other selective PYY agonists whose duration of effect was enhanced by, for example, PEGylation or by linking to Fmoc exhibited only anorectic effects and not orexigenic effects. Similarly, the orexigenic effects of these peptides are not easily ascribed to albumin-binding per se, since PYY-albumin conjugates do not exhibit this effect and are only anorectic. Nor have acylated PYY agonists that reversibly bind albumin been previously reported to stimulate food intake and weight gain.

The orexigenic effect of the class of PYY agonists typified by compounds A13 and A24 (see upper left panel of FIG. 8) will be useful in certain conditions of pathogenic weight loss or loss of body energy content. Examples of such conditions include anorexia nervosa, a condition for which there are few pharmacologic options, and which is associated with ~10% mortality, principally in young people. Other examples include forms of cachexia, associated with, and complicating the treatment of malignancy. Another example is "frailty", or the malnutrition of aging. The component of this condition represented by loss of muscle mass, termed sarcopenia, has been implicated in multiple age-related morbidities and degradation of quality of life, including loss of mobility, propensity of major bone fracture, and slow recovery of such fractures.

Figure 9:
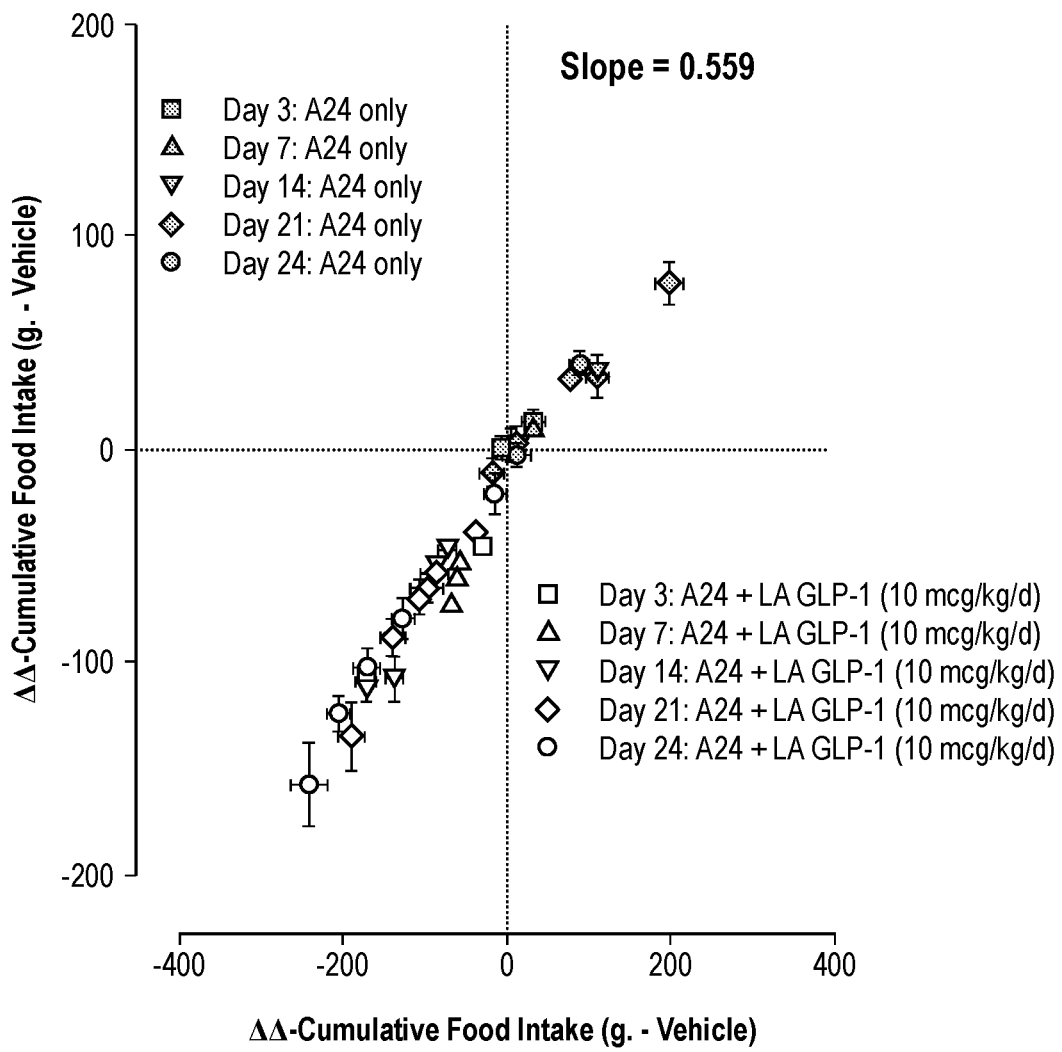
FIG. 9 replots the Y-dimension data from FIG. 8 on XY axes. Changes in body weight (ΔΔ g, Y-axis) are plotted as a function of changes in food intake (ΔΔ g, X-axis). The good fit of the relationship ($R^2$ 0.82) indicates that effects on food intake are highly predictive of effects on body weight. The slope of the relationship indicates, in this animal model, that any given change in cumulative food intake (increase or decrease) over a given period will result in a corresponding change in body weight approximately 56% as great.

Such therapeutically useful weight gain effects of the class of PYY agonists typified by compounds A13 and A24 (see upper right panel of FIG. 8 and upper right quadrant of FIG. 9) can be invoked with these agents administered singly, or in combination with other agents that invoke beneficial effects via separate mechanisms. Examples of separate beneficial agents include orexigenic agents, such as ghrelin and/or motilin agonists, or agents that promote muscle growth, such as anabolic steroids and activators of the growth hormone/inulin-like growth factor axis. Combinations that are beneficial for the abovementioned conditions do not include a PYY agonist typified by compounds A13 and A24 in association with a GLP-1 receptor agonist, since such a combination is associated with loss of body weight (lower panels of FIG. 8 and lower left quadrant of FIG. 9).

Figure 2:
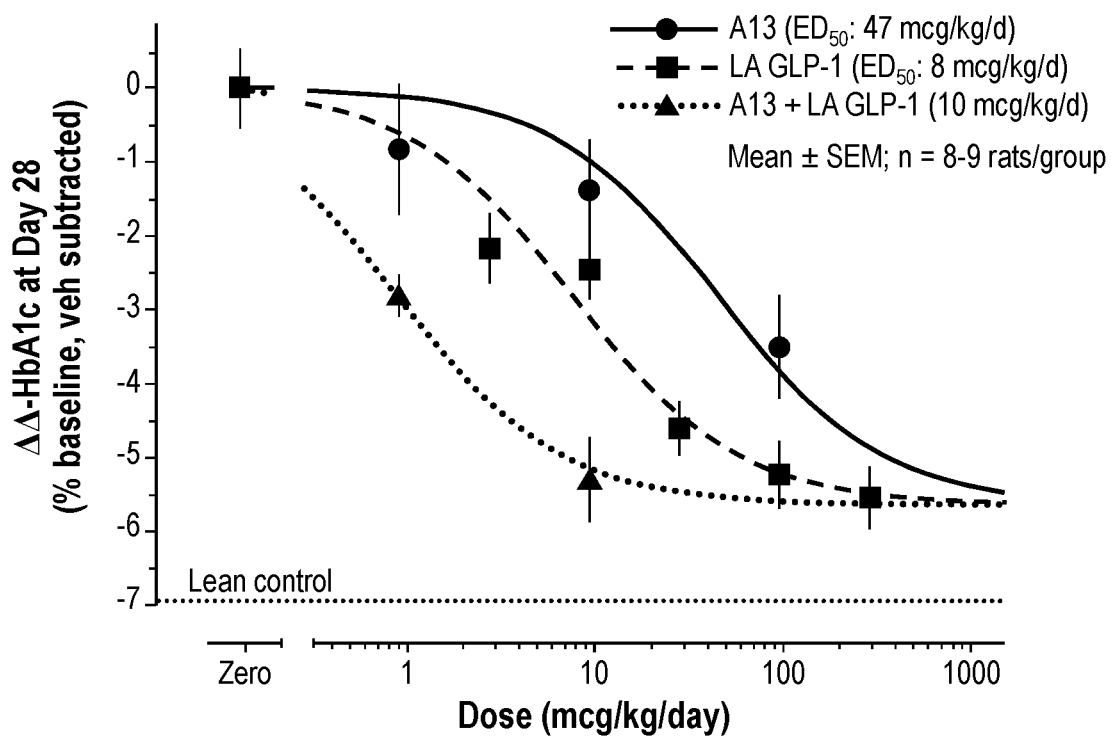
FIG. 2 depicts mean HbA1c (%) from baseline and vehicle control (ΔΔ %) of a long acting PYY analog in combination with a long acting GLP-1 analog
Figure 3:
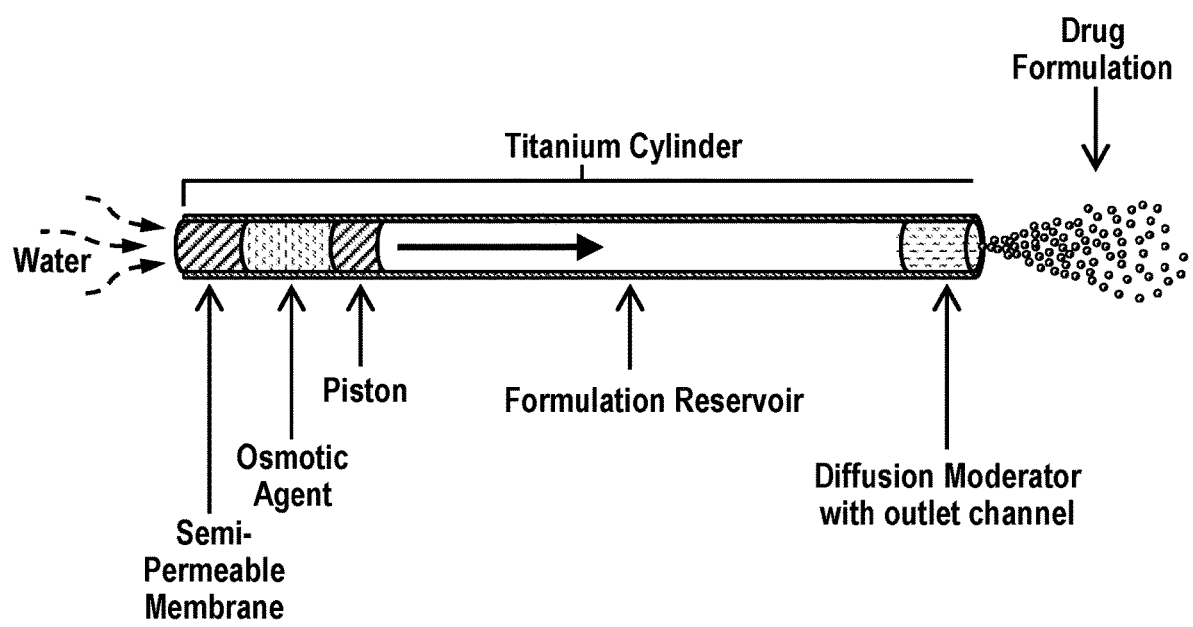
FIG. 3 depicts a cross-sectional diagram of a representative osmotic mini-pump for drug delivery.
Figure 7:
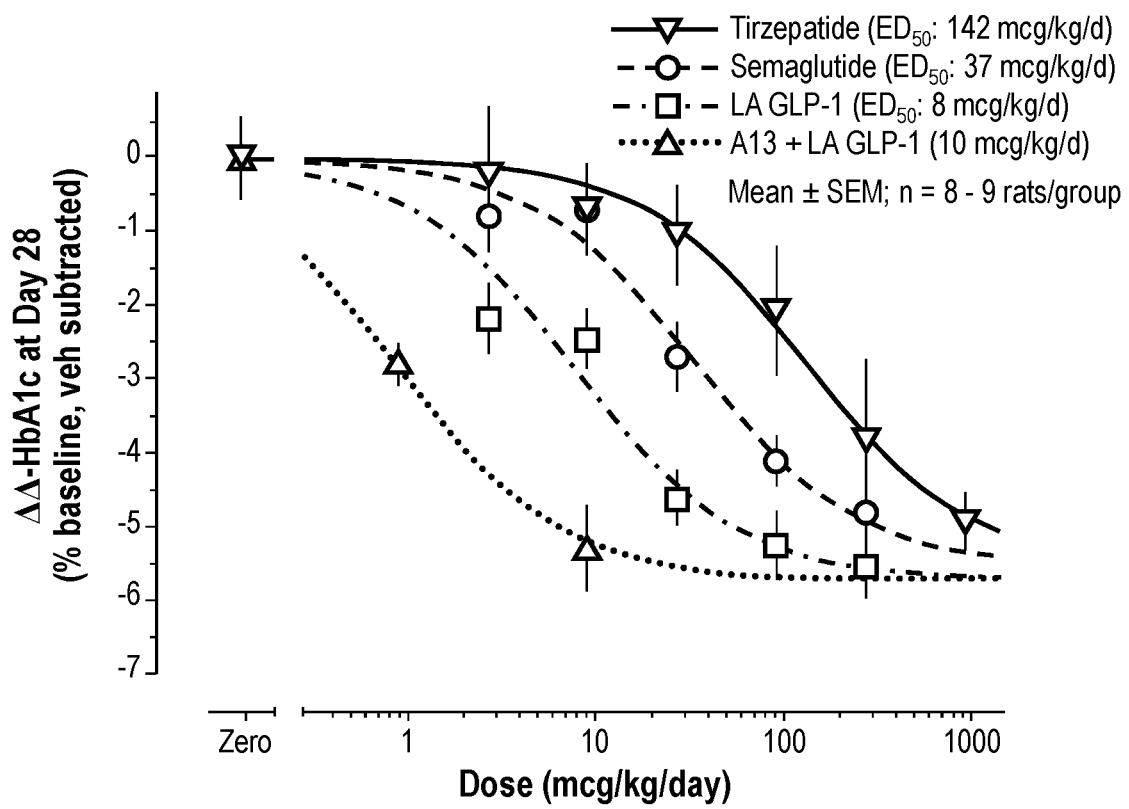
FIG. 7 is a graph depicting the antidiabetic effect in a Zucker diabetic fatty (ZDF) rat model of type 2 diabetes and highlighting that the combination of the PYY analog peptide A13 with a long acting GLP-1 receptor agonist is significantly more effective and potent than tirzepatide and semaglutide alone.

Example 8: Anti-Diabetic Efficacy PYY Analogs in in Combination with a GLP-1 Agonist in ZDF Rats Chronic studies were conducted to determine the antidiabetic effects of continuous administration of a PYY analog polypeptide in combination with a GLP-1 receptor agonist on HbA1c (a primary anti-diabetic parameter) after 27 days of treatment in Zucker Diabetic Fatty (ZDF) rats. Male ZDF rats were obtained at six (6) weeks of age (Charles River, Raleigh, NC) and used on study at eight (8) weeks old. Upon receipt, the rats were housed one animal per cage with free access to Purina 5008 chow (Lab Diet, St. Louis, MO) and water, maintained on a 12-hour light/dark cycle from 5:00 AM to 5:00 PM at 21° C. and 50% relative humidity and allowed to acclimate for nine (9) days before the start of the study. Blood samples were taken as pre-bleeds (Day −3) via tail vein to measure glucose levels and HbA1c. The ZDF rats were randomized into treatment groups (n=10/group) with similar mean HbA1c and glucose. They were subcutaneously (SC) implanted with Alzet osmotic mini-pumps (two (2) pumps/animal) containing either specified doses of PYY analog polypeptide and/or GLP-1 receptor agonist (10 mcg/kg/day) or vehicle (20% DMSO in water) (n=10 animals/treatment group). PYY analog whose PK supported every other day dosing were dosed by SC injection instead of mini-pump administration. All other procedures were the same as described for previous example. Blood samples were taken again on Days 14 and 27 (end of study) to measure glucose levels and HbA1c. Final whole blood samples were collected by cardiac puncture under isoflurane anesthesia (Day 27). HbA1c analysis was performed by using a Carolina Chemistries CLC720i Clinical Chemistry analyzer (Mindray Inc., Mahwah, NY) with the protocol and method parameters as described by the manufacturer. HbA1c results expressed as the mean % change from baseline and vehicle control (AA) from the chronic combination studies of Compound A13 (SEQ ID NO: 13) with the GLP-1 receptor agonist are shown in FIG. 2. Comparative data with respect to tirzepatide and semaglutide is provided in FIG. 7.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

```
Sequence total quantity: 814
SEQ ID NO: 1            moltype = AA  length = 34
FEATURE                 Location/Qualifiers
```

```
REGION                  1..34
                        note = Description of Artificial Sequence: Synthetic
                         polypeptide
source                  1..34
                        mol_type = protein
                        organism = synthetic construct
SEQUENCE: 1
PKPEAPGKDA SPEEWNRYYA DLRHYLNWLT RQRY                                     34

SEQ ID NO: 2            moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 2
PKPEAPGKDA SPEEWNRYYA DLRHYLNWLT RQRY                                     34

SEQ ID NO: 3            moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 3
PKPEAPGKDA SPEEWNRYYA DLRHYLNWLT RQRY                                     34

SEQ ID NO: 4            moltype = AA  length = 35
FEATURE                 Location/Qualifiers
REGION                  1..35
                        note = Description of Artificial Sequence: Synthetic
                         polypeptide
MOD_RES                 35
                        note = n-methyl Tyrosine
source                  1..35
                        mol_type = protein
                        organism = synthetic construct
SEQUENCE: 4
KPKPEAPGKD ASPEEWNRYY ADARHYLNWL TRQRY                                    35

SEQ ID NO: 5            moltype = AA  length = 34
FEATURE                 Location/Qualifiers
REGION                  1..34
                        note = Description of Artificial Sequence: Synthetic
                         polypeptide
MOD_RES                 34
                        note = n-methyl Tyrosine
source                  1..34
                        mol_type = protein
                        organism = synthetic construct
SEQUENCE: 5
PKPEAPGKDA SPEEWNRYYA DARHYLNWLT RQRY                                     34

SEQ ID NO: 6            moltype = AA  length = 34
FEATURE                 Location/Qualifiers
REGION                  1..34
                        note = Description of Artificial Sequence: Synthetic
                         polypeptide
MOD_RES                 34
                        note = n-methyl Tyrosine
source                  1..34
                        mol_type = protein
                        organism = synthetic construct
SEQUENCE: 6
PKPKAPGKDA SPEEWNRYYA DARHYLNWLT RQRY                                     34

SEQ ID NO: 7            moltype = AA  length = 34
FEATURE                 Location/Qualifiers
REGION                  1..34
                        note = Description of Artificial Sequence: Synthetic
                         polypeptide
MOD_RES                 34
                        note = n-methyl Tyrosine
source                  1..34
                        mol_type = protein
```

-continued

```
                          organism = synthetic construct
SEQUENCE: 7
PKPEAPKKDA SPEEWNRYYA DARHYLNWLT RQRY                               34

SEQ ID NO: 8              moltype = AA   length = 34
FEATURE                   Location/Qualifiers
REGION                    1..34
                          note = Description of Artificial Sequence: Synthetic
                           polypeptide
MOD_RES                   34
                          note = n-methyl Tyrosine
source                    1..34
                          mol_type = protein
                          organism = synthetic construct
SEQUENCE: 8
PKPEAPGKDA SPKEWNRYYA DARHYLNWLT RQRY                               34

SEQ ID NO: 9              moltype = AA   length = 34
FEATURE                   Location/Qualifiers
REGION                    1..34
                          note = Description of Artificial Sequence: Synthetic
                           polypeptide
MOD_RES                   34
                          note = n-methyl Tyrosine
source                    1..34
                          mol_type = protein
                          organism = synthetic construct
SEQUENCE: 9
PKPEAPGKDA SPEEWKRYYA DARHYLNWLT RQRY                               34

SEQ ID NO: 10             moltype = AA   length = 34
FEATURE                   Location/Qualifiers
REGION                    1..34
                          note = Description of Artificial Sequence: Synthetic
                           polypeptide
MOD_RES                   34
                          note = n-methyl Tyrosine
source                    1..34
                          mol_type = protein
                          organism = synthetic construct
SEQUENCE: 10
PKPEAPGKDA SPEEWNRYYA DLRHYLNWLT RQRY                               34

SEQ ID NO: 11             moltype = AA   length = 34
FEATURE                   Location/Qualifiers
REGION                    1..34
                          note = Description of Artificial Sequence: Synthetic
                           polypeptide
MOD_RES                   34
                          note = Homotyrosine
source                    1..34
                          mol_type = protein
                          organism = synthetic construct
SEQUENCE: 11
PKPEAPGKDA SPEEWNRYYA DLRHYLNWLT RQRY                               34

SEQ ID NO: 12             moltype = AA   length = 34
FEATURE                   Location/Qualifiers
REGION                    1..34
                          note = Description of Artificial Sequence: Synthetic
                           polypeptide
SITE                      34
                          note = D-Tyrosine
source                    1..34
                          mol_type = protein
                          organism = synthetic construct
SEQUENCE: 12
PKPEAPGKDA SPEEWNRYYA DLRHYLNWLT RQRY                               34

SEQ ID NO: 13             moltype = AA   length = 34
FEATURE                   Location/Qualifiers
REGION                    1..34
                          note = Description of Artificial Sequence: Synthetic
                           polypeptide
source                    1..34
                          mol_type = protein
                          organism = synthetic construct
SEQUENCE: 13
PKPEAPGKDA SPEEWNRYYA DLRHYLNWLT RQRF                               34
```

```
SEQ ID NO: 14            moltype = AA  length = 34
FEATURE                  Location/Qualifiers
REGION                   1..34
                         note = Description of Artificial Sequence: Synthetic
                         polypeptide
SITE                     20
                         note = D-Lysine
source                   1..34
                         mol_type = protein
                         organism = synthetic construct
SEQUENCE: 14
PKPEAPGKDA SPEEWNRYYK DLRHYLNWLT RQRF                                   34

SEQ ID NO: 15            moltype = AA  length = 34
FEATURE                  Location/Qualifiers
REGION                   1..34
                         note = Description of Artificial Sequence: Synthetic
                         polypeptide
SITE                     8
                         note = D-Lysine
source                   1..34
                         mol_type = protein
                         organism = synthetic construct
SEQUENCE: 15
PKPEAPGKDA SPEEWNRYYA DLRHYLNWLT RQRF                                   34

SEQ ID NO: 16            moltype = AA  length = 34
FEATURE                  Location/Qualifiers
REGION                   1..34
                         note = Description of Artificial Sequence: Synthetic
                         polypeptide
source                   1..34
                         mol_type = protein
                         organism = synthetic construct
SEQUENCE: 16
PKPEAPGKDA SPEEWNRYYK DLRHYLNWLT RQRF                                   34

SEQ ID NO: 17            moltype = AA  length = 34
FEATURE                  Location/Qualifiers
REGION                   1..34
                         note = Description of Artificial Sequence: Synthetic
                         polypeptide
source                   1..34
                         mol_type = protein
                         organism = synthetic construct
SEQUENCE: 17
PKPEAPGKDA SPEEWNRYYA DLRHYLNWLT RQRF                                   34

SEQ ID NO: 18            moltype = AA  length = 34
FEATURE                  Location/Qualifiers
REGION                   1..34
                         note = Description of Artificial Sequence: Synthetic
                         polypeptide
SITE                     8
                         note = D-Lysine
source                   1..34
                         mol_type = protein
                         organism = synthetic construct
SEQUENCE: 18
PKPEAPGKDA SPEEWNRYYA DLRHYLNWLT RQRF                                   34

SEQ ID NO: 19            moltype = AA  length = 34
FEATURE                  Location/Qualifiers
REGION                   1..34
                         note = Description of Artificial Sequence: Synthetic
                         polypeptide
source                   1..34
                         mol_type = protein
                         organism = synthetic construct
SEQUENCE: 19
PKPEKPGKDA SPEEWNRYYK DLRHYLNWLT RQRF                                   34

SEQ ID NO: 20            moltype = AA  length = 34
FEATURE                  Location/Qualifiers
REGION                   1..34
                         note = Description of Artificial Sequence: Synthetic
                         polypeptide
source                   1..34
```

```
                              mol_type = protein
                              organism = synthetic construct
SEQUENCE: 20
PKPEAPGKDA SPKEWNRYYK DLRHYLNWLT RQRF                                34

SEQ ID NO: 21             moltype = AA  length = 34
FEATURE                   Location/Qualifiers
REGION                    1..34
                          note = Description of Artificial Sequence: Synthetic
                           polypeptide
SITE                      20
                          note = D-Lysine
source                    1..34
                          mol_type = protein
                          organism = synthetic construct
SEQUENCE: 21
PKPEAPGKDA SPEEWNRYYK DLRHYLNWLT RQRF                                34

SEQ ID NO: 22             moltype = AA  length = 34
FEATURE                   Location/Qualifiers
REGION                    1..34
                          note = Description of Artificial Sequence: Synthetic
                           polypeptide
MOD_RES                   20
                          note = Diaminopimelic acid
source                    1..34
                          mol_type = protein
                          organism = synthetic construct
SEQUENCE: 22
PKPEAPGKDA SPEEWNRYYX DLRHYLNWLT RQRF                                34

SEQ ID NO: 23             moltype = AA  length = 34
FEATURE                   Location/Qualifiers
REGION                    1..34
                          note = Description of Artificial Sequence: Synthetic
                           polypeptide
source                    1..34
                          mol_type = protein
                          organism = synthetic construct
SEQUENCE: 23
PKPEAPGKDA SPEEWQRYYK DLRHYLNWLT RQRF                                34

SEQ ID NO: 24             moltype = AA  length = 34
FEATURE                   Location/Qualifiers
REGION                    1..34
                          note = Description of Artificial Sequence: Synthetic
                           polypeptide
source                    1..34
                          mol_type = protein
                          organism = synthetic construct
SEQUENCE: 24
PKPEAPGKDA SPEEWDRYYK DLRHYLNWLT RQRF                                34

SEQ ID NO: 25             moltype = AA  length = 34
FEATURE                   Location/Qualifiers
REGION                    1..34
                          note = Description of Artificial Sequence: Synthetic
                           polypeptide
source                    1..34
                          mol_type = protein
                          organism = synthetic construct
SEQUENCE: 25
PKPEAPGKDA SPEEWSRYYK DLRHYLNWLT RQRF                                34

SEQ ID NO: 26             moltype = AA  length = 34
FEATURE                   Location/Qualifiers
REGION                    1..34
                          note = Description of Artificial Sequence: Synthetic
                           polypeptide
source                    1..34
                          mol_type = protein
                          organism = synthetic construct
SEQUENCE: 26
PKPEAPGKDA SPEEWTRYYK DLRHYLNWLT RQRF                                34

SEQ ID NO: 27             moltype = AA  length = 34
FEATURE                   Location/Qualifiers
REGION                    1..34
                          note = Description of Artificial Sequence: Synthetic
```

```
                            polypeptide
source                      1..34
                            mol_type = protein
                            organism = synthetic construct
SEQUENCE: 27
PKPEKPGKDA SPKEWNRYYK DLRHYLNWLT RQRF                                   34

SEQ ID NO: 28               moltype = AA  length = 34
FEATURE                     Location/Qualifiers
REGION                      1..34
                            note = Description of Artificial Sequence: Synthetic
                             polypeptide
source                      1..34
                            mol_type = protein
                            organism = synthetic construct
SEQUENCE: 28
PKPEKPGKDA SPKEWNRYYK DLRHYLNWLT RQRF                                   34

SEQ ID NO: 29               moltype = AA  length = 34
FEATURE                     Location/Qualifiers
REGION                      1..34
                            note = Description of Artificial Sequence: Synthetic
                             polypeptide
source                      1..34
                            mol_type = protein
                            organism = synthetic construct
SEQUENCE: 29
PKPEKPGEDA SPKEWNRYYK DLRHYLNWLT RQRF                                   34

SEQ ID NO: 30               moltype = AA  length = 34
FEATURE                     Location/Qualifiers
REGION                      1..34
                            note = Description of Artificial Sequence: Synthetic
                             polypeptide
MOD_RES                     16
                            note = homoSer
source                      1..34
                            mol_type = protein
                            organism = synthetic construct
SEQUENCE: 30
PKPEAPGKDA SPEEWSRYYK DLRHYLNWLT RQRF                                   34

SEQ ID NO: 31               moltype = AA  length = 34
FEATURE                     Location/Qualifiers
REGION                      1..34
                            note = Description of Artificial Sequence: Synthetic
                             polypeptide
MOD_RES                     16
                            note = alpha-methyl-Ser
source                      1..34
                            mol_type = protein
                            organism = synthetic construct
SEQUENCE: 31
PKPEAPGKDA SPEEWSRYYK DLRHYLNWLT RQRF                                   34

SEQ ID NO: 32               moltype = AA  length = 34
FEATURE                     Location/Qualifiers
REGION                      1..34
                            note = Description of Artificial Sequence: Synthetic
                             polypeptide
source                      1..34
                            mol_type = protein
                            organism = synthetic construct
SEQUENCE: 32
PKPEAPGKDA SPEEWDRYYK DLRHYLNWLT RQRF                                   34

SEQ ID NO: 33               moltype = AA  length = 34
FEATURE                     Location/Qualifiers
REGION                      1..34
                            note = Description of Artificial Sequence: Synthetic
                             polypeptide
source                      1..34
                            mol_type = protein
                            organism = synthetic construct
SEQUENCE: 33
PKPEAPGKDA SPEEWDRYYK DLRHYLNWLT RQRF                                   34

SEQ ID NO: 34               moltype = AA  length = 34
FEATURE                     Location/Qualifiers
```

```
REGION                  1..34
                        note = Description of Artificial Sequence: Synthetic
                         polypeptide
source                  1..34
                        mol_type = protein
                        organism = synthetic construct
SEQUENCE: 34
PKPEKPGEDA SPKEWDRYYK DLRHYLNWLT RQRF                                        34

SEQ ID NO: 35           moltype = AA   length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 35
PKPEKPGEDA SPKEWDRYYK DLRHYLNWLT RQRF                                        34

SEQ ID NO: 36           moltype = AA   length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 36
PKPEKPGEDA SPKEWNRYYK DLRHYLNWLT RQRF                                        34

SEQ ID NO: 37           moltype = AA   length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 37
PKPEKPGKDA SPKEWNRYYK DLRHYLNWLT RQRF                                        34

SEQ ID NO: 38           moltype = AA   length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 38
PKPEKPGEDA SPKEWNRYYK DLRHYLNWLT RQRF                                        34

SEQ ID NO: 39           moltype = AA   length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 39
PKPEKPGKDA SPKEWERYYK DLRHYLNWLT RQRF                                        34

SEQ ID NO: 40           moltype = AA   length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 40
PKPEKPGKDA SPKEWDRYYK DLRHYLNWLT RQRF                                        34

SEQ ID NO: 41           moltype = AA   length = 34
FEATURE                 Location/Qualifiers
REGION                  1..34
                        note = Description of Artificial Sequence: Synthetic
```

```
                            polypeptide
source                      1..34
                            mol_type = protein
                            organism = synthetic construct
SEQUENCE: 41
PKPEAPGKDA SPEEWERYYK DLRHYLNWLT RQRF                                  34

SEQ ID NO: 42               moltype = AA  length = 34
FEATURE                     Location/Qualifiers
REGION                      1..34
                            note = Description of Artificial Sequence: Synthetic
                            polypeptide
source                      1..34
                            mol_type = protein
                            organism = synthetic construct
SEQUENCE: 42
PKPEAPGKDA SPEEWDRYYK DLRHYLNWLT RQRF                                  34

SEQ ID NO: 43               moltype = AA  length = 34
FEATURE                     Location/Qualifiers
REGION                      1..34
                            note = Description of Artificial Sequence: Synthetic
                            polypeptide
source                      1..34
                            mol_type = protein
                            organism = synthetic construct
SEQUENCE: 43
PKPEAPGKDA SPEEWKRYYE DLRHYLNWLT RQRF                                  34

SEQ ID NO: 44               moltype = AA  length = 34
FEATURE                     Location/Qualifiers
REGION                      1..34
                            note = Description of Artificial Sequence: Synthetic
                            polypeptide
source                      1..34
                            mol_type = protein
                            organism = synthetic construct
SEQUENCE: 44
PKPEAPGKDA SPEEWKRYYD DLRHYLNWLT RQRF                                  34

SEQ ID NO: 45               moltype = AA  length = 34
FEATURE                     Location/Qualifiers
REGION                      1..34
                            note = Description of Artificial Sequence: Synthetic
                            polypeptide
source                      1..34
                            mol_type = protein
                            organism = synthetic construct
SEQUENCE: 45
PKPEAPGKDA SPKEWDRYYK DLRHYLNWLT RQRF                                  34

SEQ ID NO: 46               moltype = AA  length = 34
FEATURE                     Location/Qualifiers
REGION                      1..34
                            note = Description of Artificial Sequence: Synthetic
                            polypeptide
source                      1..34
                            mol_type = protein
                            organism = synthetic construct
SEQUENCE: 46
PKPEAPGKKA SPEEWDRYYK DLRHYLNWLT RQRF                                  34

SEQ ID NO: 47               moltype = AA  length = 34
FEATURE                     Location/Qualifiers
REGION                      1..34
                            note = Description of Artificial Sequence: Synthetic
                            polypeptide
source                      1..34
                            mol_type = protein
                            organism = synthetic construct
SEQUENCE: 47
PKPEAPGKDA SPEEWDRYYK DDRHYKNWLT RQRF                                  34

SEQ ID NO: 48               moltype = AA  length = 34
FEATURE                     Location/Qualifiers
REGION                      1..34
                            note = Description of Artificial Sequence: Synthetic
                            polypeptide
source                      1..34
```

```
                           mol_type = protein
                           organism = synthetic construct
SEQUENCE: 48
PKPEAPGKDA SPEEWDRYYK DKRHYENWLT RQRF                                 34

SEQ ID NO: 49              moltype = AA   length = 34
FEATURE                    Location/Qualifiers
REGION                     1..34
                           note = Description of Artificial Sequence: Synthetic
                             polypeptide
MOD_RES                    34
                           note = Beta-homo-Tyr
source                     1..34
                           mol_type = protein
                           organism = synthetic construct
SEQUENCE: 49
PKPEAPGKDA SPEEWNRYYA DLRHYLNWLT RQRY                                 34

SEQ ID NO: 50              moltype = AA   length = 34
FEATURE                    Location/Qualifiers
REGION                     1..34
                           note = Description of Artificial Sequence: Synthetic
                             polypeptide
source                     1..34
                           mol_type = protein
                           organism = synthetic construct
SEQUENCE: 50
PKPEAPGKDA SPEEWNRYYA DLRHYLNWLT RKRF                                 34

SEQ ID NO: 51              moltype = AA   length = 34
FEATURE                    Location/Qualifiers
REGION                     1..34
                           note = Description of Artificial Sequence: Synthetic
                             polypeptide
source                     1..34
                           mol_type = protein
                           organism = synthetic construct
SEQUENCE: 51
PKPEAPGKDA SPEEWNRYYA DLRHYLKWLT RQRF                                 34

SEQ ID NO: 52              moltype = AA   length = 34
FEATURE                    Location/Qualifiers
REGION                     1..34
                           note = Description of Artificial Sequence: Synthetic
                             polypeptide
source                     1..34
                           mol_type = protein
                           organism = synthetic construct
SEQUENCE: 52
PKPEAPGKDA SPEEWNRYYA DLRHKLNWLT RQRF                                 34

SEQ ID NO: 53              moltype = AA   length = 34
FEATURE                    Location/Qualifiers
REGION                     1..34
                           note = Description of Artificial Sequence: Synthetic
                             polypeptide
source                     1..34
                           mol_type = protein
                           organism = synthetic construct
SEQUENCE: 53
PKPEAPGKDA SPEEWNRYYA DLKHYLNWLT RQRF                                 34

SEQ ID NO: 54              moltype = AA   length = 34
FEATURE                    Location/Qualifiers
REGION                     1..34
                           note = Description of Artificial Sequence: Synthetic
                             polypeptide
source                     1..34
                           mol_type = protein
                           organism = synthetic construct
SEQUENCE: 54
PKPEAPGKDA SPEEWNRYYK DLRHYLNWLT RQRF                                 34

SEQ ID NO: 55              moltype = AA   length = 34
FEATURE                    Location/Qualifiers
REGION                     1..34
                           note = Description of Artificial Sequence: Synthetic
                             polypeptide
source                     1..34
```

```
                            mol_type = protein
                            organism = synthetic construct
SEQUENCE: 55
PKPEAPGKDA SPEEWKRYYA DLRHYLNWLT RQRF                                          34

SEQ ID NO: 56               moltype = AA   length = 34
FEATURE                     Location/Qualifiers
REGION                      1..34
                            note = Description of Artificial Sequence: Synthetic
                             polypeptide
MOD_RES                     34
                            note = 4-pyridylAla
source                      1..34
                            mol_type = protein
                            organism = synthetic construct
SEQUENCE: 56
PKPEAPGKDA SPEEWNRYYA DLRHYLNWLT RQRA                                          34

SEQ ID NO: 57               moltype = AA   length = 34
FEATURE                     Location/Qualifiers
REGION                      1..34
                            note = Description of Artificial Sequence: Synthetic
                             polypeptide
MOD_RES                     34
                            note = 3-pyridylAla
source                      1..34
                            mol_type = protein
                            organism = synthetic construct
SEQUENCE: 57
PKPEAPGKDA SPEEWNRYYA DLRHYLNWLT RQRA                                          34

SEQ ID NO: 58               moltype = AA   length = 34
FEATURE                     Location/Qualifiers
REGION                      1..34
                            note = Description of Artificial Sequence: Synthetic
                             polypeptide
MOD_RES                     34
                            note = 4-methylPhe
source                      1..34
                            mol_type = protein
                            organism = synthetic construct
SEQUENCE: 58
PKPEAPGKDA SPEEWNRYYA DLRHYLNWLT RQRF                                          34

SEQ ID NO: 59               moltype = AA   length = 34
FEATURE                     Location/Qualifiers
REGION                      1..34
                            note = Description of Artificial Sequence: Synthetic
                             polypeptide
MOD_RES                     34
                            note = 4-carboxyPhe
source                      1..34
                            mol_type = protein
                            organism = synthetic construct
SEQUENCE: 59
PKPEAPGKDA SPEEWNRYYA DLRHYLNWLT RQRF                                          34

SEQ ID NO: 60               moltype = AA   length = 34
FEATURE                     Location/Qualifiers
REGION                      1..34
                            note = Description of Artificial Sequence: Synthetic
                             polypeptide
MOD_RES                     34
                            note = 4-fluoroPhe
source                      1..34
                            mol_type = protein
                            organism = synthetic construct
SEQUENCE: 60
PKPEAPGKDA SPEEWNRYYA DLRHYLNWLT RQRF                                          34

SEQ ID NO: 61               moltype = AA   length = 34
FEATURE                     Location/Qualifiers
REGION                      1..34
                            note = Description of Artificial Sequence: Synthetic
                             polypeptide
MOD_RES                     34
                            note = Homo-Phe
source                      1..34
                            mol_type = protein
```

```
                        organism = synthetic construct
SEQUENCE: 61
PKPEAPGKDA SPEEWNRYYA DLRHYLNWLT RQRF                                34

SEQ ID NO: 62           moltype = AA   length = 34
FEATURE                 Location/Qualifiers
REGION                  1..34
                        note = Description of Artificial Sequence: Synthetic
                         polypeptide
MOD_RES                 34
                        note = n-methylPhe
source                  1..34
                        mol_type = protein
                        organism = synthetic construct
SEQUENCE: 62
PKPEAPGKDA SPEEWNRYYA DLRHYLNWLT RQRF                                34

SEQ ID NO: 63           moltype = AA   length = 34
FEATURE                 Location/Qualifiers
REGION                  1..34
                        note = Description of Artificial Sequence: Synthetic
                         polypeptide
MOD_RES                 34
                        note = n-methylTyr
source                  1..34
                        mol_type = protein
                        organism = synthetic construct
SEQUENCE: 63
PKPEAPKKDA SPEELNRYYA DARHYLNWLT RQRY                                34

SEQ ID NO: 64           moltype = AA   length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 64
PKPEAPKKDA SPEELNRYYA DARHYLNWLT RQRF                                34

SEQ ID NO: 65           moltype = AA   length = 34
FEATURE                 Location/Qualifiers
REGION                  1..34
                        note = Description of Artificial Sequence: Synthetic
                         polypeptide
SITE                    20
                        note = D-Lysine
source                  1..34
                        mol_type = protein
                        organism = synthetic construct
SEQUENCE: 65
PKPEAPGKDA SPEEWNRYYK DLRHYLNWLT RQRF                                34

SEQ ID NO: 66           moltype = AA   length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 66
PKPEAPGKDK SPEEWNRYYK DLRHYLNWLT RQRF                                34

SEQ ID NO: 67           moltype = AA   length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 67
PKPEAPGKDA SPEKWNRYYK DLRHYLNWLT RQRF                                34

SEQ ID NO: 68           moltype = AA   length = 34
FEATURE                 Location/Qualifiers
REGION                  1..34
```

```
                        note = Description of Artificial Sequence: Synthetic
                         polypeptide
source                  1..34
                        mol_type = protein
                        organism = synthetic construct
SEQUENCE: 68
PKPEAPGKDA SPEEWNRKYK DLRHYLNWLT RQRF                              34

SEQ ID NO: 69           moltype = AA   length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 69
PKPEAPGKDA SPEEWNRYKK DLRHYLNWLT RQRF                              34

SEQ ID NO: 70           moltype = AA   length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 70
PKPEKPGKDA SPKEWNRYYK DLRHYLNWLT RQRF                              34

SEQ ID NO: 71           moltype = AA   length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 71
PKPEKPGKDA SPKEWNRYYK DLRHYLNWLT RQRF                              34

SEQ ID NO: 72           moltype = AA   length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 72
PKPEKPGEDA SPKEWNRYYK DLRHYLNWLT RQRF                              34

SEQ ID NO: 73           moltype = AA   length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 73
PKPEAPGKDA SPKEWNRYYK DLRHYLNWLT RQRF                              34

SEQ ID NO: 74           moltype = AA   length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 74
PKPEKPGKDA SPKEWNRYYK DLRHYLNWLT RQRF                              34

SEQ ID NO: 75           moltype = AA   length = 34
FEATURE                 Location/Qualifiers
REGION                  1..34
                        note = Description of Artificial Sequence: Synthetic
                         polypeptide
```

```
source                  1..34
                        mol_type = protein
                        organism = synthetic construct
SEQUENCE: 75
PKPEKPGKDA SPEEWSRYYK DLRHYLNWLT RQRF                                    34

SEQ ID NO: 76           moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 76
PKPEAPGKDA SPKEWDRYYK DLRHYLNWLT RQRF                                    34

SEQ ID NO: 77           moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 77
PKPEKPGEDA SPEEWDRYYK DLRHYLNWLT RQRF                                    34

SEQ ID NO: 78           moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 78
PKPEKPGEDA SPKEWDRYYK DLRHYLNWLT RQRF                                    34

SEQ ID NO: 79           moltype =    length =
SEQUENCE: 79
000

SEQ ID NO: 80           moltype =    length =
SEQUENCE: 80
000

SEQ ID NO: 81           moltype =    length =
SEQUENCE: 81
000

SEQ ID NO: 82           moltype =    length =
SEQUENCE: 82
000

SEQ ID NO: 83           moltype =    length =
SEQUENCE: 83
000

SEQ ID NO: 84           moltype =    length =
SEQUENCE: 84
000

SEQ ID NO: 85           moltype =    length =
SEQUENCE: 85
000

SEQ ID NO: 86           moltype =    length =
SEQUENCE: 86
000

SEQ ID NO: 87           moltype =    length =
SEQUENCE: 87
000

SEQ ID NO: 88           moltype =    length =
SEQUENCE: 88
000
```

| | | |
|---|---|---|
| SEQ ID NO: 89<br>SEQUENCE: 89<br>000 | moltype = length = | |
| SEQ ID NO: 90<br>FEATURE<br>REGION | moltype = AA length = 35<br>Location/Qualifiers<br>1..35<br>note = Description of Artificial Sequence: Synthetic<br>polypeptide | |
| VARIANT | 1<br>note = X can be K or absent | |
| VARIANT | 5<br>note = X can be E or K | |
| VARIANT | 6<br>note = X can be A or K | |
| VARIANT | 8<br>note = X can be G or K | |
| VARIANT | 9<br>note = X can be E, K, or D-Lysine | |
| VARIANT | 10<br>note = X can be D or K | |
| VARIANT | 11<br>note = X can be A or K | |
| VARIANT | 14<br>note = X can be E or K | |
| VARIANT | 15<br>note = X can be E or K | |
| VARIANT | 16<br>note = X can be L or W | |
| VARIANT | 17<br>note = X can be D, E, K, N, Q, S, T, alpha-methylserine,<br>homoserine, homotyrosine, or N-methyltyrosine | |
| VARIANT | 19<br>note = X can be K or Y | |
| VARIANT | 20<br>note = X can be K or Y | |
| VARIANT | 21<br>note = X can be A, D, E, K, D-Lysine, or Diaminopimelic acid | |
| VARIANT | 23<br>note = X can be A, D, K, or L | |
| VARIANT | 24<br>note = X can be K or R | |
| VARIANT | 26<br>note = X can be K or Y | |
| VARIANT | 27<br>note = X can be E, K, or L | |
| VARIANT | 28<br>note = X can be K or N | |
| VARIANT | 33<br>note = X can be K or Q | |
| VARIANT | 35<br>note = X can be F, y, 3-pyridinylalanine,<br>4-pyridinylalanine, 4-carboxyphenylalanine,<br>4-fluorophenylalanine, 4-methylphenylalanine,<br>N-methylphenylalanine, homophenylalanine,<br>beta-homotyrosine,homotyrosine, or N-methyltyrosine | |
| REGION | 1..35<br>note = See specification as filed for detailed description<br>of substitutions and preferred embodiments | |
| source | 1..35<br>mol_type = protein<br>organism = synthetic construct | |
| SITE | 9<br>note = D-Lysine | |
| SITE | 21<br>note = D-Lysine | |
| MOD_RES | 17<br>note = Alpha-methylserine, homoserine, homotyrosine, or<br>N-methyltyrosine | |
| MOD_RES | 35<br>note = 3-pyridinylalanine, 4-pyridinylalanine,<br>4-carboxyphenylalanine, 4-fluorophenylalanine,<br>4-methylphenylalanine, N-methylphenylalanine,<br>homophenylalanine, beta-homotyrosine,homotyrosine, or<br>N-methyltyrosine | |
| MOD_RES | 21<br>note = Diaminopimelic acid | |
| SEQUENCE: 90<br>XPKPXXPXXX XSPXXXXRXX XDXXHXXXWL TRXRX | | 35 |

```
SEQ ID NO: 91            moltype = AA  length = 34
FEATURE                  Location/Qualifiers
REGION                   1..34
                         note = Description of Artificial Sequence: Synthetic
                          polypeptide
VARIANT                  5
                         note = X can be A or K
VARIANT                  7
                         note = X can be G or K
VARIANT                  8
                         note = X can be E, K, or D-Lysine
VARIANT                  13
                         note = X can be E or K
VARIANT                  15
                         note = X can be L or W
VARIANT                  16
                         note = X can be D, E, K, N, S, alpha-methylserine, or
                          homoserine
VARIANT                  20
                         note = X can be A, D, E, K, or D-Lysine
VARIANT                  22
                         note = X can be A or L
VARIANT                  34
                         note = X can be F, 3-pyridinylalanine, 4-pyridinylalanine,
                          4-carboxyphenylalanine, 4-fluorophenylalanine,
                          4-methylphenylalanine, N-methylphenylalanine,
                          homophenylalanine, beta-homotyrosine, homotyrosine, or
                          N-methyltyrosine
REGION                   1..34
                         note = See specification as filed for detailed description
                          of substitutions and preferred embodiments
source                   1..34
                         mol_type = protein
                         organism = synthetic construct
SITE                     8
                         note = D-Lysine
SITE                     20
                         note = D-Lysine
MOD_RES                  34
                         note = 3-pyridinylalanine, 4-pyridinylalanine,
                          4-carboxyphenylalanine, 4-fluorophenylalanine,
                          4-methylphenylalanine, N-methylphenylalanine,
                          homophenylalanine, beta-homotyrosine, homotyrosine, or
                          N-methyltyrosine
MOD_RES                  16
                         note = Alpha-methylserine, or homoserine
SEQUENCE: 91
PKPEXPXXDA SPXEXXRYYX DXRHYLNWLT RQRX                                        34

SEQ ID NO: 92            moltype = AA  length = 34
FEATURE                  Location/Qualifiers
REGION                   1..34
                         note = Description of Artificial Sequence: Synthetic
                          polypeptide
VARIANT                  5
                         note = X can be A or K
VARIANT                  7
                         note = X can be G or K
VARIANT                  8
                         note = X can be E, K, or D-Lysine
VARIANT                  13
                         note = X can be E or K
VARIANT                  15
                         note = X can be L or W
VARIANT                  16
                         note = X can be D, E, K, S, alpha-methylserine, or
                          homoserine
VARIANT                  20
                         note = X can be A, D, E, K, or D-Lysine
VARIANT                  22
                         note = X can be A or L
VARIANT                  34
                         note = X can be F, 3-pyridinylalanine, 4-pyridinylalanine,
                          4-carboxyphenylalanine, 4-fluorophenylalanine,
                          4-methylphenylalanine, N-methylphenylalanine,
                          homophenylalanine, beta-homotyrosine,homotyrosine, or
                          N-methyltyrosine
REGION                   1..34
```

```
                        note = See specification as filed for detailed description
                         of substitutions and preferred embodiments
source                  1..34
                        mol_type = protein
                        organism = synthetic construct
SITE                    8
                        note = D-Lysine
SITE                    20
                        note = D-Lysine
MOD_RES                 16
                        note = Alpha-methylserine, or homoserine
MOD_RES                 34
                        note = 3-pyridinylalanine, 4-pyridinylalanine,
                         4-carboxyphenylalanine, 4-fluorophenylalanine,
                         4-methylphenylalanine, N-methylphenylalanine,
                         homophenylalanine, beta-homotyrosine,homotyrosine, or
                         N-methyltyrosine
SEQUENCE: 92
PKPEXPXXDA SPXEXXRYYX DXRHYLNWLT RQRX                                       34

SEQ ID NO: 93           moltype = AA  length = 34
FEATURE                 Location/Qualifiers
REGION                  1..34
                        note = Description of Artificial Sequence: Synthetic
                         polypeptide
VARIANT                 5
                        note = X can be A or K
VARIANT                 7
                        note = X can be G or K
VARIANT                 8
                        note = X can be E, K, or D-Lysine
VARIANT                 13
                        note = X can be E or K
VARIANT                 15
                        note = X can be L or W
VARIANT                 16
                        note = X can be D, E, K, N, S, alpha-methylserine, or
                         homoserine
VARIANT                 20
                        note = X can be D, E, K, or D-Lysine
VARIANT                 22
                        note = X can be A or L
VARIANT                 34
                        note = X can be F, 3-pyridinylalanine, 4-pyridinylalanine,
                         4-carboxyphenylalanine, 4-fluorophenylalanine,
                         4-methylphenylalanine, N-methylphenylalanine,
                         homophenylalanine, beta-homotyrosine,homotyrosine, or
                         N-methyltyrosine
REGION                  1..34
                        note = See specification as filed for detailed description
                         of substitutions and preferred embodiments
source                  1..34
                        mol_type = protein
                        organism = synthetic construct
SITE                    8
                        note = D-Lysine
SITE                    20
                        note = D-Lysine
MOD_RES                 16
                        note = Alpha-methylserine, or homoserine
MOD_RES                 34
                        note = 3-pyridinylalanine, 4-pyridinylalanine,
                         4-carboxyphenylalanine, 4-fluorophenylalanine,
                         4-methylphenylalanine, N-methylphenylalanine,
                         homophenylalanine, beta-homotyrosine,homotyrosine, or
                         N-methyltyrosine
SEQUENCE: 93
PKPEXPXXDA SPXEXXRYYX DXRHYLNWLT RQRX                                       34

SEQ ID NO: 94           moltype = AA  length = 34
FEATURE                 Location/Qualifiers
REGION                  1..34
                        note = Description of Artificial Sequence: Synthetic
                         polypeptide
VARIANT                 5
                        note = X can be A or K
VARIANT                 8
                        note = X can be E, K, or D-Lysine
VARIANT                 13
```

```
                        note = X can be E or K
VARIANT                 16
                        note = X can be D, E, K, or N
VARIANT                 20
                        note = X can be A, D, E, K, or D-Lysine
VARIANT                 22
                        note = X can be A or L
VARIANT                 34
                        note = X can be F or N-methyltyrosine
REGION                  1..34
                        note = See specification as filed for detailed description
                         of substitutions and preferred embodiments
source                  1..34
                        mol_type = protein
                        organism = synthetic construct
SITE                    8
                        note = D-Lysine
SITE                    20
                        note = D-Lysine
MOD_RES                 34
                        note = N-methyltyrosine
SEQUENCE: 94
PKPEXPGXDA SPXEWXRYYX DXRHYLNWLT RQRX                                     34

SEQ ID NO: 95           moltype = AA  length = 34
FEATURE                 Location/Qualifiers
REGION                  1..34
                        note = Description of Artificial Sequence: Synthetic
                         polypeptide
VARIANT                 5
                        note = X can be A or K
VARIANT                 13
                        note = X can be E or K
VARIANT                 16
                        note = X can be D, E, K, or N
VARIANT                 20
                        note = X can be A, D, E, K, or D-Lysine
REGION                  1..34
                        note = See specification as filed for detailed description
                         of substitutions and preferred embodiments
source                  1..34
                        mol_type = protein
                        organism = synthetic construct
SITE                    20
                        note = D-Lysine
SEQUENCE: 95
PKPEXPGKDA SPXEWXRYYX DLRHYLNWLT RQRF                                     34

SEQ ID NO: 96           moltype =     length =
SEQUENCE: 96
000

SEQ ID NO: 97           moltype =     length =
SEQUENCE: 97
000

SEQ ID NO: 98           moltype =     length =
SEQUENCE: 98
000

SEQ ID NO: 99           moltype =     length =
SEQUENCE: 99
000

SEQ ID NO: 100          moltype =     length =
SEQUENCE: 100
000

SEQ ID NO: 101          moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 101
PKPEAPGKDA SPEEWNRYYA DLRHYLNWLT RQRY                                     34
```

```
SEQ ID NO: 102          moltype =    length =
SEQUENCE: 102
000

SEQ ID NO: 103          moltype =    length =
SEQUENCE: 103
000

SEQ ID NO: 104          moltype = AA   length = 35
FEATURE                 Location/Qualifiers
REGION                  1..35
                        note = Description of Artificial Sequence: Synthetic
                         polypeptide
MOD_RES                 35
                        note = n-methyl Tyrosine
source                  1..35
                        mol_type = protein
                        organism = synthetic construct
SEQUENCE: 104
KPKPEAPGKD ASPEEWNRYY ADARHYLNWL TRQRY                                      35

SEQ ID NO: 105          moltype = AA   length = 34
FEATURE                 Location/Qualifiers
REGION                  1..34
                        note = Description of Artificial Sequence: Synthetic
                         polypeptide
MOD_RES                 34
                        note = n-methyl Tyrosine
source                  1..34
                        mol_type = protein
                        organism = synthetic construct
SEQUENCE: 105
PKPEAPGKDA SPEEWNRYYA DARHYLNWLT RQRY                                       34

SEQ ID NO: 106          moltype = AA   length = 34
FEATURE                 Location/Qualifiers
REGION                  1..34
                        note = Description of Artificial Sequence: Synthetic
                         polypeptide
MOD_RES                 34
                        note = n-methyl Tyrosine
source                  1..34
                        mol_type = protein
                        organism = synthetic construct
SEQUENCE: 106
PKPKAPGKDA SPEEWNRYYA DARHYLNWLT RQRY                                       34

SEQ ID NO: 107          moltype = AA   length = 34
FEATURE                 Location/Qualifiers
REGION                  1..34
                        note = Description of Artificial Sequence: Synthetic
                         polypeptide
MOD_RES                 34
                        note = n-methyl Tyrosine
source                  1..34
                        mol_type = protein
                        organism = synthetic construct
SEQUENCE: 107
PKPEAPKKDA SPEEWNRYYA DARHYLNWLT RQRY                                       34

SEQ ID NO: 108          moltype = AA   length = 34
FEATURE                 Location/Qualifiers
REGION                  1..34
                        note = Description of Artificial Sequence: Synthetic
                         polypeptide
MOD_RES                 34
                        note = n-methyl Tyrosine
source                  1..34
                        mol_type = protein
                        organism = synthetic construct
SEQUENCE: 108
PKPEAPGKDA SPKEWNRYYA DARHYLNWLT RQRY                                       34

SEQ ID NO: 109          moltype = AA   length = 34
FEATURE                 Location/Qualifiers
REGION                  1..34
                        note = Description of Artificial Sequence: Synthetic
                         polypeptide
MOD_RES                 34
```

```
                        note = n-methyl Tyrosine
source                  1..34
                        mol_type = protein
                        organism = synthetic construct
SEQUENCE: 109
PKPEAPGKDA SPEEWKRYYA DARHYLNWLT RQRY                              34

SEQ ID NO: 110          moltype = AA  length = 34
FEATURE                 Location/Qualifiers
REGION                  1..34
                        note = Description of Artificial Sequence: Synthetic
                         polypeptide
MOD_RES                 34
                        note = n-methyl Tyrosine
source                  1..34
                        mol_type = protein
                        organism = synthetic construct
SEQUENCE: 110
PKPEAPGKDA SPEEWNRYYA DLRHYLNWLT RQRY                              34

SEQ ID NO: 111          moltype = AA  length = 34
FEATURE                 Location/Qualifiers
REGION                  1..34
                        note = Description of Artificial Sequence: Synthetic
                         polypeptide
MOD_RES                 34
                        note = Homotyrosine
source                  1..34
                        mol_type = protein
                        organism = synthetic construct
SEQUENCE: 111
PKPEAPGKDA SPEEWNRYYA DLRHYLNWLT RQRY                              34

SEQ ID NO: 112          moltype = AA  length = 34
FEATURE                 Location/Qualifiers
REGION                  1..34
                        note = Description of Artificial Sequence: Synthetic
                         polypeptide
SITE                    34
                        note = D-Tyrosine
source                  1..34
                        mol_type = protein
                        organism = synthetic construct
SEQUENCE: 112
PKPEAPGKDA SPEEWNRYYA DLRHYLNWLT RQRY                              34

SEQ ID NO: 113          moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 113
PKPEAPGKDA SPEEWNRYYA DLRHYLNWLT RQRF                              34

SEQ ID NO: 114          moltype = AA  length = 34
FEATURE                 Location/Qualifiers
REGION                  1..34
                        note = Description of Artificial Sequence: Synthetic
                         polypeptide
SITE                    20
                        note = D-Lysine
source                  1..34
                        mol_type = protein
                        organism = synthetic construct
SEQUENCE: 114
PKPEAPGKDA SPEEWNRYYK DLRHYLNWLT RQRF                              34

SEQ ID NO: 115          moltype = AA  length = 34
FEATURE                 Location/Qualifiers
REGION                  1..34
                        note = Description of Artificial Sequence: Synthetic
                         polypeptide
SITE                    8
                        note = D-Lysine
source                  1..34
                        mol_type = protein
```

```
                              organism = synthetic construct
SEQUENCE: 115
PKPEAPGKDA SPEEWNRYYA DLRHYLNWLT RQRF                                  34

SEQ ID NO: 116           moltype = AA  length = 34
FEATURE                  Location/Qualifiers
REGION                   1..34
                         note = Description of Artificial Sequence: Synthetic
                           polypeptide
source                   1..34
                         mol_type = protein
                         organism = synthetic construct
SEQUENCE: 116
PKPEAPGKDA SPEEWNRYYK DLRHYLNWLT RQRF                                  34

SEQ ID NO: 117           moltype =   length =
SEQUENCE: 117
000

SEQ ID NO: 118           moltype =   length =
SEQUENCE: 118
000

SEQ ID NO: 119           moltype = AA  length = 34
FEATURE                  Location/Qualifiers
REGION                   1..34
                         note = Description of Artificial Sequence: Synthetic
                           polypeptide
source                   1..34
                         mol_type = protein
                         organism = synthetic construct
SEQUENCE: 119
PKPEKPGKDA SPEEWNRYYK DLRHYLNWLT RQRF                                  34

SEQ ID NO: 120           moltype = AA  length = 34
FEATURE                  Location/Qualifiers
REGION                   1..34
                         note = Description of Artificial Sequence: Synthetic
                           polypeptide
source                   1..34
                         mol_type = protein
                         organism = synthetic construct
SEQUENCE: 120
PKPEAPGKDA SPKEWNRYYK DLRHYLNWLT RQRF                                  34

SEQ ID NO: 121           moltype =   length =
SEQUENCE: 121
000

SEQ ID NO: 122           moltype = AA  length = 34
FEATURE                  Location/Qualifiers
REGION                   1..34
                         note = Description of Artificial Sequence: Synthetic
                           polypeptide
MOD_RES                  20
                         note = Diaminopimelic acid
source                   1..34
                         mol_type = protein
                         organism = synthetic construct
SEQUENCE: 122
PKPEAPGKDA SPEEWNRYYX DLRHYLNWLT RQRF                                  34

SEQ ID NO: 123           moltype = AA  length = 34
FEATURE                  Location/Qualifiers
REGION                   1..34
                         note = Description of Artificial Sequence: Synthetic
                           polypeptide
source                   1..34
                         mol_type = protein
                         organism = synthetic construct
SEQUENCE: 123
PKPEAPGKDA SPEEWQRYYK DLRHYLNWLT RQRF                                  34

SEQ ID NO: 124           moltype = AA  length = 34
FEATURE                  Location/Qualifiers
REGION                   1..34
                         note = Description of Artificial Sequence: Synthetic
                           polypeptide
source                   1..34
```

```
                        mol_type = protein
                        organism = synthetic construct
SEQUENCE: 124
PKPEAPGKDA SPEEWDRYYK DLRHYLNWLT RQRF                                    34

SEQ ID NO: 125          moltype = AA   length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 125
PKPEAPGKDA SPEEWSRYYK DLRHYLNWLT RQRF                                    34

SEQ ID NO: 126          moltype = AA   length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 126
PKPEAPGKDA SPEEWTRYYK DLRHYLNWLT RQRF                                    34

SEQ ID NO: 127          moltype = AA   length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 127
PKPEKPGKDA SPKEWNRYYK DLRHYLNWLT RQRF                                    34

SEQ ID NO: 128          moltype =     length =
SEQUENCE: 128
000

SEQ ID NO: 129          moltype = AA   length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 129
PKPEKPGEDA SPKEWNRYYK DLRHYLNWLT RQRF                                    34

SEQ ID NO: 130          moltype = AA   length = 34
FEATURE                 Location/Qualifiers
REGION                  1..34
                        note = Description of Artificial Sequence: Synthetic
                         polypeptide
MOD_RES                 16
                        note = HomoSer
source                  1..34
                        mol_type = protein
                        organism = synthetic construct
SEQUENCE: 130
PKPEAPGKDA SPEEWSRYYK DLRHYLNWLT RQRF                                    34

SEQ ID NO: 131          moltype = AA   length = 34
FEATURE                 Location/Qualifiers
REGION                  1..34
                        note = Description of Artificial Sequence: Synthetic
                         polypeptide
MOD_RES                 16
                        note = alpha-methyl-Ser
source                  1..34
                        mol_type = protein
                        organism = synthetic construct
SEQUENCE: 131
PKPEAPGKDA SPEEWSRYYK DLRHYLNWLT RQRF                                    34
```

-continued

```
SEQ ID NO: 132          moltype =    length =
SEQUENCE: 132
000

SEQ ID NO: 133          moltype =    length =
SEQUENCE: 133
000

SEQ ID NO: 134          moltype = AA   length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 134
PKPEKPGEDA SPKEWDRYYK DLRHYLNWLT RQRF                                      34

SEQ ID NO: 135          moltype =    length =
SEQUENCE: 135
000

SEQ ID NO: 136          moltype =    length =
SEQUENCE: 136
000

SEQ ID NO: 137          moltype =    length =
SEQUENCE: 137
000

SEQ ID NO: 138          moltype =    length =
SEQUENCE: 138
000

SEQ ID NO: 139          moltype = AA   length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 139
PKPEKPGKDA SPKEWERYYK DLRHYLNWLT RQRF                                      34

SEQ ID NO: 140          moltype = AA   length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 140
PKPEKPGKDA SPKEWDRYYK DLRHYLNWLT RQRF                                      34

SEQ ID NO: 141          moltype = AA   length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 141
PKPEAPGKDA SPEEWERYYK DLRHYLNWLT RQRF                                      34

SEQ ID NO: 142          moltype =    length =
SEQUENCE: 142
000

SEQ ID NO: 143          moltype = AA   length = 34
FEATURE                 Location/Qualifiers
REGION                  1..34
                        note = Description of Artificial Sequence: Synthetic
                         polypeptide
source                  1..34
                        mol_type = protein
```

```
                        organism = synthetic construct
SEQUENCE: 143
PKPEAPGKDA SPEEWKRYYE DLRHYLNWLT RQRF                                  34

SEQ ID NO: 144          moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 144
PKPEAPGKDA SPEEWKRYYD DLRHYLNWLT RQRF                                  34

SEQ ID NO: 145          moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 145
PKPEAPGKDA SPKEWDRYYK DLRHYLNWLT RQRF                                  34

SEQ ID NO: 146          moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 146
PKPEAPGKKA SPEEWDRYYK DLRHYLNWLT RQRF                                  34

SEQ ID NO: 147          moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 147
PKPEAPGKDA SPEEWDRYYK DDRHYKNWLT RQRF                                  34

SEQ ID NO: 148          moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 148
PKPEAPGKDA SPEEWDRYYK DKRHYENWLT RQRF                                  34

SEQ ID NO: 149          moltype = AA  length = 34
FEATURE                 Location/Qualifiers
REGION                  1..34
                        note = Description of Artificial Sequence: Synthetic
                         polypeptide
MOD_RES                 34
                        note = Beta-homoTyr
source                  1..34
                        mol_type = protein
                        organism = synthetic construct
SEQUENCE: 149
PKPEAPGKDA SPEEWNRYYA DLRHYLNWLT RQRY                                  34

SEQ ID NO: 150          moltype = AA  length = 34
FEATURE                 Location/Qualifiers
REGION                  1..34
                        note = Description of Artificial Sequence: Synthetic
                         polypeptide
source                  1..34
                        mol_type = protein
```

```
                        organism = synthetic construct
SEQUENCE: 150
PKPEAPGKDA SPEEWNRYYA DLRHYLNWLT RKRF                               34

SEQ ID NO: 151          moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 151
PKPEAPGKDA SPEEWNRYYA DLRHYLKWLT RQRF                               34

SEQ ID NO: 152          moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 152
PKPEAPGKDA SPEEWNRYYA DLRHKLNWLT RQRF                               34

SEQ ID NO: 153          moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 153
PKPEAPGKDA SPEEWNRYYA DLKHYLNWLT RQRF                               34

SEQ ID NO: 154          moltype =    length =
SEQUENCE: 154
000

SEQ ID NO: 155          moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 155
PKPEAPGKDA SPEEWKRYYA DLRHYLNWLT RQRF                               34

SEQ ID NO: 156          moltype = AA  length = 34
FEATURE                 Location/Qualifiers
REGION                  1..34
                        note = Description of Artificial Sequence: Synthetic
                         polypeptide
MOD_RES                 34
                        note = 4-pyridylAla
source                  1..34
                        mol_type = protein
                        organism = synthetic construct
SEQUENCE: 156
PKPEAPGKDA SPEEWNRYYA DLRHYLNWLT RQRA                               34

SEQ ID NO: 157          moltype = AA  length = 34
FEATURE                 Location/Qualifiers
REGION                  1..34
                        note = Description of Artificial Sequence: Synthetic
                         polypeptide
MOD_RES                 34
                        note = 3-pyridylAla
source                  1..34
                        mol_type = protein
                        organism = synthetic construct
SEQUENCE: 157
PKPEAPGKDA SPEEWNRYYA DLRHYLNWLT RQRA                               34

SEQ ID NO: 158          moltype = AA  length = 34
```

```
FEATURE                 Location/Qualifiers
REGION                  1..34
                        note = Description of Artificial Sequence: Synthetic
                         polypeptide
MOD_RES                 34
                        note = 4-methylPhe
source                  1..34
                        mol_type = protein
                        organism = synthetic construct
SEQUENCE: 158
PKPEAPGKDA SPEEWNRYYA DLRHYLNWLT RQRF                                       34

SEQ ID NO: 159          moltype = AA  length = 34
FEATURE                 Location/Qualifiers
REGION                  1..34
                        note = Description of Artificial Sequence: Synthetic
                         polypeptide
MOD_RES                 34
                        note = 4-carboxyPhe
source                  1..34
                        mol_type = protein
                        organism = synthetic construct
SEQUENCE: 159
PKPEAPGKDA SPEEWNRYYA DLRHYLNWLT RQRF                                       34

SEQ ID NO: 160          moltype = AA  length = 34
FEATURE                 Location/Qualifiers
REGION                  1..34
                        note = Description of Artificial Sequence: Synthetic
                         polypeptide
MOD_RES                 34
                        note = 4-fluoroPhe
source                  1..34
                        mol_type = protein
                        organism = synthetic construct
SEQUENCE: 160
PKPEAPGKDA SPEEWNRYYA DLRHYLNWLT RQRF                                       34

SEQ ID NO: 161          moltype = AA  length = 34
FEATURE                 Location/Qualifiers
REGION                  1..34
                        note = Description of Artificial Sequence: Synthetic
                         polypeptide
MOD_RES                 34
                        note = homoPhe
source                  1..34
                        mol_type = protein
                        organism = synthetic construct
SEQUENCE: 161
PKPEAPGKDA SPEEWNRYYA DLRHYLNWLT RQRF                                       34

SEQ ID NO: 162          moltype = AA  length = 34
FEATURE                 Location/Qualifiers
REGION                  1..34
                        note = Description of Artificial Sequence: Synthetic
                         polypeptide
MOD_RES                 34
                        note = n-methylPhe
source                  1..34
                        mol_type = protein
                        organism = synthetic construct
SEQUENCE: 162
PKPEAPGKDA SPEEWNRYYA DLRHYLNWLT RQRF                                       34

SEQ ID NO: 163          moltype = AA  length = 34
FEATURE                 Location/Qualifiers
REGION                  1..34
                        note = Description of Artificial Sequence: Synthetic
                         polypeptide
MOD_RES                 34
                        note = n-methylTyr
source                  1..34
                        mol_type = protein
                        organism = synthetic construct
SEQUENCE: 163
PKPEAPKKDA SPEELNRYYA DARHYLNWLT RQRY                                       34

SEQ ID NO: 164          moltype = AA  length = 34
FEATURE                 Location/Qualifiers
```

```
REGION                      1..34
                            note = Description of Artificial Sequence: Synthetic
                             polypeptide
source                      1..34
                            mol_type = protein
                            organism = synthetic construct
SEQUENCE: 164
PKPEAPKKDA SPEELNRYYA DARHYLNWLT RQRF                                     34

SEQ ID NO: 165              moltype =    length =
SEQUENCE: 165
000

SEQ ID NO: 166              moltype = AA   length = 34
FEATURE                     Location/Qualifiers
REGION                      1..34
                            note = Description of Artificial Sequence: Synthetic
                             polypeptide
source                      1..34
                            mol_type = protein
                            organism = synthetic construct
SEQUENCE: 166
PKPEAPGKDK SPEEWNRYYK DLRHYLNWLT RQRF                                     34

SEQ ID NO: 167              moltype = AA   length = 34
FEATURE                     Location/Qualifiers
REGION                      1..34
                            note = Description of Artificial Sequence: Synthetic
                             polypeptide
source                      1..34
                            mol_type = protein
                            organism = synthetic construct
SEQUENCE: 167
PKPEAPGKDA SPEKWNRYYK DLRHYLNWLT RQRF                                     34

SEQ ID NO: 168              moltype = AA   length = 34
FEATURE                     Location/Qualifiers
REGION                      1..34
                            note = Description of Artificial Sequence: Synthetic
                             polypeptide
source                      1..34
                            mol_type = protein
                            organism = synthetic construct
SEQUENCE: 168
PKPEAPGKDA SPEEWNRKYK DLRHYLNWLT RQRF                                     34

SEQ ID NO: 169              moltype = AA   length = 34
FEATURE                     Location/Qualifiers
REGION                      1..34
                            note = Description of Artificial Sequence: Synthetic
                             polypeptide
source                      1..34
                            mol_type = protein
                            organism = synthetic construct
SEQUENCE: 169
PKPEAPGKDA SPEEWNRYKK DLRHYLNWLT RQRF                                     34

SEQ ID NO: 170              moltype =    length =
SEQUENCE: 170
000

SEQ ID NO: 171              moltype =    length =
SEQUENCE: 171
000

SEQ ID NO: 172              moltype =    length =
SEQUENCE: 172
000

SEQ ID NO: 173              moltype =    length =
SEQUENCE: 173
000

SEQ ID NO: 174              moltype =    length =
SEQUENCE: 174
000

SEQ ID NO: 175              moltype = AA   length = 34
FEATURE                     Location/Qualifiers
```

```
REGION                  1..34
                        note = Description of Artificial Sequence: Synthetic
                         polypeptide
source                  1..34
                        mol_type = protein
                        organism = synthetic construct
SEQUENCE: 175
PKPEKPGKDA SPEEWSRYYK DLRHYLNWLT RQRF                                  34

SEQ ID NO: 176          moltype =    length =
SEQUENCE: 176
000

SEQ ID NO: 177          moltype = AA   length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 177
PKPEKPGEDA SPEEWDRYYK DLRHYLNWLT RQRF                                  34

SEQ ID NO: 178          moltype =    length =
SEQUENCE: 178
000

SEQ ID NO: 179          moltype = AA   length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 179
PKPEAPGKDA SPEEWDRYYK DLRHYLNWLT RQRY                                  34

SEQ ID NO: 180          moltype = AA   length = 33
FEATURE                 Location/Qualifiers
REGION                  1..33
                        note = Description of Artificial Sequence: Synthetic
                         polypeptide
source                  1..33
                        mol_type = protein
                        organism = synthetic construct
SEQUENCE: 180
PKPEAPGDAS PEEWDRYYKD LRHYLNWLTR QRF                                   33

SEQ ID NO: 181          moltype = AA   length = 33
FEATURE                 Location/Qualifiers
REGION                  1..33
                        note = Description of Artificial Sequence: Synthetic
                         polypeptide
source                  1..33
                        mol_type = protein
                        organism = synthetic construct
SEQUENCE: 181
PKPEAPGDAS PEEWKRYYED LRHYLNWLTR QRF                                   33

SEQ ID NO: 182          moltype =    length =
SEQUENCE: 182
000

SEQ ID NO: 183          moltype =    length =
SEQUENCE: 183
000

SEQ ID NO: 184          moltype =    length =
SEQUENCE: 184
000

SEQ ID NO: 185          moltype =    length =
SEQUENCE: 185
000

SEQ ID NO: 186          moltype =    length =
SEQUENCE: 186
```

000

SEQ ID NO: 187          moltype =     length =
SEQUENCE: 187
000

SEQ ID NO: 188          moltype =     length =
SEQUENCE: 188
000

SEQ ID NO: 189          moltype =     length =
SEQUENCE: 189
000

SEQ ID NO: 190          moltype =     length =
SEQUENCE: 190
000

SEQ ID NO: 191          moltype =     length =
SEQUENCE: 191
000

SEQ ID NO: 192          moltype =     length =
SEQUENCE: 192
000

SEQ ID NO: 193          moltype =     length =
SEQUENCE: 193
000

SEQ ID NO: 194          moltype =     length =
SEQUENCE: 194
000

SEQ ID NO: 195          moltype =     length =
SEQUENCE: 195
000

SEQ ID NO: 196          moltype =     length =
SEQUENCE: 196
000

SEQ ID NO: 197          moltype =     length =
SEQUENCE: 197
000

SEQ ID NO: 198          moltype =     length =
SEQUENCE: 198
000

SEQ ID NO: 199          moltype =     length =
SEQUENCE: 199
000

SEQ ID NO: 200          moltype =     length =
SEQUENCE: 200
000

SEQ ID NO: 201          moltype =     length =
SEQUENCE: 201
000

SEQ ID NO: 202          moltype =     length =
SEQUENCE: 202
000

SEQ ID NO: 203          moltype =     length =
SEQUENCE: 203
000

SEQ ID NO: 204          moltype =     length =
SEQUENCE: 204
000

SEQ ID NO: 205          moltype =     length =
SEQUENCE: 205
000

SEQ ID NO: 206          moltype =     length =

| | | |
|---|---|---|
| SEQUENCE: 206 000 | | |
| SEQ ID NO: 207 SEQUENCE: 207 000 | moltype = | length = |
| SEQ ID NO: 208 SEQUENCE: 208 000 | moltype = | length = |
| SEQ ID NO: 209 SEQUENCE: 209 000 | moltype = | length = |
| SEQ ID NO: 210 SEQUENCE: 210 000 | moltype = | length = |
| SEQ ID NO: 211 SEQUENCE: 211 000 | moltype = | length = |
| SEQ ID NO: 212 SEQUENCE: 212 000 | moltype = | length = |
| SEQ ID NO: 213 SEQUENCE: 213 000 | moltype = | length = |
| SEQ ID NO: 214 SEQUENCE: 214 000 | moltype = | length = |
| SEQ ID NO: 215 SEQUENCE: 215 000 | moltype = | length = |
| SEQ ID NO: 216 SEQUENCE: 216 000 | moltype = | length = |
| SEQ ID NO: 217 SEQUENCE: 217 000 | moltype = | length = |
| SEQ ID NO: 218 SEQUENCE: 218 000 | moltype = | length = |
| SEQ ID NO: 219 SEQUENCE: 219 000 | moltype = | length = |
| SEQ ID NO: 220 SEQUENCE: 220 000 | moltype = | length = |
| SEQ ID NO: 221 SEQUENCE: 221 000 | moltype = | length = |
| SEQ ID NO: 222 SEQUENCE: 222 000 | moltype = | length = |
| SEQ ID NO: 223 SEQUENCE: 223 000 | moltype = | length = |
| SEQ ID NO: 224 SEQUENCE: 224 000 | moltype = | length = |
| SEQ ID NO: 225 SEQUENCE: 225 000 | moltype = | length = |

```
SEQ ID NO: 226          moltype =   length =
SEQUENCE: 226
000

SEQ ID NO: 227          moltype =   length =
SEQUENCE: 227
000

SEQ ID NO: 228          moltype =   length =
SEQUENCE: 228
000

SEQ ID NO: 229          moltype =   length =
SEQUENCE: 229
000

SEQ ID NO: 230          moltype =   length =
SEQUENCE: 230
000

SEQ ID NO: 231          moltype =   length =
SEQUENCE: 231
000

SEQ ID NO: 232          moltype =   length =
SEQUENCE: 232
000

SEQ ID NO: 233          moltype =   length =
SEQUENCE: 233
000

SEQ ID NO: 234          moltype =   length =
SEQUENCE: 234
000

SEQ ID NO: 235          moltype =   length =
SEQUENCE: 235
000

SEQ ID NO: 236          moltype =   length =
SEQUENCE: 236
000

SEQ ID NO: 237          moltype =   length =
SEQUENCE: 237
000

SEQ ID NO: 238          moltype =   length =
SEQUENCE: 238
000

SEQ ID NO: 239          moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 239
PKPEKPGKDA SPKEWERYYK DLRHYLNWLT RQRF                                34

SEQ ID NO: 240          moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 240
PKPEKPGKDA SPKEWDRYYK DLRHYLNWLT RQRF                                34

SEQ ID NO: 241          moltype = AA  length = 34
FEATURE                 Location/Qualifiers
REGION                  1..34
                        note = Description of Artificial Sequence: Synthetic
                         polypeptide
```

```
source                  1..34
                        mol_type = protein
                        organism = synthetic construct
SEQUENCE: 241
PKPEAPGKDA SPEEWERYYK DLRHYLNWLT RQRF                              34

SEQ ID NO: 242          moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 242
PKPEAPGKDA SPEEWDRYYK DLRHYLNWLT RQRF                              34

SEQ ID NO: 243          moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 243
PKPEAPGKDA SPEEWKRYYE DLRHYLNWLT RQRF                              34

SEQ ID NO: 244          moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 244
PKPEAPGKDA SPEEWKRYYD DLRHYLNWLT RQRF                              34

SEQ ID NO: 245          moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 245
PKPEAPGKDA SPKEWDRYYK DLRHYLNWLT RQRF                              34

SEQ ID NO: 246          moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 246
PKPEAPGKKA SPEEWDRYYK DLRHYLNWLT RQRF                              34

SEQ ID NO: 247          moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 247
PKPEAPGKDA SPEEWDRYYK DDRHYKNWLT RQRF                              34

SEQ ID NO: 248          moltype = AA  length = 34
FEATURE                 Location/Qualifiers
REGION                  1..34
                        note = Description of Artificial Sequence: Synthetic
                         polypeptide
source                  1..34
                        mol_type = protein
```

```
                    organism = synthetic construct
SEQUENCE: 248
PKPEAPGKDA SPEEWDRYYK DKRHYENWLT RQRF                              34

SEQ ID NO: 249       moltype =   length =
SEQUENCE: 249
000

SEQ ID NO: 250       moltype =   length =
SEQUENCE: 250
000

SEQ ID NO: 251       moltype =   length =
SEQUENCE: 251
000

SEQ ID NO: 252       moltype =   length =
SEQUENCE: 252
000

SEQ ID NO: 253       moltype =   length =
SEQUENCE: 253
000

SEQ ID NO: 254       moltype =   length =
SEQUENCE: 254
000

SEQ ID NO: 255       moltype =   length =
SEQUENCE: 255
000

SEQ ID NO: 256       moltype =   length =
SEQUENCE: 256
000

SEQ ID NO: 257       moltype =   length =
SEQUENCE: 257
000

SEQ ID NO: 258       moltype =   length =
SEQUENCE: 258
000

SEQ ID NO: 259       moltype =   length =
SEQUENCE: 259
000

SEQ ID NO: 260       moltype =   length =
SEQUENCE: 260
000

SEQ ID NO: 261       moltype =   length =
SEQUENCE: 261
000

SEQ ID NO: 262       moltype =   length =
SEQUENCE: 262
000

SEQ ID NO: 263       moltype =   length =
SEQUENCE: 263
000

SEQ ID NO: 264       moltype =   length =
SEQUENCE: 264
000

SEQ ID NO: 265       moltype =   length =
SEQUENCE: 265
000

SEQ ID NO: 266       moltype =   length =
SEQUENCE: 266
000

SEQ ID NO: 267       moltype =   length =
SEQUENCE: 267
000
```

```
SEQ ID NO: 268          moltype =    length =
SEQUENCE: 268
000

SEQ ID NO: 269          moltype =    length =
SEQUENCE: 269
000

SEQ ID NO: 270          moltype =    length =
SEQUENCE: 270
000

SEQ ID NO: 271          moltype =    length =
SEQUENCE: 271
000

SEQ ID NO: 272          moltype =    length =
SEQUENCE: 272
000

SEQ ID NO: 273          moltype =    length =
SEQUENCE: 273
000

SEQ ID NO: 274          moltype =    length =
SEQUENCE: 274
000

SEQ ID NO: 275          moltype =    length =
SEQUENCE: 275
000

SEQ ID NO: 276          moltype =    length =
SEQUENCE: 276
000

SEQ ID NO: 277          moltype =    length =
SEQUENCE: 277
000

SEQ ID NO: 278          moltype =    length =
SEQUENCE: 278
000

SEQ ID NO: 279          moltype =    length =
SEQUENCE: 279
000

SEQ ID NO: 280          moltype = AA   length = 33
FEATURE                 Location/Qualifiers
REGION                  1..33
                        note = Description of Artificial Sequence: Synthetic
                         polypeptide
source                  1..33
                        mol_type = protein
                        organism = synthetic construct
SEQUENCE: 280
PKPEAPGDAS PEEWDRYYKD LRHYLNWLTR QRF                                   33

SEQ ID NO: 281          moltype = AA   length = 33
FEATURE                 Location/Qualifiers
REGION                  1..33
                        note = Description of Artificial Sequence: Synthetic
                         polypeptide
source                  1..33
                        mol_type = protein
                        organism = synthetic construct
SEQUENCE: 281
PKPEAPGDAS PEEWKRYYED LRHYLNWLTR QRF                                   33

SEQ ID NO: 282          moltype =    length =
SEQUENCE: 282
000

SEQ ID NO: 283          moltype =    length =
SEQUENCE: 283
000
```

-continued

| | | |
|---|---|---|
| SEQ ID NO: 284 SEQUENCE: 284 | moltype = | length = 000 |
| SEQ ID NO: 285 SEQUENCE: 285 | moltype = | length = 000 |
| SEQ ID NO: 286 SEQUENCE: 286 | moltype = | length = 000 |
| SEQ ID NO: 287 SEQUENCE: 287 | moltype = | length = 000 |
| SEQ ID NO: 288 SEQUENCE: 288 | moltype = | length = 000 |
| SEQ ID NO: 289 SEQUENCE: 289 | moltype = | length = 000 |
| SEQ ID NO: 290 SEQUENCE: 290 | moltype = | length = 000 |
| SEQ ID NO: 291 SEQUENCE: 291 | moltype = | length = 000 |
| SEQ ID NO: 292 SEQUENCE: 292 | moltype = | length = 000 |
| SEQ ID NO: 293 SEQUENCE: 293 | moltype = | length = 000 |
| SEQ ID NO: 294 SEQUENCE: 294 | moltype = | length = 000 |
| SEQ ID NO: 295 SEQUENCE: 295 | moltype = | length = 000 |
| SEQ ID NO: 296 SEQUENCE: 296 | moltype = | length = 000 |
| SEQ ID NO: 297 SEQUENCE: 297 | moltype = | length = 000 |
| SEQ ID NO: 298 SEQUENCE: 298 | moltype = | length = 000 |
| SEQ ID NO: 299 SEQUENCE: 299 | moltype = | length = 000 |
| SEQ ID NO: 300 SEQUENCE: 300 | moltype = | length = 000 |
| SEQ ID NO: 301 SEQUENCE: 301 | moltype = | length = 000 |
| SEQ ID NO: 302 SEQUENCE: 302 | moltype = | length = 000 |
| SEQ ID NO: 303 SEQUENCE: 303 | moltype = | length = 000 |

| | | |
|---|---|---|
| SEQ ID NO: 304 SEQUENCE: 304 | moltype = | length = 000 |
| SEQ ID NO: 305 SEQUENCE: 305 | moltype = | length = 000 |
| SEQ ID NO: 306 SEQUENCE: 306 | moltype = | length = 000 |
| SEQ ID NO: 307 SEQUENCE: 307 | moltype = | length = 000 |
| SEQ ID NO: 308 SEQUENCE: 308 | moltype = | length = 000 |
| SEQ ID NO: 309 SEQUENCE: 309 | moltype = | length = 000 |
| SEQ ID NO: 310 SEQUENCE: 310 | moltype = | length = 000 |
| SEQ ID NO: 311 SEQUENCE: 311 | moltype = | length = 000 |
| SEQ ID NO: 312 SEQUENCE: 312 | moltype = | length = 000 |
| SEQ ID NO: 313 SEQUENCE: 313 | moltype = | length = 000 |
| SEQ ID NO: 314 SEQUENCE: 314 | moltype = | length = 000 |
| SEQ ID NO: 315 SEQUENCE: 315 | moltype = | length = 000 |
| SEQ ID NO: 316 SEQUENCE: 316 | moltype = | length = 000 |
| SEQ ID NO: 317 SEQUENCE: 317 | moltype = | length = 000 |
| SEQ ID NO: 318 SEQUENCE: 318 | moltype = | length = 000 |
| SEQ ID NO: 319 SEQUENCE: 319 | moltype = | length = 000 |
| SEQ ID NO: 320 SEQUENCE: 320 | moltype = | length = 000 |
| SEQ ID NO: 321 SEQUENCE: 321 | moltype = | length = 000 |
| SEQ ID NO: 322 SEQUENCE: 322 | moltype = | length = 000 |
| SEQ ID NO: 323 SEQUENCE: 323 | moltype = | length = |

```
SEQ ID NO: 324            moltype = AA  length = 34
FEATURE                   Location/Qualifiers
REGION                    1..34
                          note = Description of Artificial Sequence: Synthetic
                          polypeptide
source                    1..34
                          mol_type = protein
                          organism = synthetic construct
SEQUENCE: 324
PKPEAPGKDA SPEEWDRYYK DLRHYLNWLT RQRF                                 34

SEQ ID NO: 325            moltype =     length =
SEQUENCE: 325
000

SEQ ID NO: 326            moltype =     length =
SEQUENCE: 326
000

SEQ ID NO: 327            moltype =     length =
SEQUENCE: 327
000

SEQ ID NO: 328            moltype =     length =
SEQUENCE: 328
000

SEQ ID NO: 329            moltype =     length =
SEQUENCE: 329
000

SEQ ID NO: 330            moltype =     length =
SEQUENCE: 330
000

SEQ ID NO: 331            moltype =     length =
SEQUENCE: 331
000

SEQ ID NO: 332            moltype =     length =
SEQUENCE: 332
000

SEQ ID NO: 333            moltype =     length =
SEQUENCE: 333
000

SEQ ID NO: 334            moltype =     length =
SEQUENCE: 334
000

SEQ ID NO: 335            moltype =     length =
SEQUENCE: 335
000

SEQ ID NO: 336            moltype =     length =
SEQUENCE: 336
000

SEQ ID NO: 337            moltype =     length =
SEQUENCE: 337
000

SEQ ID NO: 338            moltype =     length =
SEQUENCE: 338
000

SEQ ID NO: 339            moltype =     length =
SEQUENCE: 339
000

SEQ ID NO: 340            moltype =     length =
SEQUENCE: 340
000

SEQ ID NO: 341            moltype =     length =
SEQUENCE: 341
```

```
000

SEQ ID NO: 342          moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 342
PKPEAPGKDA SPEEWDRYYK DLRHYLNWLT RQRF                                 34

SEQ ID NO: 343          moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 343
PKPEAPGKDA SPEEWKRYYE DLRHYLNWLT RQRF                                 34

SEQ ID NO: 344          moltype =     length =
SEQUENCE: 344
000

SEQ ID NO: 345          moltype =     length =
SEQUENCE: 345
000

SEQ ID NO: 346          moltype =     length =
SEQUENCE: 346
000

SEQ ID NO: 347          moltype =     length =
SEQUENCE: 347
000

SEQ ID NO: 348          moltype =     length =
SEQUENCE: 348
000

SEQ ID NO: 349          moltype =     length =
SEQUENCE: 349
000

SEQ ID NO: 350          moltype =     length =
SEQUENCE: 350
000

SEQ ID NO: 351          moltype =     length =
SEQUENCE: 351
000

SEQ ID NO: 352          moltype =     length =
SEQUENCE: 352
000

SEQ ID NO: 353          moltype =     length =
SEQUENCE: 353
000

SEQ ID NO: 354          moltype =     length =
SEQUENCE: 354
000

SEQ ID NO: 355          moltype =     length =
SEQUENCE: 355
000

SEQ ID NO: 356          moltype =     length =
SEQUENCE: 356
000

SEQ ID NO: 357          moltype =     length =
SEQUENCE: 357
000
```

| | | |
|---|---|---|
| SEQ ID NO: 358<br>SEQUENCE: 358<br>000 | moltype = | length = |
| SEQ ID NO: 359<br>SEQUENCE: 359<br>000 | moltype = | length = |
| SEQ ID NO: 360<br>SEQUENCE: 360<br>000 | moltype = | length = |
| SEQ ID NO: 361<br>SEQUENCE: 361<br>000 | moltype = | length = |
| SEQ ID NO: 362<br>SEQUENCE: 362<br>000 | moltype = | length = |
| SEQ ID NO: 363<br>SEQUENCE: 363<br>000 | moltype = | length = |
| SEQ ID NO: 364<br>SEQUENCE: 364<br>000 | moltype = | length = |
| SEQ ID NO: 365<br>SEQUENCE: 365<br>000 | moltype = | length = |
| SEQ ID NO: 366<br>SEQUENCE: 366<br>000 | moltype = | length = |
| SEQ ID NO: 367<br>SEQUENCE: 367<br>000 | moltype = | length = |
| SEQ ID NO: 368<br>SEQUENCE: 368<br>000 | moltype = | length = |
| SEQ ID NO: 369<br>SEQUENCE: 369<br>000 | moltype = | length = |
| SEQ ID NO: 370<br>SEQUENCE: 370<br>000 | moltype = | length = |
| SEQ ID NO: 371<br>SEQUENCE: 371<br>000 | moltype = | length = |
| SEQ ID NO: 372<br>SEQUENCE: 372<br>000 | moltype = | length = |
| SEQ ID NO: 373<br>SEQUENCE: 373<br>000 | moltype = | length = |
| SEQ ID NO: 374<br>SEQUENCE: 374<br>000 | moltype = | length = |
| SEQ ID NO: 375<br>SEQUENCE: 375<br>000 | moltype = | length = |
| SEQ ID NO: 376<br>SEQUENCE: 376<br>000 | moltype = | length = |
| SEQ ID NO: 377<br>SEQUENCE: 377 | moltype = | length = |

```
000

SEQ ID NO: 378          moltype =   length =
SEQUENCE: 378
000

SEQ ID NO: 379          moltype =   length =
SEQUENCE: 379
000

SEQ ID NO: 380          moltype =   length =
SEQUENCE: 380
000

SEQ ID NO: 381          moltype =   length =
SEQUENCE: 381
000

SEQ ID NO: 382          moltype =   length =
SEQUENCE: 382
000

SEQ ID NO: 383          moltype =   length =
SEQUENCE: 383
000

SEQ ID NO: 384          moltype =   length =
SEQUENCE: 384
000

SEQ ID NO: 385          moltype =   length =
SEQUENCE: 385
000

SEQ ID NO: 386          moltype =   length =
SEQUENCE: 386
000

SEQ ID NO: 387          moltype =   length =
SEQUENCE: 387
000

SEQ ID NO: 388          moltype =   length =
SEQUENCE: 388
000

SEQ ID NO: 389          moltype =   length =
SEQUENCE: 389
000

SEQ ID NO: 390          moltype = AA   length = 35
FEATURE                 Location/Qualifiers
REGION                  1..35
                        note = Description of Artificial Sequence: Synthetic
                         polypeptide
VARIANT                 1
                        note = X can be K or absent
VARIANT                 5
                        note = X can be E or K
VARIANT                 6
                        note = X can be A or K
VARIANT                 8
                        note = X can be G or K
VARIANT                 9
                        note = X can be E, K, or D-Lysine
VARIANT                 10
                        note = X can be D or K
VARIANT                 11
                        note = X can be A or K
VARIANT                 14
                        note = X can be E or K
VARIANT                 15
                        note = X can be E or K
VARIANT                 16
                        note = X can be L or W
VARIANT                 17
                        note = X can be D, E, K, N, Q, S, T, alpha-methylserine, or
                         homoserine
VARIANT                 19
```

```
                        note = X can be K or Y
VARIANT                 20
                        note = X can be K or Y
VARIANT                 21
                        note = X can be A, D, E, K, D-Lysine, or Diaminopimelic acid
VARIANT                 23
                        note = X can be A, D, K, or L
VARIANT                 24
                        note = K or R
VARIANT                 26
                        note = X can be K or Y
VARIANT                 27
                        note = X can be E, K, or L
VARIANT                 28
                        note = X can be K or N
VARIANT                 33
                        note = X can be K or Q
VARIANT                 35
                        note = X can be F, y, 3-pyridinylalanine,
                         4-pyridinylalanine, 4-carboxyphenylalanine,
                         4-fluorophenylalanine, 4-methylphenylalanine,
                         N-methylphenylalanine, homophenylalanine,
                         beta-homotyrosine,homotyrosine, or N-methyltyrosine
REGION                  1..35
                        note = See specification as filed for detailed description
                         of substitutions and preferred embodiments
source                  1..35
                        mol_type = protein
                        organism = synthetic construct
SITE                    9
                        note = D-Lysine
SITE                    21
                        note = D-Lysine
MOD_RES                 17
                        note = Alpha-methylserine, or homoserine
MOD_RES                 35
                        note = 3-pyridinylalanine, 4-pyridinylalanine,
                         4-carboxyphenylalanine, 4-fluorophenylalanine,
                         4-methylphenylalanine, N-methylphenylalanine,
                         homophenylalanine, beta-homotyrosine,homotyrosine, or
                         N-methyltyrosine
MOD_RES                 21
                        note = Diaminopimelic acid
SEQUENCE: 390
XPKPXXPXXX XSPXXXXRXX XDXXHXXXWL TRXRX                                    35

SEQ ID NO: 391          moltype =    length =
SEQUENCE: 391
000

SEQ ID NO: 392          moltype =    length =
SEQUENCE: 392
000

SEQ ID NO: 393          moltype =    length =
SEQUENCE: 393
000

SEQ ID NO: 394          moltype = AA  length = 34
FEATURE                 Location/Qualifiers
REGION                  1..34
                        note = Description of Artificial Sequence: Synthetic
                         polypeptide
VARIANT                 5
                        note = X can be A or K
VARIANT                 8
                        note = X can be E, K, or D-Lysine
VARIANT                 13
                        note = X can be E or K
VARIANT                 16
                        note = X can be D, E, K, or N
VARIANT                 20
                        note = X can be A, D, E, K, or D-Lysine
VARIANT                 22
                        note = X can be A or L
VARIANT                 34
                        note = X can be F or N-methyltyrosine
REGION                  1..34
                        note = See specification as filed for detailed description
```

|  | of substitutions and preferred embodiments |
|---|---|
| source | 1..34<br>mol_type = protein<br>organism = synthetic construct |
| SITE | 8<br>note = D-Lysine |
| SITE | 20<br>note = D-Lysine |
| MOD_RES | 34<br>note = N-methyltyrosine |

SEQUENCE: 394
PKPEXPGXDA SPXEWXRYYX DXRHYLNWLT RQRX                    34

SEQ ID NO: 395   moltype =   length =
SEQUENCE: 395
000

SEQ ID NO: 396   moltype =   length =
SEQUENCE: 396
000

SEQ ID NO: 397   moltype =   length =
SEQUENCE: 397
000

SEQ ID NO: 398   moltype =   length =
SEQUENCE: 398
000

SEQ ID NO: 399   moltype =   length =
SEQUENCE: 399
000

SEQ ID NO: 400   moltype =   length =
SEQUENCE: 400
000

SEQ ID NO: 401   moltype =   length =
SEQUENCE: 401
000

SEQ ID NO: 402   moltype =   length =
SEQUENCE: 402
000

SEQ ID NO: 403   moltype =   length =
SEQUENCE: 403
000

SEQ ID NO: 404   moltype =   length =
SEQUENCE: 404
000

SEQ ID NO: 405   moltype =   length =
SEQUENCE: 405
000

SEQ ID NO: 406   moltype =   length =
SEQUENCE: 406
000

SEQ ID NO: 407   moltype =   length =
SEQUENCE: 407
000

SEQ ID NO: 408   moltype =   length =
SEQUENCE: 408
000

SEQ ID NO: 409   moltype =   length =
SEQUENCE: 409
000

SEQ ID NO: 410   moltype =   length =
SEQUENCE: 410
000

SEQ ID NO: 411   moltype =   length =
SEQUENCE: 411

```
                                         -continued

000

SEQ ID NO: 412           moltype =    length =
SEQUENCE: 412
000

SEQ ID NO: 413           moltype =    length =
SEQUENCE: 413
000

SEQ ID NO: 414           moltype =    length =
SEQUENCE: 414
000

SEQ ID NO: 415           moltype =    length =
SEQUENCE: 415
000

SEQ ID NO: 416           moltype =    length =
SEQUENCE: 416
000

SEQ ID NO: 417           moltype =    length =
SEQUENCE: 417
000

SEQ ID NO: 418           moltype =    length =
SEQUENCE: 418
000

SEQ ID NO: 419           moltype =    length =
SEQUENCE: 419
000

SEQ ID NO: 420           moltype =    length =
SEQUENCE: 420
000

SEQ ID NO: 421           moltype =    length =
SEQUENCE: 421
000

SEQ ID NO: 422           moltype =    length =
SEQUENCE: 422
000

SEQ ID NO: 423           moltype =    length =
SEQUENCE: 423
000

SEQ ID NO: 424           moltype = AA  length = 34
FEATURE                  Location/Qualifiers
REGION                   1..34
                         note = Description of Artificial Sequence: Synthetic
                          polypeptide
source                   1..34
                         mol_type = protein
                         organism = synthetic construct
SEQUENCE: 424
PKPEAPGKDA SPEEWDRYYK DLRHYLNWLT RQRF                                    34

SEQ ID NO: 425           moltype =    length =
SEQUENCE: 425
000

SEQ ID NO: 426           moltype =    length =
SEQUENCE: 426
000

SEQ ID NO: 427           moltype =    length =
SEQUENCE: 427
000

SEQ ID NO: 428           moltype =    length =
SEQUENCE: 428
000

SEQ ID NO: 429           moltype =    length =
SEQUENCE: 429
```

```
000

SEQ ID NO: 430         moltype =     length =
SEQUENCE: 430
000

SEQ ID NO: 431         moltype =     length =
SEQUENCE: 431
000

SEQ ID NO: 432         moltype =     length =
SEQUENCE: 432
000

SEQ ID NO: 433         moltype =     length =
SEQUENCE: 433
000

SEQ ID NO: 434         moltype =     length =
SEQUENCE: 434
000

SEQ ID NO: 435         moltype =     length =
SEQUENCE: 435
000

SEQ ID NO: 436         moltype =     length =
SEQUENCE: 436
000

SEQ ID NO: 437         moltype =     length =
SEQUENCE: 437
000

SEQ ID NO: 438         moltype =     length =
SEQUENCE: 438
000

SEQ ID NO: 439         moltype =     length =
SEQUENCE: 439
000

SEQ ID NO: 440         moltype =     length =
SEQUENCE: 440
000

SEQ ID NO: 441         moltype =     length =
SEQUENCE: 441
000

SEQ ID NO: 442         moltype = AA  length = 34
FEATURE                Location/Qualifiers
REGION                 1..34
                       note = Description of Artificial Sequence: Synthetic
                        polypeptide
source                 1..34
                       mol_type = protein
                       organism = synthetic construct
SEQUENCE: 442
PKPEAPGKDA SPEEWDRYYK DLRHYLNWLT RQRF                                34

SEQ ID NO: 443         moltype = AA  length = 34
FEATURE                Location/Qualifiers
REGION                 1..34
                       note = Description of Artificial Sequence: Synthetic
                        polypeptide
source                 1..34
                       mol_type = protein
                       organism = synthetic construct
SEQUENCE: 443
PKPEAPGKDA SPEEWKRYYE DLRHYLNWLT RQRF                                34

SEQ ID NO: 444         moltype =     length =
SEQUENCE: 444
000

SEQ ID NO: 445         moltype =     length =
SEQUENCE: 445
000
```

| | | |
|---|---|---|
| SEQ ID NO: 446<br>SEQUENCE: 446<br>000 | moltype = | length = |
| SEQ ID NO: 447<br>SEQUENCE: 447<br>000 | moltype = | length = |
| SEQ ID NO: 448<br>SEQUENCE: 448<br>000 | moltype = | length = |
| SEQ ID NO: 449<br>SEQUENCE: 449<br>000 | moltype = | length = |
| SEQ ID NO: 450<br>SEQUENCE: 450<br>000 | moltype = | length = |
| SEQ ID NO: 451<br>SEQUENCE: 451<br>000 | moltype = | length = |
| SEQ ID NO: 452<br>SEQUENCE: 452<br>000 | moltype = | length = |
| SEQ ID NO: 453<br>SEQUENCE: 453<br>000 | moltype = | length = |
| SEQ ID NO: 454<br>SEQUENCE: 454<br>000 | moltype = | length = |
| SEQ ID NO: 455<br>SEQUENCE: 455<br>000 | moltype = | length = |
| SEQ ID NO: 456<br>SEQUENCE: 456<br>000 | moltype = | length = |
| SEQ ID NO: 457<br>SEQUENCE: 457<br>000 | moltype = | length = |
| SEQ ID NO: 458<br>SEQUENCE: 458<br>000 | moltype = | length = |
| SEQ ID NO: 459<br>SEQUENCE: 459<br>000 | moltype = | length = |
| SEQ ID NO: 460<br>SEQUENCE: 460<br>000 | moltype = | length = |
| SEQ ID NO: 461<br>SEQUENCE: 461<br>000 | moltype = | length = |
| SEQ ID NO: 462<br>SEQUENCE: 462<br>000 | moltype = | length = |
| SEQ ID NO: 463<br>SEQUENCE: 463<br>000 | moltype = | length = |
| SEQ ID NO: 464<br>SEQUENCE: 464<br>000 | moltype = | length = |
| SEQ ID NO: 465<br>SEQUENCE: 465 | moltype = | length = |

-continued

```
000

SEQ ID NO: 466          moltype =    length =
SEQUENCE: 466
000

SEQ ID NO: 467          moltype =    length =
SEQUENCE: 467
000

SEQ ID NO: 468          moltype =    length =
SEQUENCE: 468
000

SEQ ID NO: 469          moltype =    length =
SEQUENCE: 469
000

SEQ ID NO: 470          moltype =    length =
SEQUENCE: 470
000

SEQ ID NO: 471          moltype =    length =
SEQUENCE: 471
000

SEQ ID NO: 472          moltype =    length =
SEQUENCE: 472
000

SEQ ID NO: 473          moltype =    length =
SEQUENCE: 473
000

SEQ ID NO: 474          moltype =    length =
SEQUENCE: 474
000

SEQ ID NO: 475          moltype =    length =
SEQUENCE: 475
000

SEQ ID NO: 476          moltype =    length =
SEQUENCE: 476
000

SEQ ID NO: 477          moltype =    length =
SEQUENCE: 477
000

SEQ ID NO: 478          moltype =    length =
SEQUENCE: 478
000

SEQ ID NO: 479          moltype =    length =
SEQUENCE: 479
000

SEQ ID NO: 480          moltype =    length =
SEQUENCE: 480
000

SEQ ID NO: 481          moltype =    length =
SEQUENCE: 481
000

SEQ ID NO: 482          moltype =    length =
SEQUENCE: 482
000

SEQ ID NO: 483          moltype =    length =
SEQUENCE: 483
000

SEQ ID NO: 484          moltype =    length =
SEQUENCE: 484
000

SEQ ID NO: 485          moltype =    length =
```

SEQUENCE: 485
000

SEQ ID NO: 486          moltype =      length =
SEQUENCE: 486
000

SEQ ID NO: 487          moltype =      length =
SEQUENCE: 487
000

SEQ ID NO: 488          moltype =      length =
SEQUENCE: 488
000

SEQ ID NO: 489          moltype =      length =
SEQUENCE: 489
000

SEQ ID NO: 490          moltype =      length =
SEQUENCE: 490
000

SEQ ID NO: 491          moltype =      length =
SEQUENCE: 491
000

SEQ ID NO: 492          moltype =      length =
SEQUENCE: 492
000

SEQ ID NO: 493          moltype =      length =
SEQUENCE: 493
000

SEQ ID NO: 494          moltype =      length =
SEQUENCE: 494
000

SEQ ID NO: 495          moltype =      length =
SEQUENCE: 495
000

SEQ ID NO: 496          moltype =      length =
SEQUENCE: 496
000

SEQ ID NO: 497          moltype =      length =
SEQUENCE: 497
000

SEQ ID NO: 498          moltype =      length =
SEQUENCE: 498
000

SEQ ID NO: 499          moltype =      length =
SEQUENCE: 499
000

SEQ ID NO: 500          moltype =      length =
SEQUENCE: 500
000

SEQ ID NO: 501          moltype =      length =
SEQUENCE: 501
000

SEQ ID NO: 502          moltype =      length =
SEQUENCE: 502
000

SEQ ID NO: 503          moltype =      length =
SEQUENCE: 503
000

SEQ ID NO: 504          moltype =      length =
SEQUENCE: 504
000

| | | |
|---|---|---|
| SEQ ID NO: 505 SEQUENCE: 505 | moltype = length = 000 | |
| SEQ ID NO: 506 SEQUENCE: 506 | moltype = length = 000 | |
| SEQ ID NO: 507 SEQUENCE: 507 | moltype = length = 000 | |
| SEQ ID NO: 508 SEQUENCE: 508 | moltype = length = 000 | |
| SEQ ID NO: 509 SEQUENCE: 509 | moltype = length = 000 | |
| SEQ ID NO: 510 SEQUENCE: 510 | moltype = length = 000 | |
| SEQ ID NO: 511 SEQUENCE: 511 | moltype = length = 000 | |
| SEQ ID NO: 512 SEQUENCE: 512 | moltype = length = 000 | |
| SEQ ID NO: 513 SEQUENCE: 513 | moltype = length = 000 | |
| SEQ ID NO: 514 SEQUENCE: 514 | moltype = length = 000 | |
| SEQ ID NO: 515 SEQUENCE: 515 | moltype = length = 000 | |
| SEQ ID NO: 516 SEQUENCE: 516 | moltype = length = 000 | |
| SEQ ID NO: 517 SEQUENCE: 517 | moltype = length = 000 | |
| SEQ ID NO: 518 SEQUENCE: 518 | moltype = length = 000 | |
| SEQ ID NO: 519 SEQUENCE: 519 | moltype = length = 000 | |
| SEQ ID NO: 520 SEQUENCE: 520 | moltype = length = 000 | |
| SEQ ID NO: 521 SEQUENCE: 521 | moltype = length = 000 | |
| SEQ ID NO: 522 SEQUENCE: 522 | moltype = length = 000 | |
| SEQ ID NO: 523 SEQUENCE: 523 | moltype = length = 000 | |
| SEQ ID NO: 524 FEATURE REGION | moltype = AA length = 34 Location/Qualifiers 1..34 | |

|  |  |
|---|---|
| MOD_RES | note = Description of Artificial Sequence: Synthetic polypeptide |
|  | 8 |
|  | note = K(allyloxycarbonyl protecting group) |
| source | 1..34 |
|  | mol_type = protein |
|  | organism = synthetic construct |

SEQUENCE: 524
PKPEAPGKDA SPEEWDRYYK DLRHYLNWLT RQRF 34

SEQ ID NO: 525 moltype = length =
SEQUENCE: 525
000

SEQ ID NO: 526 moltype = length =
SEQUENCE: 526
000

SEQ ID NO: 527 moltype = length =
SEQUENCE: 527
000

SEQ ID NO: 528 moltype = length =
SEQUENCE: 528
000

SEQ ID NO: 529 moltype = length =
SEQUENCE: 529
000

SEQ ID NO: 530 moltype = length =
SEQUENCE: 530
000

SEQ ID NO: 531 moltype = length =
SEQUENCE: 531
000

SEQ ID NO: 532 moltype = length =
SEQUENCE: 532
000

SEQ ID NO: 533 moltype = length =
SEQUENCE: 533
000

SEQ ID NO: 534 moltype = length =
SEQUENCE: 534
000

SEQ ID NO: 535 moltype = length =
SEQUENCE: 535
000

SEQ ID NO: 536 moltype = length =
SEQUENCE: 536
000

SEQ ID NO: 537 moltype = length =
SEQUENCE: 537
000

SEQ ID NO: 538 moltype = length =
SEQUENCE: 538
000

SEQ ID NO: 539 moltype = length =
SEQUENCE: 539
000

SEQ ID NO: 540 moltype = length =
SEQUENCE: 540
000

SEQ ID NO: 541 moltype = length =
SEQUENCE: 541
000

SEQ ID NO: 542 moltype = AA length = 34

```
FEATURE                 Location/Qualifiers
REGION                  1..34
                        note = Description of Artificial Sequence: Synthetic
                        polypeptide
MOD_RES                 8
                        note =
                        K(1-(4,4-dimethyl-2,6-dioxocyclohex-1-ylidene)-3-methylbuty
                        l protecting group)
source                  1..34
                        mol_type = protein
                        organism = synthetic construct
SEQUENCE: 542
PKPEAPGKDA SPEEWDRYYK DLRHYLNWLT RQRF                                              34

SEQ ID NO: 543          moltype = AA  length = 34
FEATURE                 Location/Qualifiers
REGION                  1..34
                        note = Description of Artificial Sequence: Synthetic
                        polypeptide
MOD_RES                 8
                        note =
                        K(1-(4,4-dimethyl-2,6-dioxocyclohex-1-ylidene)-3-methylbuty
                        l protecting group)
source                  1..34
                        mol_type = protein
                        organism = synthetic construct
SEQUENCE: 543
PKPEAPGKDA SPEEWKRYYE DLRHYLNWLT RQRF                                              34

SEQ ID NO: 544          moltype =    length =
SEQUENCE: 544
000

SEQ ID NO: 545          moltype =    length =
SEQUENCE: 545
000

SEQ ID NO: 546          moltype =    length =
SEQUENCE: 546
000

SEQ ID NO: 547          moltype =    length =
SEQUENCE: 547
000

SEQ ID NO: 548          moltype =    length =
SEQUENCE: 548
000

SEQ ID NO: 549          moltype =    length =
SEQUENCE: 549
000

SEQ ID NO: 550          moltype =    length =
SEQUENCE: 550
000

SEQ ID NO: 551          moltype =    length =
SEQUENCE: 551
000

SEQ ID NO: 552          moltype =    length =
SEQUENCE: 552
000

SEQ ID NO: 553          moltype =    length =
SEQUENCE: 553
000

SEQ ID NO: 554          moltype =    length =
SEQUENCE: 554
000

SEQ ID NO: 555          moltype =    length =
SEQUENCE: 555
000

SEQ ID NO: 556          moltype =    length =
SEQUENCE: 556
```

000

SEQ ID NO: 557         moltype =      length =
SEQUENCE: 557
000

SEQ ID NO: 558         moltype =      length =
SEQUENCE: 558
000

SEQ ID NO: 559         moltype =      length =
SEQUENCE: 559
000

SEQ ID NO: 560         moltype =      length =
SEQUENCE: 560
000

SEQ ID NO: 561         moltype =      length =
SEQUENCE: 561
000

SEQ ID NO: 562         moltype =      length =
SEQUENCE: 562
000

SEQ ID NO: 563         moltype =      length =
SEQUENCE: 563
000

SEQ ID NO: 564         moltype =      length =
SEQUENCE: 564
000

SEQ ID NO: 565         moltype =      length =
SEQUENCE: 565
000

SEQ ID NO: 566         moltype =      length =
SEQUENCE: 566
000

SEQ ID NO: 567         moltype =      length =
SEQUENCE: 567
000

SEQ ID NO: 568         moltype =      length =
SEQUENCE: 568
000

SEQ ID NO: 569         moltype =      length =
SEQUENCE: 569
000

SEQ ID NO: 570         moltype =      length =
SEQUENCE: 570
000

SEQ ID NO: 571         moltype =      length =
SEQUENCE: 571
000

SEQ ID NO: 572         moltype =      length =
SEQUENCE: 572
000

SEQ ID NO: 573         moltype =      length =
SEQUENCE: 573
000

SEQ ID NO: 574         moltype =      length =
SEQUENCE: 574
000

SEQ ID NO: 575         moltype =      length =
SEQUENCE: 575
000

SEQ ID NO: 576         moltype =      length =

-continued

| | | |
|---|---|---|
| SEQUENCE: 576 000 | | |
| SEQ ID NO: 577 SEQUENCE: 577 000 | moltype = | length = |
| SEQ ID NO: 578 SEQUENCE: 578 000 | moltype = | length = |
| SEQ ID NO: 579 SEQUENCE: 579 000 | moltype = | length = |
| SEQ ID NO: 580 SEQUENCE: 580 000 | moltype = | length = |
| SEQ ID NO: 581 SEQUENCE: 581 000 | moltype = | length = |
| SEQ ID NO: 582 SEQUENCE: 582 000 | moltype = | length = |
| SEQ ID NO: 583 SEQUENCE: 583 000 | moltype = | length = |
| SEQ ID NO: 584 SEQUENCE: 584 000 | moltype = | length = |
| SEQ ID NO: 585 SEQUENCE: 585 000 | moltype = | length = |
| SEQ ID NO: 586 SEQUENCE: 586 000 | moltype = | length = |
| SEQ ID NO: 587 SEQUENCE: 587 000 | moltype = | length = |
| SEQ ID NO: 588 SEQUENCE: 588 000 | moltype = | length = |
| SEQ ID NO: 589 SEQUENCE: 589 000 | moltype = | length = |
| SEQ ID NO: 590 SEQUENCE: 590 000 | moltype = | length = |
| SEQ ID NO: 591 SEQUENCE: 591 000 | moltype = | length = |
| SEQ ID NO: 592 SEQUENCE: 592 000 | moltype = | length = |
| SEQ ID NO: 593 SEQUENCE: 593 000 | moltype = | length = |
| SEQ ID NO: 594 SEQUENCE: 594 000 | moltype = | length = |
| SEQ ID NO: 595 SEQUENCE: 595 000 | moltype = | length = |

| SEQ ID NO: 596 | moltype = | length = |
|---|---|---|
| SEQUENCE: 596 | | |
| 000 | | |

| SEQ ID NO: 597 | moltype = | length = |
|---|---|---|
| SEQUENCE: 597 | | |
| 000 | | |

| SEQ ID NO: 598 | moltype = | length = |
|---|---|---|
| SEQUENCE: 598 | | |
| 000 | | |

| SEQ ID NO: 599 | moltype = | length = |
|---|---|---|
| SEQUENCE: 599 | | |
| 000 | | |

| SEQ ID NO: 600 | moltype = | length = |
|---|---|---|
| SEQUENCE: 600 | | |
| 000 | | |

| SEQ ID NO: 601 | moltype = | length = |
|---|---|---|
| SEQUENCE: 601 | | |
| 000 | | |

| SEQ ID NO: 602 | moltype = | length = |
|---|---|---|
| SEQUENCE: 602 | | |
| 000 | | |

| SEQ ID NO: 603 | moltype = | length = |
|---|---|---|
| SEQUENCE: 603 | | |
| 000 | | |

| SEQ ID NO: 604 | moltype = | length = |
|---|---|---|
| SEQUENCE: 604 | | |
| 000 | | |

| SEQ ID NO: 605 | moltype = | length = |
|---|---|---|
| SEQUENCE: 605 | | |
| 000 | | |

| SEQ ID NO: 606 | moltype = | length = |
|---|---|---|
| SEQUENCE: 606 | | |
| 000 | | |

| SEQ ID NO: 607 | moltype = | length = |
|---|---|---|
| SEQUENCE: 607 | | |
| 000 | | |

| SEQ ID NO: 608 | moltype = | length = |
|---|---|---|
| SEQUENCE: 608 | | |
| 000 | | |

| SEQ ID NO: 609 | moltype = | length = |
|---|---|---|
| SEQUENCE: 609 | | |
| 000 | | |

| SEQ ID NO: 610 | moltype = | length = |
|---|---|---|
| SEQUENCE: 610 | | |
| 000 | | |

| SEQ ID NO: 611 | moltype = | length = |
|---|---|---|
| SEQUENCE: 611 | | |
| 000 | | |

| SEQ ID NO: 612 | moltype = | length = |
|---|---|---|
| SEQUENCE: 612 | | |
| 000 | | |

| SEQ ID NO: 613 | moltype = | length = |
|---|---|---|
| SEQUENCE: 613 | | |
| 000 | | |

| SEQ ID NO: 614 | moltype = | length = |
|---|---|---|
| SEQUENCE: 614 | | |
| 000 | | |

| SEQ ID NO: 615 | moltype = | length = |
|---|---|---|
| SEQUENCE: 615 | | |
| 000 | | |

| | | |
|---|---|---|
| SEQ ID NO: 616<br>SEQUENCE: 616<br>000 | moltype = | length = |
| SEQ ID NO: 617<br>SEQUENCE: 617<br>000 | moltype = | length = |
| SEQ ID NO: 618<br>SEQUENCE: 618<br>000 | moltype = | length = |
| SEQ ID NO: 619<br>SEQUENCE: 619<br>000 | moltype = | length = |
| SEQ ID NO: 620<br>SEQUENCE: 620<br>000 | moltype = | length = |
| SEQ ID NO: 621<br>SEQUENCE: 621<br>000 | moltype = | length = |
| SEQ ID NO: 622<br>SEQUENCE: 622<br>000 | moltype = | length = |
| SEQ ID NO: 623<br>SEQUENCE: 623<br>000 | moltype = | length = |
| SEQ ID NO: 624<br>SEQUENCE: 624<br>000 | moltype = | length = |
| SEQ ID NO: 625<br>SEQUENCE: 625<br>000 | moltype = | length = |
| SEQ ID NO: 626<br>SEQUENCE: 626<br>000 | moltype = | length = |
| SEQ ID NO: 627<br>SEQUENCE: 627<br>000 | moltype = | length = |
| SEQ ID NO: 628<br>SEQUENCE: 628<br>000 | moltype = | length = |
| SEQ ID NO: 629<br>SEQUENCE: 629<br>000 | moltype = | length = |
| SEQ ID NO: 630<br>SEQUENCE: 630<br>000 | moltype = | length = |
| SEQ ID NO: 631<br>SEQUENCE: 631<br>000 | moltype = | length = |
| SEQ ID NO: 632<br>SEQUENCE: 632<br>000 | moltype = | length = |
| SEQ ID NO: 633<br>SEQUENCE: 633<br>000 | moltype = | length = |
| SEQ ID NO: 634<br>SEQUENCE: 634<br>000 | moltype = | length = |
| SEQ ID NO: 635<br>SEQUENCE: 635 | moltype = | length = |

```
000

SEQ ID NO: 636         moltype =    length =
SEQUENCE: 636
000

SEQ ID NO: 637         moltype =    length =
SEQUENCE: 637
000

SEQ ID NO: 638         moltype =    length =
SEQUENCE: 638
000

SEQ ID NO: 639         moltype =    length =
SEQUENCE: 639
000

SEQ ID NO: 640         moltype =    length =
SEQUENCE: 640
000

SEQ ID NO: 641         moltype =    length =
SEQUENCE: 641
000

SEQ ID NO: 642         moltype = AA  length = 34
FEATURE                Location/Qualifiers
REGION                 1..34
                       note = Description of Artificial Sequence: Synthetic
                        polypeptide
MOD_RES                8
                       note =
                        K(1-(4,4-dimethyl-2,6-dioxocyclohex-1-ylidene)-3-methylbuty
                        l protecting group)
source                 1..34
                       mol_type = protein
                       organism = synthetic construct
SEQUENCE: 642
PKPEAPGKDA SPEEWDRYYK DLRHYLNWLT RQRF                                   34

SEQ ID NO: 643         moltype = AA  length = 34
FEATURE                Location/Qualifiers
REGION                 1..34
                       note = Description of Artificial Sequence: Synthetic
                        polypeptide
MOD_RES                8
                       note =
                        K(1-(4,4-dimethyl-2,6-dioxocyclohex-1-ylidene)-3-methylbuty
                        l protecting group)
source                 1..34
                       mol_type = protein
                       organism = synthetic construct
SEQUENCE: 643
PKPEAPGKDA SPEEWKRYYE DLRHYLNWLT RQRF                                   34

SEQ ID NO: 644         moltype =    length =
SEQUENCE: 644
000

SEQ ID NO: 645         moltype =    length =
SEQUENCE: 645
000

SEQ ID NO: 646         moltype =    length =
SEQUENCE: 646
000

SEQ ID NO: 647         moltype =    length =
SEQUENCE: 647
000

SEQ ID NO: 648         moltype =    length =
SEQUENCE: 648
000

SEQ ID NO: 649         moltype =    length =
SEQUENCE: 649
000
```

| SEQ ID NO: 650 SEQUENCE: 650 | moltype = | length = 000 |
|---|---|---|
| SEQ ID NO: 651 SEQUENCE: 651 | moltype = | length = 000 |
| SEQ ID NO: 652 SEQUENCE: 652 | moltype = | length = 000 |
| SEQ ID NO: 653 SEQUENCE: 653 | moltype = | length = 000 |
| SEQ ID NO: 654 SEQUENCE: 654 | moltype = | length = 000 |
| SEQ ID NO: 655 SEQUENCE: 655 | moltype = | length = 000 |
| SEQ ID NO: 656 SEQUENCE: 656 | moltype = | length = 000 |
| SEQ ID NO: 657 SEQUENCE: 657 | moltype = | length = 000 |
| SEQ ID NO: 658 SEQUENCE: 658 | moltype = | length = 000 |
| SEQ ID NO: 659 SEQUENCE: 659 | moltype = | length = 000 |
| SEQ ID NO: 660 SEQUENCE: 660 | moltype = | length = 000 |
| SEQ ID NO: 661 SEQUENCE: 661 | moltype = | length = 000 |
| SEQ ID NO: 662 SEQUENCE: 662 | moltype = | length = 000 |
| SEQ ID NO: 663 SEQUENCE: 663 | moltype = | length = 000 |
| SEQ ID NO: 664 SEQUENCE: 664 | moltype = | length = 000 |
| SEQ ID NO: 665 SEQUENCE: 665 | moltype = | length = 000 |
| SEQ ID NO: 666 SEQUENCE: 666 | moltype = | length = 000 |
| SEQ ID NO: 667 SEQUENCE: 667 | moltype = | length = 000 |
| SEQ ID NO: 668 SEQUENCE: 668 | moltype = | length = 000 |
| SEQ ID NO: 669 SEQUENCE: 669 | moltype = | length = |

000

SEQ ID NO: 670        moltype =    length =
SEQUENCE: 670
000

SEQ ID NO: 671        moltype =    length =
SEQUENCE: 671
000

SEQ ID NO: 672        moltype =    length =
SEQUENCE: 672
000

SEQ ID NO: 673        moltype =    length =
SEQUENCE: 673
000

SEQ ID NO: 674        moltype =    length =
SEQUENCE: 674
000

SEQ ID NO: 675        moltype =    length =
SEQUENCE: 675
000

SEQ ID NO: 676        moltype =    length =
SEQUENCE: 676
000

SEQ ID NO: 677        moltype =    length =
SEQUENCE: 677
000

SEQ ID NO: 678        moltype =    length =
SEQUENCE: 678
000

SEQ ID NO: 679        moltype =    length =
SEQUENCE: 679
000

SEQ ID NO: 680        moltype =    length =
SEQUENCE: 680
000

SEQ ID NO: 681        moltype =    length =
SEQUENCE: 681
000

SEQ ID NO: 682        moltype =    length =
SEQUENCE: 682
000

SEQ ID NO: 683        moltype =    length =
SEQUENCE: 683
000

SEQ ID NO: 684        moltype =    length =
SEQUENCE: 684
000

SEQ ID NO: 685        moltype =    length =
SEQUENCE: 685
000

SEQ ID NO: 686        moltype =    length =
SEQUENCE: 686
000

SEQ ID NO: 687        moltype =    length =
SEQUENCE: 687
000

SEQ ID NO: 688        moltype =    length =
SEQUENCE: 688
000

SEQ ID NO: 689        moltype =    length =

| | | |
|---|---|---|
| SEQUENCE: 689 000 | | |
| SEQ ID NO: 690 SEQUENCE: 690 000 | moltype = | length = |
| SEQ ID NO: 691 SEQUENCE: 691 000 | moltype = | length = |
| SEQ ID NO: 692 SEQUENCE: 692 000 | moltype = | length = |
| SEQ ID NO: 693 SEQUENCE: 693 000 | moltype = | length = |
| SEQ ID NO: 694 SEQUENCE: 694 000 | moltype = | length = |
| SEQ ID NO: 695 SEQUENCE: 695 000 | moltype = | length = |
| SEQ ID NO: 696 SEQUENCE: 696 000 | moltype = | length = |
| SEQ ID NO: 697 SEQUENCE: 697 000 | moltype = | length = |
| SEQ ID NO: 698 SEQUENCE: 698 000 | moltype = | length = |
| SEQ ID NO: 699 SEQUENCE: 699 000 | moltype = | length = |
| SEQ ID NO: 700 SEQUENCE: 700 000 | moltype = | length = |
| SEQ ID NO: 701 SEQUENCE: 701 000 | moltype = | length = |
| SEQ ID NO: 702 SEQUENCE: 702 000 | moltype = | length = |
| SEQ ID NO: 703 SEQUENCE: 703 000 | moltype = | length = |
| SEQ ID NO: 704 SEQUENCE: 704 000 | moltype = | length = |
| SEQ ID NO: 705 SEQUENCE: 705 000 | moltype = | length = |
| SEQ ID NO: 706 SEQUENCE: 706 000 | moltype = | length = |
| SEQ ID NO: 707 SEQUENCE: 707 000 | moltype = | length = |
| SEQ ID NO: 708 SEQUENCE: 708 000 | moltype = | length = |

| | | |
|---|---|---|
| SEQ ID NO: 709<br>SEQUENCE: 709<br>000 | moltype = | length = |
| SEQ ID NO: 710<br>SEQUENCE: 710<br>000 | moltype = | length = |
| SEQ ID NO: 711<br>SEQUENCE: 711<br>000 | moltype = | length = |
| SEQ ID NO: 712<br>SEQUENCE: 712<br>000 | moltype = | length = |
| SEQ ID NO: 713<br>SEQUENCE: 713<br>000 | moltype = | length = |
| SEQ ID NO: 714<br>SEQUENCE: 714<br>000 | moltype = | length = |
| SEQ ID NO: 715<br>SEQUENCE: 715<br>000 | moltype = | length = |
| SEQ ID NO: 716<br>SEQUENCE: 716<br>000 | moltype = | length = |
| SEQ ID NO: 717<br>SEQUENCE: 717<br>000 | moltype = | length = |
| SEQ ID NO: 718<br>SEQUENCE: 718<br>000 | moltype = | length = |
| SEQ ID NO: 719<br>SEQUENCE: 719<br>000 | moltype = | length = |
| SEQ ID NO: 720<br>SEQUENCE: 720<br>000 | moltype = | length = |
| SEQ ID NO: 721<br>SEQUENCE: 721<br>000 | moltype = | length = |
| SEQ ID NO: 722<br>SEQUENCE: 722<br>000 | moltype = | length = |
| SEQ ID NO: 723<br>SEQUENCE: 723<br>000 | moltype = | length = |
| SEQ ID NO: 724<br>SEQUENCE: 724<br>000 | moltype = | length = |
| SEQ ID NO: 725<br>SEQUENCE: 725<br>000 | moltype = | length = |
| SEQ ID NO: 726<br>SEQUENCE: 726<br>000 | moltype = | length = |
| SEQ ID NO: 727<br>SEQUENCE: 727<br>000 | moltype = | length = |
| SEQ ID NO: 728<br>SEQUENCE: 728<br>000 | moltype = | length = |

| | | |
|---|---|---|
| SEQ ID NO: 729 | moltype = length = | |
| SEQUENCE: 729 | | |
| 000 | | |
| | | |
| SEQ ID NO: 730 | moltype = length = | |
| SEQUENCE: 730 | | |
| 000 | | |
| | | |
| SEQ ID NO: 731 | moltype = length = | |
| SEQUENCE: 731 | | |
| 000 | | |
| | | |
| SEQ ID NO: 732 | moltype = length = | |
| SEQUENCE: 732 | | |
| 000 | | |
| | | |
| SEQ ID NO: 733 | moltype = length = | |
| SEQUENCE: 733 | | |
| 000 | | |
| | | |
| SEQ ID NO: 734 | moltype = length = | |
| SEQUENCE: 734 | | |
| 000 | | |
| | | |
| SEQ ID NO: 735 | moltype = length = | |
| SEQUENCE: 735 | | |
| 000 | | |
| | | |
| SEQ ID NO: 736 | moltype = length = | |
| SEQUENCE: 736 | | |
| 000 | | |
| | | |
| SEQ ID NO: 737 | moltype = length = | |
| SEQUENCE: 737 | | |
| 000 | | |
| | | |
| SEQ ID NO: 738 | moltype = length = | |
| SEQUENCE: 738 | | |
| 000 | | |
| | | |
| SEQ ID NO: 739 | moltype = length = | |
| SEQUENCE: 739 | | |
| 000 | | |
| | | |
| SEQ ID NO: 740 | moltype = length = | |
| SEQUENCE: 740 | | |
| 000 | | |
| | | |
| SEQ ID NO: 741 | moltype = length = | |
| SEQUENCE: 741 | | |
| 000 | | |
| | | |
| SEQ ID NO: 742 | moltype = AA length = 34 | |
| FEATURE | Location/Qualifiers | |
| REGION | 1..34 | |
| | note = Description of Artificial Sequence: Synthetic polypeptide | |
| MOD_RES | 8 | |
| | note = K(1-(4,4-dimethyl-2,6-dioxocyclohex-1-ylidene)-3-methylbutyl protecting group) | |
| MOD_RES | 16 | |
| | note = D(allyl (CH2=CH-CH2- ) protecting group) | |
| MOD_RES | 20 | |
| | note = K(allyloxycarbonyl protecting group) | |
| source | 1..34 | |
| | mol_type = protein | |
| | organism = synthetic construct | |
| SEQUENCE: 742 | | |
| PKPEAPGKDA SPEEWDRYYK DLRHYLNWLT RQRF | | 34 |
| | | |
| SEQ ID NO: 743 | moltype = AA length = 34 | |
| FEATURE | Location/Qualifiers | |
| REGION | 1..34 | |
| | note = Description of Artificial Sequence: Synthetic polypeptide | |
| MOD_RES | 8 | |
| | note = | |

|  |  |
|---|---|
| MOD_RES | K(1-(4,4-dimethyl-2,6-dioxocyclohex-1-ylidene)-3-methylbutyl protecting group)<br>16<br>note = K(allyloxycarbonyl protecting group) |
| MOD_RES | 20<br>note = E(allyl (CH2=CH-CH2- ) protecting group) |
| source | 1..34<br>mol_type = protein<br>organism = synthetic construct |

SEQUENCE: 743
PKPEAPGKDA SPEEWKRYYE DLRHYLNWLT RQRF                              34

SEQ ID NO: 744         moltype =     length =
SEQUENCE: 744
000

SEQ ID NO: 745         moltype =     length =
SEQUENCE: 745
000

SEQ ID NO: 746         moltype =     length =
SEQUENCE: 746
000

SEQ ID NO: 747         moltype =     length =
SEQUENCE: 747
000

SEQ ID NO: 748         moltype =     length =
SEQUENCE: 748
000

SEQ ID NO: 749         moltype =     length =
SEQUENCE: 749
000

SEQ ID NO: 750         moltype =     length =
SEQUENCE: 750
000

SEQ ID NO: 751         moltype =     length =
SEQUENCE: 751
000

SEQ ID NO: 752         moltype =     length =
SEQUENCE: 752
000

SEQ ID NO: 753         moltype =     length =
SEQUENCE: 753
000

SEQ ID NO: 754         moltype =     length =
SEQUENCE: 754
000

SEQ ID NO: 755         moltype =     length =
SEQUENCE: 755
000

SEQ ID NO: 756         moltype =     length =
SEQUENCE: 756
000

SEQ ID NO: 757         moltype =     length =
SEQUENCE: 757
000

SEQ ID NO: 758         moltype =     length =
SEQUENCE: 758
000

SEQ ID NO: 759         moltype =     length =
SEQUENCE: 759
000

SEQ ID NO: 760         moltype =     length =
SEQUENCE: 760
000

| | | |
|---|---|---|
| SEQ ID NO: 761 SEQUENCE: 761 | moltype = | length = 000 |
| SEQ ID NO: 762 SEQUENCE: 762 | moltype = | length = 000 |
| SEQ ID NO: 763 SEQUENCE: 763 | moltype = | length = 000 |
| SEQ ID NO: 764 SEQUENCE: 764 | moltype = | length = 000 |
| SEQ ID NO: 765 SEQUENCE: 765 | moltype = | length = 000 |
| SEQ ID NO: 766 SEQUENCE: 766 | moltype = | length = 000 |
| SEQ ID NO: 767 SEQUENCE: 767 | moltype = | length = 000 |
| SEQ ID NO: 768 SEQUENCE: 768 | moltype = | length = 000 |
| SEQ ID NO: 769 SEQUENCE: 769 | moltype = | length = 000 |
| SEQ ID NO: 770 SEQUENCE: 770 | moltype = | length = 000 |
| SEQ ID NO: 771 SEQUENCE: 771 | moltype = | length = 000 |
| SEQ ID NO: 772 SEQUENCE: 772 | moltype = | length = 000 |
| SEQ ID NO: 773 SEQUENCE: 773 | moltype = | length = 000 |
| SEQ ID NO: 774 SEQUENCE: 774 | moltype = | length = 000 |
| SEQ ID NO: 775 SEQUENCE: 775 | moltype = | length = 000 |
| SEQ ID NO: 776 SEQUENCE: 776 | moltype = | length = 000 |
| SEQ ID NO: 777 SEQUENCE: 777 | moltype = | length = 000 |
| SEQ ID NO: 778 SEQUENCE: 778 | moltype = | length = 000 |
| SEQ ID NO: 779 SEQUENCE: 779 | moltype = | length = 000 |
| SEQ ID NO: 780 SEQUENCE: 780 | moltype = | length = |

```
SEQ ID NO: 781          moltype =    length =
SEQUENCE: 781
000

SEQ ID NO: 782          moltype =    length =
SEQUENCE: 782
000

SEQ ID NO: 783          moltype =    length =
SEQUENCE: 783
000

SEQ ID NO: 784          moltype =    length =
SEQUENCE: 784
000

SEQ ID NO: 785          moltype =    length =
SEQUENCE: 785
000

SEQ ID NO: 786          moltype =    length =
SEQUENCE: 786
000

SEQ ID NO: 787          moltype =    length =
SEQUENCE: 787
000

SEQ ID NO: 788          moltype =    length =
SEQUENCE: 788
000

SEQ ID NO: 789          moltype =    length =
SEQUENCE: 789
000

SEQ ID NO: 790          moltype =    length =
SEQUENCE: 790
000

SEQ ID NO: 791          moltype =    length =
SEQUENCE: 791
000

SEQ ID NO: 792          moltype =    length =
SEQUENCE: 792
000

SEQ ID NO: 793          moltype =    length =
SEQUENCE: 793
000

SEQ ID NO: 794          moltype =    length =
SEQUENCE: 794
000

SEQ ID NO: 795          moltype =    length =
SEQUENCE: 795
000

SEQ ID NO: 796          moltype =    length =
SEQUENCE: 796
000

SEQ ID NO: 797          moltype =    length =
SEQUENCE: 797
000

SEQ ID NO: 798          moltype =    length =
SEQUENCE: 798
000

SEQ ID NO: 799          moltype =    length =
SEQUENCE: 799
000

SEQ ID NO: 800          moltype = AA  length = 36
```

```
FEATURE                 Location/Qualifiers
REGION                  1..36
                        note = Description of Unknown: PYY peptide sequence
source                  1..36
                        mol_type = protein
                        organism = unidentified
SEQUENCE: 800
YPIKPEAPGE DASPEELNRY YASLRHYLNL VTRQRY                                   36

SEQ ID NO: 801          moltype = AA  length = 30
FEATURE                 Location/Qualifiers
REGION                  1..30
                        note = Description of Unknown: GLP-1 sequence
source                  1..30
                        mol_type = protein
                        organism = unidentified
SEQUENCE: 801
HAEGTFTSDV SSYLEGQAAK EFIAWLVKGR                                          30

SEQ ID NO: 802          moltype = AA  length = 39
FEATURE                 Location/Qualifiers
REGION                  1..39
                        note = Description of Unknown: Exenatide sequence
source                  1..39
                        mol_type = protein
                        organism = unidentified
SEQUENCE: 802
HGEGTFTSDL SKQMEEEAVR LFIEWLKNGG PSSGAPPPS                                39

SEQ ID NO: 803          moltype =   length =
SEQUENCE: 803
000

SEQ ID NO: 804          moltype =   length =
SEQUENCE: 804
000

SEQ ID NO: 805          moltype = AA  length = 40
FEATURE                 Location/Qualifiers
REGION                  1..40
                        note = Description of Artificial Sequence: Synthetic
                         polypeptide
MOD_RES                 2
                        note = Aib
MOD_RES                 13
                        note = Aib
MOD_RES                 20
                        note = diacid-gamma-Glu
MOD_RES                 21
                        note = (AEEA)2-Lys
source                  1..40
                        mol_type = protein
                        organism = synthetic construct
SEQUENCE: 805
YXEGTFTSDY SIXLDKIAQE KAFVQWLIAG GPSSGAPPPS                               40

SEQ ID NO: 806          moltype = AA  length = 35
FEATURE                 Location/Qualifiers
REGION                  1..35
                        note = Description of Artificial Sequence: Synthetic
                         polypeptide
VARIANT                 1
                        note = X can be K or absent
VARIANT                 5
                        note = X can be E or K
VARIANT                 6
                        note = X can be A or K
VARIANT                 8
                        note = X can be G or K
VARIANT                 9
                        note = X can be E, K, or D-Lysine
VARIANT                 11
                        note = X can be A or K
VARIANT                 14
                        note = X can be E or K
VARIANT                 15
                        note = X can be E or K
VARIANT                 16
                        note = X can be L or W
```

| | |
|---|---|
| VARIANT | 17 |
| | note = X can be D, E, K, N, Q, S, T, alpha-methylserine, or homoserine |
| VARIANT | 19 |
| | note = X can be K or Y |
| VARIANT | 20 |
| | note = X can be K or Y |
| VARIANT | 21 |
| | note = X can be A, D, E, K, D-Lysine, or Diaminopimelic acid |
| VARIANT | 23 |
| | note = X can be A, D, K, or L |
| VARIANT | 24 |
| | note = X can be K or R |
| VARIANT | 26 |
| | note = X can be K or Y |
| VARIANT | 28 |
| | note = X can be K or N |
| VARIANT | 33 |
| | note = X can be K or Q |
| VARIANT | 35 |
| | note = X can be F, y, 3-pyridinylalanine, 4-pyridinylalanine, 4-carboxyphenylalanine, 4-fluorophenylalanine, 4-methylphenylalanine, N-methylphenylalanine, homophenylalanine, beta-homotyrosine, homotyrosine, or N-methyltyrosine |
| REGION | 1..35 |
| | note = See specification as filed for detailed description of substitutions and preferred embodiments |
| source | 1..35 |
| | mol_type = protein |
| | organism = synthetic construct |
| SITE | 9 |
| | note = D-Lysine |
| SITE | 21 |
| | note = D-Lysine |
| MOD_RES | 21 |
| | note = Diaminopimelic acid |
| MOD_RES | 17 |
| | note = Alpha-methylserine, or homoserine |
| MOD_RES | 35 |
| | note = 3-pyridinylalanine, 4-pyridinylalanine, 4-carboxyphenylalanine, 4-fluorophenylalanine, 4-methylphenylalanine, N-methylphenylalanine, homophenylalanine, beta-homotyrosine, homotyrosine, or N-methyltyrosine |

SEQUENCE: 806
XPKPXXPXXD XSPXXXXRXX XDXXHXLXWL TRXRX                         35

| | |
|---|---|
| SEQ ID NO: 807 | moltype = AA  length = 7 |
| FEATURE | Location/Qualifiers |
| REGION | 1..7 |
| | note = Description of Artificial Sequence: Synthetic peptide |
| source | 1..7 |
| | mol_type = protein |
| | organism = synthetic construct |

SEQUENCE: 807
WDRYYKD                                                        7

| | |
|---|---|
| SEQ ID NO: 808 | moltype = AA  length = 10 |
| FEATURE | Location/Qualifiers |
| REGION | 1..10 |
| | note = Description of Artificial Sequence: Synthetic peptide |
| MOD_RES | 1..10 |
| | note = Gamma-Glu |
| VARIANT | 1..10 |
| | note = This sequence may encompass 1-10 residues |
| source | 1..10 |
| | mol_type = protein |
| | organism = synthetic construct |

SEQUENCE: 808
EEEEEEEEEE                                                     10

| | |
|---|---|
| SEQ ID NO: 809 | moltype = AA  length = 11 |
| FEATURE | Location/Qualifiers |
| REGION | 1..11 |
| | note = Description of Artificial Sequence: Synthetic peptide |
| MOD_RES | 1..10 |
| | note = Gamma-Glu |
| VARIANT | 1..10 |

|   |   |   |
|---|---|---|
|   | note = This sequence may encompass 1-10 "Glu" residues | |
| source | 1..11 | |
|   | mol_type = protein | |
|   | organism = synthetic construct | |
| SEQUENCE: 809 | | |
| EEEEEEEEE G | | 11 |

| | | |
|---|---|---|
| SEQ ID NO: 810 | moltype = AA   length = 4 | |
| FEATURE | Location/Qualifiers | |
| REGION | 1..4 | |
|   | note = Description of Artificial Sequence: Synthetic peptide | |
| MOD_RES | 1..4 | |
|   | note = Gamma-Glu | |
| source | 1..4 | |
|   | mol_type = protein | |
|   | organism = synthetic construct | |
| SEQUENCE: 810 | | |
| EEEE | | 4 |

| | | |
|---|---|---|
| SEQ ID NO: 811 | moltype = AA   length = 5 | |
| FEATURE | Location/Qualifiers | |
| REGION | 1..5 | |
|   | note = Description of Artificial Sequence: Synthetic peptide | |
| MOD_RES | 1..5 | |
|   | note = Gamma-Glu | |
| source | 1..5 | |
|   | mol_type = protein | |
|   | organism = synthetic construct | |
| SEQUENCE: 811 | | |
| EEEEE | | 5 |

| | | |
|---|---|---|
| SEQ ID NO: 812 | moltype = AA   length = 4 | |
| FEATURE | Location/Qualifiers | |
| REGION | 1..4 | |
|   | note = Description of Artificial Sequence: Synthetic peptide | |
| MOD_RES | 1..3 | |
|   | note = Gamma-Glu | |
| source | 1..4 | |
|   | mol_type = protein | |
|   | organism = synthetic construct | |
| SEQUENCE: 812 | | |
| EEEG | | 4 |

| | | |
|---|---|---|
| SEQ ID NO: 813 | moltype = AA   length = 11 | |
| FEATURE | Location/Qualifiers | |
| REGION | 1..11 | |
|   | note = Description of Artificial Sequence: Synthetic peptide | |
| MOD_RES | 2..11 | |
|   | note = Gamma-Glu | |
| VARIANT | 2..11 | |
|   | note = Upto nine E residues may be absent | |
| source | 1..11 | |
|   | mol_type = protein | |
|   | organism = synthetic construct | |
| SEQUENCE: 813 | | |
| GEEEEEEEEE E | | 11 |

| | | |
|---|---|---|
| SEQ ID NO: 814 | moltype = AA   length = 4 | |
| FEATURE | Location/Qualifiers | |
| REGION | 1..4 | |
|   | note = Description of Artificial Sequence: Synthetic peptide | |
| source | 1..4 | |
|   | mol_type = protein | |
|   | organism = synthetic construct | |
| SEQUENCE: 814 | | |
| EEEE | | 4 |

What is claimed is:
1. A pharmaceutical composition formulated for injection, oral administration, or for administration via an implantable delivery device, wherein said pharmaceutical composition comprises an isolated polypeptide comprising the amino acid sequence of SEQ ID NO: 90:
$X_0PX_2PX_4X_5PX_7X_8X_9X_{10}SPX_{13}X_{14}X_{15}X_{16}RX_{18}$
$X_{19}X_{20}DX_{22}X_{23}HX_{25}X_{26}X_{27}WLTRX_{32}RX_{34}$-(OH/NH$_2$) (SEQ ID NO: 90), or a pharmaceutically acceptable salt thereof, wherein:
$X_0$ is absent or K;
$X_2$ is K;
$X_4$ is E or K;
$X_5$ is A or K;
$X_7$ is G or K
$X_8$ is E, K, or k;
$X_9$ is D or K;
$X_{10}$ is A or K;
$X_{13}$ is E or K;
$X_{14}$ is E or K;
$X_{15}$ is L or W;
$X_{16}$ is D, E, K, N, Q, S, T, α-methylserine, or homoserine;
$X_{18}$ is K or Y;
$X_{19}$ is K or Y;
$X_{20}$ is A, D, E, K, k, or Dap,
$X_{22}$ is A, D, K, or L;
$X_{23}$ is K or R;
$X_{25}$ is K or Y;
$X_{26}$ is E, K, or L;
$X_{27}$ is K or N;
$X_{32}$ is K or Q;
$X_{34}$ is F, y, 3-pyridinylalanine, 4-pyridinylalanine, 4-carboxyphenylalanine, 4-fluorophenylalanine, 4-methylphenylalanine, N-methylphenylalanine, homophenylalanine, ß-homotyrosine, homotyrosine, or N-methyltyrosine;
wherein when $X_0$, $X_2$, $X_4$, $X_5$, $X_7$, $X_8$, $X_{13}$, $X_{20}$, $X_{23}$, $X_{25}$, $X_{27}$, or $X_{32}$ are K, the lysine residue is optionally covalently bound to a lipophilic substituent, optionally via a spacer, and
wherein when $X_8$ or $X_{20}$ are k, the D-lysine residue is optionally covalently bound to a lipophilic substituent, optionally via a spacer,
provided that the polypeptide comprises at least one residue covalently bound to a lipophilic substituent, optionally via a spacer; and
wherein the polypeptide optionally further comprises a lactam bridge formed via an amide bond between the side chains of a lysine and an aspartic acid or between the side chains of a lysine and a glutamic acid, wherein the residues that form the lactam bridge are located at positions $X_9$ and $X_{13}$ or at positions $X_{16}$ and $X_{20}$ or at positions $X_{22}$ and $X_{26}$.

2. The pharmaceutical composition of claim 1, wherein the isolated polypeptide comprises the amino acid sequence of SEQ ID NO: 91
PKPEX$_5$PX$_7$X:
DASPX$_{13}$EX$_{15}$X$_{16}$RYYX$_{20}$DX$_{22}$RHYLNWLTRQRX$_{34}$-(OH/NH$_2$) (SEQ ID NO: 91), or a pharmaceutically acceptable salt thereof, wherein:
$X_5$ is A or K;
$X_7$ is G or K;
$X_8$ is E, K, or k;
$X_{13}$ is E or K;
$X_{15}$ is L or W;
$X_{16}$ is D, E, K, N, S, a-methylserine, or homoserine;
$X_{20}$ is A, D, E, K, or k,
$X_{22}$ is A or L;
$X_{34}$ is F, 3-pyridinylalanine, 4-pyridinylalanine, 4-carboxyphenylalanine, 4-fluorophenylalanine, 4-methylphenylalanine, N-methylphenylalanine, homophenylalanine, ß-homotyrosine, homotyrosine, or N-methyltyrosine;
wherein when $X_5$, $X_7$, $X_8$, $X_{13}$, or $X_{20}$ are K, the lysine residue is optionally covalently bound to a lipophilic substituent, optionally via a spacer, and
wherein when $X_8$ or $X_{20}$ are k, the D-lysine residue is optionally covalently bound to a lipophilic substituent, optionally via a spacer,
provided that the polypeptide comprises at least one residue covalently bound to a lipophilic substituent, optionally via a spacer; and
wherein the polypeptide optionally further comprises a lactam bridge formed via an amide bond between the side chains of a lysine and an aspartic acid or between the side chains of a lysine and a glutamic acid, wherein the residues that form the lactam bridge are located at positions $X_{16}$ and $X_{20}$.

3. The pharmaceutical composition of claim 1, wherein the isolated polypeptide comprises the amino acid sequence of SEQ ID NO: 92:
PKPEX$_5$PX$_7$X:
DASPX$_{13}$EX$_{15}$X$_{16}$RYYX$_{20}$DX$_{22}$RHYLNWLTRQRX$_{34}$-(OH/NH$_2$) (SEQ ID NO: 92), or a pharmaceutically acceptable salt thereof, wherein:
$X_5$ is A or K;
$X_7$ is G or K;
$X_8$ is E, K, or k;
$X_{13}$ is E or K;
$X_{15}$ is L or W;
$X_{16}$ is D, E, K, S, a-methylserine, or homoserine;
$X_{20}$ is A, D, E, K, or k,
$X_{22}$ is A or L;
$X_{34}$ is F, 3-pyridinylalanine, 4-pyridinylalanine, 4-carboxyphenylalanine, 4-fluorophenylalanine, 4-methylphenylalanine, N-methylphenylalanine, homophenylalanine, ß-homotyrosine, homotyrosine, or N-methyltyrosine;
wherein when $X_5$, $X_7$, $X_8$, $X_{13}$, or $X_{20}$ are K, the lysine residue is optionally covalently bound to a lipophilic substituent, optionally via a spacer, and
wherein when $X_8$ or $X_{20}$ are k, the D-lysine residue is optionally covalently bound to a lipophilic substituent, optionally via a spacer,
provided that the polypeptide comprises at least one residue covalently bound to a lipophilic substituent, optionally via a spacer; and
wherein the polypeptide optionally further comprises a lactam bridge formed via an amide bond between the side chains of a lysine and an aspartic acid or between the side chains of a lysine and a glutamic acid, wherein the residues that form the lactam bridge are located at positions $X_{16}$ and $X_{20}$.

4. The pharmaceutical composition of claim 1, wherein the isolated polypeptide comprises the amino acid sequence of SEQ ID NO: 93:
PKPEX$_5$PX$_7$X$_8$DASPX$_{13}$EX$_{15}$X$_{16}$RYYX$_{20}$DX$_{22}$RHYLNWLTRQRX$_{34}$-(OH/NH$_2$) (SEQ ID NO: 93), or a pharmaceutically acceptable salt thereof, wherein:
$X_5$ is A or K;
$X_7$ is G or K;
$X_8$ is E, K, or k;
$X_{13}$ is E or K;
$X_{15}$ is L or W;

$X_{16}$ is D, E, K, N, S, a-methylserine, or homoserine;
$X_{20}$ is D, E, K, or k,
$X_{22}$ is A or L;
$X_{34}$ is F, 3-pyridinylalanine, 4-pyridinylalanine, 4-carboxyphenylalanine, 4-fluorophenylalanine, 4-methylphenylalanine, N-methylphenylalanine, homophenylalanine, ß-homotyrosine, homotyrosine, or N-methyltyrosine;
wherein when $X_5$, $X_7$, $X_8$, $X_{13}$, or $X_{20}$ are K, the lysine residue is optionally covalently bound to a lipophilic substituent, optionally via a spacer, and
wherein when $X_8$ or $X_{20}$ are k, the D-lysine residue is optionally covalently bound to a lipophilic substituent, optionally via a spacer,
provided that the polypeptide comprises at least one residue covalently bound to a lipophilic substituent, optionally via a spacer; and
wherein the polypeptide optionally further comprises a lactam bridge formed via an amide bond between the side chains of a lysine and an aspartic acid or between the side chains of a lysine and a glutamic acid, wherein the residues that form the lactam bridge are located at positions $X_{16}$ and $X_{20}$.

5. The pharmaceutical composition of claim 1, wherein the isolated polypeptide comprises the amino acid sequence of SEQ ID NO: 94:
PKPEX$_5$PGX$_8$DASPX$_{13}$EWX$_{16}$RYYX$_{20}$DX$_{22}$RHY-LNWLTRQRX$_{34}$-(OH/NH$_2$) (SEQ ID NO: 94), or a pharmaceutically acceptable salt thereof, wherein:
$X_5$ is A or K;
$X_8$ is E, K, or k;
$X_{13}$ is E or K;
$X_{16}$ is D, E, K, or N;
$X_{20}$ is A, D, E, K, or k,
$X_{22}$ is A or L;
$X_{34}$ is F or N-methyltyrosine;
wherein when $X_5$, $X_8$, $X_{13}$, or $X_{20}$ are K, the lysine residue is optionally covalently bound to a lipophilic substituent, optionally via a spacer, and
wherein when $X_8$ or $X_{20}$ are k, the D-lysine residue is optionally covalently bound to a lipophilic substituent, optionally via a spacer,
provided that the polypeptide comprises at least one residue covalently bound to a lipophilic substituent, optionally via a spacer; and
wherein the polypeptide optionally further comprises a lactam bridge formed via an amide bond between the side chains of a lysine and an aspartic acid or between the side chains of a lysine and a glutamic acid, wherein the residues that form the lactam bridge are located at positions $X_{16}$ and $X_{20}$.

6. The pharmaceutical composition of claim 1, wherein the isolated polypeptide comprises the amino acid sequence of SEQ ID NO: 95:
PKPEX$_5$PGK$_8$DASPX$_{13}$EWX$_{16}$RYYX$_{20}$DLRHYL-NWLTRQRF-(OH/NH$_2$) (SEQ ID NO: 95), or a pharmaceutically acceptable salt thereof, wherein:
$X_5$ is A or K;
$X_{13}$ is E or K;
$X_{16}$ is D, E, K, or N;
$X_{20}$ is A, D, E, K, or k; and
wherein when $X_5$, $X_{13}$, or $X_{20}$ are K, the lysine residue is optionally covalently bound to a lipophilic substituent, optionally via a spacer,
wherein $K_8$ is optionally covalently bound to a lipophilic substituent, optionally via a spacer, and wherein when $X_{20}$ is k, the D-lysine residue is optionally covalently bound to a lipophilic substituent, optionally via a spacer,
provided that the polypeptide comprises at least one residue covalently bound to a lipophilic substituent, optionally via a spacer; and
wherein the polypeptide optionally further comprises a lactam bridge formed via an amide bond between the side chains of a lysine and an aspartic acid or between the side chains of a lysine and a glutamic acid, wherein the residues that form the lactam bridge are located at positions $X_{16}$ and $X_{20}$.

7. The pharmaceutical composition of claim 1, wherein the lipophilic substituent is covalently bound to the isolated peptide via a spacer, and wherein the lipophilic substituent and spacer are of Formula II:

$$-(Y)_n\text{-CO-}(CH_2)_m\text{-Z} \qquad \text{Formula II}$$

wherein,
Y is selected from the group consisting of γGlu, Asp, Lys and Gly;
Z is -CH$_3$ or -CO$_2$H;
m is from 4 to 24; and
n is from 1 to 10.

8. The pharmaceutical composition of claim 7, wherein Y is γGlu, and n is 2.

9. A pharmaceutical composition formulated for injection, oral administration, or for administration via an implantable delivery device, wherein said pharmaceutical composition comprises an isolated polypeptide comprising the amino acid sequence of any of SEQ ID NOs: 1 to 78, or a pharmaceutically acceptable salt thereof.

10. The pharmaceutical composition of claim 9, wherein the isolated polypeptide comprises the amino acid sequence of SEQ ID NO: 13, or a pharmaceutically acceptable salt thereof.

11. The pharmaceutical composition of claim 9, wherein the isolated polypeptide comprises the amino acid sequence of SEQ ID NO: 24, or a pharmaceutically acceptable salt thereof.

12. The pharmaceutical composition of claim 9, wherein the isolated polypeptide comprises the amino acid sequence of SEQ ID NO: 42, or a pharmaceutically acceptable salt thereof.

13. The pharmaceutical composition of claim 9, wherein the isolated polypeptide comprises the amino acid sequence of SEQ ID NO: 43, or a pharmaceutically acceptable salt thereof.

14. A method of treating obesity, diabetes, nonalcoholic fatty liver disease (NAFLD), or nonalcoholic steatohepatitis (NASH) in a human subject; providing weight loss to the human subject; or suppressing appetite in the human subject, comprising administering to the subject the pharmaceutical composition of claim 1.

15. A method of treating obesity, diabetes, nonalcoholic fatty liver disease (NAFLD), or nonalcoholic steatohepatitis (NASH) in a human subject; providing weight loss to the human subject; or suppressing appetite in the human subject, comprising administering to the subject the pharmaceutical composition of claim 9.

16. The pharmaceutical composition of claim 1, formulated for injection.

17. The pharmaceutical composition of claim 1, formulated for oral administration.

18. The pharmaceutical composition of claim 1, formulated for administration via an implantable delivery device.

19. The pharmaceutical composition of claim 9, formulated for injection.

20. The pharmaceutical composition of claim 9, formulated for oral administration.

21. The pharmaceutical composition of claim 9, formulated for administration via an implantable delivery device.

22. A method of treating obesity, diabetes, nonalcoholic fatty liver disease (NAFLD), or nonalcoholic steatohepatitis (NASH) in a human subject; providing weight loss to the human subject; or suppressing appetite in the human subject, comprising administering to the subject the pharmaceutical composition of claim 10.

23. A method of treating obesity, diabetes, nonalcoholic fatty liver disease (NAFLD), or nonalcoholic steatohepatitis (NASH) in a human subject; providing weight loss to the human subject; or suppressing appetite in the human subject, comprising administering to the subject the pharmaceutical composition of claim 11.

24. A method of treating obesity, diabetes, nonalcoholic fatty liver disease (NAFLD), or nonalcoholic steatohepatitis (NASH) in a human subject; providing weight loss to the human subject; or suppressing appetite in the human subject, comprising administering to the subject the pharmaceutical composition of claim 12.

25. A method of treating obesity, diabetes, nonalcoholic fatty liver disease (NAFLD), or nonalcoholic steatohepatitis (NASH) in a human subject; providing weight loss to the human subject; or suppressing appetite in the human subject, comprising administering to the subject the pharmaceutical composition of claim 13.

* * * * *